US008729341B2

(12) United States Patent
Zieler et al.

(10) Patent No.: US 8,729,341 B2
(45) Date of Patent: *May 20, 2014

(54) PLANTS MODIFIED WITH MINI-CHROMOSOMES

(75) Inventors: Helge Zieler, Del Mar, CA (US); James Jin, Chesterfield, MO (US); Jennifer M. Mach, Chicago, IL (US); Gary W. Rudgers, Chicago, IL (US); Daphne Preuss, Chicago, IL (US); Mich B. Hein, Chicago, IL (US); Gregory P. Copenhaver, Chapel Hill, NC (US); Kevin Keith, Three Forks, MT (US)

(73) Assignees: University of Chicago, Chicago, IL (US); Chromatin Inc., Chicago, IL (US)

( * ) Notice: Subject to any disclaimer, the term of this patent is extended or adjusted under 35 U.S.C. 154(b) by 1195 days.

This patent is subject to a terminal disclaimer.

(21) Appl. No.: 10/590,546

(22) PCT Filed: Feb. 23, 2005

(86) PCT No.: PCT/US2005/006505
§ 371 (c)(1),
(2), (4) Date: Jul. 13, 2007

(87) PCT Pub. No.: WO2005/083096
PCT Pub. Date: Sep. 9, 2005

(65) Prior Publication Data
US 2008/0060093 A1 Mar. 6, 2008

Related U.S. Application Data

(60) Provisional application No. 60/547,256, filed on Feb. 23, 2004.

(51) Int. Cl.
*A01H 1/00* (2006.01)
*A01H 5/00* (2006.01)
*C07K 14/00* (2006.01)
*C12N 9/00* (2006.01)
*C12N 15/00* (2006.01)
*C12N 15/09* (2006.01)
*C12N 15/82* (2006.01)
*C07H 21/04* (2006.01)

(52) U.S. Cl.
USPC ........... 800/295; 800/300; 800/302; 800/278; 800/298; 435/410; 435/418; 435/419; 435/320.1; 536/23.1

(58) Field of Classification Search
None
See application file for complete search history.

(56) References Cited

U.S. PATENT DOCUMENTS

| | | |
|---|---|---|
| 4,889,806 A | 12/1989 | Olson et al. |
| 5,270,201 A | 12/1993 | Richards et al. |
| 5,288,625 A | 2/1994 | Hadlaczky |
| 5,316,931 A | 5/1994 | Donson et al. |
| 5,491,076 A | 2/1996 | Carrington et al. |
| 5,530,187 A | 6/1996 | Lamb et al. |
| 5,589,379 A | 12/1996 | Kridl et al. |
| 5,650,303 A | 7/1997 | Kridl et al. |
| 5,695,967 A | 12/1997 | Van Bokkelen et al. |
| 5,712,134 A | 1/1998 | Hadlaczky |
| 5,721,118 A | 2/1998 | Scheffler |
| 5,733,744 A | 3/1998 | Hamilton |
| 5,766,885 A | 6/1998 | Carrington et al. |
| 5,866,793 A | 2/1999 | Baga et al. |
| 5,869,294 A | 2/1999 | Harrington et al. |
| 5,877,402 A | 3/1999 | Maliga et al. |
| 5,891,625 A | 4/1999 | Buchardt et al. |
| 5,891,691 A | 4/1999 | Hadlaczky |
| 5,925,808 A | 7/1999 | Oliver et al. |
| 5,977,439 A | 11/1999 | Hamilton |
| 5,977,441 A | 11/1999 | Oliver et al. |
| 6,025,155 A | 2/2000 | Hadlaczky et al. |
| 6,077,697 A | 6/2000 | Hadlaczky et al. |
| 6,127,171 A | 10/2000 | Slilaty et al. |
| 6,156,953 A * | 12/2000 | Preuss et al. ................ 800/278 |
| 6,162,963 A | 12/2000 | Kucherlapati et al. |

(Continued)

FOREIGN PATENT DOCUMENTS

| | | |
|---|---|---|
| EP | 0320500 | 6/1989 |
| EP | 0338266 | 10/1989 |
| EP | 0442174 | 8/1991 |
| EP | 0552829 | 7/1993 |
| EP | 0959134 | 11/1999 |
| WO | WO 89/09219 | 5/1989 |
| WO | WO 91/02066 | 2/1991 |
| WO | WO 91/13994 | 9/1991 |
| WO | WO 92/07080 | 4/1992 |
| WO | WO 93/05165 | 3/1993 |

(Continued)

OTHER PUBLICATIONS

Avramova 2002 Plant Physiology 129:40-49.*
Harrington et al 1997 Nature Genetics, 15:345-354 submitted by Applicant.*
Hall et al 2004 Current Opinion in Plant Biology 7:108-114.*
Bryant et al 2001 Journal of Experimental Biology 52:193-202.*

(Continued)

*Primary Examiner* — Brent T Page
*Assistant Examiner* — Ashley K Buran
(74) *Attorney, Agent, or Firm* — Marshall, Gerstein & Borun LLP

(57) ABSTRACT

The invention is generally related to methods of generating plants transformed with novel autonomous mini-chromosomes. Mini-chromosomes with novel compositions and structures are used to transform plants cells which are in turn used to generate the plant. Methods for generating the plant include methods for delivering the mini-chromosome into plant cell to transform the cell, methods for selecting the transformed cell, and methods for isolating plants transformed with the mini-chromosome. Plants generated in the present invention contain novel genes introduced into their genome by integration into existing chromosomes.

26 Claims, 6 Drawing Sheets

(56) References Cited

U.S. PATENT DOCUMENTS

| | | |
|---|---|---|
| 6,265,211 B1 | 7/2001 | Choo et al. |
| 6,277,608 B1 | 8/2001 | Hartley et al. |
| 6,277,632 B1 | 8/2001 | Harney |
| 6,291,243 B1 | 9/2001 | Fogarty et al. |
| 6,337,431 B1 | 1/2002 | Tricoli et al. |
| 6,348,353 B1 | 2/2002 | Harrington et al. |
| 6,365,377 B1 | 4/2002 | Patten et al. |
| 6,369,296 B1 | 4/2002 | Ratcliff et al. |
| 6,376,234 B1 | 4/2002 | Grimsley et al. |
| 6,376,745 B1 | 4/2002 | Atabekov et al. |
| 6,388,168 B1 | 5/2002 | Maliga et al. |
| 6,391,639 B1 | 5/2002 | Schenk et al. |
| 6,455,315 B1 | 9/2002 | Baszczynski et al. |
| 6,472,586 B1 | 10/2002 | Maliga et al. |
| 6,475,798 B2 | 11/2002 | Fogarty et al. |
| 6,495,318 B2 | 12/2002 | Harney |
| 6,514,693 B1 | 2/2003 | Lansdorp |
| 6,573,427 B1 | 6/2003 | Atabekov et al. |
| 6,900,012 B1* | 5/2005 | Preuss et al. ............... 435/6 |
| 6,972,197 B1* | 12/2005 | Preuss et al. ............ 435/468 |
| 7,119,250 B2* | 10/2006 | Keith et al. ............... 800/278 |
| 7,226,782 B2* | 6/2007 | Mach et al. ............. 435/320.1 |
| 7,227,057 B2* | 6/2007 | Mach et al. ............. 800/312 |
| 7,235,716 B2* | 6/2007 | Mach et al. ............. 800/306 |
| 7,456,013 B2* | 11/2008 | Mach et al. ............. 435/320.1 |
| 2001/0008025 A1 | 7/2001 | Hadlaczky et al. |
| 2002/0028513 A1 | 3/2002 | Fogarty et al. |
| 2002/0034814 A1 | 3/2002 | Atabekov et al. |
| 2002/0059660 A1 | 5/2002 | Tricoli et al. |
| 2002/0072097 A1 | 6/2002 | Delcardayre et al. |
| 2002/0076811 A1 | 6/2002 | Okazaki et al. |
| 2002/0094574 A1 | 7/2002 | Hartley et al. |
| 2002/0108146 A1 | 8/2002 | Pang et al. |
| 2002/0111930 A1 | 8/2002 | Battles |
| 2002/0123053 A1* | 9/2002 | Luo et al. ............... 435/6 |
| 2002/0123145 A1 | 9/2002 | Ow |
| 2002/0128457 A1 | 9/2002 | Anderson et al. |
| 2002/0132348 A1 | 9/2002 | Bradshaw et al. |
| 2002/0151058 A1 | 10/2002 | Perkins et al. |
| 2002/0155530 A1 | 10/2002 | Szybalski et al. |
| 2002/0160410 A1 | 10/2002 | Hadlaczky et al. |
| 2002/0160970 A1 | 10/2002 | Hadlaczky et al. |
| 2002/0172997 A1 | 11/2002 | Hartley et al. |
| 2002/0174453 A1 | 11/2002 | Daniell et al. |
| 2002/0192819 A1 | 12/2002 | Hartley et al. |
| 2003/0003435 A1 | 1/2003 | DeJong et al. |
| 2003/0003466 A1 | 1/2003 | Harrington et al. |
| 2003/0022204 A1 | 1/2003 | Landsorp |
| 2003/0032186 A1 | 2/2003 | Jorgensen et al. |
| 2003/0033617 A1 | 2/2003 | Hadlaczky et al. |
| 2003/0041353 A1 | 2/2003 | Daniell et al. |
| 2003/0049665 A1 | 3/2003 | Szybalski et al. |
| 2003/0064509 A1 | 4/2003 | Marynen et al. |
| 2003/0077804 A1 | 4/2003 | Byrd et al. |
| 2003/0083293 A1 | 5/2003 | Hadlaczky et al. |
| 2003/0084482 A1 | 5/2003 | Hall et al. |
| 2003/0088081 A1 | 5/2003 | Maliga et al. |
| 2003/0097678 A1 | 5/2003 | Kushinov et al. |
| 2003/0101480 A1 | 5/2003 | Hadlaczky et al. |
| 2003/0108914 A1 | 6/2003 | Hadlaczky |
| 2003/0124561 A1 | 7/2003 | Mach et al. |

FOREIGN PATENT DOCUMENTS

| | | |
|---|---|---|
| WO | WO 95/02319 | 1/1995 |
| WO | WO 95/12669 | 5/1995 |
| WO | WO 96/40965 | 12/1996 |
| WO | WO 97/06250 | 2/1997 |
| WO | WO 97/14026 | 4/1997 |
| WO | WO 97/40183 | 10/1997 |
| WO | WO 98/02562 | 1/1998 |
| WO | WO 98/08964 | 3/1998 |
| WO | WO 98/37223 | 8/1998 |
| WO | WO 98/51790 | 11/1998 |
| WO | WO 98/54342 | 12/1998 |
| WO | WO 98/55637 | 12/1998 |
| WO | WO 99/21977 | 5/1999 |
| WO | WO 99/67374 | 12/1999 |
| WO | WO 00/06715 | 2/2000 |
| WO | WO 00/07431 | 2/2000 |
| WO | WO 00/40723 | 7/2000 |
| WO | WO 00/46350 | 8/2000 |
| WO | WO 00/52155 | 9/2000 |
| WO | WO 00/52183 | 9/2000 |
| WO | WO 00/75289 | 12/2000 |
| WO | WO 00/75299 | 12/2000 |
| WO | WO 00/78985 | 12/2000 |
| WO | WO 01/00858 | 1/2001 |
| WO | WO 01/05962 | 1/2001 |
| WO | WO 01/11020 | 2/2001 |
| WO | WO 01/20011 | 3/2001 |
| WO | WO 01/27241 | 4/2001 |
| WO | WO 01/29241 | 4/2001 |
| WO | WO 00/78976 | 8/2001 |
| WO | WO 01/59091 | 8/2001 |
| WO | WO 01/64024 | 9/2001 |
| WO | WO 01/77357 | 10/2001 |
| WO | WO 02/00842 | 1/2002 |
| WO | WO 02/04629 | 1/2002 |
| WO | WO 02/08409 | 1/2002 |
| WO | WO 02/29068 | 4/2002 |
| WO | WO 02/50288 | 6/2002 |
| WO | WO 02/057464 | 7/2002 |
| WO | WO 02/059296 | 8/2002 |
| WO | WO 02/059330 | 8/2002 |
| WO | WO 02/067655 | 9/2002 |
| WO | WO 02/072849 | 9/2002 |
| WO | WO 02/081710 | 10/2002 |
| WO | WO 02/086144 | 10/2002 |
| WO | WO 02/086146 | 10/2002 |
| WO | WO 02/096923 | 12/2002 |
| WO | WO 03/028014 | 4/2003 |

OTHER PUBLICATIONS

Ananiev et al 1998 PNAS 95:13073-13078.*

Tek et al 2010 Chromosome Research 18:337-347.*

Abdullah et al., "Efficient Plant Regeneration from Rice Protoplasts through Somatic Embryogenesis," *BioTechnology* 4: 1087-1090 (1986).

Abel et al., "Delay of Disease Development in Transgenic Plants that Express the Tobacco Mosaic Virus Coat Protein Gene," *Science* 232: 738-743 (1986).

Alfenito et al., "Molecular Characterization of a Maize B Chromosome Centric Sequence," *Genetics* 135: 589-597 (1993).

Alonso-Blanco et al., "Development of AFLP Based Linkage Map of Ler, Col and Cvi *Arabidopsis thaliana* Ecotypes and Construction of a Ler/Cvi Recombinant Inbred Line Population," *The Plant Journal* 14: 259-271 (1998).

Ananiev et al., "Chromosome-specific Molecular Organization of Maize (*Zea mays* L.) Centromeric Regions," *Proc. Natl. Acad. Sci. USA* 95: 13073-13078 (1998).

Ananiev et al., "A Knob-Associated Tandem Repeat in Maize Capable of Forming Fold-back DNA Segments: Are Chromosome Knobs Megatransposons?," *Proc. Natl. Acad. Sci. USA.* 95: 10785-10790 (1998).

Ananiev et al., "Complex Structure of Knob DNA on Maize Chromosome 9: Retrotransposon Invasion into Heterochromatin," *Genetics* 149: 2025-2037 (1998).

Ananiev et al., "Complex Structure of Knobs and Centromeric Regions in Maize Chromosomes," *Tsitol Genet.* 34: 11-5 (2000).

Aragon-Alcaide et al., "A Cereal Centromeric Sequence," *Chromosoma* 105: 261-8 (1996).

Araki et al., "Site-specific Recominanse, R, Encoded by Yeast Plasmid pSR1," *J. Mol. Biol.* 225: 25-37 (1992).

Areshchenkova et al., "Long Tomato Microsatellites are Predominantly Associated with Centromeric Regions," *Genome* 42: 536-44 (1999).

Armstrong et al., "Physical Mapping of DNA Repetitive Sequences to Mitotic and Meiotic Chromosomes of *Brassica oleracea* var. *alboglabra* by Fluorescence in situ Hybridization," *Heredity* 81: 666-673 (1998).

(56) References Cited

OTHER PUBLICATIONS

Barki-Golan et al., "Studies on Growth Inhibition by Lectins of Penicillia and *Aspergilli*," *Arch. Microbiol.* 116: 119-124 (1978).
Baum et al., "The Centromeric K-Type Repeat and the Central Core are Together Sufficient to Establish a Functional *Schizosaccharomyces pombe* Centromere," *Molecular Biology of the Cell* 5: 747-761 (1994).
Bell et al., "Assignment of 30 Microsatellite Loci to the Linkage Map of *Arabidopsis*," *Genomics* 19: 137-144 (1994).
Bernal-Lupo et al., "Changes in Soluble Carbohydrates During Seed Storage," *Plant Physiol.* 98: 1207-1210 (1992).
Berzal-Herranz et al., "In Vitro Selection of Active Hairpin Ribozymes by Sequential RNA-Catalyzed Cleavage and Ligation Reactions," *Genes & Development* 6: 129-134 (1992).
Bevan et al., "Clearing a Path Through the Jungle: Progress in *Arabidopsis* Genomics," *BioEssays* 21: 110-120 (1999).
Bevan et al., "Structure and Transcription of the Nopaline Synthase Gene Region of T-DNA," *Nucleic Acids Research* 11: 369-385 (1983).
Birchler, "Do These Sequences Make CENs Yet?" *Genome Research* 7: 1035-1037 (1997).
Blackman et al., "Maturation Proteins and Sugars in Dessiccation Tolerance of Developing Soybean Seeds," *Plant Physiol.* 100: 225-230 (1992).
Bloom, "The Centromere Frontier: Kinetochore Components, Microtubule-Based Motility, and the CEN-Value Paradox," *Cell* 73: 621-624 (1993).
Bol et al., "Plant Pathogenesis-related Proteins Induced by Virus Infection," *Annu. Rev. Phytopath.* 28: 113-138 (1990).
Bowler et al., "Superoxide Dismutase and Stress Tolerance," *Annu. Rev. Plant Physiol. Plant Mol. Biol.* 43: 83-116 (1992).
Brandes et al., "Multiple Repetitive DNA Sequences in the Paracentromeric Regions of *Arabidopsis thaliana* L.," *Chromosome Res.* 5: 238-46 (1997).
Branson et al., "Potential for Utilizing Resistance from Relatives of Cultivated Crops," *Proceedings North Central Branch Entomological Society of America* 27: 9195 (1972).
Brisson et al., "Expression of a Bacterial Gene in Plants by Using a Viral Vector," *Nature* 310:511-516 (1984).
Broach et al., "Transformation in Yeast: Development of a Hybrid Cloning Vector and Isolation of the CAN1 Gene," *Gene* 8: 121-133 (1979).
Broekaert et al., "A Chitin-Binding Lectin from Stinging Nettle Rhizomes with Antifungal Properties," *Science* 245: 1100-1102 (1989).
Buchowicz, J., "Nuclear Extrachromosomal DNA of Higher Plants," *Acta Biochim Pol.* 44: 13-19 (1977).
Burke et al., "Cloning of Large Segments of Exogenous DNA into Yeast by Means of Artificial Chromosome Vectors," *Science* 236: 806-812 (1987).
Bytebier et al., "T-DNA Organization in Tumor Cultures and Transgenic Plants of the Monocotyledon *Asparagus officinalis*," *Proc. Natl. Acad. Sci. USA* 84: 5345-5349 (1987).
Callis et al., "Introns Increase Gene Expression in Cultured Maize Cells," *Genes & Development* 1: 1183-1200 (1987).
Cambareri et al., "Structure of the Chromosome VII Centromere Region in *Neurospora crassa*: Degenerate Transposons and Simple Repeats," *Molecular and Cellular Biology* 18: 5465-5477 (1998).
Campbell, "The Production and Characterization of Rodent and Human Hybridomas," *Laboratory Techniques in Biochemistry and Molecular Biology* 13: 75-83 (1984).
Capecchi, "High Efficiency Transformation by Direct Microinjection of DNA into Cultured Mammalian Cells," *Cell* 22: 479-488 (1980).
Carbon et al., "Centromere Structure and Function in Budding and Fission Yeasts," *The New Biologist* 2: 10-19 (1990).
Carbon et al., "Structural and Functional Analysis of a Yeast Centromere (CEN3)," *J. Cell Sci. Suppl.* 1, 43-58 (1984).
Carbon et al., *Recombinant Molecules: Impact on Science and Society*, Raven Press: 335-378 (1977).
Carpenter et al., "On the Control of the Distribution of Meiotic Exchange in *Drosophila melanogaster*," *Genetics* 101: 81-89 (1982).

Cech et al., "In Vitro Splicing of the Ribosomal RNA Precursor of Tetrahymena: Involvement of a Guanosine Nucleotide in the Excision of the Intervening Sequence," *Cell* 27: 487-496 (1981).
Cepko et al., "Construction and Applications of a Highly Transmissible Murine Retrovirus Shuttle Vector," *Cell* 37: 1053-1062 (1984).
Chandler et al., "Two Regulatory Genes of the Maize Anthocyanin Pathway are Homologous: Isolation of *B* Utilizing *R* Genomic Sequences," *The Plant Cell* 1: 1175-1183 (1989).
Chang et al., "Restriction Fragment Length Polymorphism Linkage Map for *Arabidopsis thaliana*," *Proc. Natl. Acad. Sci USA* 85: 6856-6860 (1988).
Charlesworth et al., "The Evolution of Restricted Recombination and the Accumulation of Repeated DNA Sequences," *Genetics* 112: 947-962 (1986).
Charlesworth et al., "The Evolutionary Dynamics of Repetitive DNA in Eukaryotes," *Nature* 371:215-220 (1994).
Cheng et al., "Functional Rice Centromeres are Marked by a Satellite Repeat and a Centromere-Specific Retrotransposon," *Plant Cell.* 14: 1691-1704 (2002).
Choi et al., "Construction and Characterization of a Bacterial Artificial Chromosome Library of *Arabidopsis thaliana*," *Plant Molecular Biology Reporter* 13: 124-129 (1995).
Choo, "Turning on the Centromere," *Nature Genetics* 18: 3-4 (1998).
Choo, "Why Is the Centromere So Cold?" *Genome Research* 8: 81-82 (1998).
Chowrira et al., "In Vitro and In Vivo Comparison of Hammerhead, Hairpin, and Hepatitis Delta Virus Self-processing Ribozyme Cassettes," *The Journal of Biological Chemistry* 269: 25856-25864 (1994).
Christou et al., "Stable Transformation of Soybean Callus by DNA-Coated Gold Particles," *Plant Physiol.* 87: 671-674 (1988).
Chu et al., "Separation of Large DNA Molecules by Contour-Clamped Homogenous Electric Fields," *Science* 234: 1582-1585 (1986).
Chye et al., "Characterization of *TSCL*, a Nonviral Retroposon from *Arabidopsis thaliana*," *Plant Molecular Biology* 35: 893-904 (1997).
Clapp, "Somatic Gene Therapy into Hemotopoietic Cells," *Clinics in Perinatology* 20: 155-168 (1993).
Clarke et al., "Centromeres: Proteins, Protein Complexes, and Repeated Domains at Centromeres of Simple Eukaryotes," *Genetics and Development* 8: 212-218 (1998).
Clarke et al., "Analysis of Centromeric DNA in the Fission Yeast *Schizosaccharomyces pombe*," *Proc. Natl. Acad. Sci. USA* 83: 8253-8257 (1986).
Clarke et al., "Isolation of a Yeast Centromere and Construction of Functional Small Circular Chromosomes," *Nature* 287: 504-509 (1980).
Cohen et al., "Construction of Biologically Functional Bacterial Plasmids In Vitro," *Proc. Nat. Acad. Sci. USA* 70: 3240-3244 (1973).
Conkling et al., "Isolation of Transcriptionally Regulated Root-Specific Genes from Tobacco," *Current Opinion Plant Physiol.* 93: 1203-1211 (1990).
Copenhaver, et al., "Centromeres in the Genomic Era: Unraveling Paradoxes," *Plant Biology* 2: 104-108 (1999).
Copenhaver et al., "Assaying Genome-wide Recombination and Centromere Functions with *Arabidopsis* tetrads," *Proc. Natl. Acad. Sci. USA*, 95: 247-252 (1998).
Copenhaver et al., "Tetrad Analysis in Higher Plants: A Budding Technology," *Plant Physiol.*, 124: 7-16 (2000).
Copenhaver et al., "RFLP and Physical Mapping with an rDNA-specific Endonuclease Reveals that Nucleolus Organizer Regions of *Arabidopsis thaliana* Adjoin the Telomeres on Chromosomes 2 and 4," *Plant Journal* 9: 259-276 (1996).
Copenhaver et al., "Genetic Definition and Sequence Analysis of *Arabidopsis* Centromeres," *Science* 286: 2468-2474 (1999).
Copenhaver et al., "Two-dimensional RFLP analyses Reveal Megabase-sized Clusters of rRNA Gene Variants in *Arabidopsis thaliana*, Suggesting Local Spreading of Variants as the Mode for Gene Homogenization During Concerted Evolution," *The Plant Journal* 9: 273-282 (1996).

(56) References Cited

OTHER PUBLICATIONS

Copenhaver et al., "Use of RFLPs Larger than 100 kbp to Map Position and Internal Organization of the Nucleolus Organizer Region on Chromosome 2 in *Arabidopsis thaliana*," *Plant Journal* 7: 273-286 (1995).
Copenhaver, "Using *Arabidopsis* to Understand Centromere Function: Progress and Prospects," *Chromosome Res. 2993*: 11: 255-62 (2003).
Coxson et al., "Pulse Release of Sugars and Polyols from Canopy Bryophytes in Tropical Montane Rain Forest (Guadeloupe, French West Indies)," *Biotropica* 24: 121-133 (1992).
Creusot et al., "The CIC Library: A Large Insert YAC Library for Genome Mapping in *Arabidopsis thaliana*," *The Plant Journal* 8: 763-770 (1995).
Cristou et al., "Stable Transformation of Soybean Callus by DNA-Coated Gold Particles, *"Plant Physiol.* 87: 671-674 (1988).
Cuozzo et al., "Viral Protection in Transgenic Tobacco Plants Expressing the Cucumber Mosaic Virus Coat Protein or Its Antisense RNA," *BioTechnology* 6: 549-557 (1988).
Curiel et al., "High-efficiency Gene Transfer Mediated by Adenovirus Coupled to DNA-polylysine Complexes," *Hum. Gen. Ther.* 3: 147-154 (1992).
Curiel et al., "Adenovirus Enhancement of Transferrin-Polylysine-Mediated Gene Delivery," *Proc. Natl. Acad. Sci. USA* 88: 8850-8854 (1991).
Cutler et al. , "Winter Flounder Antifreeze Protein Improves the Cold Hardiness of Plant Tissues," *J. Plant Physiol.* 135: 351-354 (1989).
Czapla et al., "Effect of Plant Lectins on the Larval Development of European Corn Borer (*Lepidoptera: Pyralidae*) and Southern Corn Rootworm (*Coleoptera: Chrysomelidae*)," *J. Econ Entomol 83*: 2480-2485 (1990).
Davies et al., "Leaf Senescence in a Nonyellowing Mutant of *Festuca pratensis*," *Plant Physiol.* 93: 588-595 (1990).
Dellaporta et al., "Molecular Cloning of the Maize *R-nj* Allele by Transposon Tagging with *Ac"*: *Chromosome Structure and Function: Impact of New Concepts, 18th Stadler Genetics Symposium 11*: 263-282 (1988).
Dennis et al., "Knob Heterochromatin Homology in Maize and Its Relatives," *J. Mol. Evol.* 20: 341-350 (1984).
Depicker et al., "A Negative Selection Scheme for Tobacco Protoplast-Derived Cells Expressing the T-DNA Gene 2," *Plant Cell Reports 7*: 63-66 (1988).
Di Laurenzio et al., "The SCARECROW Gene Regulates an Asymmetric Cell Division that Is Essential for Generating the Radial Organization of the *Arabidopsis* Root," *Cell*, 86: 423-433 (1996).
Discussion with David Baltimore as Moderator, "Recombinant Molecules: Impact on Science and Society": 337-352, New York, 1977.
Donahue et al., "The Nucleotide Sequence of the *HIS4* Region of Yeast," *Gene.* 18: 47-59 (1982).
Dong et al., "Rice (*Oryza sativa*) Centromeric Regions Consist of Complex DNA," *Proc. Natl. Acad. Sci. USA 95*: 8135-40 (1998).
Dure III et al., "Common Amino Acid Sequence Domains Among the LEA Proteins of Higher Plants," *Plant Molecular Biology* 12: 475-486 (1989).
duSart et al., "A Functional Neo-centromere Formed Through Activation of a Latent Human Centromere and Consisting of Non-alpha Satellite DNA," *Nature Genetics 16*: 144-153 (1997).
Earnshaw et al., "Proteins of the Inner and Outer Centromere of Mitotic Chromosomes," *Genome 31*: 541-552 (1989).
Earnshaw et al., "When is a Centromere Not a Kinetochore?" *Journal of Cell Science* 99: 1-4 (1991).
Ebert et al., "Identification of an Essential Upstream Element in the Nopaline Synthase Promoter by Stable and Transient Assays," *Proc. Natl. Acad. Sci. USA* 84: 5745-5749 (1987).
Ecker, "PFGE and YAC Analysis of the *Arabidopsis* Genome," *Methods I*: 186-194 (1990).
Eglitis et al., "Retroviral Vectors for Introduction of Genes into Mammalian Cells," *Bio Techniques 6*: 608-614 (1988).
Eglitis et al., "Retroviral-mediated Gene Transfer into Hemapoietic Cells," *Avd. Exp. Med. Biol. 241*: 19-27 (1988).

Enomoto et al., "Mapping of the *pin* Locus Coding for a Site-Specific Recombinase that Causes Flagellar-Phase Variation in *Escherichia coli* K-12," *Journal of Bacteriology 156*: 663-668 (1983).
Erdmann et al., "Glycosylglycerol Accumulation During Salt Acclimination of Two Unicellular Cyanobacteria," *Journal of General Microbiology 138*: 363-368 (1992).
Ferrin et al., "Selective Cleavage of Human DNA: RecA-Assisted Restriction Endonuclease (RARE) Cleavage," *Science 254*: 1494-1497 (1991).
Fitzpatrick, "Pleiotropic Gene Found in Barley Plant" *Gen. Engineering News* 13(5): 1, 22 (1993).
Fleig. et al., "Functional Selection for the Centromere DNA from Yeast Chromosome VIII," *Nuc. Acids. Res 23*: 922-924 (1995).
Forster et al., "Self-Cleavage of Plus and Minus RNAs of a Virusoid and a Structural Model for the Active Sites," *Cell 49*: 211-220 (1987).
Fraley et al, "The SEV Sysem: A New Disarmed TI Plasmid Vector System for Plant Transformation," *BioTechnology 3*: 629-635 (1985).
Fransz et al., "Cytogenetics for the Model System *Arabidopsis thaliana*," *The Plant Journal 13*: 867-876 (1998).
Fransz et al., "Integrated Cytogenetic Map of Chromosome Arm 4S of *A. thaliana*: Structural Organization of Heterochromatic Knob and Centromere Region," *Cell. 100*: 367-76 (2000).
Frary et al., "Molecular Mapping of the Centromeres of Tomato Chromosomes 7 and 9," *Mol Gen Genet., 250*: 295-304 (1996).
Fromm et al., "Expression of Genes Transferred into Monocot and Dicot Plant Cells by Electroporation," *Proc. Nat. Acad. Sci. USA 82*: 5824-5828 (1985).
Fromm et al., "Stable Transformation of Maize After Gene Transfer by Electroporation," *Nature 319*: 791-793 (1986).
Fujimara et al, "Regeneration of Rice Plants from Protoplasts," *Plant Tissue Culture Letters 2*: 74 (1985).
Fukui et al., "Physical Arrangement of Retrotransposon-Related Repeats in Centromeric Regions of Wheat," *Plant Cell Physiology, 42*: 189-96 (2004).
Fynan et al., "DNA Vaccines: Protective Immunizations by Parenteral, Mucosal, and Gene-Gun Inoculations," *Proc. Nat. Acad. Sci. USA 90*: 11478-11482 (1993).
Gatehouse et al., "Effect of Seed Lectins from *Phaseolus vulgaris* on the Development of Larvae of *Callosobruchus maculates*; Mechanism of Toxicity," *J. Sci. Food. Agric.* 35: 373-380 (1984).
Gefter et al., "A Simple Method for Polyethylene Glycol-promoted Hybridization of Mouse Myeloma Cells," *Somatic Cell Genet. 3*: 231-236 (1977).
GenBank Accession No. AF013103.
GenBank Accession No. AF049110.
GenBank Accession No. AF050437.
GenBank Accession No. AF050438.
GenBank Accession No. AF050452.
GenBank Accession No. AF050453.
GenBank Accession No. AF071126.
GenBank Accession No. AF078917.
GenBank Accession No. AF078922.
GenBank Accession No. AF078923.
GenBank Accession No. AF090447.
GenBank Accession No. AF123535.
GenBank Accession No. AF242891.
GenBank Accession No. AF273104.
GenBank Accession No. AF448416.
GenBank Accession No. AY129008.
GenBank Accession No. AY173950.
GenBank Accession No. AY321491.
GenBank Accession No. K01868.
GanBank Accession No. K02202.
GenBank Accession No. M35408.
GenBank Accession No. X01365.
GenBank Accession No. U39642.
Gerlach et al., "Construction of a Plant Disease Resistance Gene from the Satellite RNA of Tobacco Ringspot Virus," *Nature 328*: 802-805 (1987).
Gindullis et al., "The Large-Scale Organization of the Centromeric Region in Beta Species," *Genome Res. 11*: 253-65 (2001).

(56) References Cited

OTHER PUBLICATIONS

Gindullis, et al., "Construction and Characterization of a BAC Library for the Molecular Dissection of a Single Wild Beet Centromere and Sugar Beet (*Beta Vulfaris*)," *Genome Analysis, 44*: 846-55 (2001).
Giordano et al., "Identification by Denaturing High-Performance Liquid Chromatography of Numerous Polymorphisms in a Candidate Region for Multiple Sclerosis Susceptibility," *Genomics, 56*: 247-253 (1999).
Goding, *Monoclonal Antibodies: Principles and Practice*, Academic Press, Orlando, Florida, 60-74 (1986).
Golic et al., "The FLP Recombinase of Yeast Catalyzes Site-Specific Recombinatioin in the *Drosophila* Genome" *Cell 59*: 499-509 (1989).
Goring et al., "Transformation of a Partial Nopaline Synthase Gene into Tobacco Suppresses the Expression of a Resident Wild-type Gene," *Proc. Natl. Acad. Aci. USA 88*, 1770-1774 (1991).
Graham et al., "Transformation of Rat Cells by DNA of Human Adenovirus 5," *Virology 54*: 536-539 (1973).
Grellet et al., "Organization and Evolution of a Higher Plant Alphoid-like Satellite DNA Sequence," *J. Mol. Biol. 187*: 495-507(1986).
Grill et al., "Construction and Characterization of a Yeast Artificial Chromosome Library of *Arabidopsis* Which Is Suitable for Chromosome Walking," *Mol. Gen. Genet. 226*: 484-490 (1991).
Guerrero et al., "Turgo-Responsive Gene Transcription and RNA Levels Increase Rapidly When Pea Shoots Are Wilted. Sequence and Expression of Three Inducible Genes," *Plant Molecular Biology 15*: 11-26 (1990).
Gupta et al., "Increased Resistance to Oxidative Stress in Transgenic Plants that Overexpress Chloroplastic Cu/Zn Superoxide Dismutase," *Proc. Natl. Acad. Sci. USA 90*: 1629-1633 (1993).
Gutierrez-Marcos et al., "Three Members of a Novel Small Gene-Family from *Arabidopsis thaliana* Able to Complement Functionally an *Escherichia coli* Mutant Defective in PAPS Reducatase Activity Encode Proteins with a Thioredoxin-like Domain and "APS Reductase" Activity," *Proc. Natl. Acad. Sci USA 93*: 13377-133824 (1996).
Haaf et al., "Integration of Human Satellite DNA into Simian Chromosomes: Centromere Protein Binding and Disruption of Normal Chromosome Segregation," *Cell 70*: 681-696 (1992).
Hadlaczky et al., "Centromere Formation in Mouse Cells Cotransformed with Human DNA and a Dominant Marker Gene," *Proc. Natl. Acad. Sci., USA 88*: 8106-8110 (1991).
Hauge et al., "Mapping the *Arabidopsis* Genome," *Symp. Society for Experimental Biology, 45*:45-56 (1991).
Hall, et al., "The Rapidly Evolving Field of Plant Centromeres," Department of Molecular Genetics and Cell Biology, The University of Chicago, Chicago, Illinois 60637, USA, *Curr. Opin Plant Biol.* 7108-14 (2002).
Hamilton et al., "Stable Transfer of Intact High Molecular Weight DNA into Plant Chromosones," *Proc. Natl. Acad. Sci. USA 93*: 9975-9979(1996).
Hamilton, "A Binary BAC System for Plant Transformation with High-Molecular-Weight DNA," *Gene 4*: 200: 107-116 (1997).
Hammock et al., "Expression and Effects of the Juvenile Hormone Esterase in a Baculovirus Vector," *Nature 344*: 458-463 (1990).
Harrington et al., "Formation of de novo Centromeres and Construction of First-generation Human Artificial Microchromosomes," *Nature Genetics 15*: 345-354 (1997).
Harrison et al., "Centromeric Repetitive DNA Sequences in the Genus *Brassica*," *Theor. Appl. Genet., 90*: 157-165 (1995).
Haseloff et al., "Removal of a Cryptic Intron and Subcellular Localization of Green Fluorescent Protein Are Required to Mark Transgenic *Arabidopsis* Plants Brightly," *Proc. Natl. Acad. Sci. USA 94*: 2122-2127 (1997).
Hegemann et al., "The Ceontromere of Budding Yeast," *BioEssays 15*: 451-460 (1998).
Heller et al., "Mini-Chromosomes Derived from the Human Y Chromosome by Telomere Directed Chromosome Breakage," *Proc. Natl. Acad. Sci. USA 93*: 7125-7130 (1996).
Hemenway et al., "Analysis of the Mechanism of Protection in Transgenic Plants Expressing the Potato Virus X Coat Protein or its Antisense RNA," *The EMBO Journal 7*: 1273-1280 (1988).
Heslop-Harrison et al., "Polymorphisms and Genomic Organization of Repetitive DNA from Centromeric Regions of *Arabidopsis* Chromosomes," *Plant Cell. 11*: 31-42 (1999).
Hilder et al., "A Novel Mechanism of Insect Resistance Engineered into Tobacco," *Nature 330*: 160-163 (1987).
Hinchee et al., "Production of Transgenic Soybean Plants Using *Agrobacterium*-Mediated DNA Transfer," *BioTechnology 6*: 915-922 (1988).
Hoess et al., "P1 Site-Specific Recombination: Nucleotide Sequence of the Recombining Sites," *Proc. Nat. Acad. Sci. USA 79*: 3398-3402 (1982).
Houben et al., "DNA and Proteins of Plant Centromeres," *Current Opinion in Plant Biology 6*: 554-560 (2003).
Hsiao et al., "High-Frequency Transformation of Yeast by Plasmids Containing the Cloned Yeast ARG4 Gene," *Proc. Nat. Acad. Sci. USA 76*: 3829-3833 (1979).
Hudakova et al., "Sequence Organization of Barley Centromeres," *Nucleic Acids Resources*, 29: 5029-35 (2001).
Hudspeth et al., "Structure and Expression of the Maize Gene Encoding the Phosphoenolpyruvate Carboxylase Isozyme Involved in $C_4$ Photosynthesis," *Plant Molecular Biology 12*: 579-589 (1989).
Hwang et al., "Identification and Map Position of YAC Clones Comprising One-third of the *Arabidopsis* genome," *The Plant Journal 1*: 367-374 (1991).
Ikeda, et al., "Genetic Studies of Avermectin Biosynthesis in *Streptomyces avermitilis*," *Journal of Bacteriology 16*: 5615-5621 (1987).
Ikeno, et al., "Construction of YAC-based Mammalian Artificial Chromosomes," *Nature Biotechnology 16*: 431-439 (1998).
Ikuta et al., "The Alpha-Amylase Gene as a Marker for Gene Cloning: Direct Screening of Recombinant Clones," *BioTechnology 8*: 241-242 (1990).
Inohara et al., "Two Genes, *atp*C1 and *atp*C2, for the Subunit of *Arabidopsis thaliana* Chloroplast ATP Synthase," *The Journal of Biological Chemistry 266*: 7333-7338 (1991).
Jiang et al., "A Conserved Repetitive DNA Element Located in the Centromeres of Cereal Chromosomes," *Proc Natl Acad Sci USA.,93*: 4210-4213 (1996).
Jiang et al., "A Molecular View of Plant Centromeres," *Trends in Plant Science 8*: 570-575 (2003).
Jin et al., Maize-Centromeres: Organization and Functional Adaptation in the Genetic Background of Oat, Department of Horticulture, University of Wisconsin-Madison, Madison, Wisconsin 53706, USA, *Plant Cell. 16*: 57-81 (2004).
Johnston et al., "Gene Gun Transfection of Animal Cells and Genetic Immunization," *Methods in Cell Biology 43*: 353-363 (1994).
Jones et al., "T-DNA Structure and Gene Expression in Petunia Plants Transformed by *Agrobacterium tumafaciens* C58 Derivatives," *Mol. Gen. Genet. 207:* 478-485 (1987).
Jones et al., "High Level Expression of Introduced Chimaeric Genes in Regenerated Transformed Plants," *The EMBO Journal 4*: 2411-2418 (1985).
Jorgensen et al., "T-DNA is Organized Predominantly in Inverted Repeat Structures in Plants Transformed with *Agrobacterium tumafaciens* C58 Derivatives," *Mol. Gen. Genet. 207*: 471-477 (1987).
Jouanin et al., "Localization and Restriction Maps of Replication Origin Regions of the Plasmids of *Agrobacterium rhizogenes* Strain $A_4$," *Mol. Gen. Genet. 201*: 370-374 (1985).
Joyce, "RNA Evolution and the Origins of Life," *Nature 338*: 217-224 (1989).
Karpen, "Position-effect Variegation and the New Biology of Heterochromatin," *Current Opinion in Genetics and Development 4*: 281-291 (1994).
Karsten et al., "Polyol Content of Bostrychia and Stictosiphonia (Rhodomelaceae, Rhodophyta) from Field and Culture," *Botanica Marina 35*: 11-19 (1992).

(56) References Cited

OTHER PUBLICATIONS

Kaasen et al., "Molecular Cloning and Physical Mapping of the otsBA Genes, Which Encode the Osmoregulatory Trehalose Pathway of *Escherichia coli*: Evidence that Transcription Is Activated by KatF (AppR)," *Journal of Bacteriology* 174: 889-898 (1992).
Kaszás et al., "Misdivision Analysis of Centromere Structure in Maize," *The EMBO Journal* 15: 5246-5255 (1996).
Kato et al., "Foreign DNA Introduced by Calcium Phosphate is Integrated into Repetitive DNA Elements of the Mouse L Cell Genome," *Molecular and Cellular Biology* 6: 1787-1795 (1986).
Katz et al., "Cloning and Expression of the Tyrosinase Gene from *Streptomyces antibioticus* in *Streptomyces lividans*," *Journal of General Microbiology* 129: 2703-2714 (1983).
Kim et al., "Three-Dimensional Model of the Active Site of the Self-Splicing rRNA Precursor of Tetrahymena," *Proc. Nat. Acad. Sci. USA* 84: 8788-8792 (1987).
Kishii, et al, "A Tandem Repetitive Sequence Located in the Centromeric Region of Common Wheat (*Triticum aestivum*) Chromosomes," *Chromosome Resources*, 9: 417-28 (2001).
Klee et al., "Vectors for Transformation of Higher Plants," *BioTechnology* 3: 637-642 (1985).
Klein et al., "High-Velocity Microprojectiles for Delivering Nucleic Acids into Living Cells," *Nature* 327: 70-73 (1987).
Klein et al., "Stable Genetic Transformation of Intact Nicotiana Cells by the Particle Bombardment Process," *Proc. Nat. Acad. Sci. USA* 85: 8502-8505 (1988).
Kohler et al., "Continous Cultures of Fused Cells Secreting Antibody of Predefined Specificity," *Nature* 256: 495-497 (1975).
Kohler et al., "Derivation of Specific Antibody-Producing Tissue Culture and Tumor Lines by Cell Fusion," *Eur. J. Immunol.* 6: 511-519 (1976).
Kolchinsky et al., "A Major Satellite DNA of Soybean is a 92-base Pairs Tandem Repeat" *Theor. Appl. Genet.* 90: 621-626 (1995).
Konieczny et al., "A Superfamily of *Arabidopsis thaliana* Retrotransposons," *Genetics* 127: 801-809 (1991).
Konieczny et al., "A Procedure for Mapping *Arabidopsis* Mutations Using Co-dominant Ectotype-specific PCR-based Markers," *The Plant Journal* 4: 403-310 (1993).
Koorneef et al., "Trisomics in *Arabidopsis thaliana* and the Location of Linkage Groups," *Genetica* 61: 41-46 (1983).
Koorneef ,"Linkage Map of *Arabidopsis thaliana* (2n=10)," In S.J. O'Brien, ed., *Genetic Maps 1987: A Compilation of Linkage and Restriction Maps of Genetically Studied Organisms*, 742-745 (1987).
Koorneef, "The Use of Telotrisomics for Centromere Mapping in *Arabidopsis thaliana* (L.) Heynh.," *Genetica* 62: 33-40 (1983).
Koster et al., "Sugars and Desiccation Tolerance in Seeds," *Plant Physiol.* 88: 829-832 (1988).
Kotani et al., "Structural Analysis and Complete Physical Map of *Arabidopsis thaliana* Chromosome 5 Including Centromeric Telomeric Regions," *DNA Research* 6: 381-386 (1999).
Kuhn et al., "Clustered tRNA Genes in *Schizosaccharomyces pombe* Centromeric DNA Sequence Repeats," *Proc. Nat. Acad. Sci. USA* 88: 1306-1310 (1991).
Kumekawa et al., "The Size and Sequence Organization of the Centromeric Region of *Arabiodpsis thaliana* Chromosome 5," *DNA Resources*, 7: 315-21 (2000).
Kurata et al.,, "Rice Genome Organization: The Centromere and Genome Interactions," *Ann Bot* 90: 427-35 (2002).
Kyte et al., "A Simple Method for Displaying the Hydropathic Character of a Protein," *J. Mol. Biol.* 157: 105-132 (1982).
Lakshmikumarin et al., "Isolation and Characterization of a Highly Repetitive DNA of *Brassica campestris*," *Plant Molecular Biology* 14: 447-448 (1990).
Lawton et al., "Expression of a Soybean-conclycinin Gene under the Control of the Cauliflower Mosaic Virus 35S and 19S Promoters in Transformed Petunia Tissues," *Plant Molecular Biology* 9: 315-324 (1987).
Lechner et al., "A 240 kd Multisubunit Protein Complex, CBF3, Is a Major Component of the Budding Yeast Centromere," *Cell* 64: 717-725 (1991).

Lee et al., "Use of Cloned *mtl* Genes of *Escherichia coli* to Introduce *mtl* Deletion Mutations into the Chromosome," *Journal of Bacteriology* 153: 685-692 (1983).
Levings III, "The Texas Cytoplasm of Maize: Cytoplasmic Male Sterility and Disease Susceptibility," *Science* 250: 942-947 (1990).
Li et al., "Direct Electrophoretic Detection of the Allelic State of Single DNA Molecules in Human Sperm by Using the Polymerase Chain Reaction," *Proc. Natl. Acad. Sci. USA* 87: 4580-4584 (1990).
Li et al., "CUE1: A Mesophyll Cell-Specific Positive Regulator of Light-Controlled Gene Expression in *Arabidopsis*," *The Plant Cell* 7: 1599-1610 (1995).
Lieber et al., "Selection of Efficient Cleavage Sites in Target RNAs by Using a Ribozyme Expression Library," *Molecular and Cellular Biology* 15: 540-551 (1995).
Lin et al., "Sequence and Analysis of Chromosome 2 of the Plant *Arabidopsis thaliana*," *Nature* 402: 761-768 (1999).
Liu, Y.G., et al., "Complementation of Plant Mutants with Large Genomic DNA Fragments by a Transformation-Competent Artificial Chromosome Vector Accelerates Positional Cloning," *Proc. Natl. Acad. Sci. USA* 96: 6535-6540 (1999).
Lohe et al., "Return of the H-word (heterochromatin)," *Current Opinion in Genetics and Development* 5: 746-755 (1995).
Loomis et al., "Cyroprotective Capacity of End Products of Anaerobic Metabolism," *The Journal of Experimental Zoology* 252: 9-15 (1989).
Lorz et al., "Gene Transfer to Cereal Cells Mediated by Protoplast Transformation," *Mol. Gen. Genet.* 199: 178-182 (1985).
Louis, "Corrected Sequence for the Right Telomere of *Saccharomyces cerevisiae* Chromosome III," *Yeast* 10: 271-274 (1994).
Lu et al., "High Efficiency Retroviral Mediated Gene Transduction into Single Isolated Immature and Replatable $CD34^{3+}$ Hemotopoietic Stem/Progenitor Cells from Human Umbilical Cord Blood," *J. Ex. Med.* 178: 2089-2096 (1993).
Maeser et al., "The Gin Recombinase of Phase Mu Can Catalyse Site-Specific Recombination in Plant Protoplasts," *Mol. Gen. Genet* 230: 170-176 (1991).
Mahtani et al., "Physical and Genetic Mapping of the Human X Chromosome Centromere: Repression of Recombination," *Genome Research* 8: 100-110 (1998).
Maloy, S.R., Experimental Techniques in Bacterial Genetics , Jones and Bartlett, *Ann. N.Y. Acad. Sci.* 646 (1991). Table of Contents only.
Maluszynska et al., "Localization of Tandemly Repeated DNA Sequences in *Arabidopsis thaliana*," *The Plant Journal* 1: 159-166 (1991).
Maluszynska et al., Molecular Cytogenetics of the Genus *Arabidopsis*: In situ Localization of rDNA Sites, Chromosome Numbers and Diversity in Centromeric Heterochromatin,: *Annals of Botany* 71: 479-484 (1993).
Marcotte et al., "Regulation of a Wheat Promoter by Abscisic Acid in Rice Protoplasts" *Nature* 335: 454 (1988).
Mariani et al., "Induction of Male Sterility in Plants by a Chimaeric Ribonuclease Gene," *Nature* 357: 737-741 (1990).
Marra et al., "A Map for Sequence Analysis of the *Arabidopsis thaliana* Genome," *Nature Genetics* 22: 265-270 (1999).
Martinex-Zapater et al., "A Highly Repeated DNA Sequence in *Arabidopsis thaliana*," *Mol. Gen. Genet* 204: 417-423 (1986).
Matsuura et al., "The *sre* Gene (ORF459) Encodes a Site-Specific Recombinase Responsible for Integration of the R4 Phage Genome," *Journal of Baceteriology* 178, 3374-3376 (1996).
McCabe et al., "Stable Transformation of Soybean (*Glycine max*) by Particle Acceleration," *BioTechnology* 6: 924-926 (1988).
Michel et al.., Modeling of the Three-dimensional Architecture of Group I Catalytic Introns Based on Comparative Sequence Analysis,: *J. Mol. Biol.* 216: 585-610 (1990).
Miller et al., "Retrotransposon-Related DNA Sequences in the Centromeres of Grass Chromosomes," *Genetics* 150: 1615-23 (1998).
Mortimer et al., "Genetic Mapping in *Saccharomyces cerevisiae*," Department of Biophysics and Medical Physics and Donner Laboratory, University of California at Berkeley: 11-26 (1981).
Mozo et al., "A Complete BAC-based Physical Map of the *Arabidopsis thaliana* Genome," *Nature Genetics* 22: 271-275 (1999).

(56) References Cited

OTHER PUBLICATIONS

Mozo et al., "Construction and Characterization of the IGF *Arabidopsis* BAC Library," *Mol. Gen. Genet. 258*: 562-570 (1998).
Mundy et al. "Abscisic Acid and Water-stress Induce the Expression of a Novel Rice Gene," *The EMBO Journal 7*: 2279-2286 (1988).
Murakarni et al., "The Bialaphos Biosynthetic Genes of *Streptomyces hygroscopicus*: Molecular Cloning and Characterization of the Gene Cluster," *Mol. Gen. Genet. 205*: 42-50 (1986).
Murata et al., "Physical Mapping of the 5S Ribosomal RNA Genes in *Arabidopsis thaliana* by Multi-Color Fluorescence in situ Hybridization with Cosmid Clones," *The Plant Journal 12*: 31-37 (1997).
Murata et al., "Centromeric Repetitive Sequences In *Arabiidopsis thaliana*," *Jpn J Genet. 69*: 361-370 (1994).
Murdock et al., "Biological Efects of Plant Lectins on the Cowpea Weevil, " *Phytochemistry 29*: 85-89 (1990).
Murphy et al., "Localization of Centromere Function in a *Drosophila* Minichromosome," *Cell 82*: 599-609 (1995).
Murray et al., "Construction of Artificial Chromosomes in Yeast,"*Nature 305*: 189-193(1983).
Mysore et al., "An *Arabidopsis* Histone H2A Mutant is Deficient in *Agrobacterium* T-DNA Integration," *Proc. Natl. Acad. Sci USA 97*: 948-953 (2000).
Mysore et al., "*Arabidopsis* Ecotypes and Mutants That Are Recalcritant to *Agrobacterium* Root Transformation Are Susceptible to Germ-line Transformation," *The Plant Journal 21*: 9-16 (2000).
Nagaki et al., "Molecular and Cytological Analysis of Large Tracks of Centrometic DNA Reveal the Structure and Evolutionary Dynamics of Maize Centromeres," *Genetics 163*: 759-70 (2003).
Nagaki et al., "Sequencing of a Rice Centromere Uncovers Active Genes", *Nature Genet. 36*: 138-145 (2004).
Nakamura et al., "Construction of an 800-KB Contig in the Near-Centromeric Region of the Rice Blast Resistance Gene *Pi-ta*2 Using a Highly Representative Rice BAC Library," *Mol Gen Genet. 254*: 611-620 (1997).
Napoli et al., "Introduction of a Chimeric Chalcone Synthase Gene into Petunia Results in Reversible Co-Suppression of Homologous Genes in trans," *The Plant Cell 2*: 279-298 (1990).
Negrutiu, et al. "Plant Protoplasts as Genetic Tool: Selectable Markers for Developmental Studies," *Int. J. Dev. Biol. 36*: 73-84 (1992).
Nester et al., "Crown Gall: A Molecular and Physiological Analysis," *Ann Rev. Plant Physiol 35*: 387-413(1984).
Nicklas, "The Forces That Move Chromosomes in Mitosis," *Ann. Rev. Biophys. Biophys. Chem. 17*: 431-449 (1988).
Nonomura et al., "Organization of the 1.9-KB Repeat Unit RCE1 in the Centromeric Region of Rice Chromosomes," *Mol Gen Genet. 261*: 1-10 (1999).
Nonomura, et al., "The Centromere Composition of Multiple Repetitive Sequences on Rice," *Chromosome 5*, 110: 284-91 (2001).
Noutoshi et al., "Designing of Plant Artificial Chromosome (PAC) by Using the Chlorella Smallest Chromosome as a Model System," *Nucleic Acids Symp. Ser. 37*: 143-4 (1997).
Nussbaum et al., "Construction and Propagation of a Defective Simian Virus 40 Genome Bearing an Operator from Bacteriophage," *Proc. Nat. Acad. Sci. USA 73*: 1068-1072 (1976).
Odell et al., "Identification of DNA Sequences Required for Activity of the Cauliflower Mosaic Virus 35S Promoter," *Nature 313*: 810-812 (1985).
Ohmori et al., "Nucleotide Sequence of the Region Required for Maintenance of Colicin E1 Plasmid," *Mol. Gen. Genet. 176*: 161-170 (1979).
Omirulleh et al., "Activity of a Chimeric Promoter with the Doubled CaMV 35S Enhancer Element in Protoplast-derived Cells and Transgenic Plants in Maize," *Plant Molecular Biology 21*: 415-428 (1993).
Ow et al., "Transient and Stable Expression of the Firefly Luciferase Gene in Plant Cells and Transgenic Plants," *Science 234*: 856-859 (1986).
Page et al., "Characterization of a Maize Chromosome 4 Centromeric Sequence: Evidence for an Evolutionary Relationship with the B Chromosome Centromere," *Genetics 159*: 291-301 (2001).

Palukaitis et al., "Characterization of a Viroid Associated with Avocado Sunblotch Disease," *Virology 99*: 145-151 (1979).
Peacock et al., "Highly Repeated DNA Sequence Limited to Knob Heterochromatin in Maize," *Proc. Nat. Acad. Sci. USA 78*: 4490-4494 (1981).
Pelissier et al., "DNA Regions Flanking the Major *Arabidopsis thaliana* Satellite Are Principally Enriched in *Athila* Retroelement Sequences," *Genetica 97*: 141-151 (1996).
Pelissier et al., "Athila, a New Retroelement from *Arabidopsis thaliana*.," *Plant Mol. Biol. 29*: 441-552 (1995).
Perkins, "The Detection of Linkage in Tetrad Analysis," *Genetics 38*: 187-197 (1953).
Perlak et al., "Modification of the Coding Sequence Enhances Plant Expression of Insect Control Protein Genes," *Proc. Natl. Acad. Sci USA 88*: 3324-3328 (1991).
Perriman et al., "Extended Target-Site Specificity for a Hammerhead Ribozyme," *Gene 113*: 157-163 (1992).
Peterson et al., "Production of Transgenic Mice with Yeast Artificial Chromosomes," *TIG 13*: 61-66 (1997).
Phi-Van et al., "The Chicken Lysozyme 5' Matrix Attachment Region Increases Transcription from a Heterologous Promoter in Heterologous Cells and Dampens Position Effects on the Expression of Transfected Genes," *Molecular and Cellular Biology 10*: 2302-2307 (1990).
Piatowski et al., "Characterization of Five Abscisic Acid-Responsive cDNA Clones Isolated from the Dessication-Tolerant Plant *Craterostigma plantagineum* and Their Relationship to Other Water-Stress Genes," *Plant Physiol. 94*: 1682-1688 (1990).
Potrykus et al., "Direct Gene Transfer to Cells of a Graminaceous Monocot," *Mol. Gen. Genet. 199*: 183-188 (1985).
Prasher et al., "Cloning and Expression of the cDNA Coding for Aequorin, a Bioluminescent Calcium-binding Protein," *Biochem Biophys. Res. Commun 126*: 1259-1268 (1985).
Presting et al., "A *Ty3/gypsy* Retrotransposon-Like Sequence Localizes to the Centromeric Regions of Cereal Chromosomes," *Plant J. 16*: 721-8 (1998).
Preuss et al., "Tetrad Analysis Possible in *Arabidopsis* with Mutation of the QUARTET (QRT) Genes," *Science 264*: 1458-1460 (1994).
Price et al.,"Systematic Relationships of *Arabidopsis*: A Molecular and Morphological Perspective," in Somerville, C. and Meyerowitz, E. (eds.), *Arabidopsis*, Cold Spring Harbor Press, New York (1995) pp. 7-19.
Prody et al.,"Autolytic Processing of Dimeric Plant Virus Satellite RNA," *Science 231*: 1577-80 (1986).
Puechberty, J., "Genetic and Physical Analyses of the Centromeric and Pericentromeric Regions of Human Chromosome 5: Recombination Across 5cen," *Genomics 56*: 274-87 (1999).
Rathore et al., "Use of *bar* as a Selectable Marker Gene and for the Production of Herbicide-Resistant Rice Plants from Protoplasts," *Plant Molecular Biology 21*: 871-884 (1993).
Rattner et al., "The Structure of the Mammalian Centromere," *BioEssays 13*: 51-56 (1991).
Ravatn et al., "Int-B13, An Unusual Site-Specific Recombinase of the Bacteriophage P4 Integrase Family, Is Responsible for Chromosomal Insertion of the 105-Kilobase *clc* Element of *Pseudomonas* sp. Strain B13," *Journal of Bacteriology 180*: 5505-5514.
Reed et al., "Carbohydrate Accumulation and Osmotic Stress in Cyanobacteria," *J. Gen. Microbiology 130*: 1-4 (1984).
Reichel et al., "Enhanced Green Fluorescence by the Expression of an Aequorea victoria Green Fluorescent Protein Mutant in Mono- and Dicotyledonous Plant Cells," *Proc. Nat. Acad. Sci. USA 93*: 5888-5893 (1996).
Reinhold-Hurek et al., "Self-splicing Introns in tRNA Genes of Widely Divergent Bacteria," *Nature 357*: 173-176 (1990).
Rensburg et al., "Proline Accumulation as Drought-tolerance Selection Criterion: Its Relationship to Membrane Integrity and Chloroplast Ultrastructure in *Nicotiana tabacum* L.," *J. Plant Physiol. 141*: 188-194 (1993).
Richards et al., "The Centomere Region of *Arabidopsis thaliana* Chromosome 1 Contains Telomere-Similar Sequences," *Nucleic Acids Research 19*: 3351-3357 (1991).
Richards et al., "Isolation of a Higher Eukaryotic Telomere from *Arabidopsis thaliana*," *Cell 53*: 127-136 (1988).

(56) References Cited

OTHER PUBLICATIONS

Richards et al.,"Plant Centromeres: Structure And Control," *Curr Opin Plant Biol.1*: 130-135 (1998).
Rieder, "The Formation, Structure, and Composition of the Mammalian Kinetochore and Kinetochore Fiber," New York State Department of Health, Division of Laboratories and Research, *Intl. Rev. Cytol.79* : 1-58 (1982).
Rogers et al., "Improved Vectors for Plant Transformation: Expression Cassette Vectors and New Selectable Markers," *Methods in Enzymology 153*: 253-277.
Rosenberg et al., ""RFLP Subtraction": A Method for Making Libraries of Polymorphic Markers," *Proc. Natl. Acad. Sci. USA 91*: 6113-6117 (1994).
Rosenfeld, "Human artificial chromosomes get real," *Nature Genetics 15*: 333-335 (1997).
Round et al., "*Arabidopsis thaliana* Centromere Regions: Genetic Map Positions and Repetitive DNA Structure," *Genome Research 7*: 1045-1053 (1997).
Sasnauskas et al., "Molecular Cloning and Analysis of Autonomous Replicating Sequence of *Candida maltosa,*" *Yeast 8*: 253-259 (1992).
Sauer, "Functional Expression of the *cre-lox* Site-Specific Recombination System in the Yeast *Saccharomyces cerevisiae*," *Molecular and Cellular Biology 7*: 2087-2096 (1987).
Schmidt et al., "Analysis of Clones Carrying Repeated DNA Sequences in Two YAC Libraries of *Arabidopsis thaliana* DNA," *The Plant Journal 5*: 735-744 (1994).
Schmidt et al., "Physical Map and Organization of *Arabidopsis thaliana* Chromosome 4," *Science, 270*: 480-483 (1995).
Schwartz et al., "New Techniques for Purifying Large DNAs and Studying Their Properties and Packaging," Department of Human Genetics and Development, Columbia University: 189-195.
Schweizer et al., "Species-specific DNA sequences for identification of somatic hybrids between *Lycopersicon esculentim* and *Solanum acaule,*" *Theor. Appl. Genet 75*: 679-684 (1988).
Sears et al., "Cytogenic Studies in *Arabidopsis thaliana*," Department of Genetics, University of Missouri, *Can. J. Genet. Cytol. 12*: 217-223 (1970).
Shagan et al., "Nucleotide Sequence of an *Arabidopsis thaliana* Turgor-Responsive cDNA Clone Encoding TMP-A, a Transmembrane Protein Containing the Major Intrinsic Protein Motif," *Plant Physiol. 101*: 1397-1398 (1993).
Sheen et al., "Green-flourescent Protein as a New Vital Marker in Plant Cells," *The Plant Journal 8*: 777-784 (1985).
Simoens et a.l, "Characterization of Highly Repetitive Sequences of *Arabidopsis thaliana,*" *Nucleic Acids Research 16*: 6753-6766 (1988).
Singh et al., "Centromere Mapping and Orientation of the Molecular Linkage Mao of Rice (*Oryza sativa* L.)," *Proc Natl Acad Sci USA. 93*: 6163-6168 (1996).
Smith et al., "Expression of Truncated Tomato Polygalacturonase Gene Inhibits Expression of the Endogenous Gene in Transgenic Plants," *Mol. Gen. Genet. 224*: 447-481 (1990).
Smithies et al., "Insertion of DNA Sequences into the Human Chromosomal-Globin Locus by Homologous Recombination," *Nature 317*: 230-234 (1985).
Smyth, "New *Arabidopsis* Mutations that Result in All Four Products of Meiosis Being Held Together as a Tetrad of Fused Pollen Grains May Facilitate Genetic Mapping and Lead to New Insights into Pollen Biology," *Current Biology 4*: 851-853 (1994).
Somerville et al., "Plant Functional Genomics," *Science 285*: 380-383 (1999).
Spielmann et al., "T-DNA Structure in Transgenic Tobacco Plants with Multiple Independent Integration Sites," *Mol. Gen. Genet. 205*: 34-43 (1986).
Stalker et al., "Herbicide Resistance in Transgenic Plants Expressing a Bacterial Detoxification Gene," *Science 242*: 419-423 (1988).
Steifel et al., Herbicide Resistance in Transgenic Plants Expressing a Bacterial Detoxification Gene,: *Nature 341*: 343 (1989).
Stinchomb et al., "Isolation and Characterisation of a Yeast Chromosomal Replicator," *Nature 282*: 39-43 (1979).
Stone et al., "Leafy Cotyledon2 Encodes a B3 Domain Transcription Factor that Induces Embryo Development," *Proc. Natl. Acad. Sci. USA, 98*:11806-11811 (2001).
Stougaard, "Substrate-Dependent Negative Selection in Plants Using a Bacterial Cytosine Deaminase Gene," *The Plant Journal 3*: 755-761 (1993).
Sullivan et al., "Isolation and Characterization of a Maize Chlorophyll a/b Binding protein Gene that Produces High Levels of mRNA in the Dark," *Mol. Gen. Genet. 215*: 431-440 (1980).
Sun et al., "Human Artificial Episomal Chromosomes for Cloning Large DNA Fragments in Human Cells," *Nature Genetics 8*: 33-41 (1994).
Sun et al., "Molecular Structure of a Functional *Drosophila* Centromere," *Cell 91*: 1007-1019 (1997).
Sutcliffe, "Nucleotide Sequence of the Ampicillin Resistance Gene of *Escherichia coli* Plasmid pBR322," *Proc. Natl Acad. Sci USA 75*: 3737-3741 (1978).
Symington et al., "Meiotic Recombination Within the Centromere of a Yeast Chromosome," *Cell 52*: 237-240 (1988).
Symons, "Avocado Sunblotch Viroid: Primary Sequence and Proposed Secondary Structure," *Nucleic Acids Research 9*: 6527-6537 (1981).
Symons, "Small Catalytic RNAs," *Annu. Rev. Biochem 61*: 641-671 (1992).
Tarczynski et al., "Expression of a Bacerial mtlD Gene in Transgenic Tobacco Leads to Production and Accumulation of Mannitol," *Proc. Nat. Acad. Sci. USA 89*: 2600-2604 (1992).
Tarczynski et al., "Stress Protection of Transgenic Tobacco by Production of the Osmolyte Mannitol," *Science 259*: 508-510 (1993).
Tavoletti et al., "Half Tetrad Analysis in Alfalfa Using Multiple Restriction Fragment Length Polymorphism Markers," *Proc. Natl. Acad. Sci. Online 93*: 10918-10922 (1996).
Thillet et al., "Site-directed Mutagenesis of Mouse Dihydrofolate Reductase. Mutants with Increased Resistance to Methotrexate and Trimethoprim," *J. Biol. Chem 263*: 12500-12508 (1988).
Thomas et al., "High-Frequency Targeting of Genes to Specific Sites in the Mammalian Genome," *Cell 44*: 419-428 (1986).
Thomas et al., "Viable Molecular Hybrids of Bacteriophage Lambda and Eukaryotic DNA," *Proc. Nat. Acad. Sci. USA 71*: 4579 (1974).
Thompson et al., "Identification and Distribution of Seven Classes of Middle-Repetitive DNA in the *Arabidopsis thaliana* Genome," *Nucleic Acids Research 24*: 3017-3022 (1996).
Thompson et al., "Decreased Expression of BRCA1 Accelerates Growth and Is Often Present During Sporadic Breast Cancer Progression," *Nature Genet. 9*: 444-450 (1995).
Thompson et al., "A Novel Repetitive Sequence Associated with the Centrometric Regions of *Arabidopsis thaliana* Chromosomes;" *Mol Gen Genet 253*: 247-252, (1996).
Tian et al., "Expression of the Green Fluorescent Protein Gene in Conifer Tissues," *Plant Cell Reports 16*: 267-271 (1997).
Tominaga, "The Site-specific Recombinase Encoded by pinD in *Shigella dysenteriae* is due to the presence of a defective Mu prophase," *Microbiol. 143*: 2057-2063 (1997).
Toriyama et al., "Haploid and Diploid Plant Regeneration from Protoplasts of Another Callus in Rice," *Theor Appl. Genet. 73*: 16-19 (1986).
Tsay et al., "Identification of a Mobile Endogenous Transposon in *Arabidopsis thaliana,*" *Science 260*: 342-344 (1993).
Tugal et al., "*Arabidopsis* 22-Kilodalton Peroxisomal Membrane Protein, Nucleotide Sequence Analysis and Biochemical Characterization," *Plant Physiology 120*: 309-320 (1999).
Twell et al., "Promoter Analysis of Genes that Are Coordinately Expressed During Pollen-Specific Enhancer Sequences and Shared Regulatory Elements," *Genes Dev. 5*: 496-507 (1991).
Twell et al., "Transient Expression of Chimeric Genes Delivered Pollen by Microprojectile Bombardment," *Plant Physiol. 91*: 1270-1274 (1989).
Tyler-Smith et al., "Localization of DNA Sequences Required for Human Centromere Function Through an Analysis of Rearranged Y Chromosomes," *Nature Genetics 5*: 368-375 (1993).
Tyler-Smith et al., "Mammalian Chromosome Structure," *Current Opin. Genetic Dev. 3*: 390-397 (1993).

(56) References Cited

OTHER PUBLICATIONS

Uchimiya et al., "Expression of a Foreign Gene in Callus Derived from DNA-treated Protoplasts of Rice," *Mol. Gen. Genet. 204*: 204 (1986).
Vahedian et al., "Genomic Organization and Evolution of the Soybean SB92 Satellite Sequence," *Plant Molecular Biology 29*: 857-862 (1995).
Valvekens et al., "*Agrobacterium tumefaciens*-Mediated Transformation of *Arabidopsis thaliana* Root Explants by Using Kanamycin Selection," *Proc. Natl. Acad. Sci. USA 85*: 5536-5540 (1988).
Van der Krol et al., "Flavonoid Genes in Petunia: Addition of a Limited Number Of Gene Copies May Lead to a Suppression of Gene Expression," *Plant Cell 2*: 291-299 (1990).
Van't Hof et al., "The Size and Number Of Replicon Families of Chromosomal DNA of *Arabidopsis thaliana*," *Chromosoma 68*: 269-285 (1978).
Vasil et al., "Herbicide Resistant Fertile Transgenic Wheat Plants Obtained by Microprojectile Bombardment of Regenerable Embryogenic Callus," *BioTechnology 10*: 667-674 (1992).
Vasil, "Progress in the Regeneration and Genetic Manipulation of Cereal Crops," *BioTechnology 6*: 397-402 (1988).
Vernon et al., "A Novel Methyl Transferase Induced by Osmotic Stress in the Faculative Halophyte *Mesembryanthemum crystallinum*," *The EMBO Journal 11*: 2077-2085 (1992).
Voytas et al., "A Copia-Like Transposable Element Family in *Arabidopsis thaliana*," *Nature 336*: 242-244 (1988).
Wagner et al., "Coupling of Adenovirus to Transferrin-Polylysine/DNA Complexes Greatly Enhances Receptor-Mediated Gene Delivery and Expression of Transfected Genes," *Proc. Natl. Acad. Sci. USA*, 89: 6099-6103(1992).
Walker et al., "DNA Sequences Required for Anaerobic Expression of the Maize Alcohol Dehydrogenase 1 Gene," *Proc. Nat. Acad. Sci. USA 84*: 6624-6628 (1987).
Wang et al., "Characterization of cis-Acting Elements Regulating Transcription from the Promoter of a Constitutively Active Rice Actin Gene," *Molecular and Cellular Biology*: 3399-3406 (1992).
Weide et al., "Paracentromeric Sequences on Tomato Chromosome 6 Show Homology to Human Satellite III and to the Mammalian CENP-B Binding Box," *Mol. Gen. Genet. 259*: 190-197 (1998).
Wensink et al., A System for Mapping DNA Sequences in the Chromosomes of *Drosophila melanogaster*: , *Cell 3*: 315-325 (1974).
Wevrick et al. "Partial Deletion of Alpha Satellite DNA Associated with Reduced Amounts of the Centromere Protein CENP-B in a Mitotically Stable Human Chromosome Rearrangement," *Molecular and Cellular Biology 102*: 6374-6380 (1990).
Whitehouse et al., "Mapping Chromosome Centromeres by the Analysis of Unordered Tetrads," *Nature* 4205: 893 (1950).
Wigler et al., "Transfer of Purified Herpes Virus Thymidine Kinase Gene to Cultured Mouse Cells," *Cell 11*: 223-232 (1977).
Willard, "Centromeres of mammalian chromosomes," *TIG 6*(12): 410-416 (1990).
Willard, "Centromeres: The Missing Link in the Development of Human Artificial Chromosomes," *Genetics & Development 8*: 219-225 (1998).

Wolter et al., "Chilling Sensitivity of *Arabidopsis thaliana* with Genetically Engineered Membrane Lipids," *The EMBO Journal 11*: 4685-4692 (1992).
Wong et al., "Electric Field Mediated Gene Transfer," *Biochim. Biophys. Res. Commun. 107*: 584-587 (1982).
Wright et al., "Multiple Non-LTR Retrotransposons in the Genome of *Arabidopsis thaliana*," *Genetics 142*: 569-578 (1996).
Wu et al., "Composition and Structure of the Centromeric Region of Rice Chromosome 8," *Plant Cell 16*: 967-76 (2004).
Xia et al., "Genomic Organization of the *canrep* Repetitive DNA in *Brassica juncea*," *Plant Molecular Biology 26*: 817-832 (1994).
Xia et al., Structure and Evolution of a Highly Repetitive DNA Sequence from *Brassica napus*, *Plant Molecular Biology 21*: 213-224 (1993).
Xiang, et al. "The Anti-*nptII* Gene," *Plant Physiol. 102*: 287-293 (1993).
Xu et al., "Expression of a Late Embryogenesis Abundant Protein Gene, HVA1, from Barley Confers Tolerance to Water Deficit and Salt Stress in Transgenic Rice," *Plant Physiol.* 110: 249-257 (1996).
Yamada et al., "Plant Regeneration from Protoplast-derived Callus of Rice," *Plant Cell Rep. 4*: 85 (1986).
Yamaguchi-Shinozaki et al., "Molecular Cloning and Characterization of 9 cDNAs for Genes that Are Responsive to a Desiccation in *Arabidopsis thaliana*: Sequence Analysis of One cDNA Clone that Encodes a Putative Transmembrane Channel Protein," *Plant Cell Physiol. 33*: 217-224 (1992).
Yang et al., "Maize Sucrose Synthase-1 Promoter Directs Phloem Cell-specific Expression of Gus Gene in Transgenic Tobacco Plants," *Proc. Natl. Acad. Sci. USA 87*: 4144-4148 (1990).
Yen et al., "CENP-E, a Novel Human Centomere-Associated Protein Required for Progression from Metaphase to Anaphase," *The EMBO Journal 10*: 1245-1254 (1991).
Young et al., "Organization of Coding Sequences in *Drosophila melanogaster*," *J. Supramolecular Struct., S1*: 211 (1977).
Young et al., Eukaryotic Genetic Systems ICNUCLA Symposia on Molecular and Cellular Biology VII: 315-331 (1977).
Yuan et al., "Selection of Guide Sequences That Direct Efficient Cleavage of mRNA by Human Ribonuclease P," *Science 263*: 1269-1273 (1994).
Yuan et al., "Targeted cleavage of mRNA by human RNase P," *Proc. Natl. Acad. Sci. USA 89*: 8006-8010 (1992).
Zatloukal et al., "Transferinfection: A Highly Efficient Way to Express Gene Constructs in Eukaryotic Cells," *Ann. N.Y. Acad. Sci. 660*: 136-153.
Zentgraf, "Telomere-binding Proteins of *Arabidopsis thaliana*," *Plant Molecular Biology 27*: 467-475 (1995).
Zhang et al., "Molecular Cloning, Nucleotide Sequence, and Function of a Site-Specific Recombinase Encoded in the Major 'Pathogenicity Island' of *Salmonella typhi*," *Gene 202*: 139-146 (1997).
Zhang et al., "*Zea mays* B Chromosome Centromere Repeat Sequence Zea__mays__MBsC216 pMBsC216," (unpublished).
Zukowski et al., "Chromogenic Identification of Genetic Regulatory Signals in *Bacillus subtilis* Based on Expression of a Cloned *Pseudomonas* Gene," *Proc. Natl. Acad. Sci., USA 80*: 1101-1105 (1983).
Zuo et al., "The *Wuschel* Gene Promotes Vegetative-to-Embryonic Transition in *Arabidopsis*," *Plant J.*, 30:349-359 (2002).

* cited by examiner

Figure 5

| | |
|---|---|
| 04 BB5R4-1 | ASCTTSATTTGGATACATAAAGTAGTGGAGAATCACCAGGAAGTTGAATAAA |
| 05 BB5R4-1 | AGCTTGATTTGGATACATAAAGTGGTGGAGAATCACCAGGAAGTTGAATAAA |
| 05 BB280R2-3 | ACCTTCATTTGGATACATAAAGTAGTGKAGAATCACCAGGAAGTTGAATAAA |
| | |
| 04 BB5R4-1 | TCTCATAGGAGTTAGGATGAAGAAGTTATCCCACTTTCAAATAAGGTGATCC |
| 05 BB5R4-1 | TCTCATAGGAGTTGGCATGAAGAAGTTATCCCMCTTTCAAATCAGGTGATTC |
| 05 BB280R2-3 | TCTCATAGGAGTTAGGATGAAGAAGTTATCCCACTTTCAAATAAGGTGATCC |
| | |
| 04 BB5R4-1 | CAGTTTYCCTGTTTGGGAATATKANAACTTHTTCGHCATTCTADTCAAACCAG |
| 05 BB5R4-1 | CAGTTTCCCAGTTTGGGAATAGCACAGCTTCTTCGTCGTTCCAATCAAACCAG |
| 05 BB280R2-3 | CAGTTTYCCTGTTTGGGAATATGACAACTTCTTCGTCATTCTAATCAAACCAG |
| | |
| 04 BB5R4-1 | GATGAATCGCGATGTAARARVCY |
| 05 BB5R4-1 | GATGAATCTCTTTGTAAGA |
| 05 BB280R2-3 | GATGAATCKYGATGTWAGA |

Figure 6

```
CrGm1     1..AAATTCAAAT GGTCATAACT TTTMACWCGG.....30
CrGm2     1..AAATTCAAAC GACAATAACT TTTTACTCGG.....30
SB12MC    1..AAAWTCAAAC GACAATAACT TTTKACTCGG.....30

CrGm1    31..AKGTCCGATT CAGGCGCATA ATATATCGAG.....60
CrGm2    31..ATGTCYGATT GAGTCCCGTA ATATATCGAG.....60
SB12MC   31..ATGTCCGATT GWGTCCCGTA RTATATCGAG.....60

CrGm1    61..ACGCTCGAAA TTGAACAAYG GAAGCTCTCG AG..92
CrGm2    61..ACGCTCGAAA TTGAATRYTG -AAGCTCTGA GC..92
SB12MC   61..ACGCTCGWAA TTGAAAACWG -AAGCTCTRA GM..92
```

PLANTS MODIFIED WITH MINI-CHROMOSOMES

RELATED APPLICATIONS

This application is a national phase filing of PCT Application No. PCT/US2005/006505, filed Feb. 23, 2005, which claims priority to U.S. Provisional Application No. 60/547,256 filed Feb. 23, 2004, which are incorporated by reference herein in its entirety.

BACKGROUND OF THE INVENTION

Two general approaches are used for introduction of new genetic information ("transformation") into cells. One approach is to introduce the new genetic information as part of another DNA molecule, referred to as an "episomal vector," or "mini-chromosome", which can be maintained as an independent unit (an episome) apart from the host chromosomal DNA molecule(s). Episomal vectors contain all the necessary DNA sequence elements required for DNA replication and maintenance of the vector within the cell. Many episomal vectors are available for use in bacterial cells (for example, see Maniatis et al., "Molecular Cloning: a Laboratory Manual," Cold Spring Harbor Laboratory, Cold Sprint Harbor, N.Y. 1982.). However, only a few episomal vectors that function in higher eukaryotic cells have been developed. Higher eukaryotic episomal vectors were primarily based on naturally occurring viruses. In higher plant systems gemini viruses are double-stranded DNA viruses that replicate through a double-stranded intermediate upon which an episomal vector could be based, although the gemini virus is limited to an approximately 800 bp insert. Although an episomal plant vector based on the Cauliflower Mosaic Virus has been developed, its capacity to carry new genetic information also is limited (Brisson et al., Nature, 310:511,1984).

The other general method of genetic transformation involves integration of introduced DNA sequences into the recipient cell's chromosomes, permitting the new information to be replicated and partitioned to the cell's progeny as a part of the natural chromosomes. The introduced DNA usually is broken and joined together in various combinations before it is integrated at random sites into the cell's chromosome (see, for example Wigler et al., Cell, 11:223, 1977). Common problems with this procedure are the rearrangement of introduced DNA sequences and unpredictable levels of expression due to the location of the transgene in the genome or so called "position effect variegation" (Shingo et al., Mol. Cell. Biol., 6:1787, 1986). Further, unlike episomal DNA, integrated DNA cannot normally be precisely removed. A more refined form of integrative transformation can be achieved by exploiting naturally occurring viruses that integrate into the host's chromosomes as part of their life cycle, such as retroviruses (see Chepko et al., Cell, 37:1053, 1984).

One common genetic transformation method used in higher plants is based on the transfer of bacterial DNA into plant chromosomes that occurs during infection by the phytopathogenic soil bacterium *Agrobacterium* (see Nester et al., Ann. Rev. Plant Phys., 35:387-413, 1984). By substituting genes of interest for the naturally transferred bacterial sequences (called T-DNA), investigators have been able to introduce new DNA into plant cells. However, even this more "refined" integrative transformation system is limited in three major ways. First, DNA sequences introduced into plant cells using the *Agrobacterium* T-DNA system are frequently rearranged (see Jones et al., Mol. Gen. Genet., 207:478, 1987). Second, the expression of the introduced DNA sequences varies between individual transformants (see Jones et al., EMBO J., 4:2411-2418, 1985). This variability is presumably caused by rearranged sequences and the influence of surrounding sequences in the plant chromosome (i.e., position effects), as well as methylation of the transgene. Finally, insertion of extra elements into the genome can disrupt the genes, promoters or other genetic elements necessary for normal plant growth and function.

Another widely used technique to genetically transform plants involves the use of micro-projectile bombardment. In this process, a nucleic acid containing the desired genetic elements to be introduced into the plant is deposited on or in small metallic particles, e.g., tungsten, platinum, or preferably gold, which are then delivered at a high velocity into the plant tissue or plant cells. However, similar problems arise as with *Agrobacterium*-mediated gene transfer, and as noted above expression of the inserted DNA can be unpredictable and insertion of extra elements into the genome can disrupt and adversely impact plant processes.

One attractive alternative to commonly used methods of transformation is the use of an artificial chromosome. Artificial chromosomes are man-made linear or circular DNA molecules constructed in part from cis-acting DNA sequence elements that provide replication and partitioning of the constructed chromosomes (see Murray et al., Nature, 305:189-193, 1983). Desired elements include: (1) origin of replication, which are the sites for initiation of DNA replication, (2) centromeres (site of kinetochore assembly and responsible for proper distribution of replicated chromosomes into daughter cells at mitosis or meiosis), and (3) if the chromosome is linear, telomeres (specialized DNA structures at the ends of linear chromosomes that function to stabilize the ends and facilitate the complete replication of the extreme termini of the DNA molecule). An additional desired element is a chromatin organizing sequence. It is well documented that centromere function is crucial for stable chromosomal inheritance in almost all eukaryotic organisms (reviewed in Nicklas 1988). The centromere accomplishes this by attaching, via centromere binding proteins, to the spindle fibers during mitosis and meiosis, thus ensuring proper gene segregation during cell divisions.

The essential chromosomal elements for construction of artificial chromosomes have been precisely characterized in lower eukaryotic species, and more recently in mouse and human. Autonomous replication sequences (ARSs) have been isolated from unicellular fungi, including *Saccharomyces cerevisiae* (brewer's yeast) and *Schizosaccharomyces pombe* (see Stinchcomb et al., 1979 and Hsiao et al., 1979). An ARS behaves like a origin of replication allowing DNA molecules that contain the ARS to be replicated in concert with the rest of the genome after introduction into the cell nuclei of these fungi. DNA molecules containing these sequences replicate, but in the absence of a centromere they are not partitioned into daughter cells in a controlled fashion that ensures efficient chromosome inheritance.

Artificial chromosomes have been constructed in yeast using the three cloned essential chromosomal elements (see Murray et al., Nature, 305:189-193, 1983). None of the essential components identified in unicellular organisms, however, function in higher eukaryotic systems. For example, a yeast centromere sequence will not confer stable inheritance upon vectors transformed into higher eukaryotes.

In contrast to the detailed studies done in yeast, less is known about the molecular structure of functional centromeric DNA of higher eukaryotes. Ultrastructural studies indicate that higher eukaryotic kinetochores, which are specialized complexes of proteins that form on the centromere during late prophase, are large structures (mammalian kinetochore plates are approximately 0.3 μm in diameter) which possess multiple microtubule attachment sites (reviewed in Rieder, 1982). It is therefore possible that the centromeric DNA regions of these organisms will be correspondingly large, although the minimal amount of DNA necessary for centromere function may be much smaller.

While the above studies have been useful in elucidating the structure and function of centromeres, it was not known whether information derived from lower eukaryotic or mammalian higher eukaryotic organisms would be applicable to plants. There exists a need for cloned centromeres from higher eukaryotic organisms, particularly plant organisms, which would represent a first step in production of artificial chromosomes. There further exists a need for plant cells, plants, seeds and progeny containing functional, stable, and autonomous artificial chromosomes capable of carrying a large number of different genes and genetic elements.

SUMMARY OF THE INVENTION

The invention provides for adchromosomal plants, described in further detail herein, comprising a mini-chromosome, wherein said mini-chromosome preferably has a transmission efficiency during mitotic division of at least 90%, for example, at least 95%. Additionally, these adchromosomal plants may comprise a mini-chromosome having a transmission efficiency during meiotic division of, e.g., at least 80%, at least 85%, at least 90% or at least 95%.

In one embodiment, the adchromosomal plants of the invention comprise a mini-chromosome that is 1000 kilobases or less in length. In exemplary embodiments, the adchromosomal plant comprises a mini-chromosome that is 600 kilobases or less in length or 500 kilobases or less in length.

In another embodiment, the mini-chromosome of any of the preceding adchromosomal plants of the invention comprises a site for site-specific recombination.

In an embodiment, the mini-chromosome of any of the preceding adchromosomal plants of the invention comprises a centromeric nucleic acid insert derived from a crop plant centromere. In an exemplary embodiment, the centromeric nucleic acid insert is derived from genomic DNA of a plant selected from the group consisting of *Brassica, Nicotiana, Lycopersicum, Glycine* or *Zea* species. In another exemplary embodiment, the centromeric nucleic acid insert is derived from genomic DNA of a plant selected from the group consisting of broccoli, canola, tobacco, tomato, soybean or corn.

In another embodiment, the invention provides for the mini-chromosome of any one of the preceding adchromosomal plants, further comprising a centromeric nucleic acid insert that comprises artificially synthesized repeated nucleotide sequences. These artificially synthesized repeated nucleotide sequences may be derived from natural centromere sequences, combinations or fragments of natural centromere sequences including a combination of repeats of different lengths, a combination of different sequences, a combination of both different repeat lengths and different sequences, a combination of repeats from two or more plant species, a combination of different artificially synthesized sequences or a combination of natural centromere sequence(s) and artificially synthesized sequence(s).

The invention also provides for a mini-chromosome of any of the preceding adchromosomal plants of the invention, wherein the mini-chromosome is derived from a donor clone or a centromere clone and has substitutions, deletions, insertions, duplications or arrangements of one or more nucleotides in the mini-chromosome compared to the nucleotide sequence of the donor clone or centromere clone. In one embodiment, the mini-chromosome is obtained by passage of the mini-chromosome through one or more hosts. In another embodiment, the mini-chromosome is obtained by passage of the mini-chromosome through two or more different hosts. The host may be selected from the group consisting of viruses, bacteria, yeasts, plants, prokaryotic organisms, or eukaryotic organisms.

The invention also provides for a mini-chromosome of any of the preceding adchromosomal plants of the invention, wherein the mini-chromosome comprises one or more exogenous nucleic acids. In further exemplary embodiments, the mini-chromosome comprises at least two or more, at least three or more, at least four or more, at least five or more or at least ten or more exogenous nucleic acids.

In one embodiment, at least one exogenous nucleic acid of any of the preceding mini-chromosomes of a plant is operably linked to a heterologous regulatory sequence functional in plant cells. The invention provides for exogenous nucleic acids linked to a plant regulatory sequence. The invention also provides for exogenous nucleic acids linked to a non-plant regulatory sequence, such as an inset or yeast regulatory sequence. Exemplary regulatory sequences comprise any one of SEQ ID NOS: 4 to 23 or a functional fragment or variant thereof.

In another embodiment, the mini-chromosome of any of the preceding adchromosomal plants comprises an exogenous nucleic acid that confers herbicide resistance, insect resistance, disease resistance, or stress resistance on the plant. The invention provides for mini-chromosomes comprising an exogenous nucleic acid that confers resistance to phosphinothricin or glyphosate herbicide. The invention also provides for mini-chromosomes comprising an exogenous nucleic acid that encodes a phosphinothricin acetyltransferase, glyphosate acetyltransferase or a mutant enolpyruvylshikimate phosphate (EPSP) synthase.

The invention also provides for the mini-chromosome of any of the preceding adchromosomal plants comprising an exogenous nucleic acid that encodes a *Bacillus thuringiensis* crystal toxin gene or *Bacillus cereus* toxin gene. The invention further provides for the mini-chromosome of any of the preceding adchromosomal plants comprising an exogenous nucleic acid that confers resistance to drought, heat, chilling, freezing, excessive moisture, ultraviolet light, ionizing radiation, toxins, pollution, mechanical stress or salt stress. The invention also provides for a mini-chromosome of any of the preceding adchromosomal plants that comprises an exogenous nucleic acid that confers resistance to a virus, bacteria, fungi or nematode.

In another embodiment, the mini-chromosome of any of the preceding adchromosomal plants comprises an exogenous nucleic acid conferring herbicide resistance, an exogenous nucleic acid conferring insect resistance, and at least one additional exogenous nucleic acid.

The invention provides for mini-chromosomes of any of the preceding adchromosomal plants comprising an exogenous nucleic acid selected from the group consisting of a nitrogen fixation gene, a plant stress-induced gene, a nutrient utilization gene, a gene that affects plant pigmentation, a gene that encodes an antisense or ribozyme molecule, a gene encoding a secretable antigen, a toxin gene, a receptor gene, a ligand gene, a seed storage gene, a hormone gene, an enzyme gene, an interleukin gene, a clotting factor gene, a cytosine gene, an antibody gene, a growth factor gene, a transcription factor gene, a transcriptional repressor gene, a DNA-binding protein gene, a recombination gene, a DNA replication gene, a programmed cell death gene, a kinase gene, a phosphatase gene, a G protein gene, a cyclin gene, a cell cycle control gene, a gene involved in transcription, a gene involved in translation, a gene involved in RNA processing, a gene involved in RNAi, an organellar gene, a intracellular trafficking gene, an integral membrane protein gene, a transporter gene, a membrane channel protein gene, a cell wall gene, a gene involved in protein processing, a gene involved in protein modification, a gene involved in protein degradation, a gene involved in metabolism, a gene involved in biosynthesis, a gene involved in assimilation of nitrogen or other elements or nutrients, a gene involved in controlling carbon flux, gene involved in respiration, a gene involved in photosynthesis, a gene involved in light sensing, a gene involved in organogenesis, a gene involved in embryogenesis, a gene involved in differentiation, a gene involved in meiotic drive, a gene involved in self incompatibility, a gene involved in development, a gene involved in nutrient, metabolite or mineral transport, a gene involved in nutrient, metabolite or mineral storage, a calcium-binding protein gene, or a lipid-binding protein gene.

The invention also provides for a mini-chromosome of any of the preceding adchromosomal plants comprising an exogenous enzyme gene selected from the group consisting of a gene that encodes an enzyme involved in metabolizing biochemical wastes for use in bioremediation, a gene that encodes an enzyme for modifying pathways that produce secondary plant metabolites, a gene that encodes an enzyme that produces a pharmaceutical, a gene that encodes an enzyme that improves changes the nutritional content of a plant, a gene that encodes an enzyme involved in vitamin synthesis, a gene that encodes an enzyme involved in carbohydrate, polysaccharide or starch synthesis, a gene that encodes an enzyme involved in mineral accumulation or availability, a gene that encodes a phytase, a gene that encodes an enzyme involved in fatty acid, fat or oil synthesis, a gene that encodes an enzyme involved in synthesis of chemicals or plastics, a gene that encodes an enzyme involved in synthesis of a fuel and a gene that encodes an enzyme involved in synthesis of a fragrance, a gene that encodes an enzyme involved in synthesis of a flavor, a gene that encodes an enzyme involved in synthesis of a pigment or dye, a gene that encodes an enzyme involved in synthesis of a hydrocarbon, a gene that encodes an enzyme involved in synthesis of a structural or fibrous compound, a gene that encodes an enzyme involved in synthesis of a food additive, a gene that encodes an enzyme involved in synthesis of a chemical insecticide, a gene that encodes an enzyme involved in synthesis of an insect repellent, or a gene controlling carbon flux in a plant.

In an embodiment of the invention, the mini-chromosomes of any one of the preceding adchromosomal plants comprise n copies of a repeated nucleotide sequence, wherein n is less than 1000. In other exemplary embodiments, the mini-chromosomes of the plants comprise n copies of a repeated nucleotide sequence, wherein n is at least 5, wherein n is at least 15, or wherein n is at least 50.

In another embodiment of the invention, the mini-chromosomes of any of the preceding adchromosomal plants comprise a telomere.

The invention also provides embodiments wherein the mini-chromosome of any of the preceding adchromosomal plants is circular.

In one embodiment of the invention, any of the preceding adchromosomal plants are a monocotyledon. In another embodiment of the invention, any of the preceding adchromosomal plants are a dicotyledone. The invention also provides that the adchromosomal plants of the invention are, e.g., crop plants, cereal plants, vegetable crops, field crops, fruit and vine crops, wood or fiber crops or ornamental plants. The invention also provides exemplary adchromosomal plants that are *Brassica, Nicotiana, Lycopersicum, Glycine* or *Zea* species.

Another embodiment of the invention is a part of any of the preceding adchromosomal plants. Exemplary plant parts of the invention include a pod, root, cutting, tuber, stem, stalk, fruit, berry, nut, flower, leaf, bark, wood, epidermis, vascular tissue, organ, protoplast, crown, callus culture, petiole, petal, sepal, stamen, stigma, style, bud, meristem, cambium, cortex, pith, sheath, silk or embryo. Other exemplary plant parts are a meiocyte or gamete or ovule or pollen or endosperm of any of the preceding adchromosomal plants. Other exemplary plant parts are a seed, embryo or propagule of any of the preceding adchromosomal plants.

An embodiment of the invention is a progeny of any of the preceding adchromosomal plants of the invention. These progeny of the invention may be the result of self-breeding, cross-breeding, apomyxis or clonal propagation. In exemplary embodiments, the invention also provides for progeny that comprise a mini-chromosome that is descended from a parental mini-chromosome that contained a centromere less than 150 kilobases in length, less than 100 kilobases in length or less than 50 kilobases in length.

In another aspect, the invention provides for methods of making a mini-chromosome for use in any of the preceding adchromosomal plants of the invention. These methods comprise identifying a centromere nucleotide sequence in a genomic DNA library using a multiplicity of diverse probes, and constructing a mini-chromosome comprising the centromere nucleotide sequence. These methods may further comprise determining hybridization scores for hybridization of the multiplicity of diverse probes to genomic clones within the genomic nucleic acid library, determining a classification for genomic clones within the genomic nucleic acid library according to the hybridization scores for at least two of the diverse probes, and selecting one or more genomic clones within one or more classifications for constructing the mini-chromosome.

In exemplary embodiments, the step of determining a classification for genomic clones within the genomic nucleic acid library may utilize the hybridization scores for at least 3, 4, 5, 6, 7, 8, 9, 10, 11, 12, 13, 14, 15, 16, 17, 18, 19, 20, 21, 22, 23, 24, 25, 26, 27, 28, 29 or 30 or more different probes. A classification may comprise a pattern of high, medium or low hybridization scores to various probes.

Exemplary embodiments of probes useful in this method include a probe that hybridizes to the centromere region of a chromosome, a probe that hybridizes to satellite repeat DNA, a probe that hybridizes to retroelement DNA, a probe that hybridizes to portions of genomic DNA that are heavily methylated, a probe that hybridizes to arrays of tandem repeats in genomic DNA, a probe that hybridizes to telomere DNA or a probe that hybridizes to a pseudogene. Other exemplary probes include, a probe that hybridizes to ribosomal DNA, a probe that hybridizes to mitochondrial DNA, or a probe that hybridizes to chloroplast DNA, for which preferably a classification comprises a low hybridization score for hybridization to said probe.

Another aspect of the invention provides for methods of making any one of the preceding adchromosomal plants comprising delivering a mini-chromosome to a plant cell using a biolistic method, wherein a particle suitable for use in biolistic method is delivered in a liquid with the mini-chromosome, and regenerating a plant from the plant cell. The liquid may further comprise a divalent ion and a di- or poly-amine. In exemplary embodiments, the liquid comprises water, CaCl$_2$, and spermidine, and the particles are gold particles. Suitable alternatives to spermidine are, e.g., spermine or other aliphatic or conjugated di- or poly-amines such as 1,5-diaminopentane, 1,6-diaminohexane, 1,7-diaminoheptane, 1,8-diaminooctane, histamine or related molecules.

A further aspect of the invention provides for methods of making any of the preceding adchromosomal plant comprising co-delivering to a plant cell a mini-chromosome and a nucleic acid encoding a growth inducing gene, wherein said nucleic acid is not part of the mini-chromosome, and regenerating a plant from the plant cell. The invention further provides for methods comprising co-delivering a nucleic acid encoding a growth inducing gene is not expressed or alternatively is not present in the regenerated plant. The invention also provides for methods wherein the co-delivered nucleic acid encodes a growth inducing gene expressed during regeneration. The growth inducing gene may a plant growth regulator gene, an organogenesis-promoting gene, an embryogenesis-promoting gene or regeneration-promoting gene, such as Agrobacterium tumefaciens isopentenyl transferase gene, Agrobacterium rhizogenes isopentenyl transferase gene, Agrobacterium tumefaciens indole-3-acetamide hydrolase (IAAH) gene or Agrobacterium tumefaciens tryptophan-2-monooxygenase (IAAM) gene.

Another aspect of the invention provides for methods of using any of the preceding adchromosomal plants for a food product, a pharmaceutical product or chemical product, according to which a suitable exogenous nucleic acid is expressed in adchromosomal plants or plant cells and the plant or plant cells are grown. The plant may secrete the product into its growth environment or the product may be contained within the plant, in which case the plant is harvested and desirable products are extracted.

Thus, the invention contemplates methods of using any of the preceding adchromosomal plants to produce a modified food product, for example, by growing a plant that expresses a exogenous nucleic acid that alters the nutritional content of the plant, and harvesting or processing the corn plant.

The invention also contemplates methods of using any of the preceding adchromosomal plants to produce a recombinant protein, by growing a plant comprising a mini-chromosome that comprises an exogenous nucleic acid encoding the recombinant protein. Optionally the plant is harvested and the desired recombinant protein is isolated from the plant. Exemplary recombinant proteins include pharmaceutical proteins or industrial enzymes.

The invention also contemplates methods of using any of the preceding adchromosomal plants to produce a recombinant protein, by growing a plant comprising a mini-chromosome that comprises an exogenous nucleic acid encoding an enzyme involved in synthesis of the chemical product. Optionally the plant is harvested and the desired chemical product is isolated from the plant. Exemplary chemical products include pharmaceutical products.

BRIEF DESCRIPTION OF THE FIGURES

FIG. 5 shows the alignment of Brassica consensus centromere satellite repeats, BB5R4-1 (SEQ ID NO:2), BB5R4-1 (SEQ ID NO:51), and BB280R2-3 (SEQ ID NO:52).

FIG. 6 shows the alignment of Glycine max (soybean) consensus centromere satellite repeats, CrGM1 (SEQ ID NO:25), CrGm2 (SEQ ID NO:26), and SB12MC (SEQ ID NO:24).

DETAILED DESCRIPTION OF THE INVENTION

Figure 1:
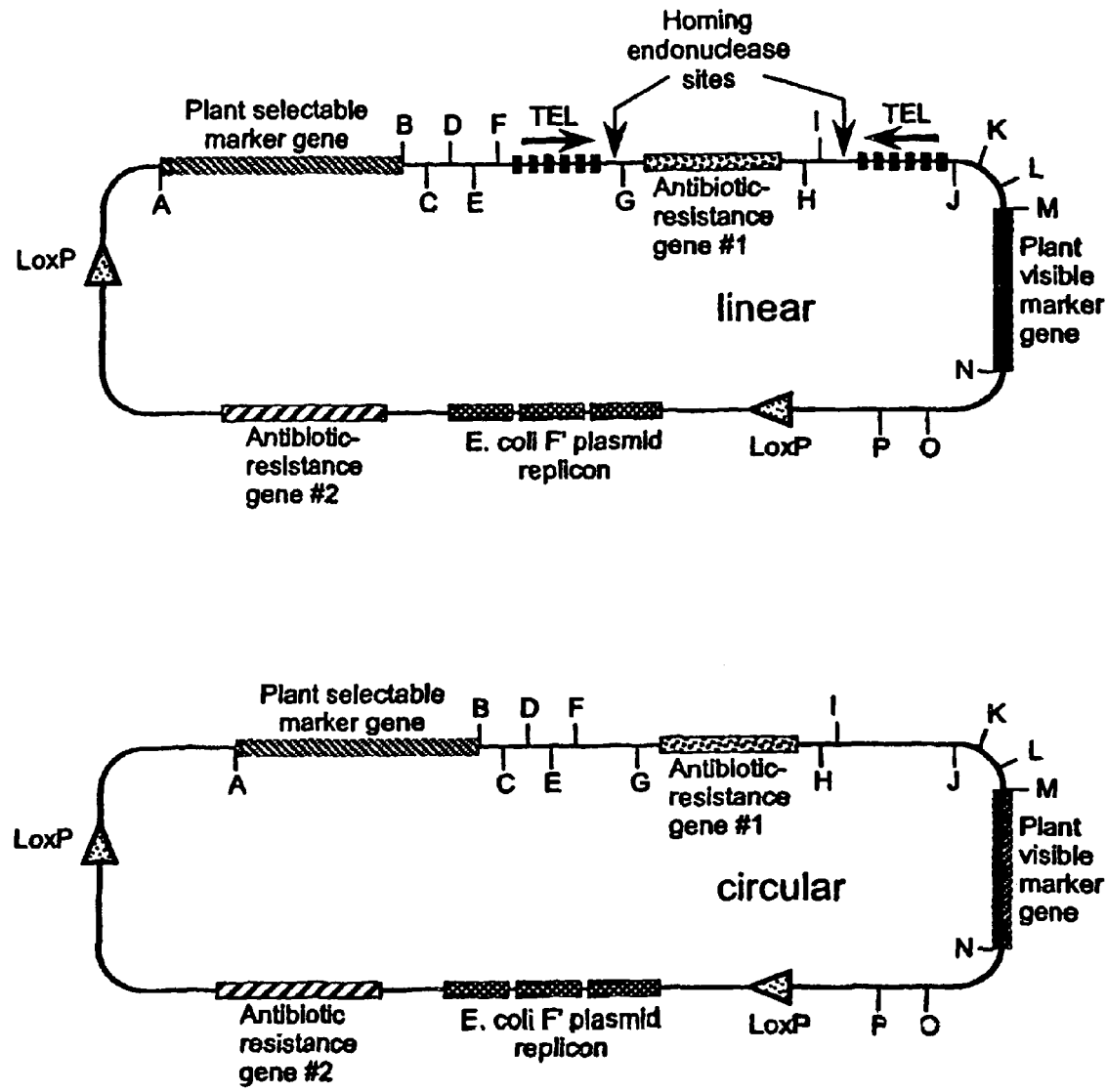
FIG. 1 is an example of a mini-chromosome vector in the present invention containing 2 genes.

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

The invention is based on the production of modified plants, containing functional, stable, autonomous mini-chromosomes. Such mini-chromosomes have been shown herein to be meiotically transmitted to progeny.

One aspect of the invention is related to plants containing functional, stable, autonomous mini-chromosomes, preferably carrying one or more nucleic acids exogenous to the cell. Such plants carrying mini-chromosomes are contrasted to transgenic plants whose genome has been altered by chromosomal integration of an exogenous nucleic acid. Preferably, expression of the exogenous nucleic acid, either constitutively or in response to a signal which may be a challenge or a stimulus, results in an altered phenotype of the plant.

The invention provides for mini-chromosomes comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 250, 500, 1000 or more exogenous nucleic acids.

The invention contemplates that any plants, including but not limited to monocots, dicots, gymnosperm, field crops, vegetable crops, fruit and vine crops, or any specific plants named herein, may be modified by carrying autonomous mini-chromosomes as described herein. A related aspect of the invention is plant parts or plant tissues, including pollen, silk, endosperm, ovule, seed, embryo, pods, roots, cuttings, tubers, stems, stalks, fruit, berries, nuts, flowers, leaves, bark, whole plant, plant cell, plant organ, protoplast, cell culture, or any group of plant cells organized into a structural and functional unit, any cells of which carry mini-chromosomes.

A related aspect of the invention is adchromosomal plant parts or plant tissues, including pollen, silk, endosperm, ovule, seed, embryo, pods, roots, cuttings, tubers, stems, stalks, crown, callus culture, petiole, petal, sepal, stamen, stigma, style, bud, fruit, berries, nuts, flowers, leaves, bark, wood, whole plant, plant cell, plant organ, protoplast, cell culture, or any group of plant cells organized into a structural and functional unit. In one preferred embodiment, the exogenous nucleic acid is primarily expressed in a specific location or tissue of a plant, for example, epidermis, vascular tissue, meristem, cambium, cortex, pith, leaf, sheath, flower, root or seed. Tissue-specific expression can be accomplished with, for example, localized presence of the mini-chromosome, selective maintenance of the mini-chromosome, or with promoters that drive tissue-specific expression.

Another related aspect of the invention is meiocytes, pollen, ovules, endosperm, seed, somatic embryos, apomyctic embryos, embryos derived from fertilization, vegetative propagules and progeny of the originally adchromosomal plant and of its filial generations that retain the functional, stable, autonomous mini-chromosome. Such progeny include clonally propagated plants, embryos and plant parts as well as filial progeny from self- and cross-breeding, and from apomyxis.

Preferably the mini-chromosome is transmitted to subsequent generations of viable daughter cells during mitotic cell division with a transmission efficiency of at least 60%, 70%, 80%, 85%, 90%, 95%, 96%, 97%, 98%, or 99%. More preferably, the mini-chromosome is transmitted to viable gametes during meiotic cell division with a transmission efficiency of at least 60%, 70%, 80%, 85%, 90%, 95%, 96%, 97%, 98%, or 99% when more than one copy of the mini-chromosome is present in the gamete mother cells of the plant. Preferably, the mini-chromosome is transmitted to viable gametes during meiotic cell division with a transmission frequency of at least 20%, 30%, 40%, 45%, 46%, 47%, 48%, or 49% when one copy of the mini-chromosome is present in the gamete mother cells of the plant. For production of seeds via sexual reproduction or by apomyxis the mini-chromosome is preferably transferred into at least 60%, 70%, 80%, 85%, 90%, 95%, 96%, 97%, 98%, or 99% of viable embryos when cells of the plant contain more than one copy of the mini-chromosome. For production of seeds via sexual reproduction or by apomyxis from plants with one mini-chromosome per cell, the mini-chromosome is preferably transferred into at least 20%, 30%, 40%, 45%, 46%, 47%, 48%, or 49% of viable embryos.

Preferably, a mini-chromosome that comprises an exogenous selectable trait or exogenous selectable marker can be employed to increase the frequency in subsequent generations of adchromosomal cells, tissues, gametes, embryos, endosperm, seeds, plants or progeny. More preferably, the frequency of transmission of mini-chromosomes into viable cells, tissues, gametes, embryos, endosperm, seeds, plants or progeny can be at least 95%, 96%, 97%, 98%, 99% or 99.5% after mitosis or meiosis by applying a selection that favors the survival of adchromosomal cells, tissues, gametes, embryos, endosperm, seeds, plants or progeny over such cells, tissues, gametes, embryos, endosperm, seeds, plants or progeny lacking the mini-chromosome.

Transmission efficiency may be measured as the percentage of progeny cells or plants that carry the mini-chromosome as measured by one of several assays taught herein including detection of reporter gene fluorescence, PCR detection of a sequence that is carried by the mini-chromosome, RT-PCR detection of a gene transcript for a gene carried on the mini-chromosome, Western analysis of a protein produced by a gene carried on the mini-chromosome, Southern analysis of the DNA (either in total or a portion thereof) carried by the mini-chromosome, fluorescence in situ hybridization (FISH) or in situ localization by repressor binding, to name a few. Any assay used to detect the presence of the mini-chromosome (or a portion of the mini-chromosome) may be used to measure the efficiency of a parental cell or plant transmits the mini-chromosome to its progeny. Efficient transmission as measured by some benchmark percentage should indicate the degree to which the mini-chromosome is stable through the mitotic and meiotic cycles.

Plants of the invention may also contain chromosomally integrated exogenous nucleic acid in addition to the autonomous mini-chromosomes. The adchromosomal plants or plant parts, including plant tissues of the invention may include plants that have chromosomal integration of some portion of the mini-chromosome in some or all cells the plant. The plant, including plant tissue or plant cell is still characterized as adchromosomal despite the occurrence of some chromosomal integration. In one aspect of the invention, the autonomous mini-chromosome can be isolated from integrated exogenous nucleic acid by crossing the adchromosomal plant containing the integrated exogenous nucleic acid with plants producing some gametes lacking the integrated exogenous nucleic acid and subsequently isolating offspring of the cross, or subsequent crosses, that are adchromosomal but lack the integrated exogenous nucleic acid. This independent segregation of the mini-chromosome is one measure of the autonomous nature of the mini-chromosome.

Another aspect of the invention relates to methods for producing and isolating such adchromosomal plants containing functional, stable, autonomous mini-chromosomes.

In one embodiment, the invention contemplates improved methods for isolating native centromere sequences. In another embodiment, the invention contemplates methods for generating variants of native or artificial centromere sequences by passage through bacterial or plant or other host cells.

In a further embodiment, the invention contemplates methods for delivering the mini-chromosome into plant cells or tissues to transform the cells or tissues.

In yet another embodiment, the invention contemplates improved methods for regenerating plants, including methods for co-delivery of growth inducing genes with mini-chromosomes. The growth delivery genes include *Agrobacterium tumefaciens* or *A. rhizogenes* isopentenyl transferase (IPT) genes involved in cytokinin biosynthesis, plant isopentenyl transferase (IPT) genes involved in cytokinin biosynthesis (from any plant), *Agrobacterium tumefaciens* IAAH, IAAM genes involved in auxin biosynthesis (indole-3-acetamide hydrolase and tryptophan-2-monooxygenase, respectively), *Agrobacterium rhizogenes* rolA, rolB and rolC genes involved in root formation, *Agrobacterium tumefaciens* Aux1, Aux2 genes involved in auxin biosynthesis (indole-3-acetamide hydrolase or tryptophan-2-monooxygenase genes), *Arabidopsis thaliana* leafy cotyledon genes (e.g. Lec1, Lec2) promoting embryogenesis and shoot formation (see Stone et al., Proc. Natl. Acad. Sci. USA 98: 11806-11811), *Arabidopsis thaliana* ESR1 gene involved in shoot formation (see Banno et al., Plant Cell 13: 2609-2618), *Arabidopsis thaliana* PGA6/WUSCHEL gene involved in embryogenesis (see Zuo et al., Plant J. 30: 349-359).

In yet a further embodiment, the invention contemplates methods for selecting modified plant cells or plant parts containing mini-chromosomes for regeneration. Such methods include assays for identifying adchromosomal plants or cells by determining that mini-chromosomes within the modified plant cell or plant are functional, stable, and autonomous. Exemplary assays for assessing mini-chromosome performance include lineage-based inheritance assays, use of chromosome loss agents to demonstrate autonomy, global mitotic mini-chromosome inheritance assays (sectoring assays) with or without the use of agents inducing chromosomal loss, assays measuring expression levels of marker genes in the mini-chromosome over time and space in a plant, physical assays for separation of autonomous mini-chromosomes from endogenous nuclear chromosomes of plants, molecular assays demonstrating conserved mini-chromosome structure, such as PCR, Southern blots, mini-chromosome rescue, cloning and characterization of mini-chromosome sequences present in the plant, cytological assays detecting mini-chromosome presence in the cell's genome (e.g. FISH) and meiotic mini-chromosome inheritance assays, which measure the levels of mini-chromosome inheritance into a subsequent generation of plants via meiosis and gametes, embryos, endosperm or seeds.

The invention also contemplates novel methods of screening for adchromosomal plant cells that involve use of relatively low, sub-killing concentrations of selection agent (e.g. sub-killing antibiotic concentrations), and also involve use of a screenable marker (e.g., a visible marker gene) to identify clusters of modified cells carrying the screenable marker, after which these screenable cells are manipulated to homogeneity. Another aspect of the present invention is related to methods of making and compositions of non-plant promoters for expressing genes in plants.

The invention further provides isolated promoter nucleic acid sequences comprising any one of SEQ ID NOS: 4 to 23, or fragments or variants thereof that retain expression-promoting activity. Mini-chromosomes comprising non-plant promoter sequences such as these that are operably linked to plant-expressed genes (e.g., genes that confer a different phenotype on plants), are contemplated as are plants comprising such mini-chromosomes.

Another aspect is related to methods for using exonuclease to enrich for circular mini-chromosome DNA in genomic DNA preparations.

Another aspect of the invention relates to methods for using such adchromosomal plants containing a mini-chromosome for producing food products, pharmaceutical products and chemical products by appropriate expression of exogenous nucleic acid(s) contained within the mini-chromosome(s).

It has also been shown herein that mini-chromosomes containing centromeres from one plant species, when inserted into plant cells of a different species or even a different genus or family, can be stable, functional and autonomous. For example, as shown herein, a broccoli centromere (*B. oleraceae*) is functional in a canola (*B. napus*) plant. Similarly, a tomato (*Lycopersicum*) centromere is functional in a tobacco (*Nicotiana*) plant. A soybean (*G. max*) centromere is functional in a broccoli (*B. oleraceae*) and tobacco plant. Tobacco and tomato are in the same family of Solanaceae plants. Soybean is in the Leguminoseae family and broccoli is in the Brassicaceae family. Thus, another aspect of the invention is an adchromosomal plant comprising a functional, stable, autonomous mini-chromosome that contains centromere sequence derived from a different taxonomic plant species, or derived from a different taxonomic plant species, genus, family, order or class.

Yet another aspect of the invention provides novel autonomous mini-chromosomes with novel compositions and structures which are used to transform plant cells which are in turn used to generate a plant (or multiple plants). Exemplary mini-chromosomes of the invention are contemplated to be of a size 2000 kb or less in length. Other exemplary sizes of mini-chromosomes include less than or equal to, e.g., 1500 kb, 1000 kb, 900 kb, 800 kb, 700 kb, 600 kb, 500 kb, 450 kb, 400 kb, 350 kb, 300 kb, 250 kb, 200 kb, 150 kb, 100 kb, 80 kb, 60 kb, or 40 kb in length.

In a related aspect, novel centromere compositions as characterized by sequence content, size or other parameters are provided. Preferably, the minimal size of centromeric sequence is utilized in mini-chromosome construction. Exemplary sizes include a centromeric nucleic acid insert derived from a portion of plant genomic DNA, that is less than or equal to 1000 kb, 900 kb, 800 kb, 700 kb, 600 kb, 500 kb, 400 kb, 300 kb, 200 kb, 150 kb, 100 kb, 95 kb, 90 kb, 85 kb, 80 kb, 75 kb, 70 kb, 65 kb, 60 kb, 55 kb, 50 kb, 45 kb, 40 kb, 35 kb, 30 kb, 25 kb, 20 kb, 15 kb, 10 kb, 5 kb, or 2 kb in length. For example, rescued functional variant soybean centromeric sequences have been shown to be less than 30 kb in size. Another related aspect is the novel structure of the mini-chromosome, particularly structures lacking bacterial sequences, e.g, required for bacterial propagation.

In exemplary embodiments the invention contemplates mini-chromosomes or other vectors comprising a repeated nucleotide sequence derived from a *Brassica* plant and adchromosomal plants or parts containing these mini-chromosomes. Exemplary repeated nucleotide sequences include (1) SEQ ID NO:1, SEQ ID NO: 2, SEQ ID NO:3, SEQ ID NO: 51 or SEQ ID NO: 52, or fragments or variants thereof, (2) combinations of any of these *Brassica* sequences or a fragment or variant thereof with another *Brassica*-derived centromeric nucleotide sequence, (3) combinations of any of these *Brassica* sequences or a fragment or variant thereof with a centromeric nucleotide sequence derived from a different plant species, and (4) combinations of any of the above with artificially synthesized centromeric nucleotide sequences.

In exemplary embodiments the invention also contemplates mini-chromosomes or other vectors comprising a repeated nucleotide sequence derived from a *Glycine max* plant and adchromosomal plants or parts containing these mini-chromosomes. Exemplary repeated nucleotide sequences include (1) SEQ ID NO: 24, SEQ ID NO: 25, SEQ ID NO:26, or fragments or variants thereof, (2) combinations of any of these soybean sequences or a fragment or variant thereof with another soybean-derived centromeric nucleotide sequence, (3) combinations of any of these soybean sequences or a fragment or variant thereof with a centromeric nucleotide sequence derived from a different plant species, and (4) combinations of any of the above with artificially synthesized centromeric nucleotide sequences.

In exemplary embodiments, the invention also contemplates mini-chromosomes or other vectors comprising fragments or variants of the genomic DNA inserts of the BAC clones [identified as BB5, SB6, TB99, ZB19, or ZB113] deposited on Feb. 23, 2005 with the American Type Culture Collection (ATCC), P.O. Box 1549 Manassas, Va. 20108, USA, under Accession Nos. PTA-6601, PTA-6602, PTA-6603, PTA-6604 and PTA-6605, respectively, or naturally occurring descendants thereof, that retain the ability to segregate during mitotic or meiotic division as described herein, as well as adchromosomal plants or parts containing these mini-chromosomes. Other exemplary embodiments include fragments or variants of the genomic DNA inserts of any of the BAC clones identified herein, or descendants thereof, and fragments or variants of the centromeric nucleic acid inserts of any of the vectors or mini-chromosomes identified herein.

In other exemplary embodiments, the invention contemplates mini-chromosomes or other vectors comprising centromeric nucleotide sequence that when hybridized to 1, 2, 3, 4, 5, 6, 7, 8 or more of the probes described in the examples herein, under hybridization conditions described herein, e.g. low, medium or high stringency, provides relative hybridization scores as described in the examples herein. Preferably the probes for which relative hybridization scores are described herein as 5/10 or greater are used, and a hybridization signal greater than background for one or more of these probes is used to select clones. Adchromosomal plants or parts containing such mini-chromosomes are contemplated.

The advantages of the present invention include: provision of an autonomous, independent genetic linkage group for accelerating breeding; lack of disruption of host genome; multiple gene "stacking" of large numbers of genes with a potentially unlimited payload; uniformity of genetic composition exogenous DNA sequences in plant cells and plants containing autonomous mini-chromosomes; defined genetic context for predictable gene expression; higher frequency occurrence and recovery of plant cells and plants containing stably maintained exogenous DNA due to elimination of inefficient integration step; and the ability to eliminate mini-chromosomes in any tissues.

I. Composition of Mini-Chromosomes and Mini-Chromosome Construction

The mini-chromosome vector of the present invention may contain a variety of elements, including (1) sequences that function as plant centromeres, (2) one or more exogenous nucleic acids, including, for example, plant-expressed genes, (3) sequences that function as an origin of replication, which may be included in the region that functions as plant centromere, (4) optionally, a bacterial plasmid backbone for propagation of the plasmid in bacteria, (5) optionally, sequences that function as plant telomeres, (6) optionally, additional "stuffer DNA" sequences that serve to separate the various components on the mini-chromosome from each other, (7) optionally "buffer" sequences such as MARs or SARs, (8) optionally marker sequences of any origin, including but not limited to plant and bacterial origin, (9) optionally, sequences that serve as recombination sites, and (10) "chromatin packaging sequences" such as cohesion and condensing binding sites.

The mini-chromosomes of the present invention may be constructed to include various components which are novel, which include, but are not limited to, the centromere comprising novel repeating centromeric sequences, and the promoters, particularly promoters derived from non-plant species, as described in further detail below.

The mini-chromosomes of the present invention may be constructed to include various components which are novel, which include, but are not limited to, the centromere comprising novel repeating centromeric sequences, and the promoters, particularly promoters derived from non-plant species, as described in further detail below.

Novel Centromere Compositions

The centromere in the mini-chromosome of the present invention may comprise novel repeating centromeric sequences. An example of the mini-chromosome in the present invention is the *Brassica* BB5R4-1 mini-chromosome. The sequences set out as SEQ ID NOS:1 to 3 are relevant to the BB5R4-mini-chromosomes. The centromere of the BB5R4-1 mini-chromosome is 50 kb of *Brassica* centromere DNA as determined by CHEF gel analysis. To determine the sequence composition of the centromere, the mini-chromosome was randomly sheared and small fragments were cloned for sequencing, from which 11,010 bases of sequence were obtained from the centromere insert, a 0.17x coverage of the centromere. Of this sequence 9,533 bases were composed of centromere satellite repeat, the consensus of which is shown in SEQ ID NO:2. The satellite repeat was found to be 180+/−2 bp long. The remaining 1,477 bases of mini-chromosome sequence covered a unique sequence set out as SEQ ID NO:3. This sequence is considered a sampling of the centromere content of BB5R4-1.

Additional sequence analysis of another sampling of the *Brassica* centromere content of BB5R4-1 analyzing 7 contigs (1,175, 176, 177, 180, 184) that contain 118 canrep repeats from BB5R4-0.1 with repeat lengths of 113×176 bp, 1×175 bp and 4×174 bp generated the consensus sequence set out in SEQ ID NO: 51. A consensus sequence was also built from 135 tandem repeats obtained from another mini-chromosome, BB280R2-3; from the largest contig (33703 kb) spanning a total of 23782 bp. The repeat lengths are: 125×176 bp, 4×182 bp, 4×175 bp and 2×177 bp and this sequence is set out as SEQ ID NO: 52. An alignment of SEQ ID NOS: 2, 51 and 52 is set out in FIG. 5.

In another example, individual satellite repeats from soybean BAC clone SB12R2-3 (SEQ ID NO: 24) showed an average of 91.3% (s.d.=11.3%) identity to each other, with specific regions showing significantly higher and lower levels of variability. Comparing the satellite repeat consensus from SB12R2-3 to that obtained from randomly sampled soybean satellite sequences ChrGm1 (SEQ ID NO: 25) and ChrGm2 (SEQ ID NO: 26), see U.S. Patent Application 20030124561: Plant centromere compositions) identified several bases that differed significantly ($\chi^2$ test, P<0.05). The SB12MC satellite repeats showed an average length of 91.07±0.40 bp, similar to the ChrGm2 91-base consensus and differing from the ChrGm1 92-base consensus. An alignment of the of consensus centromere satellite repeats is set out in FIG. 6.

Exemplary embodiments of centromere nucleic acid sequences according to the present invention include fragments or variants of the genomic DNA inserts of the BAC clones [identified as BB5, SB6, TB99, ZB19, or ZB113 deposited on Feb. 23, 2005 with the American Type Culture Collection (ATCC), P.O. Box 1549 Manassas, Va. 20108, USA, under Accession Nos. PTA-6601, PTA-6602, PTA-6603, PTA-6604 and PTA-6605, respectively, that retain the ability to segregate during mitotic or meiotic division as described herein. Variants of such sequences include artificially produced modifications as described herein and modifications produced via passaging through one or more bacterial, plant or other host cells as described herein.

Vectors comprising one, two, three, four, five, six, seven, eight, nine, ten, 15 or 20 or more of the elements contained in any of the exemplary vectors described in the examples below are also contemplated.

The invention specifically contemplates the alternative use of fragments or variants (mutants) of any of the nucleic acids described herein that retain the desired activity, including nucleic acids that function as centromeres, nucleic acids that function as promoters or other regulatory control sequences, or exogenous nucleic acids. Variants may have one or more additions, substitutions or deletions of nucleotides within the original nucleotide sequence. Variants include nucleic acid sequences that are at least 50%, 55%, 60, 65, 70, 75, 80, 81, 82, 83, 84, 85, 86, 87, 88, 89, 90, 91, 92, 93, 94, 95, 96, 97, 98, 99, or 100% identical to the original nucleic acid sequence. Variants also include nucleic acid sequences that hybridize under low, medium, high or very high stringency conditions to the original nucleic acid sequence. Similarly, the specification also contemplates the alternative use of fragments or variants of any of the polypeptides described herein.

The comparison of sequences and determination of percent identity between two nucleotide sequences can be accomplished using a mathematical algorithm. In a preferred embodiment, the percent identity between two amino acid sequences is determined using the Needleman and Wunsch (1970) J. Mol. Biol. 48:444-453 algorithm which has been incorporated into the GAP program in the GCG software package, using either a Blossum 62 matrix or a PAM250 matrix. Preferably parameters are set so as to maximize the percent identity.

As used herein, the term "hybridizes under low stringency, medium stringency, and high stringency conditions" describes conditions for hybridization and washing. Guidance for performing hybridization reactions can be found in Current Protocols in Molecular Biology (1989) John Wiley & Sons, N.Y., 6.3.1-6.3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.5× SSC, 0.1% SDS, at least at 50° C.; 2) medium stringency hybridization conditions in 6×SSC at about 45° C., followed by one or more washes in 0.2×SSC, 0.1% SDS at 55° C.; 3) high stringency hybridization conditions in 6×SSC at about 45° C., followed by one or more washes in 0.2×SSC, 0.1% SDS at 65° C.

Mini-Chromosome Sequence Content and Structure

Plant-expressed genes from non-plant sources may be modified to accommodate plant codon usage, to insert preferred motifs near the translation initiation ATG codon, to remove sequences recognized in plants as 5' or 3' splice sites, or to better reflect plant GC/AT content. Plant genes typically have a GC content of more than 35%, and coding sequences which are rich in A and T nucleotides can be problematic. For example, ATTTA motifs may destabilize mRNA; plant polyadenylation signals such as AATAAA at inappropriate positions within the message may cause premature truncation of transcription; and monocotyledons may recognize AT-rich sequences as splice sites.

Each exogenous nucleic acid or plant-expressed gene may include a promoter, a coding region and a terminator sequence, which may be separated from each other by restriction endonuclease sites or recombination sites or both. Genes may also include introns, which may be present in any number and at any position within the transcribed portion of the gene, including the 5' untranslated sequence, the coding region and the 3' untranslated sequence. Introns may be natural plant introns derived from any plant, or artificial introns based on the splice site consensus that has been defined for plant species. Some intron sequences have been shown to enhance expression in plants. Optionally the exogenous nucleic acid may include a plant transcriptional terminator, non-translated leader sequences derived from viruses that enhance expression, a minimal promoter, or a signal sequence controlling the targeting of gene products to plant compartments or organelles.

Figure 2:
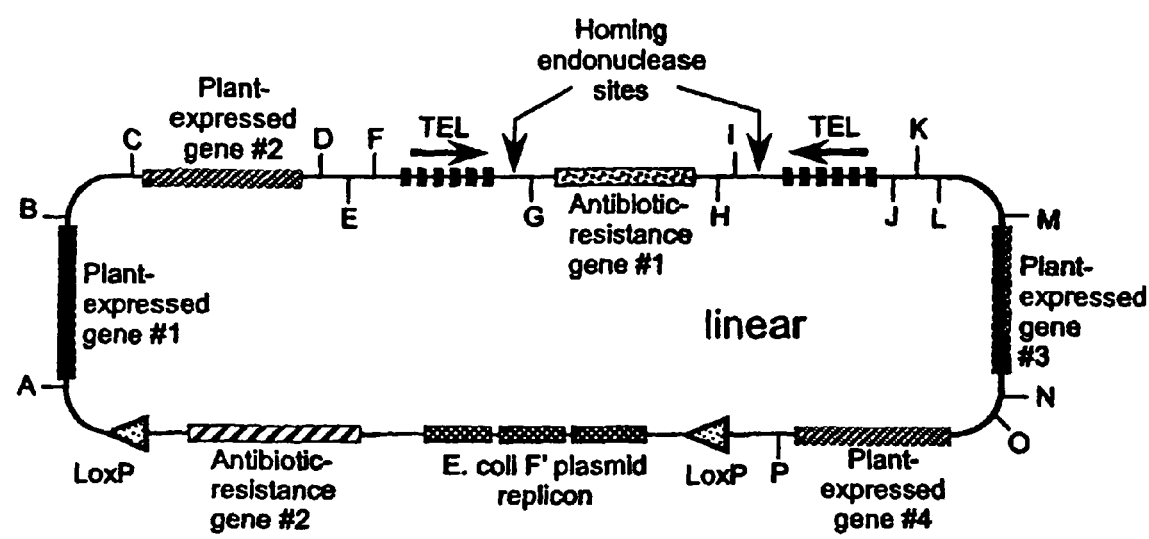
FIG. 2 is another example of a mini-chromosome vector in the present invention containing 4 genes.
Figure 2:
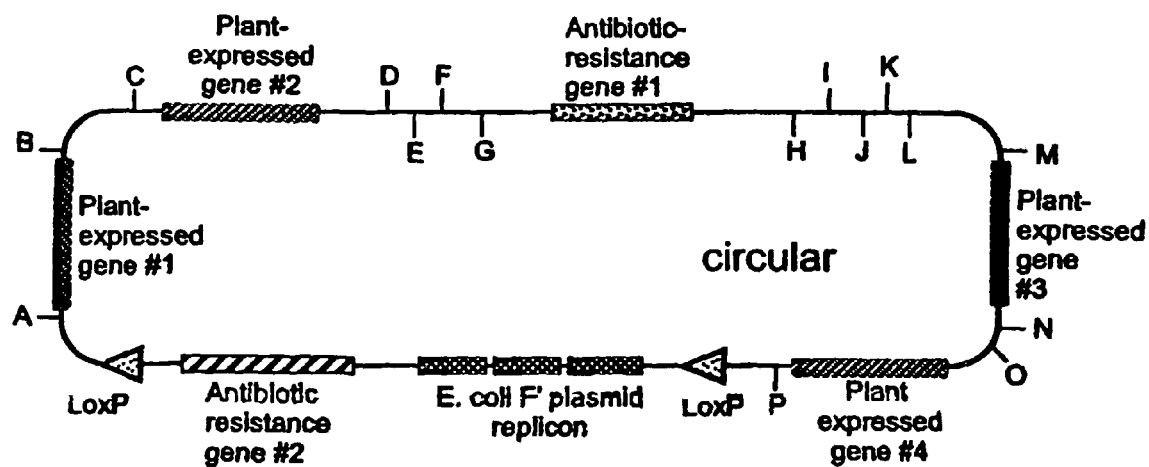

The coding regions of the genes can encode any protein, including but not limited to visible marker genes (for example, fluorescent protein genes, other genes conferring a visible phenotype to the plant) or other screenable or selectable marker genes (for example, conferring resistance to antibiotics, herbicides or other toxic compounds or encoding a protein that confers a growth advantage to the cell expressing the protein) or genes which confer some commercial or agronomic value to the adchromosomal plant. Multiple genes can be placed on the same mini-chromosome vector, limited only by the number of restriction endonuclease sites or site-specific recombination sites present in the vector. The genes may be separated from each other by restriction endonuclease sites, homing endonuclease sites, recombination sites or any combinations thereof. Any number of genes can be present. FIGS. 1 and 2 show mini-chromosome vector structures with 2 and 4 genes, respectively.

The mini-chromosome vector may also contain a bacterial plasmid backbone for propagation of the plasmid in bacteria such as E. coli, A. tumefaciens, or A. rhizogenes. The plasmid backbone may be that of a low-copy vector or in other embodiments it may be desirable to use a mid to high level copy backbone. In one embodiment of the invention, this backbone contains the replicon of the F' plasmid of E. coli. However, other plasmid replicons, such as the bacteriophage P1 replicon, or other low-copy plasmid systems such as the RK2 replication origin, may also be used. The backbone may include one or several antibiotic-resistance genes conferring resistance to a specific antibiotic to the bacterial cell in which the plasmid is present. Bacterial antibiotic-resistance genes include but are not limited to kanamycin-, ampicillin-, chloramphenicol-, streptomycin-, spectinomycin-, tetracycline- and gentamycin-resistance genes.

The mini-chromosome vector may also contain plant telomeres. An exemplary telomere sequence is TTTAGGG or its complement. Telomeres are specialized DNA structures at the ends of linear chromosomes that function to stabilize the ends and facilitate the complete replication of the extreme termini of the DNA molecule (Richards et. al., Cell. 1988 Apr. 8; 53(1):127-36; Ausubel et al., Current Protocols in Molecular Biology, Wiley & Sons, 1997).

Additionally, the mini-chromosome vector may contain "stuffer DNA" sequences that serve to separate the various components on the mini-chromosome (centromere, genes, telomeres) from each other. The stuffer DNA may be of any origin, prokaryotic or eukaryotic, and from any genome or species, plant, animal, microbe or organelle, or may be of synthetic origin. The stuffer DNA can range from 100 bp to 10 Mb in length and can be repetitive in sequence, with unit repeats from 10 to 1,000,000 bp. Examples of repetitive sequences that can be used as stuffer DNAs include but are not limited to: rDNA, satellite repeats, retroelements, transposes, pseudogenes, transcribed genes, microsatellites, tDNA genes, short sequence repeats and combinations thereof. Alternatively, the stuffer DNA can consist of unique, non-repetitive DNA of any origin or sequence. The stuffer sequences may also include DNA with the ability to form boundary domains, such as but not limited to scaffold attachment regions (SARs) or matrix attachment regions (MARs). The stuffer DNA may be entirely synthetic, composed of random sequence. In this case, the stuffer DNA may have any base composition, or any A/T or G/C content. For example, the G/C content of the stuffer DNA could resemble that of the plant (~30-40%), or could be much lower (0-30%) or much higher (40-100%). Alternatively, the stuffer sequences could be synthesized to contain an excess of any given nucleotide such as A, C, G or T. Different synthetic stuffers of different compositions may also be combined with each other. For example a fragment with low G/C content may be flanked or abutted by a fragment of medium or high G/C content, or vice versa.

Figure 3:
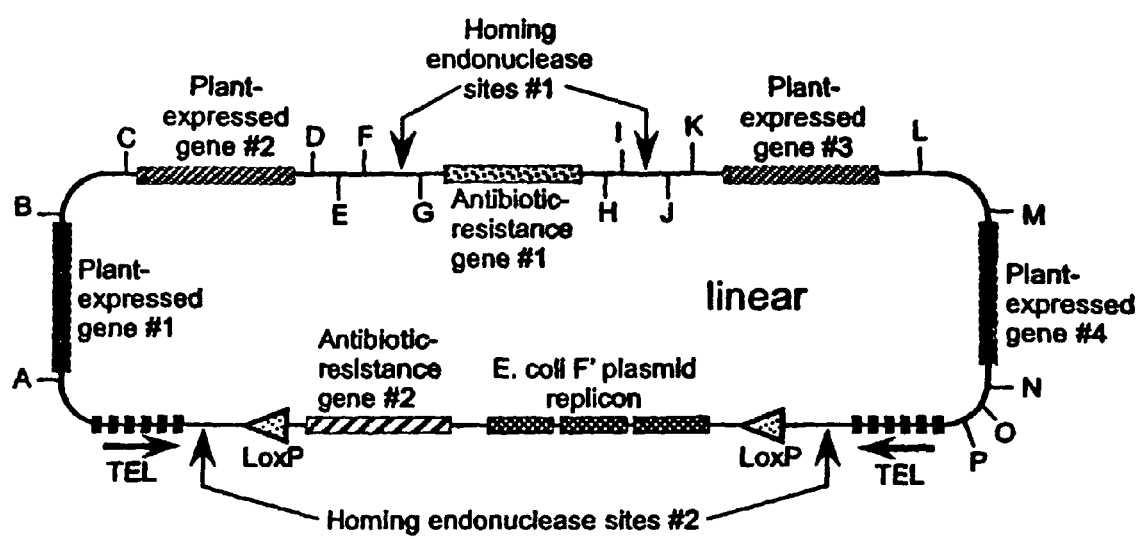
FIG. 3 is a mini-chromosome from which all bacterial sequences have been removed. In this embodiment, bacterial sequence present between or among the plant-expressed genes or other mini-chromosome sequences would be excised prior to removal of the remaining bacterial sequences, by cutting the mini-chromosome with endonuclease #1, and re-ligating the structure such that the antibiotic-resistance gene #1 has been lost.
Figure 4:
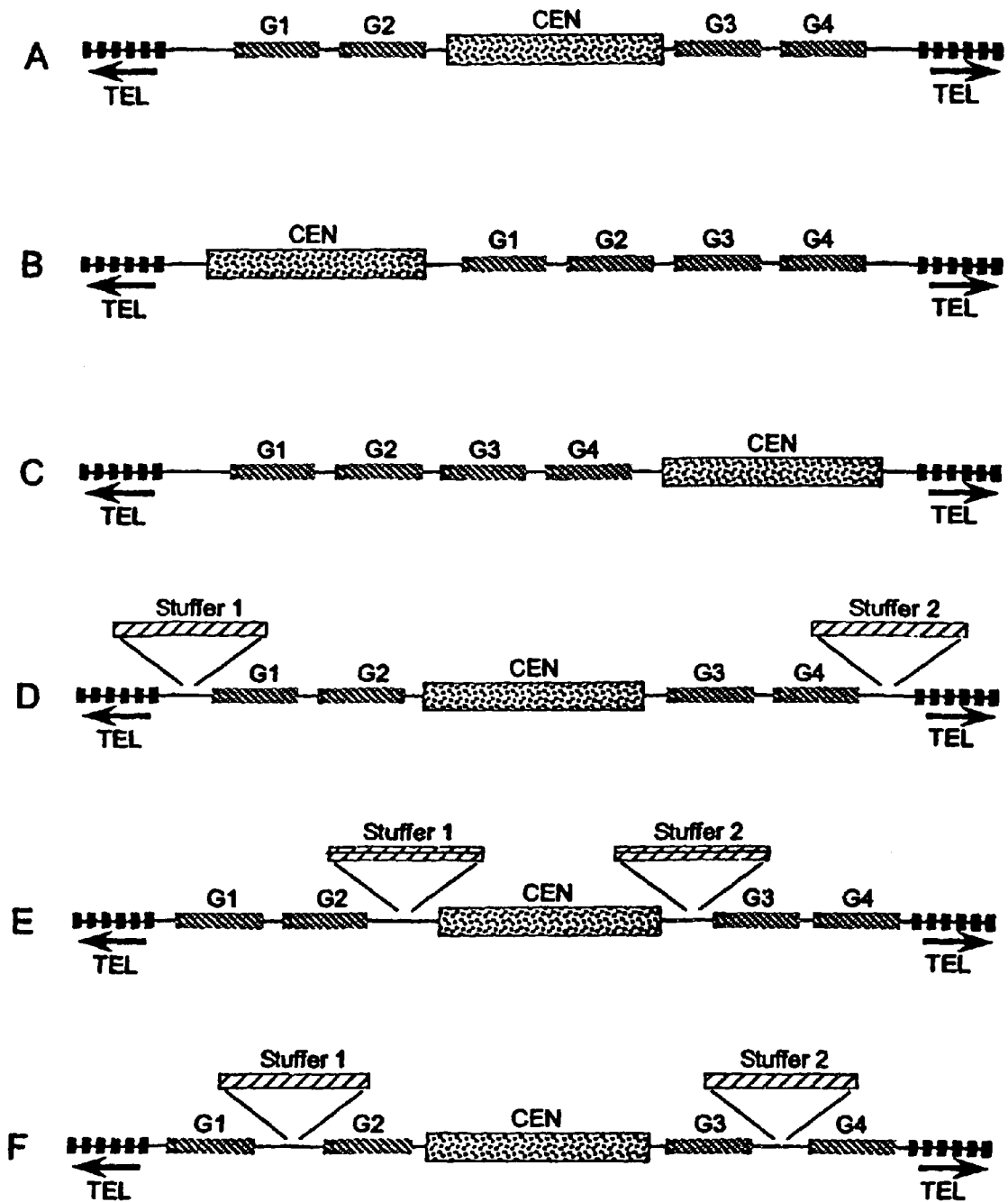
FIG. 4 shows various structural configurations by which mini-chromosome elements can be oriented with respect to each other.

In one embodiment of the invention, the mini-chromosome has a circular structure without telomeres, as shown in FIGS. 1 and 2 "circular". In another embodiment, the mini-chromosome has a circular structure with telomeres, as shown in FIGS. 1 and 2 "linear". In a third embodiment, the mini-chromosome has a linear structure with telomeres, as would result if the "linear" structure shown in FIGS. 1 and 2 were to be cut with a unique endonuclease, exposing the telomeres at the ends of a DNA molecule that contains all of the sequence contained in the original, closed construct with the exception of the antibiotic-resistance gene #1. In a fourth embodiment of the invention, the telomeres could be placed in such a manner that the bacterial replicon, backbone sequences, antibiotic-resistance genes and any other sequences of bacterial origin and present for the purposes of propagation of the mini-chromosome in bacteria, can be removed from the plant-expressed genes, the centromere, telomeres, and other sequences by cutting the structure with unique endonuclease #2 (FIG. 3). This results in a mini-chromosome from which much of, or preferably all, bacterial sequences have been removed. In this embodiment, bacterial sequence present between or among the plant-expressed genes or other mini-chromosome sequences would be excised prior to removal of the remaining bacterial sequences by cutting the mini-chromosome with homing endonuclease #1, and re-ligating the structure such that the antibiotic-resistance gene #1 has been lost (FIG. 3). In all of the structures shown in FIGS. 1, 2 and 3, the unique endonuclease site may be the recognition sequence of a homing endonuclease. Alternatively, the endonucleases and their sites can be replaced with any specific DNA cutting mechanism and its specific recognition site such as rare-cutting endonuclease or recombinase and its specific recognition site, as long as that site is present in the mini-chromosomes only at the indicated positions.

Various structural configurations are possible by which mini-chromosome elements can be oriented with respect to each other. A centromere can be placed on a mini-chromosome either between genes or outside a cluster of genes next to one telomere or next to the other telomere. Stuffer DNAs can be combined with these configurations to place the stuffer sequences inside the telomeres, around the centromere between genes or any combination thereof. Thus, a large number of alternative mini-chromosome structures are possible, depending on the relative placement of centromere DNA, genes, stuffer DNAs, bacterial sequences, telomeres, and other sequences. The sequence content of each of these variants is the same, but their structure may be different depending on how the sequences are placed. These variations in architecture are possible both for linear and for circular mini-chromosomes.

Exemplary Centromere Components

Centromere components may be isolated or derived from native plant genome, for example, modified through recombinant techniques or through the cell-based techniques described below. Alternatively, wholly artificial centromere components may be constructed using as a general guide the sequence of native centromeres. Combinations of centromere components derived from natural sources and/or combinations of naturally derived and artificial components are also contemplated As noted above, centromere sequence from one taxonomic plant species has been shown to be functional in another taxonomic plant species, genus and family.

In one embodiment, the centromere contains n copies of a repeated nucleotide sequence obtained by the methods disclosed herein, wherein n is at least 2. In another embodiment, the centromere contains n copies of interdigitated repeats. An interdigitated repeat is a DNA sequence that consists of two distinct repetitive elements that combine to create an unique permutation. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. Moreover, the copies, while largely identical, can vary from each other. Such repeat variation is commonly observed in naturally occurring centromeres. The length of the repeat may vary, but will preferably range from about 20 bp to about 360 bp, from about 20 bp to about 250 bp, from about 50 bp to about 225 bp, from about 75 bp to about 210 bp, such as a 92 bp repeat and a 97 bp repeat, from about 100 bp to about 205 bp, from about 125 bp to about 200 bp, from about 150 bp to about 195 bp, from about 160 bp to about 190 and from about 170 bp to about 185 bp including about 180 bp.

Modification of Centromeres Isolated from Native Plant Genome

Modification and changes may be made in the centromeric DNA segments of the current invention and still obtain a functional molecule with desirable characteristics. The following is a discussion based upon changing the nucleic acids of a centromere to create an equivalent, or even an improved, second generation molecule.

In particular embodiments of the invention, mutated centromeric sequences are contemplated to be useful for increasing the utility of the centromere. It is specifically contemplated that the function of the centromeres of the current invention may be based in part of in whole upon the secondary structure of the DNA sequences of the centromere, modification of the DNA with methyl groups or other adducts, and/or the proteins which interact with the centromere. By changing the DNA sequence of the centromere, one may alter the affinity of one or more centromere-associated protein(s) for the centromere and/or the secondary structure or modification of the centromeric sequences, thereby changing the activity of the centromere. Alternatively, changes may be made in the centromeres of the invention which do not affect the activity of the centromere. Changes in the centromeric sequences which reduce the size of the DNA segment needed to confer centromere activity are contemplated to be particularly useful in the current invention, as would changes which increased the fidelity with which the centromere was transmitted during mitosis and meiosis.

Modification of Centromeres by Passage Through Bacteria, Plant or Other Hosts or Processes In the methods of the present invention, the resulting mini-chromosome DNA sequence may also be a derivative of the parental clone or centromere clone having substitutions, deletions, insertions, duplications and/or rearrangements of one or more nucleotides in the nucleic acid sequence. Such nucleotide mutations may occur individually or consecutively in stretches of 1, 2, 3, 4, 5, 10, 20, 40, 80, 100, 200, 400, 800, 1000, 2000, 4000, 8000, 10000, 50000, 100000, and about 200000, including all ranges in-between.

Variations of mini-chromosomes may arise through passage of mini-chromosomes through various hosts including virus, bacteria, yeast, plant or other prokaryotic or eukaryotic organism and may occur through passage of multiple hosts or individual host. Variations may also occur by replicating the mini-chromosome in vitro.

Derivatives may be identified through sequence analysis, or variations in mini-chromosome molecular weight through electrophoresis such as, but not limited to, CHEF gel analysis, column or gradient separation, or any other methods used in the field to determine and/or analyze DNA molecular weight or sequence content. Alternately, derivatives may be identified by the altered activity of a derivative in conferring centromere function to a mini-chromosome.

Exemplary Exogenous Nucleic Acids Including Plant-Expressed Genes

Of particular interest in the present invention are exogenous nucleic acids which when introduced into plants alter the phenotype of the plant, a plant organ, plant tissue, or portion of the plant. Exemplary exogenous nucleic acids encode polypeptides involved in one or more important biological properties in plants. Other exemplary exogenous nucleic acids alter expression of exogenous or endogenous genes, either increasing or decreasing expression, optionally in response to a specific signal or stimulus.

As used herein, the term "trait" can refer either to the altered phenotype of interest or the nucleic acid which causes the altered phenotype of interest.

One of the major purposes of transformation of crop plants is to add some commercially desirable, agronomically important traits to the plant. Such traits include, but are not limited to, herbicide resistance or tolerance; insect (pest) resistance or tolerance; disease resistance or tolerance (viral, bacterial, fungal, nematode or other pathogens); stress tolerance and/or resistance, as exemplified by resistance or tolerance to drought, heat, chilling, freezing, excessive moisture, salt stress, mechanical stress, extreme acidity, alkalinity, toxins, UV light, ionizing radiation or oxidative stress; increased yields, whether in quantity or quality; enhanced or altered nutrient acquisition and enhanced or altered metabolic efficiency; enhanced or altered nutritional content and makeup of plant tissues used for food, feed, fiber or processing; physical appearance; male sterility; drydown; standability; prolificacy; starch quantity and quality; oil quantity and quality; protein quality and quantity; amino acid composition; modified chemical production; altered pharmaceutical or nutraceutical properties; altered bioremediation properties; increased biomass; altered growth rate; altered fitness; altered biodegradability; altered $CO_2$ fixation; presence of bioindicator activity; altered digestibility by humans or animals; altered allergenicity; altered mating characteristics; altered pollen dispersal; improved environmental impact; altered nitrogen fixation capability; the production of a pharmaceutically active protein; the production of a small molecule with medicinal properties; the production of a chemical including those with industrial utility; the production of nutraceuticals, food additives, carbohydrates, RNAs, lipids, fuels, dyes, pigments, vitamins, scents, flavors, vaccines, antibodies, hormones, and the like; and alterations in plant architecture or development, including changes in developmental timing, photosynthesis, signal transduction, cell growth, reproduction, or differentiation. Additionally one could create a library of an entire genome from any organism or organelle including mammals, plants, microbes, fungi, or bacteria, represented on mini-chromosomes.

In one embodiment, the modified plant may exhibit increased or decreased expression or accumulation of a product of the plant, which may be a natural product of the plant or a new or altered product of the plant. Exemplary products include an enzyme, an RNA molecule, a nutritional protein, a structural protein, an amino acid, a lipid, a fatty acid, a polysaccharide, a sugar, an alcohol, an alkaloid, a carotenoid, a propanoid, a phenylpropanoid, or terpenoid, a steroid, a flavonoid, a phenolic compound, an anthocyanin, a pigment, a vitamin or a plant hormone. In another embodiment, the modified plant has enhanced or diminished requirement for light, water, nitrogen, or trace elements. In another embodiment the modified plant has an enhance ability to capture or fix nitrogen from its environment. In yet another embodiment, the modified plant is enriched for an essential amino acid as a proportion of a protein fraction of the plant. The protein fraction may be, for example, total seed protein, soluble protein, insoluble protein, water-extractable protein, and lipid-associated protein. The modification may include overexpression, underexpression, antisense modulation, sense suppression, inducible expression, inducible repression, or inducible modulation of a gene.

A brief summary of exemplary improved properties and polypeptides of interest for either increased or decreased expression is provided below.

(i) Herbicide Resistance

A herbicide resistance (or tolerance) trait is a characteristic of a modified plant that is resistant to dosages of an herbicide that is typically lethal to a non-modified plant. Exemplary herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and glufosinate herbicides. Other herbicides would be useful as would combinations of herbicide genes on the same mini-chromosome.

The genes encoding phosphinothricin acetyltransferase (bar), glyphosate tolerant EPSP synthase genes, glyphosate acetyltransferase, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar gene codes for an enzyme, phosphinothricin acetyltransferase (PAT), which inactivates the herbicide phosphinothricin and prevents this compound from inhibiting glutamine synthetase enzymes. The enzyme 5 enolpyruvylshikimate 3 phosphate synthase (EPSP Synthase), is normally inhibited by the herbicide N (phosphonomethyl)glycine (glyphosate). However, genes are known that encode glyphosate resistant EPSP synthase enzymes. These genes are particularly contemplated for use in plant transformation. The deh gene encodes the enzyme dalapon dehalogenase and confers resistance to the herbicide dalapon. The bxn gene codes for a specific nitrilase enzyme that converts bromoxynil to a non herbicidal degradation product. The glyphosate acetyl transferase gene inactivates the herbicide glyphosate and prevents this compound from inhibiting EPSP synthase.

Polypeptides that may produce plants having tolerance to plant herbicides include polypeptides involved in the shikimate pathway, which are of interest for providing glyphosate tolerant plants. Such polypeptides include polypeptides involved in biosynthesis of chorismate, phenylalanine, tyrosine and tryptophan.

(ii) Insect Resistance

Potential insect resistance (or tolerance) genes that can be introduced include *Bacillus thuringiensis* crystal toxin genes or Bt genes (Watrud et al., In: Engineered Organisms and the Environment, 1985). Bt genes may provide resistance to lepidopteran or coleopteran pests such as European Corn Borer (ECB). Preferred Bt toxin genes for use in such embodiments include the CryIA(b) and CryIA(c) genes. Endotoxin genes from other species of *B. thuringiensis* which affect insect growth or development also may be employed in this regard.

It is contemplated that preferred Bt genes for use in the mini-chromosomes disclosed herein will be those in which the coding sequence has been modified to effect increased expression in plants, and for example, in monocot plants. Means for preparing synthetic genes are well known in the art and are disclosed in, for example, U.S. Pat. No. 5,500,365 and U.S. Pat. No. 5,689,052, each of the disclosures of which are specifically incorporated herein by reference in their entirety. Examples of such modified Bt toxin genes include a synthetic Bt CryIA(b) gene (Perlak et al., Proc. Natl. Acad. Sci. USA, 88:3324-3328, 1991), and the synthetic CryIA(c) gene termed 1800b (PCT Application WO 95/06128). Some examples of other Bt toxin genes known to those of skill in the art are given in Table 1 below.

TABLE 1

Bacillus thuringiensis Endotoxin Genes[a]

| New Nomenclature | Old Nomenclature | GenBank Accession |
|---|---|---|
| Cry1Aa | Cry1A(a) | M11250 |
| Cry1Ab | Cry1A(b) | M13898 |
| Cry1Ac | Cry1A(c) | M11068 |
| Cry1Ad | Cry1A(d) | M73250 |
| Cry1Ae | Cry1A(e) | M65252 |
| Cry1Ba | Cry1B | X06711 |
| Cry1Bb | ET5 | L32020 |
| Cry1Bc | PEG5 | Z46442 |
| Cry1Bd | CryEI | U70726 |
| Cry1Ca | Cry1C | X07518 |
| Cry1Cb | Cry1C(b) | M97880 |
| Cry1Da | Cry1D | X54160 |
| Cry1Db | PrtB | Z22511 |
| Cry1Ea | Cry1E | X53985 |
| Cry1Eb | Cry1E(b) | M73253 |
| Cry1Fa | Cry1F | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | Cry1G | X58120 |
| Cry9B | CryIX | X75019 |
| Cry9C | Cry1H | Z37527 |
| Cry10A | Cry1VC | M12662 |
| Cry11A | Cry1VD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34 kDa | M76442 |
| Cry16A | cbm71 | X94146 |
| Cry17A | cbm71 | X99478 |
| Cry18A | CryBPI | X99049 |
| Cry19A | Jeg65 | Y08920 |
| CytIAa | CytA | X03182 |
| CytIAb | CytM | X98793 |
| Cyt2A | CytB | Z14147 |
| Cyt2B | CytB | U52043 |

[a]Adapted from: Crickmore, N, Zeigler, D R, Feitelson, J. et al. 1998. Revision of the Nomenclature for the *Bacillus thuringiensis* Pesticidal Crystal Proteins. *Microbiol. Molec. Biol. Rev.* 62: 807-813.

Protease inhibitors also may provide insect resistance (Johnson et al., Proc Natl Acad Sci USA. 1989 December; 86(24): 9871-9875.), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered to produce synergistic insecticidal activity. Other genes which encode inhibitors of the insect's digestive system, or those that encode enzymes or co factors that facilitate the production of inhibitors, also may be useful. This group may be exemplified by oryzacystatin and amylase inhibitors such as those from wheat and barley.

Amylase inhibitors are found in various plant species and are used to ward off insect predation via inhibition of the digestive amylases of attacking insects. Several amylase inhibitor genes have been isolated from plants and some have been introduced as exogenous nucleic acids, conferring an insect resistant phenotype that is potentially useful ("Plants, Genes, and Crop Biotechnology" by Maarten J. Chrispeels and David E. Sadava (2003) Jones and Bartlett Press).

Genes encoding lectins may confer additional or alternative insecticide properties. Lectins are multivalent carbohydrate binding proteins which have the ability to agglutinate red blood cells from a range of species. Lectins have been identified recently as insecticidal agents with activity against weevils, ECB and rootworm (Murdock et al., Phytochemistry, 29:85-89, 1990, Czapla & Lang, J. Econ. Entomol., 83:2480-2485, 1990). Lectin genes contemplated to be useful include, for example, barley and wheat germ agglutinin (WGA) and rice lectins (Gatehouse et al., J. Sci. Food. Agric., 35:373-380, 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., Nature, 344:458-461, 1990).

Genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP glucosyl transferase, also fall within the scope of the useful exogenous nucleic acids of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti nutritional effects on insects and to reduce the nutritional quality of their diet. Therefore, further embodiments of the invention concern modified plants with enhanced lipoxygenase activity which may be resistant to insect feeding.

*Tripsacum dactyloides* is a species of grass that is resistant to certain insects, including corn root-worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, Proceedings North Central Branch Entomological Society of America, 27:91-95, 1972). It is further anticipated that other cereal, monocot or dicot plant species may have genes encoding proteins that are toxic to insects which would be useful for producing insect resistant plants.

Further genes encoding proteins characterized as having potential insecticidal activity also may be used as exogenous nucleic acids in accordance herewith. Such genes include, for example, the cowpea trypsin inhibitor (CpTI; Hilder et al., Nature, 330:160-163, 1987) which may be used as a rootworm deterrent; genes encoding avermectin (Avermectin and Abamectin., Campbell, W. C., Ed., 1989; Ikeda et al., J. Bacteriol., 169:5615-5621, 1987) which may prove particularly useful as a corn rootworm deterrent; ribosome inactivating protein genes; and even genes that regulate plant structures. Modified plants including anti insect antibody genes and genes that code for enzymes that can convert a non toxic insecticide (pro insecticide) applied to the outside of the plant into an insecticide inside the plant also are contemplated.

Polypeptides that may improve plant tolerance to effects of plant pests or pathogens include proteases, polypeptides involved in anthocyanin biosynthesis, polypeptides involved in cell wall metabolism, including cellulases, glucosidases, pectin methylesterase, pectinase, polygalacturonase, chitinase, chitosanase, and cellulose synthase, and polypeptides involved in biosynthesis of terpenoids or indole for production of bioactive metabolites to provide defense against herbivorous insects. It is also anticipated that combinations of different insect resistance genes on the same mini-chromosome will be particularly useful.

Vegetative Insecticidal Proteins (VIP) are a relatively new class of proteins originally found to be produced in the vegetative growth phase of the bacterium, *Bacillus cereus*, but do have a spectrum of insect lethality similar to the insecticidal genes found in strains of *Bacillus thuriengensis*. Both the vip1a and vip3A genes have been isolated and have demonstrated insect toxicity. It is anticipated that such genes may be used in modified plants to confer insect resistance ("Plants, Genes, and Crop Biotechnology" by Maarten J. Chrispeels and David E. Sadava (2003) Jones and Bartlett Press).

(iii) Environment or Stress Resistance

Improvement of a plant's ability to tolerate various environmental stresses such as, but not limited to, drought, excess moisture, chilling, freezing, high temperature, salt, and oxidative stress, also can be effected through expression of novel genes. It is proposed that benefits may be realized in terms of increased resistance to freezing temperatures through the introduction of an "antifreeze" protein such as that of the Winter Flounder (Cutler et al., J. Plant Physiol., 135:351-354, 1989) or synthetic gene derivatives thereof. Improved chilling tolerance also may be conferred through increased expression of glycerol 3 phosphate acetyltransferase in chloroplasts (Wolter et al., The EMBO J., 4685-4692, 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., Ann Rev. Plant Physiol., 43:83-116, 1992). Such strategies may allow for tolerance to freezing in newly emerged fields as well as extending later maturity higher yielding varieties to earlier relative maturity zones.

It is contemplated that the expression of novel genes that favorably affect plant water content, total water potential, osmotic potential, or turgor will enhance the ability of the plant to tolerate drought. As used herein, the terms "drought resistance" and "drought tolerance" are used to refer to a plant's increased resistance or tolerance to stress induced by a reduction in water availability, as compared to normal circumstances, and the ability of the plant to function and survive in lower water environments. In this aspect of the invention it is proposed, for example, that the expression of genes encoding for the biosynthesis of osmotically active solutes, such as polyol compounds, may impart protection against drought. Within this class are genes encoding for mannitol L phosphate dehydrogenase (Lee and Saier, 1982) and trehalose 6 phosphate synthase (Kaasen et al., J. Bacteriology, 174:889-898, 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., Science, 259:508-510, 1993, Tarczynski et al Proc. Natl. Acad. Sci. USA, 89:1-5, 1993).

Similarly, the efficacy of other metabolites in protecting either enzyme function (e.g., alanopine or propionic acid) or membrane integrity (e.g., alanopine) has been documented (Loomis et al., J. Expt. Zoology, 252:9-15, 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., Biotropica, 24:121-133, 1992), sorbitol, dulcitol (Karsten et al., Botanica Marina, 35:11-19, 1992), glucosyiglycerol (Reed et al., J. Gen. Microbiology, 130:1-4, 1984; Erdmann et al., J. Gen. Microbiology, 138:363-368, 1992), sucrose, stachyose (Koster and Leopold, Plant Physiol., 88:829-832, 1988; Blackman et al., Plant Physiol., 100:225-230, 1992), raffinose (Bernal Lugo and Leopold, Plant Physiol., 98:1207-1210, 1992), proline (Rensburg et al., J. Plant Physiol., 141: 188-194, 1993), glycine betaine, ononitol and pinitol (Vernon and Bohnert, The EMBO J., 11:2077-2085, 1992). Continued canopy growth and increased reproductive fitness during times of stress will be augmented by introduction and expression of genes such as those controlling the osmotically active compounds discussed above and other such compounds. Currently preferred genes which promote the synthesis of an osmotically active polyol compound are genes which encode the enzymes mannitol 1 phosphate dehydrogenase, trehalose 6 phosphate synthase and myoinositol 0 methyltransferase.

It is contemplated that the expression of specific proteins also may increase drought tolerance. Three classes of Late Embryogenic Proteins have been assigned based on structural similarities (see Dure et al., Plant Molecular Biology, 12:475-486, 1989). All three classes of LEAs have been demonstrated in maturing (e.g. desiccating) seeds. Within these 3 types of LEA proteins, the Type II (dehydrin type) have generally been implicated in drought and/or desiccation tolerance in vegetative plant parts (e.g. Mundy and Chua, The EMBO J., 7:2279-2286, 1988; Piatkowski et al., Plant Physiol., 94:1682-1688, 1990; Yamaguchi Shinozaki et al., Plant Cell Physiol., 33:217-224, 1992). Expression of a Type III LEA (HVA 1) in tobacco was found to influence plant height, maturity and drought tolerance (Fitzpatrick, Gen. Engineering News, 22:7, 1993). In rice, expression of the HVA 1 gene influenced tolerance to water deficit and salinity (Xu et al., Plant Physiol., 110:249-257, 1996). Expression of structural genes from any of the three LEA groups may therefore confer drought tolerance. Other types of proteins induced during water stress include thiol proteases, aldolases or transmembrane transporters (Guerrero et al., Plant Molecular Biology, 15:11-26, 1990), which may confer various protective and/or repair type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in plants. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor induced promoter (such as the promoters for the turgor induced genes described in Guerrero et al., Plant Molecular Biology, 15:11-26, 1990 and Shagan et al., Plant Physiol., 101:1397-1398, 1993 which are incorporated herein by reference). Spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, e.g., silks, would be of benefit. In addition it is proposed that expression of genes that minimize kernel abortion during times of stress would increase the amount of grain to be harvested and hence be of value.

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Polypeptides that may improve stress tolerance under a variety of stress conditions include polypeptides involved in gene regulation, such as serine/threonine-protein kinases, MAP kinases, MAP kinase kinases, and MAP kinase kinase kinases; polypeptides that act as receptors for signal transduction and regulation, such as receptor protein kinases; intracellular signaling proteins, such as protein phosphatases, GTP binding proteins, and phospholipid signaling proteins; polypeptides involved in arginine biosynthesis; polypeptides involved in ATP metabolism, including for example ATPase, adenylate transporters, and polypeptides involved in ATP synthesis and transport; polypeptides involved in glycine betaine, jasmonic acid, flavonoid or steroid biosynthesis; and hemoglobin. Enhanced or reduced activity of such polypeptides in modified plants will provide changes in the ability of a plant to respond to a variety of environmental stresses, such as chemical stress, drought stress and pest stress.

Other polypeptides that may improve plant tolerance to cold or freezing temperatures include polypeptides involved in biosynthesis of trehalose or raffinose, polypeptides encoded by cold induced genes, fatty acyl desaturases and other polypeptides involved in glycerolipid or membrane lipid biosynthesis, which find use in modification of membrane fatty acid composition, alternative oxidase, calcium-dependent protein kinases, LEA proteins or uncoupling protein.

Other polypeptides that may improve plant tolerance to heat include polypeptides involved in biosynthesis of trehalose, polypeptides involved in glycerolipid biosynthesis or membrane lipid metabolism (for altering membrane fatty acid composition), heat shock proteins or mitochondrial NDK.

Other polypeptides that may improve tolerance to extreme osmotic conditions include polypeptides involved in proline biosynthesis.

Other polypeptides that may improve plant tolerance to drought conditions include aquaporins, polypeptides involved in biosynthesis of trehalose or wax, LEA proteins or invertase.

(iv) Disease Resistance

It is proposed that increased resistance (or tolerance) to diseases may be realized through introduction of genes into plants, for example, into monocotyledonous plants such as maize. It is possible to produce resistance to diseases caused by viruses, viroids, bacteria, fungi and nematodes. It also is contemplated that control of mycotoxin producing organisms may be realized through expression of introduced genes. Resistance can be effected through suppression of endogenous factors that encourage disease-causing interactions, expression of exogenous factors that are toxic to or otherwise provide protection from pathogens, or expression of factors that enhance the plant's own defense responses.

Resistance to viruses may be produced through expression of novel genes. For example, it has been demonstrated that expression of a viral coat protein in a modified plant can impart resistance to infection of the plant by that virus and perhaps other closely related viruses (Cuozzo et al., Bio/Technology, 6:549-553, 1988, Hemenway et al., The EMBO J., 7:1273-1280, 1988, Abel et al., Science, 232:738-743, 1986). It is contemplated that expression of antisense genes targeted at essential viral functions may also impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Further, it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so called "peptide antibiotics," pathogenesis related (PR) proteins, toxin resistance, or proteins affecting host pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants, for example, monocots such as maize, may be useful in conferring resistance to bacterial disease. These genes are induced following pathogen attack on a host plant and have been divided into at least five classes of proteins (Bol, Linthorst, and Cornelissen, 1990). Included amongst the PR proteins are beta 1, 3 glucanases, chitinases, and osmotin and other proteins that are believed to function in plant resistance to disease organisms. Other genes have been identified that have antifungal properties, e.g., UDA (stinging nettle lectin), or hevein (Broakaert et al., 1989; Barkai Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics.

Polypeptides useful for imparting improved disease responses to plants include polypeptides encoded by cercosporin induced genes, antifungal proteins and proteins encoded by R-genes or SAR genes.

Agronomically important diseases caused by fungal phytopathogens include: glume or leaf blotch, late blight, stalk/head rot, rice blast, leaf blight and spot, corn smut, wilt, sheath blight, stem canker, root rot, blackleg or kernel rot.

Exemplary plant viruses include tobacco or cucumber mosaic virus, ringspot virus, necrosis virus, maize dwarf mosaic virus, etc. Specific fungal, bacterial and viral pathogens of major crops include, but are not limited to:

RICE: rice brown spot fungus (*Cochliobolus miyabeanus*), rice blast fungus—*Magnaporthe grisea* (*Pyricularia grisea*), *Magnaporthe salvinii* (*Sclerotium oryzae*), *Xanthomomas oryzae* pv. *oryzae*, *Xanthomomas oryzae* pv. *oryzicola*, *Rhizoctonia* spp. (including but not limited to *Rhizoctonia solani*, *Rhizoctonia oryzae* and *Rhizoctonia oryzae-sativae*), *Pseudomonas* spp. (including but not limited to *Pseudomonas plantarii*, *Pseudomonas avenae*, *Pseudomonas glumae*, *Pseudomonas fuscovaginae*, *Pseudomonas alboprecipitans*, *Pseudomonas syringae* pv. *panici*, *Pseudomonas syringae* pv. *syringae*, *Pseudomonas syringae* pv. *oryzae* and *Pseudomonas syringae* pv. *aptata*), *Erwinia* spp. (including but not limited to *Erwinia herbicola*, *Erwinia amylovaora*, *Erwinia chrysanthemi* and *Erwinia carotovora*), *Achyla* spp. (including but not limited to *Achyla conspicua* and *Achyia klebsiana*), *Pythium* spp. (including but not limited to *Pythium dissotocum*, *Pythium irregulare*, *Pythium arrhenomanes*, *Pythium myriotylum*, *Pythium catenulatum*, *Pythium graminicola* and *Pythium spinosum*), *Saprolegnia* spp., *Dictyuchus* spp., *Pythiogeton* spp., *Phytophthora* spp., *Alternaria padwickii*, *Cochliobolus miyabeanus*, *Curvularia* spp. (including but not limited to *Curvularia lunata*, *Curvularia affinis*, *Curvularia clavata*, *Curvularia eragrostidis*, *Curvularia fallax*, *Curvularia geniculata*, *Curvularia inaequalis*, *Curvularia intermedia*, *Curvularia oryzae*, *Curvularia oryzae-sativae*, *Curvularia pallescens*, *Curvularia senegalensis*, *Curvularia tuberculata*, *Curvularia uncinata* and *Curvularia verruculosa*), *Sarocladium oryzae*, *Gerlachia oryzae*, *Fusarium* spp. (including but not limited Fusarium graminearum, *Fusarium nivale* and to different pathovars of *Fusarium monoliforme*, including pvs. *fujikuroi* and *zeae*), *Sclerotium rolfsii*, *Phoma exigua*, *Mucor fragilis*, *Trichoderma viride*, *Rhizopus* spp., *Cercospora oryzae*, *Entyloma oryzae*, *Dreschlera gigantean*, *Scierophthora macrospora*, *Mycovellosiella oryzae*, *Phomopsis oryzae-sativae*, *Puccinia graminis*, *Uromyces coronatus*, *Cylindrocladium scopariurn*, *Sarocladium oryzae*, *Gaeumannomyces graminis* pv. *graminis*, *Myrothecium verrucaria*, *Pyrenochaeta oryzae*, *Ustilaginoidea virens*, *Neovossia* spp. (including but not limited to *Neovossia horrida*), *Tilletia* spp., *Balansia oryzae-sativae*, *Phoma* spp. (including but not limited to *Phoma sorghina*, *Phoma insidiosa*, *Phoma glumarum*, *Phoma glumicola* and *Phoma oryzina*), *Nigrospora* spp. (including but not limited to *Nigrospora oryzae*, *Nigrospora sphaerica*, *Nigrospora panici* and *Nigrospora padwickii*), *Epiococcum nigrum*, *Phyllostica* spp., *Wolkia decolorans*, *Monascus purpureus*, *Aspergillus* spp., *Penicillium* spp., *Absidia* spp., *Mucor* spp., *Chaetomium* spp., *Dematium* spp., *Monilia* spp., *Streptomyces* spp., *Syncephalastrum* spp., *Verticillium* spp., *Nematospora coryli*, *Nakataea sigmoidea*, *Cladosporium* spp., *Bipolaris* spp., *Coniothyrium* spp., *Diplodia oryzae*, *Exserophilum rostratum*, *Helococera oryzae*, *Melanomma glumarum*, *Metashaeria* spp., *Mycosphaerella* spp., *Oidium* spp., *Pestalotia* spp., *Phaeoseptoria* spp., *Sphaeropsis* spp., *Trematosphaerelia* spp., rice black-streaked dwarf virus, rice dwarf virus, rice gall dwarf virus, barley yellow dwarf virus, rice grassy stunt virus, rice hoja blanca virus, rice necrosis mosaic virus, rice ragged stunt virus, rice stripe virus, rice stripe necrosis virus, rice transitory yellowing virus, rice tungro bacilliform virus, rice tungro spherical virus, rice yellow mottle virus, rice tarsonemid mite virus, *Echinochloa* hoja blanca virus, *Echinochloa* ragged stunt virus, orange leaf mycoplasma-like organism, yellow dwarf mycoplasma-like organism, *Aphelenchoides besseyi*, *Ditylenchus angustus*, *Hirschmanniella* spp., *Criconemella* spp., *Meloidogyne* spp., *Heterodera* spp., *Pratylenchus* spp., *Hoplolaimus indicus*.

SOYBEANS: *Phytophthora sojae*, *Fusarium solani* f. sp. *Glycines*, *Macrophomina phaseolina*, *Fusarium*, *Pythium*, *Rhizoctonia*, *Phialophora gregata*, *Sclerotinia sclerotiorum*, *Diaporthe phaseolorum* var. *sojae*, *Colletotrichum truncatum*, *Phomopsis longicolla*, *Cercospora kikuchii*, *Diaporthe phaseolonum* var. *meridionalis* (and var. *caulivora*), *Phakopsora pachyrhyzi*, *Fusarium solani*, *Microsphaera diffusa*, *Septoria glycines*, *Cercospora kikuchii*, *Macrophomina phaseolina*, *Sclerotinia scierotiorum*, *Corynespora cassiicola*, *Rhizoctonia solani*, *Cercospora sojina*, *Phytophthora megasperma* fsp. *glycinea*, *Macrophomina phaseolina*, *Fusarium oxysporum*, *Diapothe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Phyllosticta sojicola*, *Alternaria alternata*, *Pseudomonas syringae* p.v. *glycinea*, *Xanthomonas campestris* p.v. *phaseoli*, *Microspaera diffusa*, *Fusarium semitectum*, *Phialophora gregata*, Soybean mosaic virus, *Glomerella glycines*, Tobacco Ring spot virus, Tobacco Streak virus, *Phakopsora pachyrhizi*, *Pythium aphanidermatum*, *Pythium ultimum*, *Pythium dearyanum*, Tomato spotted wilted virus, *Heterodera glycines*, *Fusarium solani*, Soybean cyst and root knot nematodes.

CORN: *Fusarium moniliforme* var. *subglutinans*, *Erwinia stewartii*, *Fusarium moniliforme*, *Gibberella zeae* (*Fusarium Graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*cochliobolus heterostrophus*), *Helminthosporium carbonum* I, II, and III (*Cochliobolus carbonum*), *Exserohilum turcicum* I, II and III, *Helminthosporium pedicellatum*, *Physoderma maydis*, *Phyllosticta maydis*, *Kabatie-maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganese* subsp. *Nebraskense*, *Trichoderma viride*, Maize dwarf Mosaic Virus A and B, Wheat Streak Mosaic Virus, Maize Chlorotic Dwarf Virus, *Claviceps sorghi, Pseudonomas avenae, Erwinia chrysantemi* p.v. *Zea, Erwinia corotovora, Cornstun spiroplasma, Diplodia macrospora, Sclerophthora macrospora, Peronosclerospora sorghi, Peronoscherospora philippinesis, Peronosclerospora maydis, Peronosclerospora sacchari, Spacelotheca reiliana, Physopella zea, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rought Dwarf Virus:

WHEAT: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f. sp. *Tritici, Puccinia graminis* f. sp. *Tritici, Puccinia recondite* f. sp. *tritici, puccinia striiformis, Pyrenophora triticirepentis, Septoria nodorum, Septoria tritici, Spetoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Virus, Wheat Spindle Streak Virus, American Wheat Striate Virus, *Claviceps purpurea, Tilletia tritici, Tilletia laevis, Pstilago tritici, Tilletia indica, Rhizoctonia solani, Pythium arrhenomannes, Pythium gramicola, Pythium aphanidermatum*, High Plains Virus, European Wheat Striate Virus:

CANOLA: *Albugo candida, Alternaria brassicae, Leptosharia maculans, Rhizoctonia solani, Sclerotinia sclerotiorum, Mycospaerella brassiccola, Pythium ultimum, Peronospora parasitica, Fusarium roseum, Fusarium oxysporum, Tilletia foetida, Tilletia caries, Alternaria alternata:*

SUNFLOWER: *Plasmophora halstedii, Scherotinia sclerotiorum*, Aster Yellows, *Septoria helianthi, Phomopsis helianthi, Alternaria helianthi, Alternaria zinniae, Botrytis cinera, Phoma macdonaldii, Macrophomina phaseolina, Erysiphe cichoracearum, Phizopus oryzae, Rhizopus arrhizus, Rhizopus stolonifer, Puccinia helianthi, Verticillium Dahliae, Erwinia carotovorum* p.v. *carotovora, Cephalosporium acremonium, Phytophthora cryptogea, Albugo tragopogonis.*

SORGHUM: *Exserohilum turcicum, Colletotrichum graminicola* (*Glomerella graminicola*), *Cercospora sorghi, Gloeocercospora sorghi, Ascochyta sorghi, Pseudomonas syringae* p.v. *syringae, Xanthomonas campestris* p.v. *holcicola, Pseudomonas andropogonis, Puccinia purpurea, Macrophomina phaseolina, Periconia circinata, Fusarium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari Sporisorium relianum* (*Sphacelotheca reliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium Oxysporum, Pythium arrhenomanes, Pythium graminicola.*

ALFALFA: *Clavibater michiganensis* subsp. *Insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Rhizoctonia solani, Uromyces striatus, Colletotrichum trifolii* race 1 and race 2, *Leptosphaerulina briosiana, Stemphylium botryosum, Stagonospora meliloti, Sclerotinia trifoliorum*, Alfalfa Mosaic Virus, *Verticillium albo-atrum, Xanthomonas campestris* p.v. *alfalfae, Aphanomyces euteiches, Stemphylium herbarum, Stemphylium alfalfae.*

(v) Plant Agronomic Characteristics

Two of the factors determining where crop plants can be grown are the average daily temperature during the growing season and the length of time between frosts. Within the areas where it is possible to grow a particular crop, there are varying limitations on the maximal time it is allowed to grow to maturity and be harvested. For example, a variety to be grown in a particular area is selected for its ability to mature and dry down to harvestable moisture content within the required period of time with maximum possible yield. Therefore, crops of varying maturities are developed for different growing locations. Apart from the need to dry down sufficiently to permit harvest, it is desirable to have maximal drying take place in the field to minimize the amount of energy required for additional drying post harvest. Also, the more readily a product such as grain can dry down, the more time there is available for growth and kernel fill. It is considered that genes that influence maturity and/or dry down can be identified and introduced into plant lines using transformation techniques to create new varieties adapted to different growing locations or the same growing location, but having improved yield to moisture ratio at harvest. Expression of genes that are involved in regulation of plant development may be especially useful.

It is contemplated that genes may be introduced into plants that would improve standability and other plant growth characteristics. Expression of novel genes in plants which confer stronger stalks, improved root systems, or prevent or reduce ear droppage or shattering would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in crop plants may be advantageous. Expression of such a gene may reduce apical dominance, confer semidwarfism on a plant, or increase shade tolerance (U.S. Pat. No. 5,268, 526). Such approaches would allow for increased plant populations in the field.

(vi) Nutrient Utilization

The ability to utilize available nutrients may be a limiting factor in growth of crop plants. It is proposed that it would be possible to alter nutrient uptake, tolerate pH extremes, mobilization through the plant, storage pools, and availability for metabolic activities by the introduction of novel genes. These modifications would allow a plant, for example, maize to more efficiently utilize available nutrients. It is contemplated that an increase in the activity of, for example, an enzyme that is normally present in the plant and involved in nutrient utilization would increase the availability of a nutrient or decrease the availability of an antinutritive factor. An example of such an enzyme would be phytase. It is further contemplated that enhanced nitrogen utilization by a plant is desirable. Expression of a glutamate dehydrogenase gene in plants, e.g., *E. coli* gdhA genes, may lead to increased fixation of nitrogen in organic compounds. Furthermore, expression of gdhA in plants may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

Polypeptides useful for improving nitrogen flow, sensing, uptake, storage and/or transport include those involved in aspartate, glutamine or glutamate biosynthesis, polypeptides involved in aspartate, glutamine or glutamate transport, polypeptides associated with the TOR (Target of Rapamycin) pathway, nitrate transporters, nitrate reductases, amino transferases, ammonium transporters, chlorate transporters or polypeptides involved in tetrapyrrole biosynthesis.

Polypeptides useful for increasing the rate of photosynthesis include phytochrome, ribulose bisphosphate carboxylase-oxygenase, Rubisco activase, photosystem I and II proteins, electron carriers, ATP synthase, NADH dehydrogenase or cytochrome oxidase.

Polypeptides useful for increasing phosphorus uptake, transport or utilization include phosphatases or phosphate transporters.

(vii) Male Sterility

Male sterility is useful in the production of hybrid seed. It is proposed that male sterility may be produced through expression of novel genes. For example, it has been shown that expression of genes that encode proteins, RNAs, or peptides that interfere with development of the male inflorescence and/or gametophyte result in male sterility. Chimeric ribonuclease genes that express in the anthers of transgenic tobacco and oilseed rape have been demonstrated to lead to male sterility (Mariani et al., Nature, 347:737-741, 1990).

A number of mutations were discovered in maize that confer cytoplasmic male sterility. One mutation in particular, referred to as T cytoplasm, also correlates with sensitivity to Southern corn leaf blight. A DNA sequence, designated TURF 13 (Levings, Science, 250:942-947, 1990), was identified that correlates with T cytoplasm. It is proposed that it would be possible through the introduction of TURF 13 via transformation, to separate male sterility from disease sensitivity. As it is necessary to be able to restore male fertility for breeding purposes and for grain production, it is proposed that genes encoding restoration of male fertility also may be introduced.

(viii). Altered Nutritional Content

Genes may be introduced into plants to improve or alter the nutrient quality or content of a particular crop. Introduction of genes that alter the nutrient composition of a crop may greatly enhance the feed or food value. For example, the protein of many grains is suboptimal for feed and food purposes, especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

Polypeptides useful for providing increased seed protein quantity and/or quality include polypeptides involved in the metabolism of amino acids in plants, particularly polypeptides involved in biosynthesis of methionine/cysteine and lysine, amino acid transporters, amino acid efflux carriers, seed storage proteins, proteases, or polypeptides involved in phytic acid metabolism.

The protein composition of a crop may be altered to improve the balance of amino acids in a variety of ways including elevating expression of native proteins, decreasing expression of those with poor composition, changing the composition of native proteins, or introducing genes encoding entirely new proteins possessing superior composition.

The introduction of genes that alter the oil content of a crop plant may also be of value. Increases in oil content may result in increases in metabolizable-energy-content and density of the seeds for use in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, alpha-ketoacyl-ACP synthase, or other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA also may encode sequences that block expression of enzymes involved in fatty acid biosynthesis, altering the proportions of fatty acids present in crops.

Genes may be introduced that enhance the nutritive value of crops, or of foods derived from crops by increasing the level of naturally occurring phytosterols, or by encoding for proteins to enable the synthesis of phytosterols in crops. The phytosterols from these crops can be processed directly into foods, or extracted and used to manufacture food products.

Genes may be introduced that enhance the nutritive value of the starch component of crops, for example by increasing the degree of branching, resulting in improved utilization of the starch in livestock by delaying its metabolism. Additionally, other major constituents of a crop may be altered, including genes that affect a variety of other nutritive, processing, or other quality aspects. For example, pigmentation may be increased or decreased.

Carbohydrate metabolism may be altered, for example by increased sucrose production and/or transport. Polypeptides useful for affecting on carbohydrate metabolism include polypeptides involved in sucrose or starch metabolism, carbon assimilation or carbohydrate transport, including, for example sucrose transporters or glucose/hexose transporters, enzymes involved in glycolysis/gluconeogenesis, the pentose phosphate cycle, or raffinose biosynthesis, or polypeptides involved in glucose signaling, such as SNF1 complex proteins.

Feed or food crops may also possess sub-optimal quantities of vitamins, antioxidants or other nutraceuticals, requiring supplementation to provide adequate nutritive value and ideal health value. Introduction of genes that enhance vitamin biosynthesis may be envisioned including, for example, vitamins A, E, B12, choline, or the like. Mineral content may also be sub-optimal. Thus genes that affect the accumulation or availability of compounds containing phosphorus, sulfur, calcium, manganese, zinc, or iron among others would be valuable.

Numerous other examples of improvements of crops may be used with the invention. The improvements may not necessarily involve grain, but may, for example, improve the value of a crop for silage. Introduction of DNA to accomplish this might include sequences that alter lignin production such as those that result in the "brown midrib" phenotype associated with superior feed value for cattle. Other genes may encode for enzymes that alter the structure of extracellular carbohydrates in the stover, or that facilitate the degradation of the carbohydrates in the non-grain portion of the crop so that it can be efficiently fermented into ethanol or other useful carbohydrates.

It may be desirable to modify the nutritional content of plants by reducing undesirable components such as fats, starches, etc. This may be done, for example, by the use of exogenous nucleic acids that encode enzymes which increase plant use or metabolism of such components so that they are present at lower quantities. Alternatively, it may be done by use of exogenous nucleic acids that reduce expression levels or activity of native plant enzymes that synthesize such components.

Likewise the elimination of certain undesirable traits may improve the food or feed value of the crop. Many undesirable traits must currently be eliminated by special post-harvest processing steps and the degree to which these can be engineered into the plant prior to harvest and processing would provide significant value. Examples of such traits are the elimination of anti-nutritionals such as phytates and phenolic compounds which are commonly found in many crop species. Also, the reduction of fats, carbohydrates and certain phytohormones may be valuable for the food and feed industries as they may allow a more efficient mechanism to meet specific dietary requirements.

In addition to direct improvements in feed or food value, genes also may be introduced which improve the processing of crops and improve the value of the products resulting from the processing. One use of crops is via wetmilling. Thus novel genes that increase the efficiency and reduce the cost of such processing, for example by decreasing steeping time, may also find use. Improving the value of wetmilling products may include altering the quantity or quality of starch, oil, corn gluten meal, or the components of gluten feed. Elevation of starch may be achieved through the identification and elimination of rate limiting steps in starch biosynthesis by expressing increased amounts of enzymes involved in biosynthesis or by decreasing levels of the other components of crops resulting in proportional increases in starch.

Oil is another product of wetmilling, the value of which may be improved by introduction and expression of genes. Oil properties may be altered to improve its performance in the production and use of cooking oil, shortenings, lubricants or other oil-derived products or improvement of its health attributes when used in the food-related applications. Novel fatty acids also may be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids (e.g. fatty acid elongases, desaturases) and the lipids possessing them or by increasing levels of native fatty acids while possibly reducing levels of precursors or breakdown products. Alternatively, DNA sequences may be introduced which slow or block steps in fatty acid biosynthesis resulting in the increase in precursor fatty acid intermediates. Genes that might be added include desaturases, epoxidases, hydratases, dehydratases, or other enzymes that catalyze reactions involving fatty acid intermediates. Representative examples of catalytic steps that might be blocked include the desaturations from stearic to oleic acid or oleic to linolenic acid resulting in the respective accumulations of stearic and oleic acids. Another example is the blockage of elongation steps resulting in the accumulation of C8 to C12 saturated fatty acids.

Polypeptides useful for providing increased seed oil quantity and/or quality include polypeptides involved in fatty acid and glycerolipid biosynthesis, beta-oxidation enzymes, enzymes involved in biosynthesis of nutritional compounds, such as carotenoids and tocopherols, or polypeptides that increase embryo size or number or thickness of aleurone.

Polypeptides involved in production of galactomannans or arabinogalactans are of interest for providing plants having increased and/or modified reserve polysaccharides for use in food, pharmaceutical, cosmetic, paper and paint industries.

Polypeptides involved in modification of flavonoid/isoflavonoid metabolism in plants include cinnamate-4-hydroxylase, chalcone synthase or flavones synthase. Enhanced or reduced activity of such polypeptides in modified plants will provide changes in the quantity and/or speed of flavonoid metabolism in plants and may improve disease resistance by enhancing synthesis of protective secondary metabolites or improving signaling pathways governing disease resistance.

Polypeptides involved in lignin biosynthesis are of interest for increasing plants' resistance to lodging and for increasing the usefulness of plant materials as befouls.

(ix) Production or Assimilation of Chemicals or Biological

It may further be considered that a modified plant prepared in accordance with the invention may be used for the production or manufacturing of useful biological compounds that were either not produced at all, or not produced at the same level, in the corn plant previously. Alternatively, plants produced in accordance with the invention may be made to metabolize or absorb and concentrate certain compounds, such as hazardous wastes, thereby allowing bioremediation of these compounds.

The novel plants producing these compounds are made possible by the introduction and expression of one or potentially many genes with the constructs provided by the invention. The vast array of possibilities include but are not limited to any biological compound which is presently produced by any organism such as proteins, nucleic acids, primary and intermediary metabolites, carbohydrate polymers, enzymes for uses in bioremediation, enzymes for modifying pathways that produce secondary plant metabolites such as falconoid or vitamins, enzymes that could produce pharmaceuticals, and for introducing enzymes that could produce compounds of interest to the manufacturing industry such as specialty chemicals and plastics.

The compounds may be produced by the plant, extracted upon harvest and/or processing, and used for any presently recognized useful purpose such as pharmaceuticals, fragrances, and industrial enzymes to name a few.

(x) Other Characteristics

Cell cycle modification: Polypeptides encoding cell cycle enzymes and regulators of the cell cycle pathway are useful for manipulating growth rate in plants to provide early vigor and accelerated maturation. Improvements in quality traits, such as seed oil content, may also be obtained by expression of cell cycle enzymes and cell cycle regulators. Polypeptides of interest for modification of cell cycle pathway include cycling and EIF5alpha pathway proteins, polypeptides involved in polyamine metabolism, polypeptides which act as regulators of the cell cycle pathway, including cyclin-dependent kinases (CDKs), CDK-activating kinases, cell cycle-dependent phosphatases, CDK-inhibitors, Rb and Rb-binding proteins, or transcription factors that activate genes involved in cell proliferation and division, such as the E2F family of transcription factors, proteins involved in degradation of cyclins, such as cullins, and plant homologs of tumor suppressor polypeptides.

Plant growth regulators: Polypeptides involved in production of substances that regulate the growth of various plant tissues are of interest in the present invention and may be used to provide modified plants having altered morphologies and improved plant growth and development profiles leading to improvements in yield and stress response. Of particular interest are polypeptides involved in the biosynthesis, or degradation of plant growth hormones, such as gibberellins, brassinosteroids, cytokinins, auxins, ethylene or abscisic acid, and other proteins involved in the activity, uptake and/or transport of such polypeptides, including for example, cytokinin oxidase, cytokinin/purine permeases, F-box proteins, G-proteins or phytosulfokines.

Transcription factors in plants: Transcription factors play a key role in plant growth and development by controlling the expression of one or more genes in temporal, spatial and physiological specific patterns. Enhanced or reduced activity of such polypeptides in modified plants will provide significant changes in gene transcription patterns and provide a variety of beneficial effects in plant growth, development and response to environmental conditions. Transcription factors of interest include, but are not limited to myb transcription factors, including helix-turn-helix proteins, homeodomain transcription factors, leucine zipper transcription factors, MADS transcription factors, transcription factors having AP2 domains, zinc finger transcription factors, CCAAT binding transcription factors, ethylene responsive transcription factors, transcription initiation factors or UV damaged DNA binding proteins.

Homologous recombination: Increasing the rate of homologous recombination in plants is useful for accelerating the introgression of transgenes into breeding varieties by backcrossing, and to enhance the conventional breeding process by allowing rare recombinants between closely linked genes in phase repulsion to be identified more easily. Polypeptides useful for expression in plants to provide increased homologous recombination include polypeptides involved in mitosis and/or meiosis, DNA replication, nucleic acid metabolism, DNA repair pathways or homologous recombination pathways including for example, recombinases, nucleases, proteins binding to DNA double-strand breaks, single-strand DNA binding proteins, strand-exchange proteins, resolvases, ligases, helicases and polypeptide members of the RAD52 epistasis group.

Non-Protein-Expressing Exogenous Nucleic Acids

Plants with decreased expression of a gene of interest can also be achieved, for example, by expression of antisense nucleic acids, dsRNA or RNAi, catalytic RNA such as ribozymes, sense expression constructs that exhibit cosuppression effects, aptamers or zinc finger proteins.

Antisense RNA reduces production of the polypeptide product of the target messenger RNA, for example by blocking translation through formation of RNA:RNA duplexes or by inducing degradation of the target mRNA. Antisense approaches are a way of preventing or reducing gene function by targeting the genetic material as disclosed in U.S. Pat. Nos. 4,801,540; 5,107,065; 5,759,829; 5,910,444; 6,184,439; and 6,198,026, all of which are incorporated herein by reference. In one approach, an antisense gene sequence is introduced that is transcribed into antisense RNA that is complementary to the target mRNA. For example, part or all of the normal gene sequences are placed under a promoter in inverted orientation so that the 'wrong' or complementary strand is transcribed into a non-protein expressing antisense RNA. The promoter used for the antisense gene may influence the level, timing, tissue, specificity, or inducibility of the antisense inhibition.

Autonomous mini-chromosomes may contain exogenous DNA bounded by recombination sites, for example lox-P sites, that can be recognized by a recombinase, e.g. Cre, and removed from the mini-chromosome. In cases where there is a homologous recombination site or sites in the host genomic DNA, the exogenous DNA excised the mini-chromosome may be integrated into the genome at one of the specific recombination-sites and the DNA bounded by the recombination sites-will become integrated into the host DNA. The use of a mini-chromosome as a platform for DNA excision or for launching such DNA integration into the host genome may include in vivo induction of the expression of a recombinase encoded in the genomic DNA of a transgenic host, or in a mini-chromosome or other episome.

RNAi gene suppression in plants by transcription of a dsRNA is described in U.S. Pat. No. 6,506,559, U.S. patent application Publication No. 2002/0168707, WO 98/53083, WO 99/53050 and WO 99/61631, all of which are incorporated herein by reference. The double-stranded RNA or RNAi constructs can trigger the sequence-specific degradation of the target messenger RNA. Suppression of a gene by RNAi can be achieved using a recombinant DNA construct having a promoter operably linked to a DNA element comprising a sense and anti-sense element of a segment of genomic DNA of the gene, e.g., a segment of at least about 23 nucleotides, more preferably about 50 to 200 nucleotides where the sense and anti-sense DNA components can be directly linked or joined by an intron or artificial DNA segment that can form a loop when the transcribed RNA hybridizes to form a hairpin structure.

Catalytic RNA molecules or ribozymes can also be used to inhibit expression of the target gene or genes or facilitate molecular reactions. Ribozymes are targeted to a given sequence by hybridization of sequences within the ribozyme to the target mRNA. Two stretches of homology are required for this targeting, and these stretches of homologous sequences flank the catalytic ribozyme structure. It is possible to design ribozymes that specifically pair with virtually any target mRNA and cleave the target mRNA at a specific location, thereby inactivating it. A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include Tobacco Ringspot Virus (Prody et al., *Science*, 231:1577-1580, 1986), Avocado Sunblotch Viroid (Palukaitis et al., *Virology*, 99:145-151, 1979; Symons, *Nucl. Acids Res.*, 9:6527-6537, 1981), and Lucerne Transient Streak Virus (Forster and Symons, *Cell*, 49:211-220, 1987), and the satellite RNAs from velvet tobacco mottle virus, *Solanum nodiflorum* mottle virus and subterranean clover mottle virus. The design and use of target RNA-specific ribozymes is described in Haseloff, et al., Nature 334:585-591 (1988). Several different ribozyme motifs have been described with RNA cleavage activity (Symons, *Annu. Rev. Biochem.*, 61:641-671, 1992). Other suitable ribozymes include sequences from RNase P with RNA cleavage activity (Yuan et al., *Proc. Natl. Acad. Sci. USA*, 89:8006-8010, 1992; Yuan and Altman, *Science*, 263:1269-1273, 1994; U.S. Pat. Nos. 5,168,053 and 5,624,824), hairpin ribozyme structures (Berzal-Herranz et al., *Genes and Devel.*, 6:129-134, 1992; Chowrira et al., *J. Biol. Chem.*, 269:25856-25864, 1994) and Hepatitis Delta virus based ribozymes (U.S. Pat. No. 5,625,047). The general design and optimization of ribozyme directed RNA cleavage activity has been discussed in detail (Haseloff and Gerlach, 1988, Nature. 1988 Aug. 18; 334 (6183):585-91, Chowrira et al., J. Biol. Chem., 269:25856-25864, 1994).

Another method of reducing protein expression utilizes the phenomenon of cosuppression or gene silencing (for example, U.S. Pat. Nos. 6,063,947; 5,686,649; or 5,283,184; each of which is incorporated herein by reference). Cosuppression of an endogenous gene using a full-length cDNA sequence as well as a partial cDNA sequence are known (for example, Napoli et al., Plant Cell 2:279-289 [1990]; van der Krol et al., Plant Cell 2:291-299 [1990]; Smith et al., Mol. Gen. Genetics 224:477-481 [1990]). The phenomenon of cosuppression has also been used to inhibit plant target genes in a tissue-specific manner.

In some embodiments, nucleic acids from one species of plant are expressed in another species of plant to effect cosuppression of a homologous gene. The introduced sequence generally will be substantially identical to the endogenous sequence intended to be repressed, for example, about 65%, 80%, 85%, 90%, or preferably 95% or greater identical. Higher identity may result in a more effective repression of expression of the endogenous sequence. A higher identity in a shorter than full length sequence compensates for a longer, less identical sequence. Furthermore, the introduced sequence need not have the same intron or exon pattern, and identity of non-coding segments will be equally effective. Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence.

Yet another method of reducing protein activity is by expressing nucleic acid ligands, so-called aptamers, which specifically bind to the protein. Aptamers may be obtained by the SELEX (Systematic Evolution of Ligands by EXponential Enrichment) method. See U.S. Pat. No. 5,270,163, incorporated herein by reference. In the SELEX method, a candidate mixture of single stranded nucleic acids having regions of randomized sequence is contacted with the protein and those nucleic acids having an increased affinity to the target are selected and amplified. After several iterations a nucleic acid with optimal affinity to the polypeptide is obtained and is used for expression in modified plants.

A zinc finger protein that binds a polypeptide-encoding sequence or its regulatory region is also used to alter expression of the nucleotide sequence. Transcription of the nucleotide sequence may be reduced or increased. Zinc finger proteins are, for example, described in Beerli et al. (1998) PNAS 95:14628-14633., or in WO 95/19431, WO 98/54311, or WO 96/06166, all incorporated herein by reference.

Other examples of non-protein expressing sequences specifically envisioned for use with the invention include tRNA sequences, for example, to alter codon usage, and rRNA variants, for example, which may confer resistance to various agents such as antibiotics.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Exemplary Plant Promoters, Regulatory Sequences and Targeting Sequences

Exemplary classes of plant promoters are described below.

Constitutive Expression promoters: Exemplary constitutive expression promoters include the ubiquitin promoter (e.g., sunflower—Binet et al. Plant Science 79: 87-94 (1991); maize—Christensen et al. Plant Molec. Biol. 12: 619-632 (1989); and *Arabidopsis*—Callis et al., J. Biol. Chem. 265: 12486-12493 (1990) and Norris et al., Plant Mol. Biol. 21: 895-906 (1993)); the CaMV 35S promoter (U.S. Pat. Nos. 5,858,742 and 5,322,938); or the actin promoter (e.g., rice— U.S. Pat. No. 5,641,876; McElroy et al. Plant Cell 2: 163-171 (1990), McElroy et al. Mol. Gen. Genet. 231: 150-160 (1991), and Chibbar et al. Plant Cell Rep. 12: 506-509 (1993)).

Inducible Expression promoters: Exemplary inducible expression promoters include the chemically regulatable tobacco PR-1 promoter (e.g., tobacco—U.S. Pat. No. 5,614, 395; *Arabidopsis*—Lebel et al., Plant J. 16: 223-233 (1998); maize—U.S. Pat. No. 6,429,362). Various chemical regulators may be employed to induce expression, including the benzothiadiazole, isonicotinic acid, and salicylic acid compounds disclosed in U.S. Pat. Nos. 5,523,311 and 5,614,395. Other promoters inducible by certain alcohols or ketones, such as ethanol, include, for example, the alcA gene promoter from *Aspergillus nidulans* (Caddick et al. (1998) Nat. Biotechnol 16:177-180). A glucocorticoid-mediated induction system is described in Aoyama and Chua (1997) The Plant Journal 11: 605-612 wherein gene expression is induced by application of a glucocorticoid, for example a dexamethasone. Another class of useful promoters are water-deficit-inducible promoters, e.g. promoters which are derived from the 5' regulatory region of genes identified as a heat shock protein 17.5 gene (HSP 17.5), an HVA22 gene (HVA22), and a cinnamic acid 4-hydroxylase (CA4H) gene (CA4H) of *Zea maize*. Another water-deficit-inducible promoter is derived from the rab-17 promoter as disclosed by Vilardell et al., Plant Molecular Biology, 17(5):985-993, 1990. See also U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, and U.S. Pat. No. 6,175,060 which discloses phosphorus deficiency inducible promoters.

As another example, numerous wound-inducible promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), Warner et al. Plant J. 3: 191-201 (1993)). Logemann describe 5' upstream sequences of the potato wun1 gene. Xu et al. show that a wound-inducible promoter from the dicotyledon potato (pin2) is active in the monocotyledon rice. Rohrmeier & Lehle describe maize Wip1 cDNA which is wound induced and which can be used to isolate the cognate promoter. Firek et al. and Warner et al. have described a wound-induced gene from the monocotyledon *Asparagus officinalis*, which is expressed at local wound and pathogen invasion sites.

Tissue-Specific Promoters: Exemplary promoters that express genes only in certain tissues are useful according to the present invention. For example root specific expression may be attained using the promoter of the maize metallothionein-like (MTL) gene described by de Framond (FEBS 290: 103-106 (1991)) and also in U.S. Pat. No. 5,466,785, incorporated herein by reference. U.S. Pat. No. 5,837,848 discloses a root specific promoter. Another exemplary promoter confers pith-preferred expression (see Int'l. Pub. No. WO 93/07278, herein incorporated by reference, which describes the maize trpA gene and promoter that is preferentially expressed in pith cells). Leaf-specific expression may be attained, for example, by using the promoter for a maize gene encoding phosphoenol carboxylase (PEPC) (see Hudspeth & Grula, Plant Molec Biol 12: 579-589 (1989)). Pollen-specific expression may be conferred by the promoter for the maize calcium-dependent protein kinase (CDPK) gene which is expressed in pollen cells (WO 93/07278). U.S. Pat. Appl. Pub. No. 20040016025 describes tissue-specific promoters. Pollen-specific expression may be conferred by the tomato LAT52 pollen-specific promoter (Bate et. al., Plan mol Biol. 1998 July; 37(5):859-69).

See also U.S. Pat. No. 6,437,217 which discloses a root-specific maize RS81 promoter, U.S. Pat. No. 6,426,446 which discloses a root specific maize RS324 promoter, U.S. Pat. No. 6,232,526 which discloses a constitutive maize A3 promoter, U.S. Pat. No. 6,177,611 which discloses constitutive maize promoters, U.S. Pat. No. 6,433,252 which discloses a maize L3 oleosin promoter that are aleurone and seed coat-specific promoters, U.S. Pat. No. 6,429,357 which discloses a constitutive rice actin 2 promoter and intron, U.S. patent application Pub. No. 20040216189 which discloses an inducible constitutive leaf specific maize chloroplast aldolase promoter.

Optionally a plant transcriptional terminator can be used in place of the plant-expressed gene native transcriptional terminator. Exemplary transcriptional terminators are those that are known to function in plants and include the CaMV 35S terminator, the tml terminator, the nopaline synthase terminator and the pea rbcS E9 terminator. These can be used in both monocotyledons and dicotyledons.

Various intron sequences have been shown to enhance expression, particularly in monocotyledonous cells. For example, the introns of the maize Adh1 gene have been found to significantly enhance expression. Intron 1 was found to be particularly effective and enhanced expression in fusion constructs with the chloramphenicol acetyltransferase gene (Callis et al., Genes Develop. 1: 1183-1200 (1987)). The intron from the maize bronze1 gene also enhances expression. Intron sequences have been routinely incorporated into plant transformation vectors, typically within the non-translated leader. U.S. Patent Application Publication 2002/0192813 discloses 5', 3' and intron elements useful in the design of effective plant expression vectors.

A number of non-translated leader sequences derived from viruses are also known to enhance expression, and these are particularly effective in dicotyledonous cells. Specifically, leader sequences from Tobacco Mosaic Virus (TMV, the "omega-sequence"), Maize Chlorotic Mottle Virus (MCMV), and Alfalfa Mosaic Virus (AMV) have been shown to be effective in enhancing expression (e.g: Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154:9-20); human immunoglobulin heavy-chain binding protein (BiP) leader, (Macejak, D. G., and Sarnow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie et al., Molecular Biology of RNA, pages 237-256 (1989); or Maize Chlorotic Mottle Virus leader (MCMV) (Lommel et al., Virology 81:382-385 (1991). See also, Della-Cioppa et al., Plant Physiology 84:965-968 (1987).

A minimal promoter may also be incorporated. Such a promoter has low background activity in plants when there is no transactivator present or when enhancer or response element binding sites are absent. One exemplary minimal promoter is the Bz1 minimal promoter, which is obtained from the bronze1 gene of maize. Roth et al., Plant Cell 3: 317 (1991). A minimal promoter may also be created by use of a synthetic TATA element. The TATA element allows recognition of the promoter by RNA polymerase factors and confers a basal level of gene expression in the absence of activation (see generally, Mukumoto (1993) Plant Mol Biol 23: 995-1003; Green (2000) Trends Biochem Sci 25: 59-63).

Sequences controlling the targeting of gene products also may be included. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein or many other proteins which are known to be chloroplast localized. Other gene products are localized to other organelles such as the mitochondrion and the peroxisome (e.g. Unger et al. Plant Molec. Biol. 13: 411-418 (1989)). Examples of sequences that target to such organelles are the nuclear-encoded ATPases or specific aspartate amino transferase isoforms for mitochondria. Targeting cellular protein bodies has been described by Rogers et al. (Proc. Natl. Acad. Sci. USA 82: 6512-6516 (1985)). In addition, amino terminal and carboxy-terminal sequences are responsible for targeting to the ER, the apoplast, and extracellular secretion from aleurone cells (Koehler & Ho, Plant Cell 2: 769-783 (1990)). Additionally, amino terminal sequences in conjunction with carboxy terminal sequences are responsible for vacuolar targeting of gene products (Shinshi et al. Plant Molec. Biol. 14: 357-368 (1990)).

Another possible element which may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the plant genome (Stief et al., Nature, 341:343, 1989; Phi-Van et al., Mol. Cell. Biol., 10:2302-2307.1990).

Use of Non-Plant Promoter Regions Isolated from *Drosophila* Melanogaster and *Saccharomyces Cerevisiae* to Express Genes in Plants The promoter in the mini-chromosome of the present invention can be derived from plant or non-plant species. In a preferred embodiment, the nucleotide sequence of the promoter is derived from non-plant species for the expression of genes in plant cells, including but not limited to dicotyledon plant cells such as tobacco, tomato, potato, soybean, canola, sunflower, alfalfa, cotton and *Arabidopsis*, or monocotyledonous plant cell, such as wheat, maize, rye, rice, turf grass, oat, barley, sorghum, millet, and sugarcane. In one embodiment, the non-plant promoters are constitutive or inducible promoters derived from insect, e.g., *Drosophila melanogaster* or yeast, e.g., *Saccharomyces cerevisiae*. Table 2 lists the promoters from *Drosophila melanogaster* and *Saccharomyces cerevisiae* that are used to derive the examples of non-plant promoters in the present invention. Promoters derived from any animal, protist, or fungi are also contemplated. SEQ ID NOS: 4-23 are examples of promoter sequences derived from *Drosophila melanogaster* or *Saccharomyces cerevisiae*. These non-plant promoters can be operably-linked to nucleic acid sequences encoding polypeptides or non-protein-expressing sequences including, but not limited to, antisense RNA and ribozymes, to form nucleic acid constructs, vectors, and host cells (prokaryotic or eukaryotic), comprising the promoters.

TABLE 2

*Drosophila melanogaster* Promoters (adapted from the *Drosophila* FlyBase, referenced in Grumbling, G. and Strelets, V. FlyBase: anatomical data, images and queries. *Nucl. Acids Rsrch*. 34: D484-8.

| Seq Id No. | Symbol | Flybase ID | Standard promoter gene name | Gene Product | Chromosome |
|---|---|---|---|---|---|
| 4 | gd | FBgn0004654 | Phosphogluconate dehydrogenase | 6-phosphogluconate dehydrogenase | X |
| 5 | rim | FBgn0015946 | grim | grim-P138 | 3 |
| 5 | ro | FBgn0003961 | Urate oxidase | Uro-P1 | 2 |
| 7 | na | FBgn0003448 | snail | sna-P1 | 2 |
| 8 | h3 | FBgn0003249 | Rhodopsin 3 | Rh3 | 3 |
| 9 | sp-1 γ | FBgn0002564 | Larval serum protein 1 γ | Lsp1γ-PI | 3 |

*Saccharomyces cerevisiae* Promoters (adapted from information available from the *Saccharomyces* Genome Database, referenced in Dwight S S, Balakrishnan R, Christie K R, et al. 2004. *Saccharomyces* genome database: underlying principles and organisation. *Brief Bioinform*. 5: 9-22).

| Seq Id No. | Symbol | Systematic Name | Standard promoter gene name | Gene Product | Chromosome |
|---|---|---|---|---|---|
| 10 | ef-2 | YBR118W | TEF2 (Translation elongation factor promoter) | Translation elongation factor EF-1 alpha | 2 |
| 11 | eu-1 | YGL009C | LEU1 (LEUcine biosynthesis) | isopropylmalate isomerase | 7 |
| 12 | et16 | YPR167C | METhionine requiring | 3'phosphoadenylyl-sulfate reductase | 16 |
| 13 | eu-2 | YCL018W | LEU2 (leucine biosynthesis) | beta-IPM (isopropylmalate) dehydrogenase | 3 |
| 14 | is-4 | YCL030C | HIS4 (HIStidine requiring) | histidinol dehydrogenase | 3 |
| 15 | et-2 | YNL277W | MET2 (methionine requiring) | L-homoserine-O-acetyltransferase | 14 |
| 16 | te-3 | YKL178C | STE3 (alias DAF2 Sterile) | a-factor receptor | 11 |
| 17 | rg-1 | YOL058W | ARG1 (alias ARG10 ARGinine requiring) | arginosuccinate synthetase | 15 |
| 18 | gk-1 | YCR012W | PGK1 (phosphoglycerate kinase) | phosphoglycerate kinase | 3 |
| 19 | PD-1 | YDL022W | GPD1 (alias DAR1/HOR1/OSG1/OSR5: glycerol-3-phosphate dehydrogenase activity | glycerol-3-phosphate dehydrogenase | 4 |
| 20 | DH1 | YOL086C | ADH1 (alias ADC1) | alcohol dehydrogenase | 15 |
| 21 | PD-2 | YOL059W | GPD2 (alias GPD3: glycerol-3-phosphate dehydrogenase activity | glycerol-3-phosphate dehydrogenase | 15 |
| 22 | rg-4 | YHR018C | ARGinine requiring | argininosuccinate lyase | 8 |
| 23 | at-1 | YAR035W | YAT-1 (carnitine acetyltransferase) | carnitine acetyltransferase | 1 |

The present invention relates to methods for producing a polypeptide, comprising cultivating plant material for the production of the polypeptide at any level, wherein the plant host cells comprises a first nucleic acid sequence encoding the polypeptide operably linked to a second nucleic acid sequence comprising a heterologous promoter foreign to the nucleic acid sequence, wherein the promoter comprises a sequence selected from the group consisting of SEQ ID NOS:4 to 23 or subsequences thereof; and mutant, hybrid, or tandem promoters thereof that retain promoter activity.

The present invention also relates to methods for producing non-protein expressed sequences, comprising cultivating plant material for the production of the non-protein expressed sequence, wherein the plant host cell comprises a first nucleic acid sequence encoding the non-protein expressed sequences operably linked to a second nucleic acid sequence comprising a heterologous promoter foreign to the nucleic acid sequence, wherein the promoter comprises a sequence selected from the group consisting of SEQ ID NOS:4 to 23 or subsequences thereof; and mutant, hybrid, or tandem promoters thereof.

The present invention also relates to isolated promoter sequences and to constructs, vectors, or plant host cells comprising one or more of the promoters operably linked to a nucleic acid sequence encoding a polypeptide or non-protein expressing sequence.

In the methods of the present invention, the promoter may also be a mutant of the promoters having a substitution, deletion, and/or insertion of one or more nucleotides in the nucleic acid sequence of SEQ ID NOS:4 to 23.

The present invention also relates to methods for obtaining derivative promoters of SEQ ID NOS:4 to 23.

The techniques used to isolate or clone a nucleic acid sequence comprising a promoter of interest are known in the art and include isolation from genomic DNA. The cloning procedures may involve excision or amplification, for example by polymerase chain reaction, and isolation of a desired nucleic acid fragment comprising the nucleic acid sequence encoding the promoter, insertion of the fragment into a vector molecule, and incorporation of the recombinant vector into the plant cell.

Definitions

The term "adchromosomal" plant or plant part, as used herein means a plant or plant part that contains functional, stable and autonomous mini-chromosomes. Adchromosomal plants or plant parts may be chimeric or not chimeric (chimeric meaning that mini-chromosomes are only in certain portions of the plant, and are not uniformly distributed throughout the plant). An adchromosomal plant cell contains at least one functional, stable and autonomous mini-chromosome.

The term "autonomous" as used herein means that when delivered to plant cells, at least some mini-chromosomes are transmitted through mitotic division to daughter cells and are episomal in the daughter plant cells, i.e. are not chromosomally integrated in the daughter plant cells. Daughter plant cells that contain autonomous mini-chromosomes can be selected for further replication using, for example, selectable or screenable markers. During the introduction into a cell of a mini-chromosome, or during subsequent stages of the cell cycle, there may be chromosomal integration of some portion or all of the DNA derived from a mini-chromosome in some cells. The mini-chromosome is still characterized as autonomous despite the occurrence of such events if a plant may be regenerated that contains episomal descendants of the mini-chromosome distributed throughout its parts, or if gametes or progeny can be derived from the plant that contain episomal descendants of the mini-chromosome distributed through its parts.

As used herein, a "centromere" is any DNA sequence that confers an ability to segregate to daughter cells through cell division. In one context, this sequence may produce a transmission efficiency to daughter cells ranging from about 1% to about 100%, including to about 5%, 10%, 20%, 30%, 40%, 50%, 60%, 70%, 80%, 90% or about 95% of daughter cells. Variations in such a transmission efficiency may find important applications within the scope of the invention; for example, mini-chromosomes carrying centromeres that confer 100% stability could be maintained in all daughter cells without selection, while those that confer 1% stability could be temporarily introduced into a transgenic organism, but be eliminated when desired. In particular embodiments of the invention, the centromere may confer stable transmission to daughter cells of a nucleic acid sequence, including a recombinant construct comprising the centromere, through mitotic or meiotic divisions, including through both meiotic and meiotic divisions. A plant centromere is not necessarily derived from plants, but has the ability to promote DNA transmission to daughter plant cells.

As used herein, the term "circular permutations" refer to variants of a sequence that begin at base n within the sequence, proceed to the end of the sequence, resume with base number one of the sequence, and proceed to base n–1. For this analysis, n may be any number less than or equal to the length of the sequence. For example, circular permutations of the sequence ABCD are: ABCD, BCDA, CDAB, and DABC.

The term "co-delivery" as used herein refers to the delivery of two nucleic acid segments to a cell. In co-delivery of plant growth inducing genes and mini-chromosomes, the two nucleic acid segments are delivered simultaneously using the same delivery method. Alternatively, the nucleic acid segment containing the growth inducing gene, optionally as part of an episomal vector, such as a viral vector or a plasmid vector, may be delivered to the plant cells before or after delivery of the mini-chromosome, and the mini-chromosome may carry an exogenous nucleic acid that induces expression of the earlier-delivered growth inducing gene. In this embodiment, the two nucleic acid segments may be delivered separately at different times provided the encoded growth inducing factors are functional during the appropriate time period.

The term "coding sequence" is defined herein as a nucleic acid sequence that is transcribed into mRNA which is translated into a polypeptide when placed under the control of promoter sequences. The boundaries of the coding sequence are generally determined by the ATG start codon located at the start of the open reading frame, near the 5' end of the mRNA, and TAG, TGA or TAA stop codons at the end of the coding sequence, near the 3' end f the mRNA, and in some cases, a transcription terminator sequence located just downstream of the open reading frame at the 3' end of the mRNA. A coding sequence can include, but is not limited to, genomic DNA, cDNA, semisynthetic, synthetic, or recombinant nucleic acid sequences.

As used herein the term "consensus" refers to a nucleic acid sequence derived by comparing two or more related sequences. A consensus sequence defines both the conserved and variable sites between the sequences being compared. Any one of the sequences used to derive the consensus or any permutation defined by the consensus may be useful in construction of mini-chromosomes.

The term "exogenous" when used in reference to a nucleic acid, for example, is intended to refer to any nucleic acid that has been introduced into a recipient cell, regardless of whether the same or similar nucleic acid is already present in such a cell. Thus, as an example, "exogenous DNA" can include an additional copy of DNA that is already present in the plant cell, DNA from another plant, DNA from a different organism, or a DNA generated externally, such as a DNA sequence containing an antisense message of a gene, or a DNA sequence encoding a synthetic or modified version of a gene. An "exogenous gene" can be a gene not normally found in the host genome in an identical context, or an extra copy of a host gene. The gene may be isolated from a different species than that of the host genome, or alternatively, isolated from the host genome but operably linked to one or more regulatory regions which differ from those found in the unaltered, native gene.

The term "functional" as used herein to describe a mini-chromosome means that when an exogenous nucleic acid is present within the mini-chromosome the exogenous nucleic acid can function in a detectable manner when the mini-chromosome is within a plant cell; exemplary functions of the exogenous nucleic acid include transcription of the exogenous nucleic acid, expression of the exogenous nucleic acid, regulatory control of expression of other exogenous nucleic acids, recognition by a restriction enzyme or other endonuclease, ribozyme or recombinase; providing a substrate for DNA methylation, DNA glycolation or other DNA chemical modification; binding to proteins such as histones, helix-loop-helix proteins, zinc binding proteins, leucine zipper proteins, MADS box proteins, topoisomerases, helicases, transposases, TATA box binding proteins, viral protein, reverse transcriptases, or cohesins; providing an integration site for homologous recombination; providing an integration site for a transposon, T-DNA or retrovirus; providing a substrate for RNAi synthesis; priming of DNA replication; aptamer binding; or kinetochore binding. if multiple exogenous nucleic acids are present within the mini-chromosome, the function of one or preferably more of the exogenous nucleic acids can be detected under suitable conditions permitting function thereof.

As used herein, a "library" is a pool of cloned DNA fragments that represents some or all DNA sequences collected, prepared or purified from a specific source. Each library may contain the DNA of a given organism inserted as discrete restriction enzyme generated fragments or as randomly sheared fragments into many thousands of plasmid vectors. For purposes of the present invention, *E. coli*, yeast, and *Salmonella* plasmids are particularly useful for propagating the genome inserts from other organisms. In principle, any gene or sequence present in the starting DNA preparation can be isolated by screening the library with a specific hybridization probe (see, for example, Young et al., In: Eukaryotic Genetic Systems ICN-UCLA Symposia on Molecular and Cellular Biology, VII, 315-331, 1977).

As used herein, the term "linker" refers to a DNA molecule, generally up to 50 or 60 nucleotides long and composed of two or more complementary oligonucleotides that have been synthesized chemically, or excised or amplified from existing plasmids or vectors. In a preferred embodiment, this fragment contains one, or preferably more than one, restriction enzyme site for a blunt cutting enzyme and/or a staggered cutting enzyme, such as BamHI. One end of the linker is designed to be ligatable to one end of a linear DNA molecule and the other end is designed to be ligatable to the other end of the linear molecule, or both ends may be designed to be ligatable to both ends of the linear DNA molecule.

As used herein, a "mini-chromosome" is a recombinant DNA construct including a centromere and capable of transmission to daughter cells. A mini-chromosome may remain separate from the host genome (as episomes) or may integrate into host chromosomes. The stability of this construct through cell division could range between from about 1% to about 100%, including about 5%, 10%, 20%, 30%, 40%, 50%, 60%, 70%, 80%, 90% and about 95%. The mini-chromosome construct may be a circular or linear molecule. It may include elements such as one or more telomeres, origin of replication sequences, stuffer sequences, buffer sequences, chromatin packaging sequences, linkers and genes. The number of such sequences included is only limited by the physical size limitations of the construct itself. It could contain DNA derived from a natural centromere, although it may be preferable to limit the amount of DNA to the minimal amount required to obtain a transmission efficiency in the range of 1-100%. The mini-chromosome could also contain a synthetic centromere composed of tandem arrays of repeats of any sequence, either derived from a natural centromere, or of synthetic DNA. The mini-chromosome could also contain DNA derived from multiple natural centromeres. The mini-chromosome may be inherited through mitosis or meiosis, or through both meiosis and mitosis. As used herein, the term mini-chromosome specifically encompasses and includes the terms "plant artificial chromosome" or "PLAC," or engineered chromosomes or microchromosomes and all teachings relevant to a PLAC or plant artificial chromosome specifically apply to constructs within the meaning of the term mini-chromosome.

The term "non-protein expressing sequence" or "non-protein coding sequence" is defined herein as a nucleic acid sequence that is not eventually translated into protein. The nucleic acid may or may not be transcribed into RNA. Exemplary sequences include ribozymes or antisense RNA.

The term "operably linked" is defined herein as a configuration in which a control sequence, e.g., a promoter sequence, directs transcription or translation of another sequence, for example a coding sequence. For example, a promoter sequence could be appropriately placed at a position relative to a coding sequence such that the control sequence directs the production of a polypeptide encoded by the coding sequence.

"Phenotype" or "phenotypic trait(s)", as used herein, refers to an observable property or set of properties resulting from the expression of a gene. The set of properties may be observed visually or after biological or biochemical testing, and may be constantly present or may only manifest upon challenge with the appropriate stimulus or activation with the appropriate signal.

The term "plant," as used herein, refers to any type of plant. Exemplary types of plants are listed below, but other types of plants will be known to those of skill in the art and could be used with the invention. Modified plants of the invention include, for example, dicots, gymnosperm, monocots, mosses, ferns, horsetails, club mosses, liverworts, hornworts, red algae, brown algae, gametophytes and sporophytes of pteridophytes, and green algae.

The term "crop plant" refers to plants grown for agricultural or commercial rather than experimental purposes and specifically excludes *Arabidopsis thaliana*. Some plants grown for experimental purposes may take on commercial importance when used to produce pharmaceutical or chemical products. Centromeres "derived from crop plants" according to the present invention specifically exclude centromeres that are fragments of naturally occurring *Arabidopsis thaliana* centromeres or naturally occurring descendants thereof. Centromeres derived from crop plants include variants (mutants) of *Arabidopsis thaliana* centromeres, or artificial centromeres synthesized based on nucleotide sequences of *Arabidopsis thaliana* centromeres.

A common class of plants exploited in agriculture are vegetable crops, including artichokes, kohlrabi, arugula, leeks, asparagus, lettuce (e.g., head, leaf, romaine), bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, chinese cabbage, peppers, collards, potatoes, cucumber plants (marrows, cucumbers), pumpkins, cucurbits, radishes, dry bulb onions, rutabaga, eggplant, salsify, escarole, shallots, endive, garlic, spinach, green onions, squash, greens, beet (sugar beet or fodder beet), sweet potatoes, swiss chard, horseradish, tomatoes, kale, turnips, or spices.

Other types of plants frequently finding commercial use include fruit and vine crops such as apples, grapes, apricots, cherries, nectarines, peaches, pears, plums, prunes, quince, almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, or lychee.

Modified wood and fiber or pulp plants of particular interest include, but are not limited to maple, oak, cherry, mahogany, poplar, aspen, birch, beech, spruce, fir, kenaf, pine, walnut, cedar, redwood, chestnut, acacia, bombax, alder, eucalyptus, catalpa, mulberry, persimmon, ash, honeylocust, sweetgum, privet, sycamore, magnolia, sourwood, cottonwood, mesquite, buckthorn, locust, willow, elderberry, teak, linden, bubing a, basswood or elm.

Modified flowers and ornamental plants of particular interest, include, but are not limited to, roses, petunias, pansy, peony, olive, begonias, violets, phlox, nasturtiums, irises, lilies, orchids, vinca, philodendron, poinsettias, opuntia, cyclamen, magnolia, dogwood, azalea, redbud, boxwood, Viburnum, maple, elderberry, hosta, agave, asters, sunflower, pansies, hibiscus, morning glory, alstromeria, zinnia, geranium, *Prosopis*, artemesia, clematis, delphinium, *dianthus*, gallium, coreopsis, iberis, lamium, poppy, lavender, leucophyllum, sedum, salvia, verbascum, digitalis, penstemon, savory, pythrethrum, or oenothera. Modified nut-bearing trees of particular interest include, but are not limited to pecans, walnuts, *macadamia* nuts, hazelnuts, almonds, or pistachios, cashews, pignolas or chestnuts.

Many of the most widely grown plants are field crop plants such as evening primrose, meadow foam, corn (field, sweet, popcorn), hops, jojoba, peanuts, rice, safflower, small grains (barley, oats, rye, wheat, etc.), sorghum, tobacco, kapok, leguminous plants (beans, lentils, peas, soybeans), oil plants (rape, mustard, poppy, olives, sunflowers, coconut, castor oil plants, cocoa beans, groundnuts, oil palms), fibre plants (cotton, flax, hemp, jute), lauraceae (cinnamon, camphor), or plants such as coffee, sugarcane, cocoa, tea, or natural rubber plants. Still other examples of plants include bedding plants such as flowers, cactus, succulents or ornamental plants, as well as trees such as forest (broad-leaved trees or evergreens, such as conifers), fruit, ornamental, or nut-bearing trees, as well as shrubs or other nursery stock.

Still other examples of plants include bedding plants such as flowers, cactus, succulents or ornamental plants, as well as trees such as forest (broad-leaved trees or evergreens, such as conifers), fruit, ornamental, or nut-bearing trees, as well as shrubs or other nursery stock.

Modified crop plants of particular interest in the present invention include, but are not limited to, soybean (including the variety known as *Glycine max*), cotton, canola (also known as rape), wheat, sunflower, sorghum, alfalfa, barley, safflower, millet, rice, tobacco, fruit and vegetable crops or turfgrasses. Exemplary cereals include maize, wheat, barley, oats, rye, millet, sorghum, rice triticale, *secale*, einkorn, spelt, emmer, teff, milo, flax, gramma grass, *Tripsacum* sp., or teosinte. Oil-producing plants include plant species that produce and store triacylglycerol in specific organs, primarily in seeds. Such species include soybean (*Glycine max*), rapeseed or canola (including *Brassica napus, Brassica rapa* or *Brassica campestris*), *Brassica juncea, Brassica* carinata, sunflower (Helianthus annus), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) or peanut (*Arachis hypogaea*).

The term "plant part" as used herein includes pollen, silk, endosperm, ovule, seed, embryo, pods, roots, cuttings, tubers, stems, stalks, fruit, berries, nuts, flowers, leaves, bark, wood, whole plant, plant cell, plant organ, protoplast, cell culture, crown, callus culture, petiole, petal, sepal, stamen, stigma, style, bud, or any group of plant cells organized into a structural and functional unit. In one preferred embodiment, the exogenous nucleic acid is expressed in a specific location or tissue of a plant, for example, epidermis, vascular tissue, meristem, cambium, cortex, pith, leaf, sheath, flower, root or seed.

The term "promoter" is defined herein as a DNA sequence that allows the binding of RNA polymerase (including but not limited to RNA polymerase I, RNA polymerase II and RNA polymerase III from eukaryotes) and directs the polymerase to a downstream transcriptional start site of a nucleic acid sequence encoding a polypeptide to initiate transcription. RNA polymerase effectively catalyzes the assembly of messenger RNA complementary to the appropriate DNA strand of the coding region.

A "promoter operably linked to a heterologous gene" is a promoter that is operably linked to a gene that is different from the gene to which the promoter is normally operably linked in its native state. Similarly, an "exogenous nucleic acid operably linked to a heterologous regulatory sequence" is a nucleic acid that is operably linked to a regulatory control sequence to which it is not normally linked in its native state.

The term "hybrid promoter" is defined herein as parts of two or more promoters that are fused together to generate a sequence that is a fusion of the two or more promoters, which is operably linked to a coding sequence and mediates the transcription of the coding sequence into mRNA.

The term "tandem promoter" is defined herein as two or more promoter sequences each of which is operably linked to a coding sequence and mediates the transcription of the coding sequence into mRNA.

The term "constitutive active promoter" is defined herein as a promoter that allows permanent stable expression of the gene of interest.

The term "Inducible promoter" is defined herein as a promoter induced by the presence or absence of biotic or an abiotic factor.

The term "polypeptide" does not refer to a specific length of the encoded product and, therefore, encompasses peptides, oligopeptides, and proteins. The term "exogenous polypeptide" is defined as a polypeptide which is not native to the plant cell, a native polypeptide in which modifications have been made to alter the native sequence, or a native polypeptide whose expression is quantitatively altered as a result of a manipulation of the plant cell by recombinant DNA techniques.

As used herein, the term "pseudogene" refers to a non-functional copy of a protein-coding gene; pseudogenes found in the genomes of eukaryotic organisms are often inactivated by mutations and are thus presumed to be non-essential to that organism; pseudogenes of reverse transcriptase and other open reading frames found in retroelements are abundant in the centromeric regions of *Arabidopsis* and other organisms and are often present in complex clusters of related sequences.

As used herein the term "regulatory sequence" refers to any DNA sequence that influences the efficiency of transcription or translation of any gene. The term includes, but is not limited to, sequences comprising promoters, enhancers and terminators.

As used herein the term "repeated nucleotide sequence" refers to any nucleic acid sequence of at least 25 bp present in a genome or a recombinant molecule, other than a telomere repeat, that occurs at least two or more times and that are preferably at least 80% identical either in head to tail or head to head orientation either with or without intervening sequence between repeat units.

As used herein, the term "retroelement" or "retrotransposon" refers to a genetic element related to retroviruses that disperse through an RNA stage; the abundant retroelements present in plant genomes contain long terminal repeats (LTR retrotransposons) and encode a polyprotein gene that is processed into several proteins including a reverse transcriptase. Specific retroelements (complete or partial sequences) can be found in and around plant centromeres and can be present as dispersed copies or complex repeat clusters. Individual copies of retroelements may be truncated or contain mutations; intact retroelements are rarely encountered.

As used herein the term "satellite DNA" refers to short DNA sequences (typically <1000 bp) present in a genome as multiple repeats, mostly arranged in a tandemly repeated fashion, as opposed to a dispersed fashion. Repetitive arrays of specific satellite repeats are abundant in the centromeres of many higher eukaryotic organisms.

As used herein, a "screenable marker" is a gene whose presence results in an identifiable phenotype. This phenotype may be observable under standard conditions, altered conditions such as elevated temperature, or in the presence of certain chemicals used to detect the phenotype. The use of a screenable marker allows for the use of lower, sub-killing antibiotic concentrations and the use of a visible marker gene to identify clusters of transformed cells, and then manipulation of these cells to homogeneity. Preferred screenable markers of the present include genes that encode fluorescent proteins that are detectable by a visual microscope such as the fluorescent reporter genes DsRed, ZsGreen, ZsYellow, AmCyan, Green Fluorescent Protein (GFP). An additional preferred screenable marker gene is lac.

The invention also contemplates novel methods of screening for adchromosomal plant cells that involve use of relatively low, sub-killing concentrations of selection agent (e.g. sub-killing antibiotic concentrations), and also involve use of a screenable marker (e.g., a visible marker gene) to identify clusters of modified cells carrying the screenable marker, after which these screenable cells are manipulated to homogeneity. As used herein, a "selectable marker" is a gene whose presence results in a clear phenotype, and most often a growth advantage for cells that contain the marker. This growth advantage may be present under standard conditions, altered conditions such as elevated temperature, specialized media compositions, or in the presence of certain chemicals such as herbicides or antibiotics. Use of selectable markers is described, for example, in Broach et al. Gene, 8:121-133, 1979. Examples of selectable markers include the thymidine kinase gene, the cellular adenine phosphoribosyltransferase gene and the dihydrylfolate reductase gene, hygromycin phosphotransferase genes, the bar gene, neomycin phosphotransferase genes and phosphomannose isomerase, among others. Preferred selectable markers in the present invention include genes whose expression confer antibiotic or herbicide resistance to the host cell, or proteins allowing utilization of a carbon source not normally utilized by plant cells. Expression of one of these markers should be sufficient to enable the maintenance of a vector within the host cell, and facilitate the manipulation of the plasmid into new host cells. Of particular interest in the present invention are proteins conferring cellular resistance to kanamycin, G 418, paramomycin, hygromycin, bialaphos, and glyphosate for example, or proteins allowing utilization of a carbon source, such as mannose, not normally utilized by plant cells.

The term "stable" as used herein means that the mini-chromosome can be transmitted to daughter cells over at least 8 mitotic generations. Some embodiments of mini-chromosomes may be transmitted as functional, autonomous units for less than 8 mitotic generations, e.g. 1, 2, 3, 4, 5, 6, or 7. Preferred mini-chromosomes can be transmitted over at least 8, 9, 10, 11, 12, 13, 14, 15, 16, 17, 18, 19, 20, 21, 22, 23, 24, 25, 26, 27, 28, 29 or 30 generations, for example, through the regeneration or differentiation of an entire plant, and preferably are transmitted through meiotic division to gametes. Other preferred mini-chromosomes can be further maintained in the zygote derived from such a gamete or in an embryo or endosperm derived from one or more such gametes. A "functional and stable" mini-chromosome is one in which functional mini-chromosomes can be detected after transmission of the mini-chromosomes over at least 8 mitotic generations, or after inheritance through a meiotic division. During mitotic division, as occurs occasionally with native chromosomes, there may be some non-transmission of mini-chromosomes; the mini-chromosome may still be characterized as stable despite the occurrence of such events if an adchromosomal plant that contains descendants of the mini-chromosome distributed throughout its parts may be regenerated from cells, cuttings, propagules, or cell cultures containing the mini-chromosome, or if an adchromosomal plant can be identified in progeny of the plant containing the mini-chromosome.

As used herein, a "structural gene" is a sequence which codes for a polypeptide or RNA and includes 5' and 3' ends. The structural gene may be from the host into which the structural gene is transformed or from another species. A structural gene will preferably, but not necessarily, include one or more regulatory sequences which modulate the expression of the structural gene, such as a promoter, terminator or enhancer. A structural gene will preferably, but not necessarily, confer some useful phenotype upon an organism comprising the structural gene, for example, herbicide resistance. In one embodiment of the invention, a structural gene may encode an RNA sequence which is not translated into a protein, for example a tRNA or rRNA gene.

As used herein, the term "telomere" or "telomere DNA" refers to a sequence capable of capping the ends of a chromosome, thereby preventing degradation of the chromosome end, ensuring replication and preventing fusion to other chromosome sequences. Telomeres can include naturally occurring telomere sequences or synthetic sequences. Telomeres from one species may confer telomere activity in another species. An exemplary telomere DNA is a heptanucleotide telomere repeat TTTAGGG (and its complement) found in the majority of plants.

"Transformed," "transgenic," "modified," and "recombinant" refer to a host organism such as a plant into which an exogenous or heterologous nucleic acid molecule has been introduced, and includes meiocytes, seeds, zygotes, embryos, endosperm, or progeny of such plant that retain the exogenous or heterologous nucleic acid molecule but which have not themselves been subjected to the transformation process.

When the phrase "transmission efficiency" of a certain percent is used, transmission percent efficiency is calculated by measuring mini-chromosome presence through one or more mitotic or meiotic generations. It is directly measured as the ratio (expressed as a percentage) of the daughter cells or plants demonstrating presence of the mini-chromosome to parental cells or plants demonstrating presence of the mini-chromosome. Presence of the mini-chromosome in parental and daughter cells is demonstrated with assays that detect the presence of an exogenous nucleic acid carried on the mini-chromosome. Exemplary assays can be the detection of a screenable marker (e.g. presence of a fluorescent protein or any gene whose expression results in an observable phenotype), a selectable marker, or PCR amplification of any exogenous nucleic acid carried on the mini-chromosome.

Constructing Mini-Chromosomes by Site-Specific Recombination

Plant mini-chromosomes may be constructed using site-specific recombination sequences (for example those recognized by the bacteriophage P1 Cre recombinase, or the bacteriophage lambda integrase, or similar recombination enzymes). A compatible recombination site, or a pair of such sites, is present on both the centromere containing DNA clones and the donor DNA clones. Incubation of the donor clone and the centromere clone in the presence of the recombinase enzyme causes strand exchange to occur between the recombination sites in the two plasmids; the resulting mini-chromosomes contain centromere sequences as well as mini-chromosome vector sequences. The DNA molecules formed in such recombination reactions is introduced into E. coli, other bacteria, yeast or plant cells by common methods in the field including, but not limited to, heat shock, chemical transformation, electroporation, particle bombardment, whiskers, or other transformation method followed by selection for marker genes including chemical, enzymatic, color, or other marker present on either parental plasmid, allowing for the selection of transformants harboring mini-chromosomes.

II. Methods of Detecting and Characterizing Mini-Chromosomes in Plant Cells or of Scoring Mini-Chromosome Performance in Plant Cells:

Identification of Candidate Centromere Fragments by Probing BAC Libraries

Centromere clones are identified from a large genomic insert library such as a Bacterial Artificial Chromosome library. Probes are labeled using nick-translation in the presence of radioactively labeled dCTP, dATP, dGTP or dTTP as in, for example, the commercially available Rediprime kit (Amersham) as per the manufacturer's instructions. Other labeling methods familiar to those skilled in the art could be substituted. The libraries are screened and deconvoluted. Genomic clones are screened by probing with small centromere-specific clones (for example 14F1 was used) which shows high homology to the satellite sequence (14F1 showed homology to "BJCANRD", Genbank ID X68786.1). Other embodiments of this procedure would involve hybridizing a library with other centromere sequences. Of the BAC clones identified using this procedure, a representative set are identified as having high hybridization signals to some probes, and optionally low hybridization signals to other probes. These are selected, the bacterial clones grown up in cultures and DNA prepared by methods familiar to those skilled in the art such as alkaline lysis. The DNA composition of purified clones are surveyed using for example fingerprinting by digesting with restriction enzymes such as, but not limited to, HinfI or HindIII. In a preferred embodiment the restriction enzyme cuts within the tandem centromere satellite repeat (see below). A variety of clones showing different fingerprints are selected for conversion into mini-chromosomes and inheritance testing. It can also be informative to use multiple restriction enzymes for fingerprinting or other enzymes which can cleave DNA.

Fingerprinting Analysis of BACs and Mini-Chromosomes

Centromere function may be associated with large tandem arrays of satellite repeats. To assess the composition and architecture of the centromere BACs, the candidate BACs are digested with a restriction enzyme, such as HindIII, which cuts with known frequency within the consensus sequence of the unit repeat of the tandemly repeated centromere satellite. Digestion products are then separated by agarose gel electrophoresis. Large insert clones containing a large array of tandem repeats will produce a strong band of the unit repeat size, as well as less intense bands at 2× and 3× the unit repeat size, and further multiples of the repeat size. These methods are well-known and there are many possible variations known to those skilled in the art.

Determining Sequence Composition of Mini-Chromosomes by Shotgun Cloning/Sequencing, Sequence Analysis To determine the sequence composition of the mini-chromosome, the insert is sequenced. To generate DNA suitable for sequencing mini-chromosomes are fragmented, for example by using a random shearing method (such as sonication, nebulization, etc). Other fragmentation techniques may also be used such as enzymatic digestion. These fragments are then cloned into a plasmid vector and sequenced. The resulting DNA sequence is trimmed of poor-quality sequence and of sequence corresponding to the plasmid vector. The sequence is then compared to the known DNA sequences using an algorithm such as BLAST to search a sequence database such as GenBank.

To determine the consensus of the satellite repeat in the mini-chromosome, the sequences containing satellite repeat are aligned using a DNA sequence alignment program such as ContigExpress from Vector NTI. The sequences may also be aligned to previously determined repeats for that species. The sequences are trimmed to unit repeat length using the consensus as a template. Sequences trimmed from the ends of the alignment are realigned with the consensus and further trimmed until all sequences are at or below the consensus length. The sequences are then aligned with each other. The consensus is determined by the frequency of a specific nucleotide at each position; if the most frequent base is three times more frequent than the next most frequent base, it was considered the consensus.

Methods for determining consensus sequence are well known in the art, see, e.g., U.S. Pat. App. Pub. No. 20030124561; Hall & Preuss (2002). These methods, including DNA sequencing, assembly, and analysis, are well-known and there are many possible variations known to those skilled in the art. Other alignment parameters may also be useful such as using more or less stringent definitions of consensus.

Non-Selective Mini-Chromosome Mitotic Inheritance Assays

The following list of assays and potential outcomes illustrates how various assays can be used to distinguish autonomous events from integrated events.

Assay #1: Transient Assay

Mini-chromosomes are tested for their ability to become established as chromosomes and their ability to be inherited in mitotic cell divisions. In this assay, mini-chromosomes are delivered to plant cells, for example Brassica suspension cells in liquid culture. The cells used can be at various stages of growth. In this example, a population in which some cells were undergoing division was used. The mini-chromosome is then assessed over the course of several cell divisions, by tracking the presence of a screenable marker, e.g. a visible marker gene such as a fluorescent protein. Mini-chromosomes that are inherited well may show an initial delivery into many single cells; after several cell divisions, these single cells divide to form clusters of mini-chromosome-containing cells. Other exemplary embodiments of this method include delivering mini-chromosomes to other mitotic cell types, including roots and shoot meristems.

Assay #2: Non-Lineage Based Inheritance Assays on Modified Transformed Cells and Plants Mini-chromosome inheritance is assessed on modified cell lines and plants by following the presence of the mini-chromosome over the course of multiple cell divisions. An initial population of mini-chromosome containing cells is assayed for the presence of the mini-chromosome, by the presence of a marker gene, including but not limited to a fluorescent protein, a colored protein, a protein assayable by histochemical assay, and a gene affecting cell morphology. All nuclei are stained with a DNA-specific dye including but not limited to DAPI, Hoechst 33258, OliGreen, Giemsa YOYO, or TOTO, allowing a determination of the number of cells that do not contain the mini-chromosome. After the initial determination of the percent of cells carrying the mini-chromosome, the cells are allowed to divide over the course of several cell divisions. The number of cell divisions, n, is determined by a method including but not limited to monitoring the change in total weight of cells, and monitoring the change in volume of the cells or by directly counting cells in an aliquot of the culture. After a number of cell divisions, the population of cells is again assayed for the presence of the mini-chromosome. The loss rate per generation is calculated by the equation:

$$\text{Loss rate per generation} = 1 - (F/1)^{1/n}$$

The population of mini-chromosome-containing cells may include suspension cells, roots, leaves, meristems, flowers, or any other tissue of modified plants, or any other cell type containing a mini-chromosome.

These methods are well-known and there are many possible variations known to those skilled in the art; they have been used before with human cells and yeast cells.

Assay #3: Lineage Based Inheritance Assays on Modified Cells and Plants

Mini-chromosome inheritance is assessed on modified cell lines and plants by following the presence of the mini-chromosome over the course of multiple cell divisions. In cell types that allow for tracking of cell lineage, including but not limited to root cell files, trichomes, and leaf stomata guard cells, mini-chromosome loss per generation does not need to be determined statistically over a population, it can be discerned directly through successive cell divisions. In other manifestations of this method, cell lineage can be discerned from cell position, or methods including but not limited to the use of histological lineage tracing dyes, and the induction of genetic mosaics in dividing cells.

In one simple example, the two guard cells of the stomata are daughters of a single precursor cell. To assay mini-chromosome inheritance in this cell type, the epidermis of the leaf of a plant containing a mini-chromosome is examined for the presence of the mini-chromosome by the presence of a marker gene, including but not limited to a fluorescent protein, a colored protein, a protein assayable by histochemical assay, and a gene affecting cell morphology. The number of loss events in which one guard cell contains the mini-chromosome (L) and the number of cell divisions in which both guard cells contain the mini-chromosome (B) are counted. The loss rate per cell division is determined as $L/(L+B)$. Other lineage-based cell types are assayed in similar fashion. These methods are well-known and there are many possible variations known to those skilled in the art; they have been used before with yeast cells.

Lineal mini-chromosome inheritance may also be assessed by examining root files (e.g. *Brassica* root files) or clustered cells in callus (e.g. soybean callus) over time. Changes in the percent of cells carrying the mini-chromosome will indicate the mitotic inheritance.

Assay #4: Inheritance Assays on Modified Cells and Plants in the Presence of Chromosome Loss Agents Any of the above three assays can be done in the presence of chromosome loss agents. (including but not limited to colchicine, colcemid, caffeine, etopocide, nocodazole, oryzalin, trifluran). It is likely that an autonomous mini-chromosome will prove more susceptible to loss induced by chromosome loss agents; therefore, autonomous mini-chromosomes should show a lower rate of inheritance in the presence of chromosome loss agents. These methods have been used to study chromosome loss in fruit flies and yeast; there are many possible variations known to those skilled in the art.

III. Transformation of Plant Cells and Plant Regeneration

Various methods may be used to deliver DNA into plant cells. These include biological methods, such as *Agrobacterium, E. coli*, and viruses, physical methods such as biolistic particle bombardment, nanocopoiea device, the Stein beam gun silicon, carbide whiskers and microinjection, electrical methods such as electroporation, and chemical methods such as the use of poly-ethylene glycol and other compounds known to stimulate DNA uptake into cells. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). Transformation using silicon carbide whiskers, e.g. in maize, is described in Brisibe, J. Exp. Bot. 51(343):187-196 (2000) and Dunwell, Methods Mol. Biol. 111:375-82 (1999) and U.S. Pat. No. 5,464,765.

*Agrobacterium*-Mediated Delivery

*Agrobacterium*-mediated transformation is one method for introducing a desired genetic element into a plant. Several *Agrobacterium* species mediate the transfer of a specific DNA known as "T-DNA" that can be genetically engineered to carry a desired piece of DNA into many plant species. Plasmids used for delivery contain the T-DNA flanking the nucleic acid to be inserted into the plant. The major events marking the process of T-DNA mediated pathogenesis are induction of virulence genes, processing and transfer of T-DNA.

There are three common methods to transform plant cells with *Agrobacterium*. The first method is co-cultivation of *Agrobacterium* with cultured isolated protoplasts. This method requires an established culture system that allows culturing protoplasts and plant regeneration from cultured protoplasts. The second method is transformation of cells or tissues with *Agrobacterium*. This method requires (a) that the plant cells or tissues can be modified by *Agrobacterium* and (b) that the modified cells or tissues can be induced to regenerate into whole plants. The third method is transformation of seeds, apices or meristems with *Agrobacterium*. This method requires exposure of the meristematic cells of these tissues to *Agrobacterium* and micropropagation of the shoots or plan organs arising from these meristematic cells.

Those of skill in the art are familiar with procedures for growth and suitable culture conditions for *Agrobacterium* as well as subsequent inoculation procedures. Liquid or semisolid culture media can be used. The density of the *Agrobacterium* culture used for inoculation and the ratio of *Agrobacterium* cells to explant can vary from one system to the next, as can media, growth procedures, timing and lighting conditions.

Transformation of dicotyledons using *Agrobacterium* has long been known in the art, and transformation of monocotyledons using *Agrobacterium* has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

A number of wild-type and disarmed strains of *Agrobacterium tumefaciens* and *Agrobacterium rhizogenes* harboring Ti or Ri plasmids can be used for gene transfer into plants. Preferably, the *Agrobacterium* hosts contain disarmed Ti and Ri plasmids that do not contain the oncogenes that cause tumorigenesis or rhizogenesis. Exemplary strains include *Agrobacterium tumefaciens* strain C58, a nopaline-type strain that is used to mediate the transfer of DNA into a plant cell, octopine-type strains such as LBA4404 or succinamopine-type strains, e.g., EHA101 or EHA105. The use of these strains for plant transformation has been reported and the methods are familiar to those of skill in the art.

U.S. Application No. 20040244075 published Dec. 2, 2004 describes improved methods of *Agrobacterium*-mediated transformation. The efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla et al., (1987) Plant Molec. Biol. 8:291-298). Alternatively, transformation efficiency may be enhanced by wounding the target tissue to be modified or transformed. Wounding of plant tissue may be achieved, for example, by punching, maceration, bombardment with microprojectiles, etc. (See e.g., Bidney et al., (1992) Plant Molec. Biol. 18:301-313).

In addition, a recent method described by Broothaerts, et. al. (Nature 433: 629-633, 2005) expands the bacterial genera that can be used to transfer genes into plants. This work involved the transfer of a disarmed Ti plasmid without T-DNA and another vector with T-DNA containing the marker enzyme beta-glucuronidase, into three different bacteria. Gene transfer was successful and this method significantly expands the tools available for gene delivery into plants.

Microprojectile Bombardment Delivery

Another widely used technique to genetically transform plants involves the use of microprojectile bombardment. In this process, a nucleic acid containing the desired genetic elements to be introduced into the plant is deposited on or in small dense particles, e.g., tungsten, platinum, or preferably 1 micron gold particles, which are then delivered at a high velocity into the plant tissue or plant cells using a specialized biolistics device. Many such devices have been designed and constructed; one in particular, the PDS1000/He sold by Bio-Rad, is the instrument most commonly used for biolistics of plant cells. The advantage of this method is that no specialized sequences need to be present on the nucleic acid molecule to be delivered into plant cells; delivery of any nucleic acid sequence is theoretically possible.

For the bombardment, cells in suspension are concentrated on filters or solid culture medium. Alternatively, immature embryos, seedling explants, or any plant tissue or target cells may be arranged on solid culture medium. The cells to be bombarded are positioned at an appropriate distance below the microprojectile stopping plate.

Various biolistics protocols have been described that differ in the type of particle or the manner in which DNA is coated onto the particle. Any technique for coating microprojectiles that allows for delivery of transforming DNA to the target cells may be used. For example, particles may be prepared by functionalizing the surface of a gold oxide particle, providing free amine groups. DNA, having a strong negative charge, binds to the functionalized particles.

Parameters such as the concentration of DNA used to coat microprojectiles may influence the recovery of transformants containing a single copy of the transgene. For example, a lower concentration of DNA may not necessarily change the efficiency of the transformation but may instead increase the proportion of single copy insertion events. In this regard, ranges of approximately 1 ng to approximately 10 μg (10,000 ng), approximately 5 ng to 8 μg or approximately 20 ng, 50 ng, 100 ng, 200 ng, 500 ng, 1 μg, 2 μg, 5 μg, or 7 μg of transforming DNA may be used per each 1.0-2.0 mg of starting 1.0 micron gold particles.

Other physical and biological parameters may be varied, such as manipulation of the DNA/microprojectile precipitate, factors that affect the flight and velocity of the projectiles, manipulation of the cells before and immediately after bombardment (including osmotic state, tissue hydration and the subculture stage or cell cycle of the recipient cells), the orientation of an immature embryo or other target tissue relative to the particle trajectory, and also the nature of the transforming DNA, such as linearized DNA or intact supercoiled plasmids. One may particularly wish to adjust physical parameters such as DNA concentration, gap distance, flight distance, tissue distance, and helium pressure.

The particles delivered via biolistics can be "dry" or "wet." In the "dry" method, the mini-chromosome DNA-coated particles such as gold are applied onto a macrocarrier (such as a metal plate, or a carrier sheet made of a fragile material such as mylar) and dried. The gas discharge then accelerates the macrocarrier into a stopping screen, which halts the macrocarrier but allows the particles to pass through; the particles then continue their trajectory until they impact the tissue being bombarded. For the "wet" method, the droplet containing the mini-chromosome DNA-coated particles is applied to the bottom part of a filter holder, which is attached to a base which is itself attached to a rupture disk holder used to hold the rupture disk to the helium egress tube for bombardment. The gas discharge directly displaces the DNA/gold droplet from the filter holder and accelerates the particles and their DNA cargo into the tissue being bombarded. The wet biolistics method has been described in detail elsewhere but has not previously been applied in the context of plants (Mialhe et al., Mol Mar Biol Biotechnol. 4(4):275-831995). The concentrations of the various components for coating particles and the physical parameters for delivery can be optimized using procedures known in the art.

A variety of plant cells/tissues are suitable for transformation, including immature embryos, scutellar tissue, suspension cell cultures, immature inflorescence, shoot meristem, epithelial peels, nodal explants, callus tissue, hypocotyl tissue, cotyledons, roots, and leaves, meristem cells, and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspore-derived embryos, roots, hypocotyls, cotyledons and the like.

Those cells which are capable of proliferating as callus also are recipient cells for genetic transformation.

Any suitable plant culture medium can be used. Examples of suitable media would include but are not limited to MS-based media (Murashige and Skoog, Physiol. Plant, 15:473-497, 1962) or N6-based media(Chu et al., Scientia Sinica 18:659, 1975) supplemented with additional plant growth regulators including but not limited to auxins such as picloram (4-amino-3,5,6-trichloropicolinic acid), 2,4-D (2,4-dichlorophenoxyacetic acid), naphalene-acetic acid (NAA) and dicamba (3,6-dichloroanisic acid), cytokinins such as BAP (6-benzylaminopurine) and kinetin, and gibberellins. Other media additives can include but are not limited to amino acids, macroelements, iron, microelements, vitamins and organics, carbohydrates, undefined media components such as casein hydrolysates, an appropriate gelling agent such as a form of agar, a low melting point agarose or Gelrite if desired. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog (Mursahige and Skoog, Physiol. Plant, 15:473-497, 1962), N6 (Chu et al., Scientia Sinica 18:659, 1975), Linsmaier and Skoog (Linsmaier and Skoog, Physio. Plant., 18:100, 1965), Uchimiya and Murashige (Uchimiya and Murashige, Plant Physiol. 15:473, 1962), Gamborg's B5 media (Gamborg et al., Exp. Cell Res., 50:151, 1968), D medium (Duncan et al., Planta, 165:322-332, 1985), Mc-Cown's Woody plant media (McCown and Lloyd, HortScience 6:453, 1981), Nitsch and Nitsch (Nitsch and Nitsch, Science 163:85-87, 1969), and Schenk and Hildebrandt (Schenk and Hildebrandt, Can. J. Bot. 50:199-204, 1972) or derivations of these media supplemented accordingly. Those of skill in the art are aware that media and media supplements such as nutrients and growth regulators for use in transformation and regeneration and other culture conditions such as light intensity during incubation, pH, and incubation temperatures can be varied.

Those of skill in the art are aware of the numerous modifications in selective regimes, media, and growth conditions that can be varied depending on the plant system and the selective agent. Typical selective agents include but are not limited to antibiotics such as geneticin (G418), kanamycin, paromomycin or other chemicals such as glyphosate or other herbicides. Consequently, such media and culture conditions disclosed in the present invention can be modified or substituted with nutritionally equivalent components, or similar processes for selection and recovery of transgenic events, and still fall within the scope of the present invention.

Mini-Chromosome Delivery without Selection

Mini-chromosome is delivered to plant cells or tissues, e.g., plant cells in suspension to obtain stably modified callus clones for inheritance assay. Suspension cells are maintained in a growth media, for example Murashige and Skoog (MS) liquid medium containing an auxin such as 2,4-dichlorophenoxyacetic acid (2,4-D). Cells are bombarded using a particle bombardment process, such as the helium-driven PDS-1000/He system, and propagated in the same liquid medium to permit the growth of modified and non-modified cells. Portions of each bombardment are monitored for formation of fluorescent clusters, which are isolated by micromanipulation and cultured on solid medium. Clones modified with mini-chromosome are expanded and homogenous clones are used in inheritance assays, or assays measuring mini-chromosome structure or autonomy.

Mini-Chromosome Transformation with Selectable Marker Gene

Isolation of mini-chromosome-modified cells in bombarded calluses or explants can be facilitated by the use of a selectable marker gene. The bombarded tissues are transferred to a medium containing an appropriate selective agent for a particular selectable marker gene. Such a transfer usually occurs between 0 and about 7 days after bombardment. The transfer could also take place any number of days after bombardment. The amount of selective agent and timing of incorporation of such an agent in selection medium can be optimized by using procedures known in the art. Selection inhibits the growth of non-modified cells, thus providing an advantage to the growth of modified cells, which can be further monitored by tracking the presence of a fluorescent marker gene or by the appearance of modified explants (modified cells on explants may be green under light in selection medium, while surrounding non-modified cells are weakly pigmented). In plants that develop through shoot organogenesis (e.g. Brassica, tomato or tobacco), the modified cells can form shoots directly, or alternatively, can be isolated and expanded for regeneration of multiple shoots transgenic for mini-chromosome. In plants that develop through embryogenesis (e.g. corn or soybean), additional culturing steps may be necessary to induce the modified cells to form an embryo and to regenerate in the appropriate media.

Useful selectable marker genes are well known in the art and include, for example, herbicide and antibiotic resistance genes including but not limited to neomycin phosphotransferase II (conferring resistance to kanamycin, paramomycin and G418), hygromycin phosphotransferase (conferring resistance to hygromycin), 5-enolpyruvylshikimate-3-phosphate synthase (EPSPS, conferring resistance to glyphosate), phosphinothricin acetyltransferase (conferring resistance to phosphinothricin/bialophos), MerA (conferring resistance to mercuric ions). Selectable marker genes may be transformed using standard methods in the art.

The first step in the production of plants containing novel genes involves delivery of DNA into a suitable plant tissue (described in the previous section) and selection of the tissue under conditions that allow preferential growth of any cells containing the novel genes. Selection is typically achieved with a selectable marker gene present in the delivered DNA, which may be a gene conferring resistance to an antibiotic, herbicide or other killing agent, or a gene allowing utilization of a carbon source not normally metabolized by plant cells. For selection to be effective, the plant cells or tissue need to be grown on selective medium containing the appropriate concentration of antibiotic or killing agent, and the cells need to be plated at a defined and constant density. The concentration of selective agent and cell density are generally chosen to cause complete growth inhibition of wild type plant tissue that does not express the selectable marker gene; but allowing cells containing the introduced DNA to grow and expand into adchromosomal clones. This critical concentration of selective agent typically is the lowest concentration at which there is complete growth inhibition of wild type cells, at the cell density used in the experiments. However, in some cases, sub-killing concentrations of the selective agent may be equally or more effective for the isolation of plant cells containing mini-chromosome DNA, especially in cases where the identification of such cells is assisted by a visible marker gene (e.g., fluorescent protein gene) present on the mini-chromosome.

In some species (e.g., tobacco or tomato), a homogenous clone of modified cells can also arise spontaneously when bombarded cells are placed under the appropriate selection.

An exemplary selective agent is the neomycin phosphotransferase II (nptII) marker gene, which is commonly used in plant biotechnology and confers resistance to the antibiotics kanamycin, G418 (geneticin) and paramomycin. In other species, or in certain plant tissues or when using particular selectable markers, homogeneous clones may not arise spontaneously under selection; in this case the clusters of modified cells can be manipulated to homogeneity using the visible marker genes present on the mini-chromosomes as an indication of which cells contain mini-chromosome DNA.

Regeneration of Adchromosomal Plants from Explants to Mature, Rooted Plants

For plants that develop through shoot organogenesis (e.g. *Brassica*, tomato and tobacco), regeneration of a whole plant involves culturing of regenerable explant tissues taken from sterile organogenic callus tissue, seedlings or mature plants on a shoot regeneration medium for shoot organogenesis, and rooting of the regenerated shoots in a rooting medium to obtain intact whole plants with a fully developed root system. These plants are potted in soil and grown to maturity in a greenhouse.

For plant species, such as corn and soybean, regeneration of a whole plant occurs via an embryogenic step that is not necessary for plant species where shoot organogenesis is efficient. In these plants the explant tissue is cultured on an appropriate media for embryogenesis, and the embryo is cultured until shoots form. The regenerated shoots are cultured in a rooting medium to obtain intact whole plants with a fully developed root system. These plants are potted in soil and grown to maturity in a greenhouse.

Explants are obtained from any tissues of a plant suitable for regeneration. Exemplary tissues include hypocotyls, internodes, roots, cotyledons, petioles, cotyledonary petioles, leaves and peduncles, prepared from sterile seedlings or mature plants. *Brassica* tissue can be from any *Brassica* species such as *Brassica napus, Brassica oleraceae, Brassica nigra, Brassica carinata, Brassica juncea*, and *Brassica campestris*.

Explants are wounded (for example with a scalpel or razor blade) and cultured on a shoot regeneration medium (SRM) containing Murashige and Skoog (MS) medium as well as a cytokinin, e.g., 6-benzylaminopurine (BA), and an auxin, e.g., α-naphthaleneacetic acid (NAA), and an anti-ethylene agent, e.g., silver nitrate ($AgNO_3$). For example, 2 mg/L of BA, 0.05 mg/L of NAA, and 2 mg/L of $AgNO_3$ can be added to MS medium for shoot organogenesis. The most efficient shoot regeneration is obtained from longitudinal sections of internode explants.

Shoots regenerated via organogenesis are rooted in a MS medium containing low concentration of an auxin such as NAA. Plants are potted and grown in a greenhouse to sexual maturity for seed harvest.

To regenerate a whole plant with a mini-chromosome, explants are pre-incubated for 1 to 7 days (or longer) on the shoot regeneration medium prior to bombardment with mini-chromosome (see below). Following bombardment, explants are incubated on the same shoot regeneration medium for a recovery period up to 7 days (or longer), followed by selection for transformed shoots or clusters on the same medium but with a selective agent appropriate for a particular selectable marker gene (see below).

Method of Co-Delivering Growth Inducing Genes to Facilitate Isolation of Adchromosomal Plant Cell Clones Another method used in the generation of cell clones containing mini-chromosomes involves the co-delivery of DNA containing genes that are capable of activating growth of plant cells, or that promote the formation of a specific organ, embryo or plant structure that is capable of self-sustaining growth. In one embodiment, the recipient cell receives simultaneously the mini-chromosome, and a separate DNA molecule encoding one or more growth promoting, organogenesis-promoting, embryogenesis-promoting or regeneration-promoting genes. Following DNA delivery, expression of the plant growth regulator genes stimulates the plant cells to divide, or to initiate differentiation into a specific organ, embryo, or other cell types or tissues capable of regeneration. Multiple plant growth regulator genes can be combined on the same molecule, or co-bombarded on separate molecules. Use of these genes can also be combined with application of plant growth regulator molecules into the medium used to culture the plant cells, or of precursors to such molecules that are converted to functional plant growth regulators by the plant cell's biosynthetic machinery, or by the genes delivered into the plant cell.

The co-bombardment strategy of mini-chromosomes with separate DNA molecules encoding plant growth regulators transiently supplies the plant growth regulator genes for several generations of plant cells following DNA delivery. During this time, the mini-chromosome may be stabilized by virtue of its centromere, but the DNA molecules encoding plant growth regulator genes, or organogenesis-promoting, embryogenesis-promoting or regeneration-promoting genes will tend to be lost. The transient expression of these genes, prior to their loss, may give the cells containing mini-chromosome DNA a sufficient growth advantage, or sufficient tendency to develop into plant organs, embryos or a regenerable cell cluster, to outgrow the non-modified cells in their vicinity, or to form a readily identifiable structure that is not formed by non-modified cells. Loss of the DNA molecule encoding these genes will prevent phenotypes from manifesting themselves that may be caused by these genes if present through the remainder of plant regeneration. In rare cases, the DNA molecules encoding plant growth regulator genes will integrate into the host plant's genome or into the mini-chromosome.

As described in Example 3, mini-chromosome DNA has been be co-delivered into plant cells together with DNA encoding genes that promote plant cell growth. Under a different embodiment of this invention, the genes promoting plant cell growth may be genes promoting shoot formation or embryogenesis, or giving rise to any identifiable organ, tissue or structure that can be regenerated into a plant. In this case, it may be possible to obtain embryos or shoots harboring mini-chromosomes directly after DNA delivery, without the need to induce shoot formation with growth activators supplied into the medium, or lowering the growth activator treatment necessary to regenerate plants. The advantages of this method are more rapid regeneration, higher transformation efficiency, lower background growth of non-modified tissue, and lower rates of morphologic abnormalities in the regenerated plants (due to shorter and less intense treatments of the tissue with chemical plant growth activators added to the growth medium).

Determination of Mini-Chromosome Structure an Autonomy in Adchromosomal Plants and Tissues The structure and autonomy of the mini-chromosome in adchromosomal plants and tissues can be determined by methods including but not limited to: conventional and pulsed-field Southern blot hybridization to genomic DNA from modified tissue subjected or not subjected to restriction endonuclease digestion, dot blot hybridization of genomic DNA from modified tissue hybridized with different mini-chromosome specific sequences, PCR on DNA from modified tissues with probes specific to the mini-chromosome, or Fluorescence In Situ Hybridization to nuclei of modified cells. The table below summarizes these methods.

| Assay | Assay details | Potential outcome | Interpretation |
|---|---|---|---|
| Southern blot | Restriction digest of genomic DNA* compared to purified mini-C | Native sizes and pattern of bands | Autonomous or integrated via CEN fragment |
| | | Altered sizes or pattern of bands | Integrated or rearranged |
| CHEF gel Southern blot | Restriction digest of genomic DNA compared to purified mini-C | Native sizes and pattern of bands | Autonomous or integrated via CEN fragment |
| | | Altered sizes or pattern of bands | Integrated or rearranged |
| | Native genomic DNA (no digest) | Mini-C band migrating ahead of genomic DNA | Autonomous circles or linears present in plant |
| | | Mini-C band co-migrating with genomic DNA | Integrated |
| | | >1 mini-C bands observed | Various possibilities |
| Exonuclease assay | Exonuclease digestion of genomic DNA followed by detection of circular mini-chromosome by PCR, dot blot, or restriction digest (optional), electrophoresis and southern blot (useful for circular mini-chromosomes) | Signal strength close to that w/o exonuclease | Autonomous circles present |
| | | No signal or signal strength lower that w/o exonuclease | Integrated |
| Mini-chromosome rescue | Transformation of plant genomic DNA into E. coli followed by selection for antibiotic resistance genes on mini-C | Colonies isolated only from mini-C plants with mini-Cs, not from controls; mini-C structure matches that of the parental mini-C | Autonomous circles present, native mini-C structure |
| | | Colonies isolated only from mini-C plants with mini-Cs, not from controls; mini-C structure different from parental mini-C | Autonomous circles present, rearranged mini-C structure OR mini-Cs integrated via centromere fragment |
| | | Colonies observed both in mini-C-modified plants and in controls | Various possibilities |
| PCR | PCR amplification of various parts of the mini-chromosome | All mini-c parts detected by PCR | Complete mini-C sequences present in plant |
| | | Subset of mini-c parts detected by PCR | Partial mini-C sequences present in plant |
| FISH | Detection of mini-chromosome sequences in mitotic or meiotic nuclei by fluorescence in situ hybridization | Mini-C sequences detected, free of genome | autonomous |
| | | Mini-C sequences detected, associated with genome | integrated |
| | | Mini-C sequences detected, both free and associated with genome | Both autonomous and integrated mini-C sequences present |
| | | No mini-C sequences detected | Mini-C DNA not visible by FISH |

*Genomic DNA refers to total DNA extracted from plants containing a mini-chromosome Furthermore, mini-chromosome structure can be examined by characterizing mini-chromosomes 'rescued' from adchromosomal cells. Circular mini-chromosomes that contain bacterial sequences for their selection and propagation in bacteria can be rescued from an adchromosomal plant or plant cell and re-introduced into bacteria. If no loss of sequences has occurred during replication of the mini-chromosome in plant cells, the mini-chromosome is able to replicate in bacteria and confer antibiotic resistance. Total genomic DNA is isolated from the adchromosomal plant cells by any method for DNA isolation known to those skilled in the art, including but not limited to a standard cetyltrimethy-lammonium bromide (CTAB) based method (Current Protocols in Molecular Biology (1994) John Wiley & Sons, N.Y., 2.3) The purified genomic DNA is introduced into bacteria (e.g., E. coli) using methods familiar to one skilled in the art (for example heat shock or electroporation). The transformed bacteria are plated on solid medium containing antibiotics to select bacterial clones modified with mini-chromosome DNA. Modified bacterial clones are grown up, the plasmid DNA purified (by alkaline lysis for example), and DNA analyzed by restriction enzyme digestion and gel electrophoresis or by sequencing. Because plant-methylated DNA containing methylcytosine residues will be degraded by wild-type strains of E. coli, bacterial strains (e.g. DH10B) deficient in the genes encoding methylation restriction nucleases (e.g. the mcr and mrr gene loci in *E. coli*) are best suited for this type of analysis. Mini-chromosome rescue can be performed on any plant tissue or clone of plant cells modified with a mini-chromosome.

Circular mini-chromosomes that contain bacterial sequences for their selection and propagation in bacteria can be rescued from an adchromosomal plant or plant cell and re-introduced into bacteria. If no loss of sequences has occurred during replication of the mini-chromosome in plant cells, the mini-chromosome is able to replicate in bacteria and confer antibiotic resistance. Total genomic DNA is isolated from the adchromosomal plant cells by any method for DNA isolation known to those skilled in the art, including but not limited to a standard cetyltrimethylammonium bromide (CTAB) based method (Current Protocols in Molecular Biology (1994) John Wiley & Sons, N.Y., 2.3) The purified genomic DNA is introduced into bacteria (e.g. *E. coli*) using methods familiar to one skilled in the art (for example heat shock or electroporation). The transformed bacteria are plated on solid medium containing antibiotics to select bacterial clones modified with mini-chromosome DNA. Modified bacterial clones are grown up, the plasmid DNA purified (by alkaline lysis for example), and DNA analyzed by restriction enzyme digestion and gel electrophoresis or by sequencing. Because plant-methylated DNA containing methylcytosine residues will be degraded by wild-type strains of *E. coli*, bacterial strains (e.g. DH10B) deficient in the genes encoding methylation restriction nucleases (e.g. the mcr and mrr gene loci in *E. coli*) are best suited for this type of analysis. Mini-chromosome rescue can be performed on any plant tissue or clone of plant cells modified with a mini-chromosome.

Mini-Chromosome Autonomy Demonstration by In Situ Hybridization (ISH)

To assess whether the mini-chromosome is autonomous from the native plant chromosomes, or has integrated into the plant genome, In Situ Hybridization is carried out (Fluorescent In Situ Hybridization or FISH is particularly well suited to this purpose). In this assay, mitotic or meiotic tissue, such as root tips or meiocytes from the anther, possibly treated with metaphase arrest agents such as colchicines is obtained, and standard FISH methods are used to label both the centromere and sequences specific to the mini-chromosome. For example, for *Brassica*, the *Brassica* centromere is labeled using probes from sequence 14F1, which labels all *Brassica* chromosomes with one fluorescent tag (Molecular Probes Alexafluor 568, for example), and sequences specific to the mini-chromosome are labeled with another fluorescent tag (Alexafluor 488, for example). All centromere sequences are detected with the first tag; only mini-chromosomes are detected with both the first and second tag. Chromosomes are stained with a DNA-specific dye including but not limited to DAN., Hoechst 33258, OliGreen, Giemsa YOYO, and TOTO. An autonomous mini-chromosome is visualized as a body that shows hybridization signal with both centromere probes and mini-chromosome specific probes and is separate from the native chromosomes. Similar procedures can be carried out for centromeres derived from other plant species.

Determination of Gene Expression Levels

The expression level of any gene present on the mini-chromosome can be determined by methods including but not limited to one of the following. The mRNA level of the gene can be determined by Northern Blot hybridization, Reverse Transcriptase-Polymerase Chain Reaction, binding levels of a specific RNA-binding protein, in situ hybridization, or dot blot hybridization.

The protein level of the gene product can be determined by Western blot hybridization, Enzyme-Linked Immunosorbant Assay (ELISA), fluorescent quantitation of a fluorescent gene product, enzymatic quantitation of an enzymatic gene product, immunohistochemical quantitation, or spectroscopic quantitation of a gene product that absorbs a specific wavelength of light.

Use of Exonuclease to Isolate Circular Mini-Chromosome DNA from Genomic DNA:

Exonucleases may be used to obtain pure mini-chromosome DNA, suitable for isolation of mini-chromosomes from *E. coli* or from plant cells. The method assumes a circular structure of the mini-chromosome. A DNA preparation containing mini-chromosome DNA and genomic DNA from the source organism is treated with exonuclease, for example lambda exonuclease combined with *E. coli* exonuclease I, or the ATP-dependent exonuclease (Qiagen Inc). Because the exonuclease is only active on DNA ends, it will specifically degrade the linear genomic DNA fragments, but will not affect the circular mini-chromosome DNA. The result is mini-chromosome DNA in pure form. The resultant mini-chromosome DNA can be detected by a number of methods for DNA detection known to those skilled in the art, including but not limited to PCR, dot blot followed by hybridization analysis, and southern blot followed by hybridization analysis. Exonuclease treatment followed by detection of resultant circular mini-chromosome may be used as a method to determine mini-chromosome autonomy.

Structural Analysis of Mini-Chromosomes by BAC-End Sequencing:

BAC-end sequencing procedures, known to those skilled in the art, can be applied to characterize mini-chromosome clones for a variety of purposes, such as structural characterization, determination of sequence content, and determination of the precise sequence at a unique site on the chromosome (for example the specific sequence signature found at the junction between a centromere fragment and the vector sequences). In particular, this method is useful to prove the relationship between a parental mini-chromosome and the mini-chromosomes descended from it and isolated from plant cells by mini-chromosome rescue, described above.

Methods for Scoring Meiotic Mini-Chromosome Inheritance

A variety of methods can be used to assess the efficiency of meiotic mini-chromosome transmission. In one embodiment of the method, gene expression of genes encoded by the mini-chromosome (marker genes or non-marker genes) can be scored by any method for detection of gene expression know to those skilled in the art, including but not limited to visible methods (e.g. fluorescence of fluorescent protein markers, scoring of visible phenotypes of the plant), scoring resistance of the plant or plant tissues to antibiotics, herbicides or other selective agents, by measuring enzyme activity of proteins encoded by the mini-chromosome, or measuring non-visible plant phenotypes, or directly measuring the RNA and protein products of gene expression using microarray, northern blots, in situ hybridization, dot blot hybridization, RT-PCR, western blots, immunoprecipitation, Enzyme-Linked Immunosorbant Assay (ELISA), immunofluorescence and radio-immunoassays (RIA). Gene expression can be scored in the post-meiotic stages of microspore, pollen, pollen tube or female gametophyte, or the post-zygotic stages such as embryo, seed, or progeny seedlings and plants. In another embodiment of the method, the mini-chromosome can de directly detected or visualized in post-meiotic, zygotic, embryonal or other cells in by a number of methods for DNA detection known to those skilled in the art, including but not limited to fluorescence in situ hybridization, in situ PCR, PCR, southern blot, or by mini-chromosome rescue described above.

FISH Analysis of Mini-Chromosome Copy Number in Meiocytes, Roots or Other Tissues of Adchromosomal Plants The copy number of the mini-chromosome can be assessed in any cell or plant tissue by In Situ Hybridization (Fluorescent In Situ Hybridization or FISH is Particularly well suited to this purpose). In an exemplary assay, standard FISH methods are used to label the centromere (e.g., for *Brassica*, using probes from sequence 14F1 which labels all *Brassica* chromosomes with one fluorescent tag (Molecular Probes Alexafluor 568, for example)), and to label sequences specific to the mini-chromosome with another fluorescent tag (Alexafluor 488, for example). All centromere sequences are detected with the first tag; only mini-chromosomes are detected with both the first and second tag. Nuclei are stained with a DNA-specific dye including but not limited to DAPI, Hoechst 33258, OliGreen, Giemsa YOYO, and TOTO. Mini-chromosome copy number is determined by counting the number of fluorescent foci that label with both tags.

Induction of Callus and Roots from Adchromosomal Plants Tissues for Inheritance Assays Mini-chromosome inheritance is assessed using callus and roots induced from transformed plants. To induce roots and callus, tissues such as leaf pieces are prepared from adchromosomal plants and cultured on a Murashige and Skoog (MS) medium containing a cytokinin, e.g., 6-benzylaminopurine (BA), and an auxin, e.g., α-naphthaleneacetic acid (NAA). Any tissue of an adchromosomal plant can be used for callus and root induction, and the medium recipe for tissue culture can be optimized using procedures known in the art.

Clonal Propagation of Adchromosomal Plants

To produce multiple clones of plants from a mini-chromosome-transformed plant, any tissue of the plant can be tissue-cultured for shoot organogenesis using regeneration procedures described under the section regeneration of plants from explants to mature, rooted plants (see above). Alternatively, multiple auxiliary buds can induced from a mini-chromosome-modified plant by excising the shoot tip, which can be rooted for a whole plant; each auxiliary bud can be rooted for a whole plant.

Scoring of Antibiotic- or Herbicide Resistance in Seedlings and Plants (Progeny of Self- and Out-Crossed Transformants Progeny seeds harvested from mini-chromosome-modified plants can be scored for antibiotic- or herbicide resistance by seed germination under sterile conditions on a growth media (for example Murashige and Skoog (MS) medium) containing an appropriate selective agent for a particular selectable marker gene. Only seeds containing the mini-chromosome can germinate on the medium and further grow and develop into whole plants. Alternatively, seeds can be germinated in soil, and the germinating seedlings can then be sprayed with a selective agent appropriate for a selectable marker gene. Seedlings that do not contain mini-chromosome do not survive; only seedlings containing mini-chromosome can survive and develop into mature plants.

Genetic Methods for Analyzing Mini-Chromosome Performance:

In addition to direct transformation of a plant with a mini-chromosome, plants containing a mini-chromosome can be prepared by crossing a first plant containing the functional, stable, autonomous mini-chromosome with a second plant lacking the construct.

Fertile plants modified with mini-chromosomes can be crossed to other plant lines or plant varieties to study mini-chromosome performance and inheritance. In the first embodiment of this method, pollen from an adchromosomal plant can be used to fertilize the stigma of a non-adchromosomal plant. Mini-chromosome presence is scored in the progeny of this cross using the methods outlines in the preceding section. In the second embodiment, the reciprocal cross is performed by using pollen from a non-adchromosomal plant to fertilize the flowers of a adchromosomal plant. The rate of mini-chromosome inheritance in both crosses can be used to establish the frequencies of meiotic inheritance in male and female meiosis. In the third embodiment of this method, the progeny of one of the crosses just described are back-crossed to the non-adchromosomal parental line, and the progeny of this second cross are scored for the presence of genetic markers in the plant's natural chromosomes as well as the mini-chromosome. Scoring of a sufficient marker set against a sufficiently large set of progeny allows the determination of linkage or co-segregation of the mini-chromosome to specific chromosomes or chromosomal loci in the plant's genome. Genetic crosses performed for testing genetic linkage can be done with a variety of combinations of parental lines; such variations of the methods described are known to those skilled in the art.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

Example 1

*Brassica* Centromere Construction

BAC Library Construction

A Bacterial Artificial Chromosome (BAC) library was constructed from *Brassica* genomic DNA isolated from *B. oleraceae* variety "Wisconsin fastplants" and digested with the restriction enzyme MboI. This enzyme was chosen because it is methylation insensitive and therefore can be used to enrich BAC libraries for centromere DNA sequences.

Probe Identification and Selection

Three groups of *Brassica* repetitive genomic DNA including specific centromere-localized sequences, were initially compiled as candidate probes for hybridization with the BAC libraries (Table 3). These probes represented various classes of *Brassica* repetitive sequences including satellite repeats (heterochromatic/centromere-specific), rDNA, and hypermethylated DNA fractions.

Four probes were picked to interrogate the BAC libraries. These probes represented different groups of commonly found repetitive sequences in the *Brassica* genome. The probes selected (Table 3) were CANREP (the *Brassica* centromere satellite), rRNA (18S), HpaII (bulk methylated DNA purified from genomic DNA by failure to digest with the methylation-sensitive enzyme HpaII) and Sau3A (bulk methylated DNA purified from genomic DNA by failure to digest with the methylation-sensitive enzyme Sau3A1). The probes were prepared from cloned fragments or from bulk methylated DNA prepared from *Brassica* genomic DNA. Sequences from the clones used to prepare each probe are shown in Table 3. Probes were prepared and labeled with standard molecular biology methods.

TABLE 3

Brassica repetitive genomic sequence and BAC library probes

| Group # | Group Name | Probe Name | Description | Clone used for hyb | GenBank accession* | Reference or comment |
|---|---|---|---|---|---|---|
| 1 | rDNA | B6A10 (SEQ ID NO: 27) | 18S rRNA | 5012-5-6-A10 | AF207007.1 | |
| 2 | Cen repeat | BF1 (SEQ ID NO: 28) | CANREP | 5012-5-14-F01 | X68786.1 | CANREP is one of a large family of sequences hit by this sequence: gi\|860800\|emb\|X68786.1\|BJCANRD *B. juncea* Xle7-2EB gene gi\|860798\|emb\|X68784.1\|BJCANRB *B. juncea* Xle4-7B gene gi\|17706\|emb\|X12736.1\|BCREPC *Brassica campestris* DNA for satellite |
| 3 | Bulk repetitive DNA | Bhpaii | Purified methylated DNA fraction | N/A | N/A | |
| | | Bsau | Purified methylated DNA fraction | N/A | N/A | |

*Accession number of BLAST hit; actual sequence has not been deposited in Genbank

Library Interrogation and Data Analysis

The BAC clones from the libraries were spotted onto filters and the filters were hybridized with each of the probes to identify specific BAC clones that contain DNA from the group of sequences represented by the probe(s).

A total of 18,432 BAC clones from the library were interrogated with each of the probes described above using the following hybridization conditions: 0.5×SSC 0.25% SDS at 65 degrees for 15 minutes, followed by a wash at 65 degrees for a half hour. The hybridization intensities of the BAC clones with each probe were scanned to quantitate hybridization intensity for each clone. The outputs (scores of 1 to 10 based on the hybridization intensities, with 10 being the strongest hybridization intensity) were imported into a relational database, for further analysis and classification. The database contained a total of four tables. Each table contained at total of 18,432 entries: the hybridization scores of each BAC clone from the library to one of the probes used to interrogate the library. Data analysis was done using standard SQL (Structured Query Language) routines to find BACs that contain different groups of repetitive sequences.

Classification and Selection of BAC Clones for Mini-chromosome Construction

BAC clones containing centromeric/heterochromatic DNA were identified by their hybridization scores to different probes. The goal was to select BAC clones that contained a diverse set of various repetitive sequences. Nine classes of centromeric BAC clones were eventually chosen to cover the broadest possible range of centromeric/heterochromatic sequences for mini-chromosome construction. Detailed descriptions of each class and probe hybridization values for each class are shown in Table 4.

TABLE 4

Classification of *Brassica* BAC clones containing centromeric DNA

| Class | Properties | CANREP | HpaII | Sau3A | rDNA | # clones identified |
|---|---|---|---|---|---|---|
| A | Hi CANREP Hi Sau + Hpa | >=7 | >=7 | >=7 | N/A | 33 |
| B | Hi CANREP and Sau, Low rDNA | >=7 | N/A | >=7 | <=4 | 7 |
| C | Hi Sau and Hpa | N/A | >=8 | >=8 | N/A | 43 |
| D | Hi CANREP and Hpa | >=8 | >=7 | N/A | N/A | 123 |
| E | Hi CANREP and Sau | >=8 | N/A | >=7 | N/A | 59 |
| F | Hi CANREP only | >=7 | <=4 | <=4 | N/A | 15 |
| G | Hi Sau only | <=4 | <=4 | >=7 | N/A | 8 |
| H | Hi Hpa only | <=4 | >=7 | <=4 | N/A | 58 |
| I | Hi CANREP, middle meth | >=7 | 4 to 6 | 4 to 6 | N/A | 210 |
| Total** | | | | | | 556 |

*Values represent hybridization intensities of an individual BAC to each probe on a scale of 1 to 10. Values were normalized.
N/A = not applicable A number of representative clones from each class were chosen to yield a total of 190 BAC clones for further analysis by restriction digest fingerprinting. The BAC clones were fingerprinted based on restriction sites found in the centromere specific sequence(s). Fingerprinting was used to evaluate the sequence composition of the large numbers of BAC clones and to compare their similarity to each other by comparing the restriction enzyme digest fragment patterns. A sequence with a tandem repeated sequence will show a single intense band of unit repeat size when digested with a restriction enzyme that cuts within the unit repeat. Second, BAC clones with similar sequences will show similar patterns of restriction fragments in a digest.

BAC DNA was extracted from bacteria using methods familiar to those skilled in the art. For *Brassica*, the restriction enzyme HindIII was used to digest the BAC clones. Colonies containing the BAC clones were grown overnight at 37° C. with shaking at 250-300 rpm. DNA from the colonies was isolated using Qiagen solution P1, Qiagen solution P2, Qiagen solution P3, followed by phenol/chloroform extraction. Subsequently, 10 µl of each DNA sample was inserted in into a well on a 96-well plate. The DNA samples were mixed with 10 µl of the following mixture: 200 µl 10× buffer (New England Biolabs), 50 ul 100×BSA (New England Biolabs), 30 µl enzyme (varies depending on Class of BAC clone) and 750 µl water. The samples were covered and incubated at 37° C. 1-4 hours. After the incubation, loading dye was added to each sample and the DNA was analyzed on a 1% agarose gel in 1×TBE, 23 volts for 14-18 hours.

For *Brassica*, the restriction enzyme HindIII was used to digest the BAC clones. After fingerprinting, 100 BACs were selected based on the fingerprint analysis in order to represent the hybridization classes, with an emphasis on the different classes containing the centromere tandem repeat. Within the hybridization classes, fingerprints showing the 'simple ladder' of 'complex ladder' patterns of bands at integer multiples of the unit centromere tandem repeat were favored. Additionally, within the hybridization classes, BAC clones that represent the diversity of fingerprints were preferred. Also, clones with matching fingerprints were not chosen. In some cases, after a round of functional testing, additional BACs were selected for their similarity of hybridization class and fingerprint to a BAC that showed good centromere function.

Twenty five BAC clones (from the original 190) were selected for mini-chromosome construction based on the fingerprint class. These BACs are listed in Table 5. Fingerprints were classified into 3 classes: 1. high complexity (multiple large bands with no indication of laddering), 2. low ladder (predominant bands at multiples of the unit repeat size for the centromere satellite, and 3. complex ladder (features of both previous types). Subsequent to testing, 4 additional BACs (BB221., BB222, BB229 and BB280) were chosen from the library based on their similarity to BB5 in both hybridization pattern and fingerprint. The preferred BACS have an *. Table 6 lists the fingerprint classes for 11 selected *Brassica* BACs.

TABLE 5

Restriction endonuclease fingerprinting of 25 *Brassica* BACs

| BAC Number | BAC Class | Class Properties | Hind III Fingerprint Class | MiniC tested |
|---|---|---|---|---|
| BB2 | A | Hi CANREP, Meth | 3. Complex ladder | BB2R1-1 |
| BB5* | A | Hi CANREP, Meth | 3. Complex ladder | BB5R4-1 |
|  |  |  |  | BB5R4-3 |
| BB7 | B | Hi CANREP, Meth, low rDNA | 1. Complex | BB7R2-1 |
| BB11 | D | Hi CANREP, Meth (Hpa) | 2. Simple ladder | BB11R1-2 |
| BB15 | C | Hi Meth | 3. Complex ladder | BB15R4-1 |
| BB16* | D | Hi CANREP, Meth (Hpa) | 1. Complex | BB16R1-2 |
|  |  |  |  | BB16R1-3 |
| BB18* | D | Hi CANREP, Meth (Hpa) | 1. Complex | BB18R1-2 |
|  |  |  |  | BB18R2-3 |
| BB38* | F | Hi CANREP only | 3. Complex ladder | BB38R1-3 |
| BB39 | C | Hi Meth | n/d* | BB39R1-3 |
| BB40 | C | Hi Meth | n/d* | BB40R1-2 |
|  |  |  |  | BB40R1-3 |
|  |  |  |  | BB40R2-1 |
|  |  |  |  | BB40R3-1 |
| BB47* | D | Hi CANREP, Meth (Hpa) | 2. Simple ladder | BB47R1-2 |
| BB52 | E | Hi CANREP, Meth (Sau) | 1. Complex | BB52R1-1 |
| BB60* | D | Hi CANREP, Meth (Hpa) | 3. Complex ladder | BB60R1-1 |
| BB63* | D | Hi CANREP, Meth (Hpa) | 2. Simple ladder | BB63R1-1 |

TABLE 5-continued

Restriction endonuclease fingerprinting of 25 *Brassica* BACs

| BAC Number | BAC Class | Class Properties | Hind III Fingerprint Class | MiniC tested |
|---|---|---|---|---|
| BB64 | I | Hi CANREP, Moderate Meth | 1. Complex | BB64R1-1 |
| BB70* | I | Hi CANREP, Moderate Meth | 2. Simple ladder | BB70R1-3 |
| BB71* | E | Hi CANREP, Meth (Sau) | 3. Complex ladder | BB71R1-1 |
| BB76* | I | Hi CANREP, Moderate Meth | 1. Complex | BB76R1-3 |
| BB102 | D | Hi CANREP, Meth (Hpa) | n/d* | BB102R1-1 |
| BB104* | I | Hi CANREP, Moderate Meth | n/d* | BB104R1-2 |
| BB105 | I | Hi CANREP, Moderate Meth | 2. Simple ladder | BB105R1-2 |
| BB106 | D | Hi CANREP, Meth (Hpa) | 2. Simple ladder | BB106R1-2 |
| BB119 | I | Hi CANREP, Moderate Meth | 3. Complex ladder | BB119R1-1 |
| BB129 | D | Hi CANREP, Meth (Hpa) | n/d* | BB129R1-1 |
| BB140 | A | Hi CANREP, Meth | 2. Simple ladder | BB140R1-3 |
| BB221 | A | Hi CANREP, Meth | 3. Complex ladder | BB221R2-1 |
| BB222 | A | Hi CANREP, Meth | 3. Complex ladder | BB222R2-7 |
| BB229 | A | Hi CANREP, Meth | 3. Complex ladder | BB229R2-6 |
| BB280 | A | Hi CANREP, Meth | 3. Complex ladder | BB280R2-3 | n/d*: Gel too faint to score

TABLE 6

Restriction endonuclease fingerprint classification for 11 selected *Brassica* BACs

| BAC Number | Class | Class Properties | Hind III fingerprint class |
|---|---|---|---|
| BB5 | A | Hi CANREP, Meth | 3. Complex ladder |
| BB16 | D | Hi CANREP, Meth (Hpa) | 1. Complex |
| BB18 | D | Hi CANREP, Meth (Hpa) | 1. Complex |
| BB38 | F | Hi CANREP only | 3. Complex ladder |
| BB47 | D | Hi CANREP, Meth (Hpa) | 2. Simple ladder |
| BB60 | D | Hi CANREP, Meth (Hpa) | 3. Complex ladder |
| BB63 | D | Hi CANREP, Meth (Hpa) | 2. Simple ladder |
| BB70 | I | Hi CANREP, Moderate Meth | 2. Simple ladder |
| BB71 | E | Hi CANREP, Meth (Sau) | 3. Complex ladder |
| BB76 | I | Hi CANREP, Moderate Meth | 1. Complex |
| BB104 | I | Hi CANREP, Moderate Meth | n/d* | n/d*: Gel too faint to score

*B. oleraceae* (broccoli) BAC BB5 was deposited with the American Type Culture Collection (ATCC) P.O. Box 1549 Manassas, Va. 20108, USA on Feb. 23, 2005 and assigned Accession No. PT-6601.

To determine the molecular weight of centromere fragments in the BAC libraries, a frozen sample of bacteria harboring a BAC clone was grown in selective liquid media and the BAC DNA harvested using a standard alkaline lysis method. The recovered BAC DNA was restriction digested and resolved on an agarose gel. Centromere fragment size was determined by comparing to a molecular weight standard.

Cre/lox recombined donor DNA and BAC centromere DNA was delivered into bacteria and plated on selective solid media. To determine the molecular weight of centromere fragments in retrofitted mini-chromosomes, three bacterial colonies harboring a mini-chromosome were independently grown in selective liquid media and the BAC DNA harvested using a standard alkaline lysis method. The recovered BAC DNA was restriction digested and resolved on an agarose gel. Centromere fragment size was determined by comparing to a molecular weight standard. If variation in centromere size was noted, the mini-chromosome with the largest centromere insert was used for further experimentation.

Example 2

Assembly and Components of Brassica Mini-Chromosomes

Two methods have been developed to construct plant mini-chromosomes. The first method relies on cre/lox recombination in which a bacterial mini-chromosome (BAC) vector containing plant centromeric DNA and a loxP recombination site is recombined, by the action of cre recombinase, with a donor vector carrying plant gene expression cassettes to generate a plant mini-chromosome. The second method uses restriction enzyme digestion and ligation to produce two DNA fragments with compatible cohesive ends: 1) a vector fragment containing plant gene expression cassettes and ii) a centromere fragment. The two fragments are ligated into a circular structure to form a plant mini-chromosomes.

The components of the Brassica mini-chromosomes include fluorescent reporter genes, a selectable maker gene, a Brassica centromere sequence identified in a Brassica BAC library, a telomere sequence, a cloning vector and a donor vector. These components are described in detail below.

Mini-Chromosome Construction by Cre-Lox Recombination

Cre recombinase-mediated exchange was used to construct mini chromosomes by combining the plant centromere fragments cloned in pBeloBACT1 with a donor plasmid (e.g. pCHR151, Table 10). The recipient BAC vector carrying the plant centromere fragment contained a loxP recombination site; the donor plasmid contained two such sites, flanking the sequences to be inserted into the recipient BAC. Mini-chromosomes were constructed using a two-step method. First, the donor plasmid was linearized to allow free contact between the two loxP site; in this step the backbone of the donor plasmid is eliminated. In the second step, the donor molecules were combined with centromere BACs and were treated with Cre recombinase, generating circular mini-chromosomes with all the components of the donor and recipient DNA. Mini-chromosomes were delivered into E. coli and selected on medium containing kanamycin and chloramphenicol. Only vectors that successfully cre recombined and contained both selectable markers survived in the medium. Mini-chromosomes were extracted from bacteria and restriction digested to verify DNA composition and calculate centromere insert size (Table 7).

TABLE 7

Cre/Lox Recombined Mini-chromosomes for Brassica

| Mini-Chromosome | Brassica Centromere Fragment | Centromere insert (kbp) | Donor Vector |
|---|---|---|---|
| BB5R4-1 | 5 | 64 | pCHR151 |
| BB5R10-1 | 5 | 48 | pCHR171A |
| BB5R14-6 | 5 | 52 | pCHR487 |
| BB5R15-4 | 5 | 52 | pCHR488 |
| BB5R16-6 | 5 | 50 | pCHR489 |
| BB71R1-1 | 71 | 30 | pCHR151 |
| BB221R2-1 | 221 | 70 | pCHR487 |
| BB222R2-7 | 222 | 60 | pCHR487 |
| BB229R2-6 | 229 | 60 | pCHR487 |
| BB280R2-3 | 280 | 97 | pCHR487 |

Mini-chromosome Construction by Restriction-Ligation

Mini-chromosomes were also constructed using standard cloning procedures. For example, a BAC containing a centromere fragment was digested with a restriction endonuclease that created sticky ends, as for example, but not limited to NotI, which was commonly used for this purpose. The digested DNA was then electrophoresed to purify the centromere fragment into a single band. The electrophoresis was carried out with either conventional agarose gel electrophoresis with a linear electric field, or CHEF gel electrophoresis using an electric field that switches its orientation in the course of the run. When the electrophoresis was complete, the centromere fragment was visualized by ethidium bromide staining and illumination under ultraviolet light. The band corresponding to centromere DNA was excised, and the DNA was purified from the gel using conventional method for gel-purifying DNA fragments from agarose gels. The purified fragment was then ligated with a vector fragment that contains a low-copy E. coli backbone (e.g. the F' plasmid replicon) and one or more plant-expressed genes. The vector fragment was digested with a restriction endonuclease leaving compatible sticky ends to those present on the centromere fragment. Alternatively, both fragments may be blunt.

To achieve a high rate of insertion of the centromere fragment into the vector, the phosphate groups were removed from the ends of the vector molecule by treating this DNA molecule with phosphatase; this step prevented ligation of the vector molecule to itself or to other vector molecules. After ligating vector DNA and centromere fragment, the mini-chromosomes were delivered into E. coli and selected on medium containing antibiotics corresponding to the antibiotic-resistance genes present on the vector molecule (e.g. kanamycin and chloramphenicol). Mini-chromosomes are extracted from bacteria and restriction digested to verify DNA composition and calculate centromere insert size (Table 8).

TABLE 8

Restriction-Ligation Mini-chromosomes

| Mini-Chromosome | Brassica Centromere Fragment | Centromere insert (kbp) | Donor Vector |
|---|---|---|---|
| pCHR543 | 5R4-1 | 64 | pCHR510 |
| pCHR591 | 5R4-1 | 64 | pCHR579 |
| pCHR593 | 5R4-1 | 64 | pCHR581 |
| pCHR816 | 5R4-1 | 64 | pCHR806 |
| pCHR817 | 5R4-1 | 64 | pCHR807 |
| pCHR818 | 5R4-1 | 64 | pCHR808 |
| pCHR819 | 5R4-1 | 64 | pCHR809 |
| pCHR820 | 5R4-1 | 64 | pCHR810 |
| pCHR821 | 5R4-1 | 64 | pCHR811 |
| pCHR823 | 5R4-1 | 64 | pCHR813 |
| pCHR824 | 5R4-1 | 64 | pCHR814 |
| pCHR825 | 5R4-1 | 64 | pCHR815 |
| pCHR955 | 5R4-1 | 64 | pCHR945 |
| pCHR958 | 5R4-1 | 64 | pCHR948 |
| pCHR964 | 15R4-1 | 121 | pCHR807 |
| pCHR965 | 15R4-1 | 121 | pCHR815 |
| pCHR967 | 16R1-2 | 156 | pCHR815 |
| pCHR970 | 52R1-1 | 99 | pCHR807 |
| pCHR972 | 60R1-1 | 49 | pCHR807 |
| pCHR973 | 60R1-1 | 49 | pCHR815 |

Cloning Vector

The vector, pBeloBAC11, is an E. coli plasmid cloning vector based on the F' plasmid replicon of E. coli. The vector contained a chloramphenicol resistance gene for selection of the plasmid in bacteria, repE, sopA/B/and C for maintenance of the plasmid in bacteria, and a LoxP recombination site for specific cleavage by Cre recombinase. A description of all the genes contained within the vector and the location of the gene within the vector are set out in Table 9.

TABLE 9 pBeloBAC11 components

| Genetic Element | Size (base pair) | Location (bp) | Details |
|---|---|---|---|
| Bacterial Chloramphenicol resistance | 660 | 766-1425 (complementary) | Bacterial selectable marker |
| ori2 | 67 | 2370-2436 | F' plasmid origin of replication from E. coli |
| repE | 755 | 2765-3520 | mediation of replication complex at Ori2 (Mori, H et. al, J Mol Biol. 1986 Nov. 5; 192(1): 1-15) |
| SopA | 1166 | 4108-5274 | partition of plasmid to bacterial daughter cells (Mori, H et. al, J Mol Biol. 1986 Nov. 5; 192(1): 1-15) |
| SopB | 971 | 5274-6245 | partition of plasmid to bacterial daughter cells (Mori, H et. al, J Mol Biol. 1986 Nov. 5; 192(1): 1-15) |
| SopC | 474 | 6318-6791 | partition of plasmid to bacterial daughter cells (Mori, H et. al, J Mol Biol. 1986 Nov. 5; 192(1): 1-15) |
| cos | 400 | 7050-7449 | Lambda DNA recognition sequence for phage packaging |
| LoxP | 34 | 7467-7500 | Recombination site for Cre mediated recombination (Arenski et. al 1983, Abremski et. al 1984) |

Source of Coding Regions Used in Plant-Expressed Genes

The fluorescent reporter genes DsRed, and AmCyan were isolated from Athozoa species; and ZsYellow and ZsGreen were isolated from *Zoanthus* sp (Matz et. al. *Nature Biotechnol.* 1999 October; 17:969). These reporter genes express proteins that are homologous to Green Fluorescent Protein (GFP), which is a commonly used reporter gene in various biological systems, including plants. All fluorescent reporter genes were obtained from Clontech Corporation (Palo Alto, Calif.).

The selectable marker gene MerA is a mercuric ion reductase which converts toxic $Hg^{2+}$ to less toxic metallic mercury. This gene was originally isolated from *E. coli* and then modified to accommodate improved expression in plants (Rugh et. al. *PNAS* 1996 93:318).

The selectable marker gene NPTII (neomycin phosphotransferase II) has been commonly used in plants as a selectable agent (Bevan et. al. *Nature* 1983 304:184). The original source of this gene is *E. coli*.

Donor Vectors Used to Construct Mini-Chromosomes Via Cre/Lox Recombinations pCHR151

The plasmid pCHR151 was developed using the commercially available high copy number *E. coli* cloning vector pUC19 (Yanisch-Perron et al., (1985) Gene 33, 103-119). The plasmid backbone was modified with the bacterial kanamycin selectable marker for maintenance of the plasmid in bacterial hosts, a pair of complementary loxP sites and a polylinker that facilitated the modular assembly of several plant-expressed genes for expression in plant mini-chromosomes. Using standard cloning methods, plant-expressed gene cassettes were introduced into the modified pUC19 vector to construct pCHR151. This vector includes DsRed with a nuclear localization signal (Clontech Corporation, Palo Alto Calif.), which was regulated by the *Arabidopsis* UBQ10 promoter (At4g05320) and the *Arabidopsis* pyruvate kinase terminator (At5g52920). The vector also included the *E. coli* MerA gene regulated by the *Arabidopsis thaliana* ACT2 promoter and terminator. The vector also contains a high-copy *E. coli* replication origin and an ampicillin bacterial selectable marker. Mini-chromosome genetic elements within the pCHR151 vector are set out in Table 10.

Prior to using pCHR151 to construct plant mini-chromosomes, pCHR151 was digested with restriction endonucleases to linearize the pCHR151 plasmid and remove the high copy origin of replication and the bacterial ampicillin selectable marker, leaving loxP recombination sites on each end of the linear fragment. The resulting linearized vector was cre recombined in vitro to generate circular donor pCHR151 plasmids lacking a bacterial origin of replication and the ampicillin selectable marker. The donor pCHR151 construct was used to construct plant mini-chromosomes.

TABLE 10

Donor Components of pCHR151

| Genetic Element | Size (bp) | Location (bp) | Details |
|---|---|---|---|
| Act2 promoter + intron | 1482 | 7473-8954 (complementary) | The *Arabidopsis thaliana* promoter Actin 2 plus natural intron. |
| MerA | 1695 | 5776-7470 (complementary) | Plant selectable marker providing resistance to mercuric ions (Rugh et.al. PNAS 1996 93: 3182). |
| Act2 terminator | 800 | 4823-5622 (complementary) | *Arabidopsis thaliana* Actin 2 terminator. |
| Bacterial Kanamycin | 817 | 3825-4641 (complementary) | Bacterial kanamycin selectable marker |
| Pyruvate kinase terminator | 332 | 3349-3680 | *Arabidopsis thaliana* Pyruvate kinase terminator (At5g52920) |
| DsRed2 + NLS | 780 | 2435-3214 | Nuclear localized red fluorescent protein from *Discosoma* sp. (Matz, M et. al *Nat Biotechnol* 1999 Dec.; 17(12): 1227). |
| UBQ10 Promoter | 2038 | 361-2398 | *Arabidopsis thaliana* polyubiquitin promoter (At4g05320) |
| LoxP | 34 | 346-379 and 9005-9038 | Recombination site for Cre mediated recombination (Arenski et. al 1983, Abremski et. al 1984) | pCHR171A

The vector pCHR171A vector was used to generate linear mini-chromosomes by introducing plant telomere sequences. The donor region of pCHR171A is identical to pCHR151 (described above) with the exception of two plant telomeric regions located on both sides of the bacterial kanamycin gene. pCHR171A was constructed using standard cloning methods. Similar to construction of pCHR151, the low copy bacterial backbone of pBeloBAC11 was used in place of the pUC19 high copy backbone to stabilize the addition of the highly repetitive plant telomeric sequences. The bacterial tetracycline gene replaced the pBeloBAC11 chloramphenicol gene for bacterial selection.

Naturally occurring plant telomeres are composed of a seven nucleotide repeat (TAAACCC). Plant telomeres were polymerized using standard PCR methods to generate approximately 800 base pair telomere arrays. The telomere sequences were ligated using standard methods on both sides of the bacterial kanamycin gene. Two unique I-PpoI homing endonuclease restriction sites were introduced between each telomere and the kanamycin gene for linearization of the final mini-chromosome construct. Mini-chromosome genetic elements within the pCHR171 vector are set out in Table 11 below.

kanamycin and chloramphenicol. Only vectors that successfully cre recombined contained both selectable markers and were easily selected from non-recombined events. Mini-chromosomes were extracted from bacteria and restriction digested to verify DNA composition and calculate centromere insert size.

To generate linear mini-chromosomes constructed with donor pCHR171A, *E. coli* harboring the mini-chromosomes were grown in selective bacterial growth medium and purified using standard alkaline lysis procedures. Purified mini-chromosomes were restriction digested in vitro with homing endonuclease enzyme I-PpoI following standard restriction digest procedures. Linearization of the mini-chromosome results in the removal of the bacterial kanamycin gene cassette leaving plant telomeres flanking both ends of the linear mini-chromosome. Linear mini-chromosomes were ethanol precipitated and used for plant transformation.

TABLE 11

Donor Components of pCHR171A

| Genetic Element | Size (base pair) | Location (bp) | Details |
| --- | --- | --- | --- |
| Act2 promoter + intron | 1482 | 97-1578 | The *Arabidopsis thaliana* promoter Actin 2 plus natural intron. |
| MerA | 1695 | 1581-3275 | Plant selectable marker providing resistance to mercuric ions (Rugh et.al. PNAS 1996 93: 3182). |
| Act2 terminator | 800 | 3429-4228 | *Arabidopsis thaliana* Actin 2 terminator. |
| Plant telomere | 759 | 4277-5035 | Plant telomere PCR based on plant consensus telomere sequence |
| Bacterial Kanamycin | 817 | 5211-6027 | Bacterial kanamycin selectable marker |
| Plant telomere | 760 | 6161-6920 | Plant telomere PCR based on plant consensus telomere sequence |
| Pyruvate kinase terminator | 332 | 6968-7299 | *Arabidopsis thaliana* Pyruvate kinase terminator (At5g52920) |
| DsRed2 + NLS | 780 | 7434-8213 | Nuclear localized red fluorescent protein from *Discosoma* sp. (Matz, M et. al *Nat Biotechnol* 1999 Dec.; 17(12): 1227). |
| UBQ10 Promoter | 2038 | 8250-10287 | *Arabidopsis thaliana* polyubiquitin promoter (At4g05320) |
| LoxP | 34 | 47-80 and 10303-10336 | Recombination site for Cre mediated recombination (Arenski et. al 1983, Abremski et. al 1984) |

To generate plant mini-chromosomes with pCHR171A, the vector was digested and cre treated using the same methods as described for pCHR151 to generate donor pCHR171A. Restriction digests of pCHR171A removed the low copy origin of replication and the bacterial tetracycline selectable marker, leaving loxP recombination sites on each end of the linear fragment. The resulting linearized vector was cre recombined in vitro to generate circular donor pCHR171A plasmids lacking a bacterial origin of replication and the tetracycline selectable marker.

Cre recombinase-mediated exchange was used to construct mini-chromosomes by combining the plant centromere fragments of pBeloBAC11 with the donor vector pCHR171A. The recipient BAC vector carrying the plant centromere fragment contained a loxP recombination site, facilitating the introduction of donor DNA via the action of cre recombinase. Using purified cre recombinase in vitro, BAC centromere recipients were combined with donor pCHR171A DNA, generating circular mini-chromosomes with all the components of the donor and recipient DNA. Mini-chromosomes were delivered into *E. coli* and selected on medium containing Other Donor Vectors used via Cre/Lox Recombination The pCHR487 mini-chromosome donor vector was also used to generate *Brassica* mini-chromosomes. In this vector, the Act2 promoter-MerA gene cassette of pCHR151 was replaced with the yeast TEF2 promoter from *Saccharomyces cerevisiae* and the plant kanamycin selectable marker NptII from *E. coli*. To enhance the stability of the NptII transcript, the *Arabidopsis thaliana* UBQ10 intron was inserted 5' of the yeast TEF2 promoter and 3' of the NptII gene. The UBQ10 intron is a naturally occurring component of the transcribed sequences from the *Arabidopsis thaliana* UBQ10 gene and was present in the UB10 promoter in pCHR151. Standard restriction digest and cloning methods were used to generate pCHR487. Construction of plant mini-chromosomes using pCHR487 was performed as described for pCHR151. As with pCHR151, the circular donor pCHR487 lacked a bacterial origin of replication and the bacterial ampicillin selectable marker. Mini-chromosome genetic elements within the pCHR487 vector are set out in Table 12.

TABLE 12

Donor Components of pCHR487

| Genetic Element | Size (base pair) | Location (bp) | Details |
|---|---|---|---|
| UBQ10 promoter | 2038 | 361-2398 | *Arabidopsis thaliana* polyubiquitin promoter (At4g05320) |
| DsRed2 + NLS | 780 | 2435-3214 | Nuclear localized red fluorescent protein from *Discosoma* sp. (Matz, M et. al *Nat Biotechnol* 1999 Dec.; 17(12): 1227). |
| Pyruvate kinase terminator | 332 | 3349-3680 | *Arabidopsis thaliana* pyruvate kinase terminator (At5g52920) |
| Bacterial Kanamycin | 817 | 3825-4641 | Bacterial kanamycin selectable marker |
| Act2 terminator | 800 | 4823-5622 | *Arabidopsis thaliana* Actin 2 terminator |
| NptII | 795 | 5685-6479 | Neomycin phosphotransferase II plant selectable marker |
| UBQ10 intron | 359 | 6507-6865 | PCR amplified *Arabidopsis thaliana* intron from UBQ10 gene (At4g05320) for stabilization of NptII gene transcript and increase protein expression levels |
| TEF2 Promoter | 2000 | 6880-8879 | *Saccharomyces cerevisiae* translation elongation factor alpha promoter for expression of NptII |
| LoxP | 34 | 312-345 & 8898-8931 | Recombination site for Cre mediated recombination (Arenski et. al 1983, Abremski et. al 1984) |

In the pCHR488 mini-chromosome donor vector, the yeast TEF2 promoter of pCHR487 was replaced with the yeast GPD1 promoter which drove the plant selectable marker NptII. The yeast GPD1 promoter was PCR amplified from *Saccharomyces cerevisiae* genomic DNA using standard PCR methods. Standard cloning methods were also used to replace the TEF2 promoter and insert the yeast GPD1 promoter. For construction of mini-chromosomes, donor pCHR488 was generated as described for pCHR151. As with pCHR151, the circular donor pCHR488 lacks a bacterial origin of replication and the bacterial ampicillin selectable marker. The donor pCHR488 construct was used to construct plant mini-chromosomes as described for pCHR151. Mini-chromosome genetic elements within the pCHR488 vector are set out in Table 13

TABLE 13

Donor Components of pCHR488

| Genetic Element | Size (base pair) | Location (bp) | Details |
|---|---|---|---|
| UBQ10 promoter | 2038 | 361-2398 | *Arabidopsis thaliana* polyubiquitin promoter (At4g05320) |
| DsRed2 + NLS | 780 | 2435-3214 | Nuclear localized red fluorescent protein from *Discosoma* sp. (Matz, M et. al *Nat Biotechnol* 1999 Dec.; 17(12): 1227). |
| Pyruvate kinase terminator | 332 | 3349-3680 | *Arabidopsis thaliana* pyruvate kinase terminator (At5g52920) |
| Bacterial Kanamycin | 817 | 3825-4641 | Bacterial kanamycin selectable marker |
| Act2 terminator | 800 | 4823-5622 | *Arabidopsis thaliana* Actin 2 terminator |
| NptII | 795 | 5685-6479 | Neomycin phosphotransferase II plant selectable marker |
| UBQ10 intron | 359 | 6500-6859 | PCR amplified *Arabidopsis thaliana* intron from UBQ10 gene (At4g05320) for stabilization of NptII gene transcript and increase protein expression levels |
| GPD1 Promoter | 2000 | 6880-8879 | *Saccharomyces cerevisiae* glycerol-3-phosphate dehydrogenase (NAD+) promoter for expression of NptII |
| LoxP | 34 | 312-345 & 8898-8931 | Recombination site for Cre mediated recombination (Arenski et. al 1983, Abremski et. al 1984) |

In the pCHR489 mini-chromosome donor vector, the yeast TEF2 promoter of pCHR487 was replaced with the *Drosophila melanogaster* Grim fly promoter for driving the plant selectable marker NptII. The Grim fly promoter was PCR amplified from *Drosophila melanogaster* genomic DNA using standard PCR methods. Standard cloning methods were used to replace the TEF2 promoter in pCHR487 with the Grim fly promoter to generate pCHR489. For construction of mini-chromosomes, donor pCHR489 was generated as described for pCHR151. As with pCHR151, the circular donor pCHR489 lacks a bacterial origin of replication and the bacterial ampicillin selectable marker. The donor pCHR489 construct was used to construct plant mini-chromosomes as described for pCHR151. Mini-chromosome genetic elements within the pCHR489 vector are set out in Table 14.

TABLE 14

Donor Components of pCHR489

| Genetic Element | Size (base pair) | Location (bp) | Details |
| --- | --- | --- | --- |
| UBQ10 promoter | 2038 | 361-2398 | *Arabidopsis thaliana* polyubiquitin promoter (At4g05320) |
| DsRed2 + NLS | 780 | 2435-3214 | Nuclear localized red fluorescent protein from *Discosoma* sp. (Matz, M et. al *Nat Biotechnol* 1999 Dec.; 17(12): 1227). |
| Pyruvate kinase terminator | 332 | 3349-3680 | *Arabidopsis thaliana* pyruvate kinase terminator (At5g52920) |
| Bacterial Kanamycin | 817 | 3825-4641 | Bacterial kanamycin selectable marker |
| Act2 terminator | 800 | 4823-5622 | *Arabidopsis thaliana* Actin 2 terminator |
| NptII | 795 | 5685-6479 | Neomycin phosphotransferase II plant selectable marker |
| UBQ10 intron | 359 | 6507-6865 | PCR amplified *Arabidopsis thaliana* intron from UBQ10 gene (At4g05320) for stabilization of NptII gene transcript and increase protein expression levels |
| Grim Fly Promoter | 2191 | 6880-8879 | PCR amplified promoter of grim (AKA BcDNA: RE28551) from *Drosophila melanogaster* |
| LoxP | 34 | 312-345 & 9081-9114 | Recombination site for Cre mediated recombination (Arenski et. al 1983, Abremski et. al 1984) |

Vectors Used to Construct Mini-Chromosomes Via Standard Cloning Methods:

pCHR510

As in pCHR151, pCHR510 contains DsRed with a nuclear localization signal and is regulated by the *Arabidopsis* UBQ10 promoter. The *Arabidopsis* pyruvate kinase terminator (At5g52920) was replaced by standard cloning procedures with the *Arabidopsis thaliana* triose phosphate isomerase terminator to prevent redundant use of the *Arabidopsis* pyruvate kinase terminator (At5g52920) in pCHR510. In addition, the *E. coli* MerA gene cassette was replaced with the plant selectable marker NptII regulated by the *Drosophila melanogaster* Grim fly promoter plus *Arabidopsis* UBQ10 intron and the *Arabidopsis* pyruvate kinase terminator (At5g52920). The vector also included a ZsGreen fluorescent gene (Clontech Corporation, Palo Alto Calif.) regulated by the *Arabidopsis* Act2 promoter plus naturally occurring intron and the *Arabidopsis* Act2 terminator. The high-copy *E. coli* backbone of pUC19 and ampicillin bacterial selectable marker were replaced with the low copy pBeloBAC11 backbone with the bacterial streptomycin resistance gene replacing the chloramphenicol resistance gene. An *Arabidopsis thaliana* ST11 sub-telomeric fragment was introduced upstream of the Grim fly promoter to isolate the Grim fly promoter from possible promoter silencing when a centromere fragment was ligated into the donor vector. Mini-chromosome genetic elements within the pCHR510 vector are set out in Table 15 below.

TABLE 15 pCHR510 DNA donor components

| Genetic Element | Size (base pairs) | Location (bp) | Details |
| --- | --- | --- | --- |
| Bacterial streptomycin resistance | 10111 | 16912-17922 | Bacterial selectable marker |
| ori2 | 67 | 19158-19224 | F' plasmid origin of replication from E. coli |
| repE | 755 | 19553-20308 | mediation of replication complex at Ori2 (Mori, H et. al, J Mol Biol. 1986 Nov. 5; 192(1): 1-15) |
| SopA | 1166 | 20896-22062 | partition of plasmid to bacterial daughter cells (Mori, H et. al, J Mol Biol. 1986 Nov. 5; 192(1): 1-15) |
| SopB | 971 | 22062-23033 | partition of plasmid to bacterial daughter cells (Mori, H et. al, J Mol Biol. 1986 Nov. 5; 192(1): 1-15) |
| SopC | 517 | 23106-23623 | partition of plasmid to bacterial daughter cells (Mori, H et. al, J Mol Biol. 1986 Nov. 5; 192(1): 1-15) |
| LoxP | 34 | 26-59 and 16212-16245 | Recombination site for Cre mediated recombination (Arenski et. al 1983, Abremski et. al 1984) |
| ST11 subtelomeric DNA | 4682 | 69-4750 (complementary) | Arabidopsis thaliana subtelomenic DNA from Chromosome 5 |
| Grim Promoter | 2187 | 4766-6956 | PCR amplified Drosophila melanogaster Grim gene promoter for expression of NptII gene in plants. |
| UBQ10 intron | 359 | 6963-7322 | PCR amplified Arabidopsis thaliana intron from UBQ10 gene (At4g05320) for stabilization of NptII gene transcript and increase protein expression levels. |
| NptII | 795 | 7350-8144 | Neomycin phosphotransferase II plant selectable marker |
| Pyruvate kinase terminator | 332 | 8212-8543 | Arabidopsis thaliana Pyruvate kinase terminator (At5g52920) |
| Bacterial Kanamycin | 817 | 8731-9547 | Bacterial kanamycin selectable marker |
| Act2 promoter + intron | 1482 | 9690-11171 | The Arabidopsis thaliana promoter Actin 2 plus natural intron. |
| ZsGreen | 695 | 11195-11890 | Matz et. al. Nature Biotechnol. 1999 Oct.; 17: 969 |
| Act2 terminator | 800 | 11931-12730 | Arabidopsis thaliana Actin2 gene terminator. |
| Triose phosphate isomerase | 450 | 12759-13208 (complementary) | Arabidopsis thaliana Triose phosphate isomerase gene terminator |
| DsRed2 + NLS | 780 | 13343-14122 (complementary) | Nuclear localized red fluorescent protein from Discosoma sp. (Matz, M et. al Nat Biotechnol 1999 Dec.; 17(12): 1227). |
| UBQ10 Promoter | 2038 | 14159-16196 (complementary) | Arabidopsis thaliana polyubiquitin promoter (At4g05320) |

To construct mini-chromosomes using pCHR510, the vector was linearized using standard restriction digestion procedures. The Brassica centromere fragment from mini-chromosome BB5R4-1 was restriction digested using Not I and ligated into pCHR510 using standard cloning procedures to generate the mini-chromosome pCHR543. Mini-chromosomes were delivered into E. coli and grown in selective medium. Mini-chromosomes were extracted from bacteria and restriction digested to verify DNA composition and verify centromere insert size.

pCHR579

The pCHR579 mini-chromosome donor vector was constructed using the same method to construct the pCHR510, without replacing the bacterial chloramphenicol gene in the low copy pBeloBAC11 backbone. Using standard cloning methods the bacterial kanamycin gene was replaced with a bacterial kanamycin selectable marker surrounded by two plant telomere sequences and two unique 1-PpoI homing endonuclease sequences as described in pCHR171A. Mini-chromosomes using pCHR579 were constructed as described for pCHR510 using BB5R4-1 centromeric DNA to construct pCHR591. pCHR591 was linearized as described for mini-chromosomes described above for pCHR171A. Mini-chromosome genetic elements within the pCHR579 vector are set out in Table 16 below.

TABLE 16 pCHR579 DNA donor components

| Genetic Element | Size (base pairs) | Location (bp) | Details |
|---|---|---|---|
| Bacterial chloramphenicol resistance | 660 | 18022-18681 | Bacterial selectable marker |
| ori2 | 67 | 19685-19751 | F factor origin of replication from *E. coli* |
| repE | 755 | 20080-20835 | mediation of replication complex at Ori2 (Mori, H et. al, J Mol Biol. 1986 Nov. 5; 192(1): 1-15) |
| SopA | 1166 | 214230-22589 | partition of plasmid to bacterial daughter cells (Mori, H et. al, J Mol Biol. 1986 Nov. 5; 192(1): 1-15) |
| SopB | 971 | 22589-23560 | partition of plasmid to bacterial daughter cells (Mori, H et. al, J Mol Biol. 1986 Nov. 5; 192(1): 1-15) |
| SopC | 517 | 23633-24150 | partition of plasmid to bacterial daughter cells (Mori, H et. al, J Mol Biol. 1986 Nov. 5; 192(1): 1-15) |
| LoxP | 34 | 26-59 | Recombination site for Cre mediated recombination (Arenski et. al 1983, Abremski et. al 1984) |
| ST11 sub-telomeric DNA | 4682 | 69-4750 (complementary) | *Arabidopsis thaliana* subtelomeric DNA from Chromosome 5 |
| Grim Fly Promoter | 2187 | 4766-6956 | PCR amplified *Drosophila melanogaster* Grim gene promoter for expression of NptII gene in plants. |
| UBQ10 intron | 359 | 6963-7322 | PCR amplified *Arabidopsis thaliana* intron from UBQ10 promoter (At4g05320) for stabilization of NptII gene transcript and increase protein expression levels. |
| NptII | 795 | 7350-8144 | Kanamycin plant selectable marker |
| Pyruvate kinase terminator | 332 | 8212-8543 | *Arabidopsis thaliana* Pyruvate kinase terminator (At5g52920) |
| Plant telomere | 759 | 8598-9356 | Plant telomere PCR based on plant consensus telomere sequence |
| Bacterial Kanamycin | 817 | 9532-10348 | Bacterial kanamycin selectable marker |
| Plant telomere | 759 | 10482-11241 | Plant telomere PCR based on plant consensus telomere sequence |
| Act2 promoter + intron | 1482 | 11287-12768 | The *Arabidopsis thaliana* promoter Actin 2 plus natural intron. |
| ZsGreen | 695 | 12792-13487 | Matz et.al. *Nature Biotechnol.* 1999 Oct.; 17: 969 |
| Act2 terminator | 800 | 13528-14327 | *Arabidopsis thaliana* Actin2 gene terminator. |
| Triose phosphate isomerase | 450 | 14356-14805 (complementary) | *Arabidopsis thaliana* Triose phosphate isomerase gene terminator |
| DsRed2 + NLS | 780 | 14940-15719 (complementary) | Nuclear localized red fluorescent protein from *Discosoma* sp. (Matz, M et. al *Nat Biotechnol* 1999 Dec.; 17(12): 1227). |
| UBQ10 Promoter | 2038 | 15756-17793 (complementary) | *Arabidopsis thaliana* polyubiquitin promoter (At4g05320) | pCHR581

The pCHR581 mini-chromosome donor vector was constructed using standard cloning procedures. The vector was constructed as pCHR579 with no ST11 sub-telomeric DNA. Mini-chromosome genetic elements within the pCHR581 vector are set out in Table 17 below.

ST9 is an *Arabidopsis thaliana* sub-telomeric sequence from centromere 5 (bases 3708-195 (3513 bp); Database: ATH1_chr5.1con), which was amplified with the following oligo nucleotides: CHHZ-199 (GGTGGTCGGCCGGAG-CACAA GCGGGCCAAGCCCATGCTTG; SEQ ID NO: 29) and CHHZ-202 (GGTGGTCGGCCGCAGGTTG-CATATGAATCTTTA ACTGACAG; SEQ ID NO: 30). ST10 is an *Arabidopsis thaliana* sub-telomeric sequence from centromere 5 (bases 195-3708 (3513 bp); Database: ATH1_chr5.1con), which was amplified with the following oligo nucleotides: CHHZ-200 (GGTGGTCGGCCGCGAG-CACAAGCGGGCCAAGCCCATGCTTG; SEQ ID NO: 31) and CHHZ-201 (GGTGGTCGGCCGTCAGGTTGCATAT-GAATCTT TAACTGACAG: SEQ ID NO: 32). ST11 is an *Arabidopsis thaliana* sub-telomeric sequence from centromere 5 (bases 26,987,774-26,992,453 (4681 bp); Database: ATH1_chr5.1 con), which was amplified with the following oligo nucleotides: CHHZ-203 (GGTGGTCGGCCGTCGTCGGCACTTG-GCAGCGAAATCTCC; SEQ ID NO: 33) and CHHZ-206 (GGTGGTCGGCCGCATTATCATATAATTATGTTT TGCTGCTTC: SEQ ID NO: 34). ST12 is an *Arabidopsis thaliana* sub-telomeric sequence from centromere 5 (bases 26,992,453-26,987,774 (4681 bp); Database: ATH1_chr5.1con), which was amplified with the following oligo nucleotides: CHHZ-204 (GGTGGTCGGC-CGCGTCGGCACTTGGCAGCGAAATCTCC; SEQ ID NO: 35) and CHHZ-205 (GGTGGTCGGCCGATTAT-CATATAATTATGT TTTGCTGCTTC: SEQ ID NO: 36). These sub-telomeric sequences were included in the pCRR581 vector.

TABLE 17 pCHR581 DNA donor components

| Genetic Element | Size (base pairs) | Location (bp) | Details |
|---|---|---|---|
| Bacterial chloramphenicol resistance | 660 | 13333-13992 | Bacterial selectable marker |
| ori2 | 67 | 14996-15062 | F' plasmid origin of replication from *E. coli* |
| repE | 755 | 15391-16146 | mediation of replication complex at Ori2 (Mori, H et. al, J Mol Biol. 1986 Nov. 5; 192(1): 1-15) |
| SopA | 1166 | 16734-17900 | partition of plasmid to bacterial daughter cells (Mori, H et. al, J Mol Biol. 1986 Nov. 5; 192(1): 1-15) |
| SopB | 971 | 17900-18871 | partition of plasmid to bacterial daughter cells (Mori, H et. al, J Mol Biol. 1986 Nov. 5; 192(1): 1-15) |
| SopC | 517 | 18944-19461 | partition of plasmid to bacterial daughter cells (Mori, H et. al, J Mol Biol. 1986 Nov. 5; 192(1): 1-15) |
| LoxP | 34 | 26-59 | Recombination site for Cre mediated recombination (Arenski et. al 1983, Abremski et. al 1984) |
| Grim Promoter | 2187 | 77-2267 | PCR amplified *Drosophila melanogaster* Grim gene promoter for expression of NptII gene in plants |
| UBQ10 intron | 359 | 2274-2633 | PCR amplified *Arabidopsis thaliana* intron from UBQ10 gene (At4g05320) for stabilization of NptII gene transcript and increase protein expression levels. |
| NptII | 795 | 2661-3455 | Neomycin phosphotransferase II plant selectable marker |
| Pyruvate kinase terminator | 332 | 3523-3854 | *Arabidopsis thaliana* Pyruvate kinase terminator (At5g52920) |
| Plant telomere | 759 | 3909-4667 | Plant telomere PCR based on plant consensus telomere sequence |
| Bacterial Kanamycin | 817 | 4843-5659 | Bacterial kanamycin selectable marker |
| Plant telomere | 759 | 5793-6552 | Plant telomere PCR based on plant consensus telomere sequence |
| Act2 promoter + intron | 1482 | 6598-8079 | The *Arabidopsis thaliana* promoter Actin 2 plus natural intron. |
| ZsGreen | 695 | 8103-8798 | Matz et. al. *Nature Biotechnol.* 1999 Oct.; 17: 969 |
| Act2 terminator | 800 | 8839-9638 | *Arabidopsis thaliana* Actin2 gene terminator. |
| Triose phosphate isomerase | 450 | 9667-10116 (complementary) | *Arabidopsis thaliana* Triose phosphate isomerase gene terminator |
| DsRed2 + NLS | 780 | 10251-11030 (complementary) | Nuclear localized red fluorescent protein from *Discosoma* sp. (Matz, M et al *Nat Biotechnol* 1999 Dec.; 17(12): 1227). |
| UBQ10 Promoter | 2038 | 11067-13104 (complementary) | *Arabidopsis thaliana* polyubiquitin promoter (At4g05320) | pCHR806

The pCHR806 mini-chromosome vector was constructed using standard cloning procedures. The vector was composed similarly to that of pCHR510 using the pBeloBAC11 low copy backbone containing the bacterial chloramphenicol gene and without the addition of the ST11 sub-telomeric DNA. An additional plant gene cassette was introduced containing the *Anemonia* sp. cyan fluorescence (AmCyan) gene regulated by the tomato Lat52 promoter and terminator. Mini-chromosome genetic elements within the pCHR806 vector are set out in Table 18.

TABLE 18

| | pCHR806 | | |
|---|---|---|---|
| Genetic Element | Size (base pairs) | Location (bp) | Details |
| Bacterial chloramphenicol resistance | 660 | 13372-14031 | Bacterial selectable marker |
| ori2 | 67 | 15035-15101 | F' plasmid origin of replication from *E. coli* |
| repE | 755 | 15430-16185 | mediation of replication complex at Ori2 (Mori, H et. al, J Mol Biol. 1986 Nov. 5; 192(1): 1-15) |
| SopA | 1166 | 16773-17939 | partition of plasmid to bacterial daughter cells (Mori, H et. al, J Mol Biol. 1986 Nov. 5; 192(1): 1-15) |
| SopB | 971 | 17939-18910 | partition of plasmid to bacterial daughter cells (Mori, H et. al, J Mol Biol. 1986 Nov. 5; 192(1): 1-15) |
| SopC | 517 | 18983-19500 | partition of plasmid to bacterial daughter cells (Mori, H et. al, J Mol Biol. 1986 Nov. 5; 192(1): 1-15) |
| LoxP | 34 | 26-59 | Recombination site for Cre mediated recombination (Arenski et. al 1983, Abremski et. al 1984) |
| Grim Promoter | 2187 | 77-2267 | PCR amplified *Drosophila melanogaster* Grim gene promoter for expression of NptII gene in plants. |
| UBQ10 intron | 359 | 2274-2633 | PCR amplified *Arabidopsis thaliana* intron from UBQ10 gene (At4g05320) for stabilization of NptII gene transcript and increase protein expression levels. |
| NptII | 795 | 2661-3455 | Neomycin phosphotransferase II plant selectable marker |
| Pyruvate kinase terminator | 332 | | *Arabidopsis thaliana* Pyruvate kinase terminator (At5g52920) |
| Lat52 terminator | 200 | 3883-4082 (complementary) | Tomato Lat52 terminator |
| AmCyan | 690 | 4123-4812 (complementary) | Visible cyan fluorescent protein from *Anemonia majano* (Matz, M et. al *Nat Biotechnol* 1999 Dec.; 17(12): 1227). |
| Tomato Lat52 promoter | 668 | 4836-5503 (complementary) | Tomato Lat52 promoter |
| Bacterial Kanamycin | 817 | 5678-6494 | Bacterial kanamycin selectable marker |
| Act2 promoter + intron | 1482 | 6637-8118 | The *Arabidopsis thaliana* promoter Actin 2 plus natural intron. |
| ZsGreen | 695 | 8142-8837 | Matz et. al. *Nature Biotechnol.* 1999 Oct.; 17: 969 |
| Act2 terminator | 800 | 8878-9677 | *Arabidopsis thaliana* Actin2 gene terminator. |
| Triose phosphate isomerase | 450 | 9706-10155 | *Arabidopsis thaliana* Triose phosphate isomerase gene terminator |
| DsRed2 + NLS | 780 | 10290-11069 (complementary) | Nuclear localized red fluorescent protein from *Discosoma* sp. (Matz, M et. al *Nat Biotechnol* 1999 Dec.; 17(12): 1227). |
| UBQ10 Promoter | 2038 | 11106-13143 (complementary) | *Arabidopsis thaliana* polyubiquitin promoter (At4g05320) | pCHR807

The pCHR807 mini-chromosome donor vector was constructed using standard cloning procedures and is identical to pCHR806. The vector was composed similar to that of pCHR510 using the pBelloBAC11 low copy backbone containing the bacterial chloramphenicol gene and without the addition of the ST11 sub-telomeric DNA. An additional plant gene cassette was introduced containing the Zoanthus sp. yellow fluorescent gene (ZsYellow) regulated by the tomato Lat52 promoter and terminator. Mini-chromosome genetic elements within the pCHR807 vector are set out in Table 19.

TABLE 19 pCHR807 DNA donor components

| Genetic Element | Size (base pairs) | Location (bp) | Details |
| --- | --- | --- | --- |
| Bacterial chloramphenicol resistance | 660 | 13378-14037 | Bacterial selectable marker |
| ori2 | 67 | 15041-15107 | F' plasmid origin of replication from E. coli |
| repE | 755 | 15436-16191 | mediation of replication complex at Ori2 (Mori, H et. al, J Mol Biol. 1986 Nov. 5; 192(1): 1-15) |
| SopA | 1166 | 16779-17945 | partition of plasmid to bacterial daughter cells (Mori, H et. al, J Mol Biol. 1986 Nov. 5; 192(1): 1-15) |
| SopB | 971 | 17945-18916 | partition of plasmid to bacterial daughter cells (Mori, H et. al, J Mol Biol. 1986 Nov. 5; 192(1): 1-15) |
| SopC | 517 | 18989-19506 | partition of plasmid to bacterial daughter cells (Mori, H et. al, J Mol Biol. 1986 Nov. 5; 192(1): 1-15) |
| LoxP | 34 | 26-59 | Recombination site for Cre mediated recombination (Arenski et. al 1983, Abremski et. al 1984) |
| Grim Promoter | 2187 | 77-2267 | PCR amplified Drosophila melanogaster Grim gene promoter for expression of NptII gene in plants. |
| UBQ10 intron | 359 | 2274-2633 | PCR amplified Arabidopsis thaliana intron from UBQ10 gene (At4g05320) for stabilization of NptII gene transcript and increase protein expression levels. |
| NptII | 795 | 2661-3455 | Neomycin phosphotransferase II plant selectable marker |
| Pyruvate kinase terminator | 332 | 3523-2854 | Arabidopsis thaliana Pyruvate kinase terminator (At5g52920) |
| Lat52 terminator | 200 | 3883-4082 (complementary) | Tomato Lat52 terminator |
| ZsYellow | 696 | 4123-4818 (complementary) | Visible yellow fluorescent protein from Zoanthus sp. (Matz, M et. al Nat Biotechnol 1999 Dec.; 17(12): 1227). |
| Tomato Lat52 promoter | 668 | 4842-5509 | Tomato Lat52 promoter |
| Bacterial Kanamycin | 817 | 5684-6500 | Bacterial kanamycin selectable marker |
| Act2 promoter + intron | 1482 | 6643-8124 | The Arabidopsis thaliana promoter Actin 2 plus natural intron. |
| ZsGreen | 695 | 8148-8843 | Matz et. al. Nature Biotechnol. 1999 Oct.; 17: 969 |
| Act2 terminator | 800 | 8884-9683 | Arabidopsis thaliana Actin2 gene terminator. |
| Triose phosphate isomerase | 450 | 9712-10161 | Arabidopsis thaliana Triose phosphate isomerase gene terminator |
| DsRed2 + NLS | 780 | 10296-11075 | Nuclear localized red fluorescent protein from Discosoma sp. (Matz, M et. al Nat Biotechnol 1999 Dec.; 17(12): 1227). |

TABLE 19-continued pCHR807 DNA donor components

| Genetic Element | Size (base pairs) | Location (bp) | Details |
|---|---|---|---|
| UBQ10 Promoter | 2038 | 11112-13149 | *Arabidopsis thaliana* polyubiquitin promoter (At4g05320) | pCHR808

The pCHR808 mini-chromosome donor vector was constructed using standard cloning procedures and is identical to pCHR806, but with the addition of the *Arabidopsis thaliana* ST9 sub-telomeric DNA. The ST9 sub-telomeric fragment was introduced upstream of the Grim fly promoter to isolate the Grim fly promoter from possible promoter silencing when a centromere fragment is ligated into the donor vector. Mini-chromosome genetic elements within the pCHR808 vector are set out in Table 20.

TABLE 20 pCHR808 DNA donor components

| Genetic Element | Size (base pairs) | Location (bp) | Details |
|---|---|---|---|
| Bacterial chloramphenicol resistance | 660 | 16892-17551 | Bacterial selectable marker |
| ori2 | 67 | 18555-18621 | F' plasmid origin of replication from *E. coli* |
| repE | 755 | 18950-19705 | mediation of replication complex at Ori2 (Mori, H et. al, J Mol Biol. 1986 Nov. 5; 192(1): 1-15) |
| SopA | 1166 | 20293-21459 | partition of plasmid to bacterial daughter cells (Mori, H et. al, J Mol Biol. 1986 Nov. 5; 192(1): 1-15) |
| SopB | 971 | 21459-22430 | partition of plasmid to bacterial daughter cells (Mori, H et. al, J Mol Biol. 1986 Nov. 5; 192(1): 1-15) |
| SopC | 517 | 22503-23020 | partition of plasmid to bacterial daughter cells (Mori, H et. al, J Mol Biol. 1986 Nov. 5; 192(1): 1-15) |
| LoxP | 34 | 26-59 | Recombination site for Cre mediated recombination (Arenski et. al 1983, Abremski et. al 1984) |
| ST9 subtelomeric DNA | 3513 | 69-3581 | *Arabidopsis thaliana* subtelomeric DNA from Chromosome 5 |
| Grim Promoter | 2187 | 3597-5787 | PCR amplified *Drosophila melanogaster* Grim gene promoter for expression of NptII gene in plants. |
| UBQ10 intron | 359 | 5794-6153 | PCR amplified *Arabidopsis thaliana* intron from UBQ10 gene (At4g05320) for stabilization of NptII gene transcript and increase protein expression levels. |

TABLE 20-continued pCHR808 DNA donor components

| Genetic Element | Size (base pairs) | Location (bp) | Details |
|---|---|---|---|
| NptII | 795 | 6181-6975 | Neomycin phosphotransferase II plant selectable marker |
| Pyruvate kinase terminator | 332 | 7043-7374 | *Arabidopsis thaliana* Pyruvate kinase terminator (At5g52920) |
| Lat52 terminator | 200 | 7403-7602 (complementary) | Tomato Lat52 terminator |
| AmCyan | 690 | 7643-8332 | Visible cyan fluorescent protein from *Anemonia majano* (Matz, M et. al *Nat Biotechnol* 1999 Dec.; 17(12): 1227). |
| Tomato Lat52 promoter | 668 | 8356-9023 (complementary) | Tomato Lat52 promoter |
| Bacterial Kanamycin | 817 | 9198-10014 | Bacterial kanamycin selectable marker |
| Act2 promoter + intron | 1482 | 10157-11638 | The *Arabidopsis thaliana* promoter Actin 2 plus natural intron. |
| ZsGreen | 695 | 11662-12357 | Matz et.al. *Nature Biotechnol.* 1999 Oct.; 17: 969 |
| Act2 terminator | 800 | 12398-13197 | *Arabidopsis thaliana* Actin2 gene terminator. |
| Triose phosphate isomerase | 450 | 13226-13675 | *Arabidopsis thaliana* Triose phosphate isomerase gene terminator |
| DsRed2 + NLS | 780 | 13810-14589 | Nuclear localized red fluorescent protein from *Discosoma* sp. (Matz, M et. al *Nat Biotechnol* 1999 Dec.; 17(12): 1227). |
| UBQ10 Promoter | 2038 | 14626-16663 | *Arabidopsis thaliana* polyubiquitin promoter (At4g05320) | pCHR945

The pCHR945 mini-chromosome donor vector was constructed using standard cloning procedures and is identical to pCHR807 with the replacement of the bacterial kanamycin gene with a bacterial kanamycin selectable marker gene surrounded by two plant telomere sequences and two unique I-Ppo I homing endonuclease sequences as described in pCHR171A. Mini-chromosomes using pCHR945 were constructed as described for pCHR510 using BB5R4-1 centromeric DNA to construct pCHR955. pCHR955 was linearized as described for mini-chromosomes constructed with pCHR171A. Mini-chromosome genetic elements within the pCHR845 vector are set out in Table 21.

TABLE 21

| Genetic Element | Size (base pairs) | Location (bp) | Details |
|---|---|---|---|
| | pCHR945 DNA donor components |
| Bacterial chloramphenicol resistance | 660 | 14992-15651 | Bacterial selectable marker |
| ori2 | 67 | 16655-16721 | F' plasmid origin of replication from *E. coli* |
| repE | 755 | 17050-17805 | mediation of replication complex at Ori2 (Mori, H et. al, J Mol Biol. 1986 Nov. 5; 192(1): 1-15) |
| SopA | 1166 | 18393-19559 | partition of plasmid to bacterial daughter cells (Mori, H et. al, J Mol Biol. 1986 Nov. 5; 192(1): 1-15) |
| SopB | 971 | 19559-20530 | partition of plasmid to bacterial daughter cells (Mori, H et. al, J Mol Biol. 1986 Nov. 5; 192(1): 1-15) |
| SopC | 517 | 20603-21120 | partition of plasmid to bacterial daughter cells (Mori, H et. al, J Mol Biol. 1986 Nov. 5; 192(1): 1-15) |
| LoxP | 34 | 26-59 | Recombination site for Cre mediated recombination (Arenski et. al 1983, Abremski et. al 1984) |
| Grim Promoter | 2187 | 77-2267 | PCR amplified *Drosophila melanogaster* Grim gene promoter for expression of NptII gene in plants. |
| UBQ10 intron | 359 | 2274-2633 | PCR amplified *Arabidopsis thaliana* intron from UBQ10 gene (At4g05320) for stabilization of NptII gene transcript and increase protein expression levels. |
| NptII | 795 | 2661-3455 | Neomycin phosphotransferase II plant selectable marker |
| Pyruvate kinase terminator | 332 | 3523-3854 | *Arabidopsis thaliana* Pyruvate kinase terminator (At5g52920) |
| Lat52 terminator | 200 | 3883-4082 (complementary) | Tomato Lat52 terminator |
| ZsYellow | 696 | 4123-4818 (complementary) | Visible yellow fluorescent protein from *Zoanthus* sp. (Matz, M et. al *Nat Biotechnol* 1999 Dec.; 17(12): 1227). |
| Tomato Lat52 promoter | 668 | 4842-5509 (complementary) | Tomato Lat52 promoter |
| Plant telomere | 759 | 5568-6326 | Plant telomere PCR based on plant consensus telomere sequence |
| Bacterial Kanamycin | 817 | 6502-7318 | Bacterial kanamycin selectable marker |
| Plant telomere | 759 | 7452-8211 | Plant telomere PCR based on plant consensus telomere sequence |
| Act2 promoter + intron | 1482 | 8257-9738 | The *Arabidopsis thaliana* promoter Actin 2 plus natural intron. |
| ZsGreen | 695 | 9762-10457 | Matz et.al. *Nature Biotechnol.* 1999 Oct.; 17: 969 |
| Act2 terminator | 800 | 10498-11297 | *Arabidopsis thaliana* Actin2 gene terminator. |
| Triose phosphate isomerase terminator | 450 | 11326-11775 (complementary) | *Arabidopsis thaliana* Triose phosphate isomerase gene terminator |
| DsRed2 + NLS | 780 | 11910-12689 (complementary) | Nuclear localized red fluorescent protein from *Discosoma* sp. (Matz, M et. al *Nat Biotechnol* 1999 Dec.; 17(12): 1227). |

TABLE 21-continued pCHR945 DNA donor components

| Genetic Element | Size (base pairs) | Location (bp) | Details |
| --- | --- | --- | --- |
| UBQ10 Promoter | 2038 | 12726-14763 (complementary) | *Arabidopsis thaliana* polyubiquitin promoter (At4g05320) |

Other Vectors

The pCHR809 mini-chromosome donor vector was constructed using standard cloning procedures and is identical to pCHR807, but with the addition of the *Arabidopsis thaliana* ST9 sub-telomeric DNA. The ST9 sub-telomeric fragment was introduced upstream of the Grim fly promoter to isolate the Grim fly promoter from possible promoter silencing when a centromere fragment was ligated into the donor vector.

The pCHR810 mini-chromosome donor vector was constructed using standard cloning procedures and is identical to pCHR806, but with the addition of the *Arabidopsis thaliana* ST10 sub-telomeric DNA. The ST10 sub-telomeric fragment was introduced upstream of the Grim fly promoter to isolate the Grim fly promoter from possible promoter silencing when a centromere fragment was ligated into the donor vector.

The pCHR811 mini-chromosome donor vector was constructed using standard cloning procedures and is identical to pCHR807, but with the addition of the *Arabidopsis thaliana* ST10 sub-telomeric DNA. The ST10 sub-telomeric fragment was introduced upstream of the Grim fly promoter to isolate the Grim fly promoter from possible promoter silencing when a centromere fragment was ligated into the donor vector.

The pCHR813 mini-chromosome donor vector was constructed using standard cloning procedures and is identical to pCHR807, but with the addition of the *Arabidopsis thaliana* ST11 sub-telomeric DNA. The ST11 sub-telomeric fragment was introduced upstream of the Grim fly promoter to isolate the Grim fly promoter from possible promoter silencing when a centromere fragment was ligated into the donor vector.

The pCHR814 mini-chromosome donor vector was constructed using standard cloning procedures and is identical to pCHR806, but with the addition of the *Arabidopsis thaliana* STI 1 sub-telomeric DNA. The ST12 sub-telomeric fragment was introduced upstream of the Grim fly promoter to isolate the Grim fly promoter from possible promoter silencing when a centromere fragment was ligated into the donor vector.

The pCHR815 mini-chromosome donor vector was constructed using standard cloning procedures and is identical to pCHR807, but with the addition of the *Arabidopsis thaliana* ST11 sub-telomeric DNA. The ST12 sub-telomeric fragment was introduced upstream of the Grim fly promoter to isolate the Grim fly promoter from possible promoter silencing when a centromere fragment was ligated into the donor vector.

The pCHR948 mini-chromosome donor vector was constructed using standard cloning procedures and is identical to pCHR810 with the replacement of the bacterial kanamycin gene with a bacterial kanamycin selectable marker gene surrounded by two plant telomere sequences and two unique I-Ppo I homing endonuclease sequences as described in pCHR171A. Mini-chromosomes using pCHR948 were constructed as described for pCHR510 using BB5R4-1 centromeric DNA. pCHR958 was linearized as described for mini-chromosomes constructed with pCHR171A.

Example 3

Mini-Chromosome Delivery into *Brassica* Cells

Various methods may be used to deliver DNA into plant cells. These include biological methods, such as *Agrobacterium* and viruses, physical methods such as biolistic particle bombardment and silicon carbide whiskers, electrical methods such as electroporation, and chemical methods such as the use of poly-ethylene glycol and other compounds known to stimulate DNA uptake into cells. *Agrobacterium* and biolistic particle bombardment have been the methods that have found most widespread use in plant biotechnology. See, e.g., Broothaerts, et. al. Nature 433: 629-633, 2005.

Biolistic Particle Delivery of Mini-Chromosomes

A biolistic delivery method using wet gold particles kept in an aqueous DNA suspension was adapted from the teachings of Milahe and Miller (Biotechniques 16: 924-931, 1994) and used to transform *B. oleracea* (Broccoli) cells. To prepare the wet gold particles for bombardment, 1.0 µm gold particles were washed by mixing with 100% ethanol on a vortex followed by spinning the particles in a microfuge at 4000 rpm in order to remove supernatant. Subsequently, the gold particles were washed with sterile distilled water three times, followed by spinning in a microfuge to remove supernatant. The washed gold particles were resuspend in sterile distilled water at a final concentration of 90 mg/ml and stored at 4° C. until use. For bombardment, the gold particle suspension (90 mg/ml) was then mixed rapidly with 1 µg/µl DNA solution (in $dH_2O$ or TE), 2.5M $CaCl_2$, and 1M spermidine. When two or more plasmids were contained within the DNA solution, equal amounts of each plasmids was added to the gold suspension.

To prepare explant tissues for DNA delivery, three days prior to bombardment, an internode of the *Brassica* plant (Broccoli) were cut. The internode explant was cut longitudinally with a scalpel to cut a thin slice (⅙-¼ of the internode) off one side of the explant. The prepared internodes were placed wound side down on Petri dishes with regeneration media. The Petri dishes were wrapped with tape and placed wound side up under the light. The explants grew for 3 days prior to bombardment.

For bombardment of *Brassica* suspension cells, the cells were harvested by centrifugation (1200 rpm for 2 minutes) on the day of bombardment. The cells were plated onto 50 mm circular polyester screen cloth disks placed on petri plates with solid medium. The solid medium used was the same medium that the cells are normally grown in (MS salts, Gamborg's vitamins, 3% sucrose, 2 mg/liter 2,4D (2,4-Dichlorophenoxyacetic acid), 0.5 mM MES pH 5.8+(solid medium only), plus 0.26% gelrite, or 0.6% tissue culture agar, added before autoclaving. Approximately 1.5 ml packed cells were placed on each filter disk, and dispersed uniformly into a very even spot approximately 1 inch in diameter.

Bombardment of the cells was carried out in the BioRad PDS-1000/He Biolistic Particle Delivery System (BioRad). The DNA/gold suspension was resuspended and immediately inserted onto the grid of the filter holder. A 50 mm circular polyester screen cloth disk containing the cells was placed into a fresh 60 mm petri dish and the cells were covered with a 10×10 cm square of sterile nylon or Dacron chiffon netting. The metal cylinder was inserted into the petri dish and used to push the netting down to the bottom of the dish. This weight prevented the cells from being dislodged from the plate during bombardment. The petri dish containing the cells was then placed onto the sample holder, and positioned in the sample chamber of the gene gun and bombarded with the DNA/gold suspension. After the bombardment, the cells were scraped off the filter circle in the petri dish containing solid medium with a sterile spatula and transferred to fresh medium in a 125 ml blue-capped glass bottle. The bottles were transferred onto a shaker and grown while shaking at 150 rpm.

A biolistic delivery method using dry gold particles was also carried out to deliver mini-chromosomes to Brassica cells. For this method, 1.0 or 0.6µ gold particles were washed in 70% ethanol with vigorous shaking on a vortex for 3 to 5 minutes, followed by an soaking in 70% ethanol for 15 minutes. The gold particles were spun in a microfuge to remove the supernatant and washed three times in sterile distilled water. The gold particles were suspended in 50% glycerol at a concentration of 60 mg/ml and stored at 4° C. For bombardment, the dry gold particles were resuspended on a vortex for 5 minutes to disrupt agglomerated particles. Subsequently, the dry gold particles were mixed rapidly with DNA, 2.5M $CaCl_2$ and 0.2M spermidine in a siliconized, sterile eppendorf tube. The sample was allowed to settle for 1 minute and then spun in a microfuge for 10 seconds to remove supernatant. Subsequently, the DNA/gold particles were washed once with 70% ethanol, followed by two washed in 100% ethanol. A portion of the DNA/gold mixture was evenly placed on a macrocarrier. The macrocarrier was then placed in the Bio-Rad PDS-1000/He Biolistic Particle Delivery System, and the bombardment was done at rupture disk pressures ranging from 450 psi to 2,200 psi. The dry biolistic method did not result in the generation of adchromosomal plants or cell lines.

Example 4

Selection of Brassica Cell Clones Stably Containing Mini-chromosome DNA Use of Visible Marker Genes The presence of visible marker genes allowed for visual selection of Brassica cells stably containing mini-chromosome DNA because any adchromosomal cells or cell clusters were readily identified by virtue of fluorescent protein expression.

Transient assays were used to test mini-chromosomes for their ability to become established in cells following DNA delivery, and for their ability to be inherited in mitotic cell divisions. Expression of a visible marker encoded by a gene present on the mini-chromosome, such as a fluorescent protein gene, is used to detect mini-chromosome presence in the cell, and to follow mitotic inheritance of the mini-chromosome. In this assay, mini-chromosomes were delivered to Brassica cells of a population that is undergoing cell division, in this case Brassica suspension cells grown in liquid culture.

After DNA delivery, the cell population was monitored for fluorescent protein expression over the course of one to several weeks. Mini-chromosomes containing active centromeres were observed through the formation of fluorescent cell clusters, which were derived from a single progenitor cell that had divide and passed the mini-chromosomes to its daughter cells. Accordingly, single fluorescent cells and clusters of fluorescent cells of various sizes were scored in the growing cell population after DNA delivery. A total of 25 Brassica mini-chromosomes (see Table 23), constructed using the cre-lox assembly process, were tested in this manner in several different Brassica cell lines. A number of mini-chromosomes showed indications of stable mitotic inheritance in this assay and are listed in Table 22; in addition several stable cell lines were obtained from suspension cell lines following the delivery of the same mini-chromosomes; these are also listed in Table 22.

TABLE 22

Preferred Brassica BACs, centromeres (CEN), and mini-chromosomes (MC) based upon transient expression assays and generation of stable Brassica cell lines

| BAC Number | CEN Number | MC Number | BAC Class | Stable clones generated | # of times tested in transient deliveries | # of positive transient deliveries |
|---|---|---|---|---|---|---|
| BB5 | BB5R4-1 | BB5R4-1 | Hi CANREP, Meth | 7 | 3 | 2 |
| BB16 | BB16R1-2 | BB16R1-2 | Hi CANREP, Meth (Hpa) | 0 | 2 | 1 |
| | BB16R1-3 | BB16R1-3 | | 1 | 1 | 1 |
| BB18 | BB18R1-2 | BB18R1-2 | Hi CANREP, Meth (Hpa) | 1 | 1 | 1 |
| | BB18R2-3 | BB18R2-3 | | 1 | 4 | 2 |
| BB38 | BB38R1-3 | BB38R1-3 | Hi CANREP only | 0 | 4 | 3 |
| BB47 | BB47R1-2 | BB47R1-2 | Hi CANREP, Meth (Hpa) | 0 | 4 | 2 |
| BB60 | BB60R1-1 | BB60R1-1 | Hi CANREP, Meth (Hpa) | 1 | 3 | 3 |
| BB63 | BB63R1-1 | BB63R1-1 | Hi CANREP, Meth (Hpa) | 1 | 5 | 4 |
| BB70 | BB70R1-3 | BB70R1-3 | Hi CANREP, Moderate Meth | 0 | 4 | 2 |
| BB71 | BB71R1-3 | BB71R1-1 | Hi CANREP, Meth (Sau) | 0 | 2 | 2 |

TABLE 22-continued

Preferred *Brassica* BACs, centromeres (CEN), and mini-chromosomes (MC) based upon transient expression assays and generation of stable *Brassica* cell lines

| BAC Number | CEN Number | MC Number | BAC Class | Stable clones generated | # of times tested in transient deliveries | # of positive transient deliveries |
|---|---|---|---|---|---|---|
| BB76 | BB76R1-3 | BB76R1-3 | Hi CANREP, Moderate Meth | 0 | 5 | 4 |
| BB104 | BB104R1-2 | BB104R1-2 | Hi CANREP, Moderate Meth | 1 | 3 | 3 |

Manipulation of Adchromosomal Tissue to Homogeneity

After identifying clusters of fluorescent cells in bombarded suspension cell cultures, physical manipulations were carried out to allow for the preferential expansion of cells harboring the delivered genes. Non-fluorescent tissue surrounding the fluorescent clusters was trimmed to avoid overgrowth of fluorescent cells by non-fluorescent ones, while retaining a minimum tissue size capable of rapid growth. These manipulations were performed under sterile conditions with the use of a fluorescence stereomicroscope that allows for visualization of the fluorescent cells and cell clumps in the larger pieces of tissue. In between the mechanical purification steps, the tissue was allowed growth on appropriate media, either in the presence or absence of selection. Over time, a pure population of fluorescent cells was obtained.

Example 5

Regeneration of *Brassica* Plants from Adchromosomal Cell Clones

A total of 28 *Brassica* mini-chromosomes were used in stable transformation to successfully regenerate transchromosomal broccoli plants that are listed in Table 23. These *Brassica* mini-chromosomes represent candidate *Brassica* centromere sequences for the delivery and transmission of stable *Brassica* mini-chromosomes. *B. oleracea* plant (broccoli) regeneration was achieved by cultivating pieces of sterile plant tissue (explants) on medium containing plant growth activators (auxins, cytokinins and other compounds) that induce embryogenesis or shoot formation. Particularly, *Brassica* tissue proliferation was carried out with a medium containing high cytokinin regeneration medium (Murashige and Skooge salts, MES, sucrose, gelrite, Gamborg vitamins, 6-benzylaminopurine hydrochloride, non-essential amino acids, thidiazuron (TDZ) and silver nitrate, pH 5.7) through all culturing phases.

TABLE 23

| Centromere | MC | cofig | # genes | #explants[5] | size of cen | size of MC | In Growth Room # events | In Growth Room # plants | visual[2] | PCR[3] # events | RT[3] # events | Western[3] # events |
|---|---|---|---|---|---|---|---|---|---|---|---|---|
| BB15R4-1 | 964-4 | O-O | 4 | 77 | 60 | 80 | 1 | 1 | √ | 1 | 0 | 1 |
| BB15R4-1 | 965-1 | O-O | 4 | 93 | 55 | 80 | 1 | 2 | √ | 1 | 0 | 1 |
| BB16R1-2 | 967-1 | O-O | 4 | 105 | 55 | 60 | 1 | 1 | √ | 0 | 0 | 1 |
| BB221 | BB221R2-1 | O-O | 2 | 78 | 59 | 70 | 1 | 2 | √ | 0 | 0 | 1 |
| BB222 | BB222R2-7 | O-O | 2 | 102 | 49 | 60 | 1 | 2 | √ | 1 | 0 | 0 |
| BB229 | BB229R2-6 | O-O | 2 | 118 | 49 | 60 | 3 | 8 | √ | 2 | 0 | 1 |
| BB280 | BB280R2-3 | O-O | 2 | 79 | 86 | 97 | 3 | 6 | √ | 2 | 0 | 3 |
| BB5 | BB5R10-1 | I-I | 2 | 337 | 48 | 65 | 1 | 1 | √ | 1 | 0 | 0 |
| BB5 | BB5R14-6 | O-O | 2 | 213 | 52 | 68 | 1 | 1 | √ | 1 | 0 | 0 |
| BB5 | BB5R15-4 | O-O | 2 | 144 | 52 | 68 | 1 | 2 | √ | 1 | 0 | 0 |
| BB5 | BB5R16-6 | O-O | 2 | 152 | 50 | 66 | 2 | 6 | √ | 1 | 1 | 1 |
| BB5R4-1 | 543-6 | O-O | 3 | 101 | 50 | 74 | 2 | 4 | √ | 1 | 0 | 0 |
| BB5R4-1 | 591-1 | I-O | 3 | 76 | 50 | 75 | 1 | 2 | √ | 1 | 0 | 0 |
| BB5R4-1 | 591-1L | I-I | 3 | 207 | 50 | 73 | 2 | 4 | √ | 2 | 1 | 1 |
| BB5R4-1 | 593-3L | I-I | 3 | 78 | 50 | 69 | 1 | 4 | √ | 1 | 1 | 1 |
| BB5R4-1 | 593-4L | I-I | 3 | 82 | 50 | 69 | 1 | 3 | √ | 1 | 1 | 1 |
| BB5 | BB5R4-1 | O-O | 2 | 564 | 50 | 61 | 7 | 46 | √ | 7 | 6 | 6 |
| BB5R4-1 | 816-2 | O-O | 4 | 107 | 50 | 70 | 2 | 5 | √ | 2 | 1 | 1 |
| BB5R4-1 | 817-1 | O-O | 4 | 143 | 50 | 70 | 2 | 16 | √ | 2 | 2 | 2 |
| BB5R4-1 | 818-1 | O-O | 4 | 78 | 50 | 73 | 1 | 1 | √ | 1 | 0 | 0 |
| BB5R4-1 | 819-1 | O-O | 4 | 117 | 50 | 73 | 4 | 14 | √ | 4 | 4 | 4 |
| BB5R4-1 | 820-1 | O-O | 4 | 406 | 50 | 73 | 2 | 3 | √ | 2 | 0 | 1 |
| BB5R4-1 | 823-2 | O-O | 4 | 50 | 50 | 75 | 3 | 16 | √ | 3 | 0 | 3 |
| BB5R4-1 | 824-9 | O-O | 4 | 129 | 50 | 75 | 2 | 4 | √ | 2 | 2 | 2 |
| BB5R4-1 | 825-1 | O-O | 4 | 168 | 50 | 75 | 1 | 1 | √ | 0 | 0 | 1 |
| BB5R4-1 | 958-2L | I-I | 4 | 169 | 50 | 74 | 1 | 1 | √ | 1 | 0 | 1 |
| BB60R1-1 | 972-5 | O-O | 4 | 123 | 60 | 80 | 1 | 2 | √ | 1 | 0 | 1 |

TABLE 23-continued

| Centromere | MC | cofig | # genes | #explants[5] | size of cen | size of MC | In Growth Room # events | # plants | visual[2] | PCR[3] # events | RT[3] # events | Western[3] # events |
|---|---|---|---|---|---|---|---|---|---|---|---|---|
| BB71 | BB71R1-1 | O-O | 2 | 162 | 24 | 35 | 1 | 3 | √ | 1 | 1 | 1 |
| integrative | 489 | O-O | 2 | 306 | 0 | 11 | 1 | 1 | √ | 1 | 1 | 1 |
| SB38R2-2 | 986-1 | O-O | 2 | 61 | 63 | 83 | 3 | 5 | √ | 3 | 0 | 3 |
|  |  |  |  |  |  |  |  | 167 |  |  |  |  |

After bombardment, explants were returned to the high cytokinin regeneration medium with the wound side down on the plate. The explants were transferred to selection medium (regeneration medium containing 150 μM $HgCl_2$ or 100 mg/L of kanamycin) three days after bombardment with wound side up. The explants were visually screened under a fluorescent dissecting microscope for red fluorescent cluster formation 10 days after selection was started. In addition to facilitating the transient assays, the use of fluorescent protein expression allowed for the use of sub-killing concentrations of selective agent during growth of plant tissue on selective medium. This flexibility allowed for the use of a wider range of antibiotic concentrations than possible in the absence of a visible marker gene, without having to consider the amount of background growth observed in wild type plant tissue. Fluorescent cell clusters could be visually identified after one to several weeks of growth on selective media. Clusters with some unmodified surrounding explant tissue were carved out and placed on medium containing 50 μM $HgCl_2$ or 50 mg/L of kanamycin.

The subcultures were continued on selection medium and the non-modified tissues were parsed out from the clusters every week for a month. Once the clusters were approximately 3 mm in size, they were cultured on regeneration medium without any Hg or kanamycin in order to induce shoot regeneration. Subsequently, shoot primordia were transferred to seed germination medium for enlargement and expansion. Once the shoots elongated and developed about 2-4 leaves, the shoots with the leaves were cut off for rooting in rooting medium (MS salts, sucrose, 0.7% tissue culture agar and non-essential amino acids, pH 5.7). Once the shoots developed good root systems, they were potted and transferred to a plant growth facility.

Example 6

Regeneration of *B. napus* (Canola) Plants Modified with Mini-chromosome DNA

The biolistic delivery method using dry gold particles, described in example 3, was used to deliver mini-chromosomes to *B. napus* hypocotyl sections for the purpose of regenerating modified *B. napus* (hereinafter "canola") plants. The canola hypocotyls were modified with mini-chromosomes generated with *Brassica* centromere inserts described in Example 1 using the vectors described in Example 1.

Canola seeds were grown in germination medium (1× Murashige and Skoog (MS) salts, 1× micro-salts with Gamborg's B5 vitamins (B5), 2% sucrose, 2 g/liter gelrite, pH 5.8) for one week. The resulting hypocotyls were harvested and sliced longitudinally; the pieces were cultured on callus induction medium (1× MS salts, 1×MS vitamins, 1 mg/liter 2,4-dichlorophenoxyacetic acid (2,4D), 3% sucrose, 2 g/liter gelrite, pH 5.8) for 7 days.

The hypocotyls were bombarded with dry gold particle/DNA suspensions as described in Example 2 using 1300 psi rupture disks; the bombarded tissues were returned to callus induction medium for 3 days and then transferred to callus induction medium containing 10 mg/ml of G418. They were kept on this medium with sub-culturing every 1-2 weeks for 4-6 weeks. The subcultures were then visually analyzed for expression of the fluorescent protein as described in Example 3.

Cultures positive for expression of the fluorescent protein were further subcultured on callus induction medium containing 10 mg/ml of G418 for 4-6 weeks. During this time, fluorescent tissue was selectively isolated from non-fluorescent tissue by manipulation. Subsequently, the positive tissues were transferred to organogenesis induction media (MS salts, B5 vitamins, 6-benzylaminopurine, zeatin, sucrose, g/l gelrite, pH 5.8) containing 10 mg/ml of G418) and were kept on this medium until shoots appeared. The shoots were grown in hormone-free media to promote normal shoot development.

Developing green shoots with a defined morphology were excised and incubated in shoot elongation medium, differing from organogenesis medium by having lower cytokinin concentrations. Most callus was removed from the developing shoots, which were subcultured in fresh shoot elongation medium every 2-3 weeks. As the developing shoots became normal and exhibited apical dominance, they were transferred to rooting medium containing indolebutyric acid; the remaining callus was removed also at this time. The shoots were arranged to stand in the medium with an exposed apex. The roots began to appear in 1-3 weeks.

The rooted shoots were transferred to soil in which the basal portion of the plant was planted to soil to grow out. The shoot were gently removed from the agar and large chunks of agar were removed by rinsing gently in tap water. The roots were placed in wet RediEarth or other suitable growth medium. Roots were covered with the growth medium and packed gently. The shoots were hardened-off and acclimated to growing in soil by covering the shoot with a clear container. The shoots were placed into a greenhouse or plant growth room. After being covered for 3-4 days, the shoots were gradually exposed to room air by partial removal of the cover. Once the plant stopped wilting, the cover was removed entirely.

Several adchromosomal events and approximately 30 adchromosomal plants were obtained by this protocol; these are further discussed in example 12 and table 45. To visually analyze the presence of the marker gene in *Brassica* cells or tissue, a piece of leaf or other plant part was removed from a modified and control (non-modified) *Brassica* plant. The leaf or plant part was then examined with a fluorescence stereomicroscope using 20-100× magnification and a rhodamine filter set.

Example 7

Tomato Centromere Discovery and Mini-Chromosome Construction BAC Library Construction A Bacterial Artificial Chromosome (BAC) library was constructed from Tomato genomic DNA isolated from Tomato variety "Microtom" and digested with the restriction enzyme MboI. This enzyme was chosen because it is methylation insensitive and therefore can be used to enrich BAC libraries for centromere DNA sequences.

Probe Identification and Selection

Tomato repetitive genomic or plastid sequences, including specific centromere-localized sequences, were initially compiled as candidate probes for hybridization with the BAC libraries. These probes represented various classes of Tomato repetitive sequences including satellite repeats (heterochromatic/centromere-specific), rDNA, and hypermethylated and highly repetitive DNA fractions.

Six probes were picked to interrogate the BAC libraries. These probes represent different groups of commonly found repetitive sequences in the Tomato genome. The probes selected are shown in Table 24 and were LESAT (the Tomato centromere satellite, in two different variants; SEQ ID NOS: 37 and 38), a tomato microsatellite (LEGATAREP; SEQ ID NO: 39), HpaII (bulk methylated DNA purified from genomic DNA by failure to digest with the methylation-sensitive enzyme HpaII), bulk repetitive DNA purified from genomic DNA by reassociation kinetics (Cot), and telomere. The probes were prepared by PCR, from cloned fragments, or from bulk methylated or repetitive DNA prepared from Tomato genomic DNA. The telomere probe sequence (SEQ ID NO: 40) was generated by PCR using the following primers: CHHZ-97 (AGGCGCGCCACCTGCAGGA GAGCTCGGTCTCA TCGAGACAC; SEQ ID NO: 41) and CHHZ-98 (GGTCGACGGCCCGGGCGTT TAAAC-CCGGGCTCAC; SEQ ID NO: 42). Probes were prepared and labeled with standard molecular biology methods.

Library Interrogation and Data Analysis

The BAC clones from the libraries were spotted onto filters and these filters were hybridized with each of the probes to identify specific BAC clones that contain DNA from the group of sequences represented by the probe(s).

A total of 18,432 BAC clones from the library were interrogated with each of the probes described above sing the following hybridization conditions: 0.5×SSC 0.25% SDS at 65 degrees for 15 minutes, followed by a wash at 65 degrees for a half hour. The hybridization intensities of the BAC clones with each probe were scanned to quantitate hybridization intensity for each clone. The outputs (scores of 1 to 10 based on the hybridization intensities, with 10 being the highest intensity) were imported into a relational database, for further analysis and classification. The database contained a total of five tables that were used for BAC selection. Each table contains a total of 18,432 entries: the hybridization scores of each BAC clone from the library to one of the probes used to interrogate the library. Data analysis was done using standard SQL (Structured Query Language) routines to find BACs that contain different groups of repetitive sequences.

Classification and Selection of BAC Clones from Mini-Chromosome Construction

BAC clones containing centromeric/heterochromatic DNA were identified by their hybridization scores to different probes. The goal was to select BAC clones that contained a diverse set of various repetitive sequences. Eleven classes of centromeric BAC clones, some of which overlap, were eventually chosen to cover the broadest possible range of centromeric/heterochromatic sequences for mini-chromosome construction. Detailed descriptions of each class and probe hybridization values for each class are shown in Table 25.

TABLE 24

Tomato Repetitive Sequences and BAC Library Probes

| group # | group name | probe name | Description | clone used for hyb | GenBank accession* |
|---|---|---|---|---|---|
| 1 | centromere repeat | TC2 (SEQ ID NO: 37) | LESAT, tomato centromere satellite (different variant) | 5012-5-11-C02 | X87233.1 |
| | | TE1 (SEQ ID NO: 38) | LESAT, tomato centromere satellite (different variant) | 5012-5-11-E01 | X87233.1 |
| 2 | microsatellite repeat | TE12 (SEQ ID NO: 39) | LEGATAREP, tomato microsatellite repeat | 5012-5-11-E12 | X90937.1 |
| 3 | bulk repetitive DNA | TCot6 | Purified repetitive DNA fraction | N/A | N/A |
| | | T HpaII | Purified methylated DNA fraction | N/A | N/A |
| 4 | telomere | TTel (SEQ ID NO: 40) | Telomere | PCR product | N/A |

*Accession number of BLAST hit; actual sequence has not been deposited in Genbank

TABLE 25

Classification of tomato BAC clones containing centromeric DNA

| Class | Class Properties | Probe Hybridization Range | | | | | # clones identified |
|---|---|---|---|---|---|---|---|
| | | LESAT C2 | LESAT E1 | LEGATA REP E12 | Hpa II (METH) | TEL | |
| A | High Meth, E1, E12 | N/A | >=6 | >=6 | >=6 | N/A | 30 |
| B | High Meth, E1, TEL | N/A | >=7 | N/A | >=7 | >=7 | 36 |
| C | High Meth, TEL; low C2 | <=5 | N/A | N/A | >=7 | >=7 | 9 |
| D | High Meth and E1 | N/A | >=8 | N/A | >=7 | N/A | 103 |
| E | High Meth and E12 | N/A | N/A | >=6 | >=6 | N/A | 35 |
| F | High E1 and E12 | N/A | >=6 | >=6 | N/A | N/A | 75 |
| G | High E1 and TEL | N/A | >=8 | N/A | N/A | >=8 | 8 |
| H | High E1 only | N/A | >=8 | <=4 | <=6 | N/A | 89 |
| I | High TEL only | N/A | <=4 | N/A | <=4 | >=8 | 49 |
| J | High Meth only | N/A | N/A | <=4 | >=7 | <=4 | 15 |
| K | High E12 only | N/A | N/A | >=7 | <=4 | <=4 | 2 |
| Total** | | | | | | | 451 |

*Values represent hybridization intensities of an individual BAC to each probe on a scale of 1 to 10. Values were normalized
N/A = not applicable A number of representative clones from each class were chosen to yield a total of 278 BAC clones for further analysis by restriction digest fingerprinting. The BAC clones were fingerprinted (Table 26) based on restriction sites found in the centromere specific sequence(s) as described in Example 1. The restriction enzyme HinfI was used to digest the BAC clones. After fingerprinting, 100 BACs were selected for further testing using the method described in Example 1.

*L. esculentum* (tomato) BAC TB99 was deposited with the American Type Culture Collection (ATCC) P.O. Box 1549 Manassas, Va. 20108, USA on Feb. 23, 2005 and assigned Accession No. PTA-6603.

Thirty BAC clones (from the original 278) were selected for mini-chromosome construction based on the fingerprint class which was defined as a simple or complex laddering pattern. Table 26 lists the fingerprint patterns for a selected set of 26 Tomato BAC clones. Tomato fingerprints were classified into 3 classes: 1. high complexity (multiple large bands with no indication of laddering), 2. low ladder (predominant bands at multiples of the unit repeat size for the centromere satellite, and 3. complex ladder (features of both previous types). Table 27 lists the fingerprint classes for 7 selected tomato BACS. The preferred BACS have an *. Table 27 lists the fingerprint classes for 11 selected *Brassica* BACs.

TABLE 26

Restriction Endonuclease Fingerprinting of 26 Tomato BACs

| BAC Number | BAC Class | Class Properties | Fingerprint Class* | MiniC tested |
|---|---|---|---|---|
| TB1 | G | Hi LE SAT/Tel | 2. Low ladder | TB1R4-3 |
| TB4* | G | Hi LE SAT/Tel | 2. Low ladder | TB4R1-2 |
| TB6 | J | Hi Hpa only | 1. complex | TB6R4-1 |
| TB10 | I | Hi Tel only | 1. complex | TB10R4-1 |
| TB12 | I | Hi Tel only | 1. complex | TB12R1-1 |
| TB16 | F | Hi LESAT/LE Gata rep | 2. Low ladder | TB16R4-5 |
| TB17 | J | Hi Hpa only | 1. complex | TB17R1-1 |
| TB21 | D | Hi Hpa/LESAT | 2. Low ladder | TB21R1-2 |
| TB22 | D | Hi Hpa/LESAT | 2. Low ladder | TB22R1-1 |
| TB23* | G | Hi LESAT/Tel | 2. Low ladder | TB23R1-5 |
| TB29 | J | Hi Hpa only | 3. complex/ladder | TB29R1-1 |
| TB47 | D | Hi Hpa/LESAT | 2. Low ladder | TB47R1-1 |
| TB55 | B | Hi LESAT/Hpa/TEL | 2. Low ladder | TB55R1-5 |
| TB56 | D | Hi Hpa/LESAT | 3. complex/ladder | TB56R1-3 |
| TB67 | H | Hi LESAT only | 2. Low ladder | TB67R1-1 |
| TB72 | H | Hi LESAT only | 3. complex/ladder | TB72R1-3 |
| TB73 | D | Hi Hpa/LESAT | 2. Low ladder | TB73R1-2 |
| TB80* | D | Hi Hpa/LESAT | 3. complex/ladder | TB80R1-2 |
| TB82* | H | Hi LESAT only | 2. Low ladder | TB82R1-4 |
| TB91 | H | Hi LESAT only | 2. Low ladder | TB91R1-2 |
| TB92 | H | Hi LESAT only | 3. complex/ladder | TB92R1-3 |
| TB99* | H | Hi LESAT only | 2. Low ladder | TB99R1-5 |
| TB101* | B | Hi LESAT/Hpa/TEL | 2. Low ladder | TB101R1-5 |
| TB114 | H | Hi LESAT only | 2. Low ladder | TB114R1-1 |

TABLE 26-continued

Restriction Endonuclease Fingerprinting of 26 Tomato BACs

| BAC Number | BAC Class | Class Properties | Fingerprint Class* | MiniC tested |
|---|---|---|---|---|
| TB115 | H | Hi LESAT only | 2. Low ladder | TB115R4-2 |
| TB132* | F | Hi LESAT/LE Gata rep | 2. Low ladder | TB132R1-3 |

TABLE 27

Restriction endonuclease fingerprint classification for 7 selected tomato BACs

| BAC Number | Hyb Class | Class Properties | Fingerprint Class |
|---|---|---|---|
| TB4 | G | Hi LE SAT/Tel | 2. Low ladder |
| TB23 | G | Hi LESAT/Tel | 2. Low ladder |
| TB80 | D | Hi Hpa/LESAT | 3. complex/ladder |
| TB82 | H | Hi LESAT only | 2. Low ladder |
| TB99 | H | Hi LESAT only | 2. Low ladder |
| TB101 | B | Hi LESAT/Hpa/TEL | 2. Low ladder |
| TB132 | F | Hi LESAT/LE Gata rep | 2. Low ladder |

Construction of Mini-Chromosomes

For each BAC identified above, a mini-chromosome was constructed using a Cre-Lox Recombination-Donor vectors as described in Example 2. Tomato mini-chromosomes were constructed from a total of 30 BACs using donor vector 151 and 153 in this assembly process, and were subsequently tested in several different tomato cell lines. Mini-chromosome genetic elements within the pCHR151 and pCHR153 vector are set out in Tables 10 and 28.

TABLE 28

Donor Components of pCHR153

| Genetic Element | Size (base pair) | Location (bp) | Details |
|---|---|---|---|
| EF1αA3 Promoter | 2051 | 361-2411 | Arabidopsis thaliana elongation factor 1 alpha A3 promoter (At1g07940) |
| DsRed2 + NLS | 780 | 2448-3227 | Nuclear localized red fluorescent protein from Discosoma sp. (Matz, M et. al Nat Biotechnol 1999 Dec.; 17(12): 1227). |
| Pyruvate kinase terminator | 332 | 3362-3693 | Arabidopsis thaliana pyruvate kinase terminator (At5g52920) |
| Bacterial Kanamycin | 817 | 3838-4654 | Bacterial kanamycin selectable marker |
| Act2 terminator | 800 | 4836-5635 | Arabidopsis thaliana Actin 2 terminator |
| MerA | 1695 | 5789-7483 | Plant selectable marker providing resistance to mercuric ions (Rugh et. al. PNAS 1996 93: 3182) |
| Act2 promoter + intron | 1482 | 7486-8967 | The Arabidopsis thaliana promoter Actin 2 plus natural intron |
| LoxP | 34 | 312-345 & 8984-9017 | Recombination site for Cre mediated recombination (Arenski et. al 1983, Abremski et. al 1984) |

Example 8

Testing of Tomato Mini-Chromosomes and Regeneration of Tomato Plants Modified with Mini-Chromosome DNA The biolistic delivery method using wet gold particles, described in Example 2, was used to deliver mini-chromosomes to tomato cells. Functional testing of mini-chromosomes using transient assays as described in Example 3. In the transient assay, mini-chromosomes were delivered to tomato cells of a population that is undergoing cell division, in this case tomato suspension cells grown in liquid culture or callus cells grown on plates. PC703, a publicly available tomato callus cell line, was routinely used in transient assays described above. However, any actively dividing cell type can be used for this assay, such as root tissue, meristem tissue, or callus derived from any plant tissue.

After DNA delivery, the cell population was then monitored for fluorescent protein expression over the course of one to several weeks. Mini-chromosomes containing active centromeres allowed the formation of fluorescent cell clusters, which are derived from a single progenitor cell that has divided and passed the mini-c to its daughter cells. Accordingly, single fluorescent cells and clusters of fluorescent cells of various sizes were scored in the growing cell population after DNA delivery. A number of stable cell lines were obtained following the delivery of the mini-chromosomes listed in Table 29.

TABLE 29

Preferred Chromatin tomato BACs, centromeres (CEN), and mini-chromosomes (MC) based upon transient expression assays and generation of stable tomato cell lines.

| BAC Number | CEN Number | MC Number | BAC Class | Stable clones generated |
|---|---|---|---|---|
| TB4 | TB4 | TB4R1-2 | Hi LE SAT/Tel | yes |
| TB23 | TB23 | TB23R1-5 | Hi LESAT/Tel | yes |
| TB80 | TB80 | TB80R1-2 | Hi Hpa/LESAT | yes |
| TB82 | TB82 | TB82R1-4 | Hi LESAT only | yes |
| TB99 | TB99 | TB99R1-5 | Hi LESAT only | yes |
| TB101 | TB101 | TB101R1-5 | Hi LESAT/Hpa/TEL | yes |
| TB132 | TB132 | TB132R1-3 | Hi LESAT/LE Gata rep | yes |

To obtain trans-chromosomal tomato plants, the promising centromeres identified above were combined with a different set of genes than those present in donor vector 151 or 153 which were used in the construction of the initial set of 26 mini-chromosomes. The mini-chromosome construction procedure was thus repeated for BACs TB99 and TB132 using donor vectors 487-489 (See Example 2 and Tables 12-14 for description) and 531 (see Table 30 below for descriptions of the 531 donor vector), following the same steps as described above. Five mini-chromosomes were obtained that contain nptII, summarized below:

TABLE 30

Donor Components of pCHR531

| Genetic Element | Size (base pair) | Location (bp) | Details |
|---|---|---|---|
| UBQ10 promoter | 359 | 361-2398 | Arabidopsis thaliana polyubiquitin promoter (At4g05320) |
| DsRed2 + NLS | 780 | 2435-3214 | Nuclear localized red fluorescent protein from Discosoma sp. (Matz, M et. al Nat Biotechnol 1999 Dec.; 17(12): 1227). |

TABLE 30-continued

Donor Components of pCHR531

| Genetic Element | Size (base pair) | Location (bp) | Details |
|---|---|---|---|
| Pyruvate kinase terminator | 332 | 3349-3680 | *Arabidopsis thaliana* pyruvate kinase terminator (At5g52920) |
| Bacterial Kanamycin | 817 | 3825-4641 | Bacterial kanamycin selectable marker |
| Act2 terminator | 800 | 4823-5622 | *Arabidopsis thaliana* Actin 2 terminator |
| NptII | 795 | 5685-6479 | Neomycin phosphotransferase II plant selectable marker |
| UBQ10 intron | 359 | 6507-6865 | PCR amplified *Arabidopsis thaliana* intron from UBQ10 gene (At4g05320) for stabilization of NptII gene transcript and increase protein expression levels |
| Pgd Fly promoter | 2140 | 6873-9012 | PCR amplified promoter of phosphogluconate dehydrogenase gene from *Drosophila melanogaster* |
| LoxP | | 312-345 & 9029-9062 | Recombination site for Cre mediated recombination (Arenski et. al 1983, Abremski et. al 1984) |

| Mini-C | Cen name | Cen size | Donor vector | Promoter driving nptII* |
|---|---|---|---|---|
| TB99R7-1 | TB99 | 50 kb | pCHR487 | Tef2 |
| TB99R8-1 | TB99 | 15 kb | pCHR488 | GPD-1 |
| TB99R10-1 | TB99 | 48 kb | pCHR531 | Pgd-1 |
| TB132R8-1 | TB132 | 48 kb | pCHR488 | GPD-1 |
| TB132R10-2 | TB132 | 27 kb | pCHR531 | Pgd-1 |

For tomato modification with these mini-chromosomes (derived from TB99 and TB132 combined with donor vectors 487, 488 and 531), the following procedure was developed. Tomato seeds were surface sterilized in 10% bleach for 15 minutes and washed 4 times with sterile distilled water. The seeds were placed in sterile Petri dishes and dried under sterile air flow in a tissue culture hood. The seeds were germinated in magenta containers on solid medium (0.5×MS salts, 1×MS vitamins, 10 g/l sucrose, 8 g/l tissue culture agar, 0.5 mM MES, 1.3 g/liter calcium gluconate, pH 5.8) for 8 days at ambient temperature under lights.

Cotyledons and hypocotyls were removed from the seedlings for explants. The cotyledon pieces were cut into slices approximately 3-4 mm wide and the hypocotyls were cut longitudinally. Both types of explants were grown on preculture medium (1× MS salts, 1×MS vitamins, 3% sucrose, 1 mM MES, 8 g/liter tissue culture agar; pH 5.7-5.8) The medium also contained either 1 mg/l BA+0.1 mg/l non-essential amino acids or 0.75 mg/l zeatin+1 mg/l IAA. The cotyledon pieces were cultured with the abaxial side in contact with the medium; while the hypocotyls pieces were cultured with the wounded side away from the medium. The explants were pre-cultured for 3-6 days under lights.

The explants were then transferred to 5 cm polyethylene mesh circles and bombarded using the wet biolistics method as described in Example 2. The same surface was bombarded as facing upwards (away from the medium) during pre-culturing. After bombardment, the explants were transferred back onto preculture medium and kept under light.

Two days after bombardment, the explants were transferred onto preculture medium containing 100 mg/liter kanamycin. The explants were cultured on this medium under light for 6 weeks to three months with sub-culturing onto fresh medium every 3 weeks. Starting at 6 weeks after the onset of selection, the explants were screened with a fluorescence stereomicroscope for appearance of fluorescent calli or shoots.

The presence of fluorescent protein expression was detected as described in Example 3. Fluorescent calli or shoots were removed from the explants and transferred to plates with MS3 basal medium (1× MS salts, 1× Gamborg's vitamins, 3% sucrose, 0.5 mM MES, 8 g/liter tissue culture agar, pH 5.8)+0.75 mg/l zeatin. The calli were grown on this medium until visible shoots formed. The shoots arising directly from the kanamycin plates were kept on this medium for only 1-2 weeks. The shoots were then transferred to MS3 basal medium+0.1 mg/liter zeatin and were subcultured on this medium until the shoots elongated (1-3 cm shoot length, at least 5 mm of stem length), with medium changes every 2 weeks.

The elongated shoots were transferred to magenta containers containing 0.5×MS salts, 1×MS vitamins, 1% sucrose, 0.1 mg/liter IBA, 1 mM MES, pH 5.7-5.8. Rooting was allowed to proceed until well-formed roots generated (2 weeks to 2 months). Plantlets were then transferred to soil.

Table 31 lists the number of trans-chromosomal events for tomato and tobacco.

TABLE 31

| Construct | # events |
|---|---|
| Tobacco transformants with tomato mini-C's - summary of events | |
| TB99R7-1 | 9 |
| TB99R10-1 | 3 |
| TB132R10-2 | 2 |
| TB99R8-1 | 1 |
| TB132R8-1 | 2 |
| Tomato transformants with tomato mini-C's - summary of events | |
| TB99R7-1 | 13* |
| TB132R10-2 | 10* |

*not all events fully regenerated, some of them still in organogenic phase

Example 9

Regeneration of Tobacco Plants Modified with Mini-chromosome DNA

The biolistic delivery method using wet gold particles, described in Example 2, was used to deliver tomato mini-chromosomes (described in Example 7) to Tobacco cells.

An explant from a tobacco leaf was cut using a cork borer. The leaves were immersed in MS medium during cutting to avoid tissue dehydration. The leaf disks were placed adaxial side up onto plates containing callus inducing medium with vitamins (4.44 g/L MS Basal Medium w/Gamborg Vitamins, 0.5 g/L MES, 3% sucrose, 0.5% tissue culture agar, non-essential amino acids, kinetin and 4 ml of 1000× Gamborg Vitamins, pH 5.8). After four days, the explants were bombarded with wet gold particles/DNA suspension as described in Example 2 using 450 psi rupture disks with the sample tray in the lowest position. For bombardment, explants were transferred onto 50 mm polyethylene mesh circles, and covered with mosquito netting.

Immediately after bombardment, all explants were returned to their original plates for 24 hours. Subsequently, the explants were transferred to MBNV plates (4.44 g/L MS Basal Medium w/Gamborg Vitamins, 0.5 g/L MES, 3% sucrose, 0.5% tissue culture agar, 0:1 mg/L NAA, 2.0 mg/L BA, 4 ml of 1000× Gamborg Vitamins pH 5.8) containing 50 µg/ml of kanamycin. After 5 days of selection, the explants were transferred to fresh MBNV plates containing 100 µg/ml kanamycin for 10 days. Subsequently, the explants were transferred to MBN plates (MBNV plates described above but without the added vitamins; 1× final concentration of Gamborg's vitamins), containing 100 µg/ml of kanamycin. These plates were subsequently subcultured about every 2 weeks afterwards, onto the same MBN plates containing 100 µg/ml of kanamycin.

The presence of fluorescent protein expression was detected as described in Example 3. A pea-sized fluorescent calli was removed from the plate and transferred to MBN medium without kanamycin. Fluorescent shoots were removed from the callus as they developed, and these shoots were transferred to Magenta containers containing 1×MS salts, 1×MS vitamins and 2% sucrose, pH 5.8. As the shoots enlarged and root formed, they were transferred to Magenta containers containing 0.5×MS salts, 0.5×MS vitamins and 1% sucrose. The transchromosomal events for tobacco plants are described above in Table 31.

Example 10

Soybean Centromere Discovery and
Mini-Chromosome Assembly and Construction

BAC Library Construction

A Bacterial Artificial Chromosome (BAC) library was constructed from Soybean genomic DNA isolated from *Glycine max* variety "Williams 82" and digested with the restriction enzyme MboI This enzyme was chosen because it is methylation insensitive and therefore can be used to enrich BAC libraries for centromere DNA sequences.

Probe Identification and Selection

Five groups of soybean repetitive genomic or plastid sequences, including specific centromere-localized sequences, were initially compiled as candidate probes for hybridization with the BAC libraries (Table 32). These probes represented various classes of Soybean repetitive sequences including satellite repeats (heterochromatic/centromere-specific), retroelements, telomeres, rDNA, and hypermethylated DNA fractions.

Seven probes were picked to interrogate the BAC libraries. These probes represent different groups of commonly found repetitive sequences in the Soybean genome. The probes selected are shown in Table 32 and were: two variants of the soybean centromere satellite (TRS and 3×1), 5S ribosomal DNA, plant telomeres, HpaII (bulk methylated DNA purified from genomic DNA by failure to digest with the methylation-sensitive enzyme HpaII) and Sau3A (bulk methylated DNA purified from genomic DNA by failure to digest with the methylation-sensitive enzyme Sau3A), and retroelement. The probes were prepared from cloned fragments isolated or from bulk methylated DNA prepared from Soybean genomic DNA. Sequences from the or PCR primes clones used to prepare each probe are shown in Table 32. The telomere probe sequence (SEQ ID NO: 40) was generated by PCR using the following primers: CHHZ-97 (AGGCGCGCCACCTG-CAGGAGAGCTCGGTCTCA TCGAGACAC; SEQ ID NO: 41) and CHHZ-98 (GGTCGACGGCCCGGGCGTT TAAACCCGGGCTCAC; SEQ ID NO: 42). Probes were prepared and labeled with standard molecular biology methods.

TABLE 32

Soybean Genetic Repetitive Sequences and BAC Library Probes

| Group # | Group Name | Probe Name | Description | Clone used for hyb | GenBank accession* |
|---|---|---|---|---|---|
| 1 | Cen repeat | SC2 (SEQ ID NO: 43) | TRS (centromere satellite repeat variant) | 5012-5-9-C02 | gi\|11464861\|gb\|AF297984.1\|AF297984 *Glycine max* clone TRS2 gi\|11464862\|gb\|AF297985.1\|AF297985 *Glycine max* clone TRS3 gi\|11464860\|gb\|AF297983.1\|AF297983 *Glycine max* clone TRS1 (SEQ ID NO: X) |
|  |  | SE7 (SEQ ID NO: 44) | 3X1(centromere satellite repeat variant) | 5012-5-9-E07 | Z26334.1\|GMP3X1SAT (SEQ ID NO: X) |
| 2 | rDNA | SC11 (SEQ ID NO: 45) | 5S rDNA | 5012-5-9-C11T | X06044.1\|GMRN45SI Soybean 4.5 - 5S rRNA intergenic (SEQ ID NO: X) |
| 3 | retroelement | SG12 (SEQ ID NO: 46) | retrovirus-like element | 5012-5-9-G12T | AF186186 (SEQ ID NO: X) |
| 4 | bulk repetitive DNA | SHpaII | Purified methylated DNA fraction | N/A | N/A |
|  |  | SSau | Purified methylated DNA fraction | N/A | N/A |
| 5 | telomere | Stel (SEQ ID NO: 40) | Telomere | PCR product | N/A |

*Accession number of BLAST hit; actual sequence has not been deposited in Genbank Library Interrogation and Data Analysis The BAC clones from the libraries were spotted onto filters and these filters were hybridized with each of the probes to identify specific BAC clones that contain DNA from the group of sequences represented by the probe(s).

A total of 18,432 BAC clones from the library were interrogated with each of the probes described above sing the following hybridization conditions: 0.5×SSC 0.25% SDS at 65 degrees for 15 minutes, followed by a wash at 65 degrees for a half hour. The hybridization intensities of the BAC clones with each probe were scanned to quantitate hybridization intensity for each clone. The outputs (scores of 1 to 10 based on the hybridization intensities, with 10 being the strongest intensity) were imported into a relational database, for further analysis and classification. The database contained a total of seven tables. Each table contains at total of 18,432 entries: the hybridization scores of each BAC clone from the library to one of the probes used to interrogate the library. Data analysis was done using standard SQL (Structured Query Language) routines to find BACs that contain different groups of repetitive sequences.

Classification and Selection of BAC Clones for Mini-Chromosome Construction

BAC clones containing centromeric/heterochromatic DNA were identified by their hybridization scores to different probes. The goal was to select BAC clones that contained a diverse set of various repetitive sequences. Twelve classes of centromeric BAC clones, some of which overlap, were eventually chosen to cover the broadest possible range of centromeric/heterochromatic sequences for mini-chromosome construction. Detailed descriptions of each class and probe hybridization values for each class are shown in Table 33.

A number of representative clones from each class were chosen to yield a total of 230 BAC clones for further analysis by restriction digest fingerprinting. The BAC clones were fingerprinted (Table 34) based on restriction sites found in the centromere specific sequence(s) as described in Example 1. The restriction enzymes HinfI and DdeI were used to digest the BAC clones. After fingerprinting, 33 BACs were selected for further testing using the method described in Example 1.

Thirty-three BAC clones (from the original 230) were selected for mini-chromosome construction and testing based on the fingerprint class which was defined as a simple or complex laddering pattern. Soybean fingerprints were classified into 3 classes: 1. high complexity (multiple large bands with no indication of laddering), 2. low ladder (predominant bands at multiples of the unit repeat size for the centromere satellite, and 3. complex ladder (features of both previous types). Table 34 lists the fingerprint patterns for this selected set of Soybean mini-chromosomes. The preferred BACs have an *. Table 35 lists the fingerprint classes for 10 selected soybean BACs.

TABLE 34

Restriction endonuclease fingerprinting of 33 soybean BACs

| BAC Number | BAC Class | Class Properties | HinfI Fingerprint Class | DdeI Fingerprint Class | MiniC tested |
|---|---|---|---|---|---|
| SB1 | J | High TRS, 3X1, HpaII | n/d* | 4. 6 bands/9 bands | SB1R3-1 |

TABLE 33

Classification of Soybean BAC clones containing centromeric DNA

| | | | | Probe Hybridization Range | | | | | |
|---|---|---|---|---|---|---|---|---|---|
| Class | Class Properties | TRS (C2) | 3X1 (E7) | 5S rDNA (C11) | RE (G12) | Meth (HpaII) | Meth (Sau3A) | TEL | # clones identified |
| A | High 3X1 | <=4 | >=10 | N/A | N/A | >=1 | N/A | N/A | 155 |
| B | High TRS | >=10 | <=4 | N/A | N/A | >=1 | N/A | N/A | 114 |
| C | High HpaII | <=10 | <=10 | N/A | N/A | >=7 | N/A | N/A | 43 |
| D | High HpaII only | <=4 | <=4 | N/A | N/A | >=5 | N/A | N/A | 44 |
| E | High TRS and HpaII | >=6 | N/A | N/A | N/A | >=5 | N/A | N/A | 34 |
| F | Highest 3X1 and High HpaII | N/A | >=6 | N/A | N/A | >=5 | N/A | N/A | 103 |
| G | High 3X1 and Highest HpaII | N/A | >=6 | N/A | N/A | >=5 | N/A | N/A | 103 |
| H | High TRS and 3X1 | >=8 | >=8 | N/A | N/A | >=1 | N/A | N/A | 54 |
| I | High TRS, 3X1, HpaII | >=7 | >=7 | N/A | N/A | >=4 | N/A | N/A | 5 |
| J | High TRS, 3X1, HpaII | >=6 | >=6 | N/A | N/A | >=4 | N/A | N/A | 33 |
| K | High TEL | >=1 | >=1 | N/A | N/A | >=1 | N/A | >=8 | 6 |
| L | High RE | >=1 | >=1 | N/A | >=8 | >=1 | N/A | N/A | 105 |
| Total** | | | | | | | | | 642 |

N/A = not applicable; This is functionally equivalent to >=1, as well as <=10

Classes F and G have the same threshold values but the selected clones for class F show the highest 3X1 scores of all the clones in the class; For class G, the selected clones show the highest HpaII scores for the class., and Classes I and J have the same criteria, but slightly different thresholds.

TABLE 34-continued

Restriction endonuclease fingerprinting of 33 soybean BACs

| BAC Number | BAC Class | Class Properties | HinfI Fingerprint Class | DdeI Fingerprint Class | MiniC tested |
|---|---|---|---|---|---|
| SB2 | D | High HpaII only | 4. 6 bands/ 9 bands | 4. 6 bands/9 bands | SB2R5-1 |
| SB3* | H | High TRS and 3X1 | 3. complex ladder | 3. complex ladder | SB3R1-1 |
| SB6* | B | High TRS | 2. simple ladder | 2. simple ladder | SB6R15-3 |
| SB8 | A | High 3X1 | 1. complex | 1. complex | SB8R3-1 |
| SB9* | H | High TRS and 3X1 | 3. complex ladder | 2. simple ladder | SB9R8-1 |
| SB10 | L | High RE | 1. complex | 1. complex | SB10R4-1 |
| SB11* | B | High TRS | 3. complex ladder | 3. complex ladder | SB11R3-1 |
|  |  |  |  |  | SB11R3-2 |
|  |  |  |  |  | SB11R3-3 |
| SB12* | B | High TRS | 3. complex ladder | n/d* | SB12R2-1 |
|  |  |  |  |  | SB12R2-2 |
|  |  |  |  |  | SB12R2-3 |
| SB21 | K | High TEL | 2. simple ladder | 1. complex | SB21R1-2 |
| SB22* | A/L | High 3X1/RE | 2. simple ladder | 1. complex | SB22R2-1 |
| SB24 | A/L | High 3X1/RE | 2. simple ladder | 1. complex | SB24R2-3 |
| SB29 | B | High TRS | n/d* | 3. complex ladder | SB29R2-2 |
| SB38* | H | High TRS and 3X1 | n/d* | 3. complex ladder | SB38R2-1 |
|  |  |  |  |  | SB38R2-2 |
| SB41 | H | High TRS and 3X1 | n/d* | 2. simple ladder | SB41R3-1 |
| SB45 | J | High TRS, 3X1, HpaII | 4. 6 bands/ 9 bands | 4. 6 bands/9 bands | SB45R5-1 |
| SB50* | B | High TRS | 3. Complex ladder | n/d* | SB50R1-1 |
| SB62 | A | High 3X1 | 2. Simple ladder | n/d* | SB62R1-2 |
| SB93 | B | High TRS | 3. complex ladder | n/d* | SB93R3-2 |
|  |  |  |  |  | SB93R3-3 |
| SB97 | A | High 3X1 | 2. simple ladder | n/d* | SB97R3-2 |
| SB102 | A | High 3X1 | 2. simple ladder | n/d* | SB102R3-1 |
| SB107 | B | High TRS | 2. simple ladder | n/d* | SB107R3-1 |
| SB111 | A | High 3X1 | 2. simple ladder | n/d* | SB111R3-1 |
| SB112 | A | High 3X1 | 3. complex ladder | n/d* | SB112R3-1 |
| SB116* | A | High 3X1 | 2. simple ladder | n/d* | SB116R3-1 |
| SB118 | A | High 3X1 | 2. simple ladder | n/d* | SB118R3-1 |
| SB119 | A | High 3X1 | 2. simple ladder | n/d* | SB119R3-2 |
| SB123 | A | High 3X1 | 2. simple ladder | n/d* | SB123R3-2 |
| SB125* | B | High TRS | 3. complex ladder | n/d* | SB125R3-1 |
| SB135 | B | High TRS | 2. simple ladder | n/d* | SB135R3-2 |
| SB138 | A | High 3X1 | 2. simple ladder | n/d* | SB138R3-1 |
| SB178 | B | High TRS | 2. simple ladder | n/d* | SB178R3-1 |
| SB219 | B | High TRS | 2. simple ladder | n/d* | SB219R3-3 |

TABLE 35

Restriction endonuclease fingerprint classification for 10 selected soybean BACs

| BAC Number | Class | Class Properties | Fingerprint Class HinfI | Fingerprint Class DdeI |
|---|---|---|---|---|
| SB3 | H | High TRS and 3X1 | 3. complex ladder | 3. complex ladder |
| SB6 | B | High TRS | 2. simple ladder | 2. simple ladder |
| SB9 | H | High TRS and 3X1 | 3. complex ladder | 2. simple ladder |
| SB11 | B | High TRS | 3. complex ladder | 3. complex ladder |
| SB12 | B | High TRS | 3. complex ladder | n/d* |
| SB22 | A/L | High 3X1/RE | 2. simple ladder | 1. complex |
| SB38 | H | High TRS and 3X1 | n/d* | 3. complex ladder |
| SB50 | B | High TRS | 3. Complex ladder | n/d* |
| SB116 | A | High 3X1 | 2. simple ladder | n/d* |
| SB125 | B | High TRS | 3. complex ladder | n/d* |

*G. Max* (soybean) BAC SB6 was deposited with the American Type Culture Collection (ATCC) on P.O. Box 1549 Manassas, Va. 20108, USA on Feb. 23, 2005 and was assigned Accession No. PTA-6602.

Construction of Mini-Chromosome

Each of the soybean BAC clones identified above were constructed using a Cre-Lox Recombination-Donor as described in Example 2. Soybean mini-chromosomes were constructed from a total of 33 BACs using donor vector pCHR151 in this assembly process, and were subsequently tested in several different soybean cell lines. Mini-chromosome genetic elements within the pCHR151 are described above in Table 10. The Soybean mini-chromosomes were used to transform broccoli plants (see Table 37 below).

Identification of Functional Soybean Centromeres

Functional testing of mini-chromosomes using transient assays as described may be carried out as in Example 3. Mini-chromosomes are delivered to the soybean cells using wet biolistic as described in Example 2. After DNA delivery, the cell population is then monitored for fluorescent protein expression over the course of one to several weeks. Mini-chromosomes containing active centromeres will allow the formation of fluorescent cell clusters, which are derived from a single progenitor cell that has divided and inherited the mini-chromosome to its daughter cells. Accordingly, single fluorescent cells and clusters of fluorescent cells of various sizes are scored in the growing cell population after DNA delivery. Standard protocols for soybean tissue culture and transformation, including those available at the University of Iowa, School of Agriculture web site, are used to regenerate adchromosomal soybean plants.

Mini-Chromosome Autonomy.

As a direct demonstration of mini-chromosome autonomy, circular constructs were recovered from fluorescent soybean cell lines that had been propagated for 5 months (~25 generations) following bombardment. Genomic DNA was extracted from a cell line containing SB12MC, and the DNA was treated with a highly processive exonuclease, resulting in degradation of all linear DNA fragments including those derived from host chromosomes. Surviving DNA molecules were introduced into *E. coli* and transformants were selected on antibiotic-containing medium.

Genomic DNA from unmodified soybean cells did not result in any antibiotic-resistant colonies, while DNA purified from the line containing mini-chromosomes yielded 13 independent modified colonies (2 from exonuclease-treated DNA and 11 from untreated DNA, R1-R13). DNA was extracted from each transformed E. coli clone and characterized by gel electrophoresis and sequencing. While the vector backbone of the rescued mini-chromosomes was typically unchanged (9/13 transformants). BAC-end sequencing demonstrated that 11/13 of the recovered clones retained the same DNA sequence junctions at the centromere cloning boundaries as the parental molecule (600/600 bp sequenced at each junction), including two of the mini-chromosomes with altered vector sequences.

Fluorescence in situ hybridization (FISH) was carried out to examine mini-chromosome autonomy and copy number. Cells containing mini-chromosomes were arrested in metaphase, spread on slides and probed with labeled soybean centromere satellite DNA (red) and mini-chromosome vector sequences. In cells hybridizing to both the centromere and vector probes, only one autonomous mini-chromosome was identified; similar signals were not detected in non-transgenic controls. Only a subset of the native centromeres were labeled, suggesting that the satellite sequence used as a probe is chromosome-specific. Strong vector hybridization signals were not detected within the host chromosomes, providing further evidence that the mini-chromosome DNA remained autonomous.

Satellite Sequences from Mini-Chromosomes

The identified soybean mini-chromosomes defined DNA sequences sufficient for centromere activity. The sequence content of the centromere-containing BAC clones and the mini-chromosomes derived from them with quantitative dot blots, using probes that correspond to i) vector sequences, ii) soybean satellites, iii) the SIRE retroelement, and iv) 28S rDNA, all of which are highly repetitive sequences present in the soybean centromeric region. BAC SB1 lacked centromere activity and has a high rDNA content with undetectable satellite and retroelement sequences. By contrast, the mini-chromosome derivatives of SB6 and SB12 had similar compositions, with 6.4 and 11.8 kb of centromere satellite, respectively. The recovered SB12 derivatives retained the parental composition (R4, R6, R7, R10), had a two-fold decrease in satellite (R1, R2, R3, R5), or had little or no satellite (R8, R9, R11, R12, R13). The SIRE retroelements present in SB12 were retained in most of the derivatives, suggesting little selective pressure to eliminate this sequence during growth of the modified cell culture. In addition, each mini-chromosome also contained ~8.5 kb of gene sequence from pCHR151 (Table 10).

DNA sequencing of SB12R2-3 (1.4-fold insert coverage) revealed ~80% of the insert was composed of tandem satellite repeats (Genbank U11026 and Z26334), ~9.9% was made up of retroelement-related sequences, and ~10.1% represented novel, contiguous sequence. The same analysis also produced 1.6-fold vector sequence coverage, indicating little if any cloning bias against fragments from the centromere. Individual satellite repeats showed an average of 91.3% (s.d.=11.3%) identity to each other, with specific regions showing significantly higher and lower levels of variability. Comparing the satellite repeat consensus from SB12R2-3 to that obtained from random satellite sequences (CrGm1 and CrGm2) identified several bases that differed significantly ($\chi^2$ test, P<0.05). The SB12R2-3 satellite repeats showed an average length of 91.07±0.40 bp, similar to the CrGm2 91-base consensus and differing from the CrGm1 92-base consensus. FIG. 6 shows an alignment of these consensus sequences.

Example 11

Analysis of Mini-Chromosomal DNA Expression in Transgenic Plants Visual Scoring

The adchromosomal plants described above in Example 4 (broccoli), Example 5 (canola), Example 6 (tobacco) and Example 7 (tomato) were tested to determine if the mini-chromosome DNA was being expressed. The presence of visible marker genes allowed for visual analysis to determine if the regenerated plants were expressing the fluorescent protein present on the mini-chromosome. For visual analysis, a piece of a leaf or other plant part was cut from the adchromosomal plant. A similar part is cut from a control plant (non-adchromosomal). The plants were analyzed under a fluorescence stereo-microscope as described in Example 3.

Table 37 displays the results of visual scoring of T0 adchromosomal plants.

TABLE 37

| Host | No. of Centromeres Tested and Origin of Centromere | No. of Positives | Scored In |
|---|---|---|---|
| Broccoli | 15 (13 broccoli, 1 soybean and 1 tobacco) | 12 (10 broccoli, 1 soybean and 1 tobacco) | plants |
| Broccoli | 15 (13 broccoli, 1 soybean and 1 tobacco) | 14 (12 broccoli, 1 soybean and 1 tobacco) | cluster formation |
| Canola | 1 (broccoli) | 1 | plant |
| Canola | 34 (broccoli) | 10 | cell culture |
| Tobacco | 2 (tomato) | 2 | plants |
| Tomato | 8 (tomato) | 2 | plants |
| Tomato | 20 (tomato) | 2 | cell culture |

Expression of the fluorescent protein gene encoded by the mini-chromosome was readily observed in the cells of a piece of tissue such as leaf or root taken from a transchromosomal plant under a fluorescence stereo-microscope. Fluorescence was very high and uniform throughout the tissue. Sectoring of fluorescence protein expression was observed in some cases.

PCR Analysis

PCR was used to amplify sequences within the mini-chromosome. This method allowed for detection of all mini-chromosome parts or a subset of parts. PCR analysis was also carried out in DNA samples isolated from whole cell DNA preparations from adchromosomal broccoli, canola and tobacco plants. A piece of leaf was cut from the plant and ground by hand using a pestle and a microcentrifuge tube. The DNA was isolated using Qiagen Kit (catalog no. 69106) according to the manufacturer's instructions. PCR reactions were carried out as follows: 3 μl template DNA, 2.5 μl of 10× Termopol buffer (New England Bioscience, Catalog No. B9004S), 0.5 μl dNTP's (10 mM each), 1.5 μl oligo 1 (20 μM), 1.5 μl oligo 2 (20 μM), 15.5 μl dH$_2$O and 0.5 μl Taq polymerase (New England Bioscience, Catalog No. M0267S). The Oligos used either detected the DsRed gene (CHHZ 150 and 152) or the UBQ10 promoter (CHHZ 467 and 469). To detect DsRed oligo CHHZ 150 (TGAACGGC-CACGAGTTCGAGATCG; SEQ ID NO: 47) and oligo CHHZ 150 (GTCCTCGTTGTGGGAGGTGATGTC; SEQ ID NO: 48) were used. To detect the UBQ10 promoter oligo CHHZ467 (CTGCCACTCCATTTCCTTCTCGGC; SEQ ID NO: 49) and oligo CHH469 (ACTTATCCGGTCCTAGAT-CATCAG; SEQ ID NO: 50) were used. The results of the PCR analysis are displayed in Table 38.

TABLE 38

| Host | No. of Events | No. of Plants Tested | No. of PCR Positives | No. of Visual Positives |
|---|---|---|---|---|
| Broccoli | 74 | 140 | 127 | 128 |
| Canola | 6 | 55 | 35 | 32 |
| Tobacco | 24 | 61 | 16 | 20 |

Western Blot

Expression of the fluorescent protein DsRed in the adchromosomal broccoli plants was measured by Western blot analysis. Leaf tissue, obtained using a cork borer, was ground to a fine powder using a chilled pestle and the leaf tissue was lysed using Novex Tris-Glycine SDS Sample Buffer (2×) on ice. The protein sample concentration was determined using the BAC assay and the samples were separated on a tris-glycine gel (4-20%) according to the manufacturer's instructions (Novex). A protein sample from a non-adchromosomal broccoli plant was run as a negative control. Boiled purified *E. coli* purified DsRed was run as a positive control. The protein was transferred from the gel to filter paper (nitrocellulose or PVDF). The filter was immunoblotted with an anti-DsRed primary antibody (Clontech), which was detected with an HRP-labeled secondary antibody and developed with Pierce Supersignal West Pico Chemiluminescent Substrate. Table 39 summarizes the Western Blot analysis.

TABLE 39

| | Broccoli Centromeres in Broccoli | | Soy Centromeres in Broccoli | |
|---|---|---|---|---|
| | No. tested | No. positive | No. tested | No. positive |
| Centromere | 9 | 9 | 1 | 1 |
| Mini-chromosomes | 28 | 28 | 1 | 1 |
| Events | 51 | 47 | 3 | 3 |
| Plants | 136 | 119 | 4 | 4 |

Expression of the DsRed mRNA in the adchromosomal broccoli plants was also analyzed by RT-PCR. Total RNA was isolated from plant tissue using the Qiagen mini-kit (catalog no. 74104) according to the manufacturer's instructions. The reverse transcriptase reaction was carried out with 11 µl DNAase I-treated total RNA, 1 µl oligo-DT (oligo CHR152 specific for DsRed), 1 µldNTP (10 mM each). The reaction was heated to 62° C. for 2 minutes and chill on ice, then the following was added: 4 µl 5×1$^{st}$ stand buffer (Invitrogen), 2 µl DTT (Invitrogen) and 1 µl Superscript II reverse transcriptase. The mixture was incubated at 42° C. for 1 hour. Subsequently, 80 µl of dH2O was added and the mixture was heat inactivated for 15 minutes at 70° C.

The cDNA samples generated by the reverse transcriptase reaction were amplified with a PCR reaction carried out with 5 µl cDNA, 2.5 µl 10× Themopol buffer (New England Bioscience), 0.5 µl dNTPs (10 mM each), 1.5 µM oligo 1 (20 µM each), 1.5 µl oligo 2 (20 mM each) 13.5 µl H2O and 0.5 µl Taq polymerase (New England Bioscience). 83 adchromosomal broccoli plants were tested and 69 were positive for DsRed mRNA expression (73 were positive by visual analysis).

Table 40 is a summary of the visual, PCR, Western, and RT-PCR data for the adchromosomal broccoli plants.

TABLE 40

| Event | PCR | RT | Western | Visual | Construct | Centromere | # Genes | # Plants |
|---|---|---|---|---|---|---|---|---|
| 4 | + | + | + | + | 5R4-1 | BB5 | 2 | 8 |
| 6 | + | + | + | + | 5R4-1 | BB51 | 2 | 5 |
| 7 | + | + | + | + | 5R4-1 | BB5 | 2 | 22 |
| 10 | + | + | + | + | 5R4-1 | BB5 | 2 | 16 |
| 15 | + | + | + | + | 5R4-1 | BB5 | 2 | 10 |
| 17 | + | + | + | + | 5R4-1 | BB5 | 2 | 17 |
| 18 | + | + | + | + | 71R1-1 | BB71 | 2 | 4 |
| 23 | + | + | + | + | 489 | integrative | 2 | 1 |
| 35 | + | + | + | + | 816-2 | BB5 | 4 | 4 |
| 39 | − | − | − | − | 817-A | BB5 | 4 | 13 |
| 40 | + | + | + | + | 817-A | BB5 | 4 | 3 |
| 51 | + | + | + | + | 817-A | BB5 | 4 | 7 |
| 52 | + | + | + | + | 819-A | BB5 | 4 | 4 |
| 53 | + | + | + | + | 819-A | BB5 | 4 | 3 |
| 55 | + | + | + | + | 819-A | BB5 | 4 | 6 |
| 67 | + | + | + | + | 824-9 | BB5 | 4 | 2 |
| 69 | + | + | + | + | 824-9 | BB5 | 4 | 5 |
| 83 | − | − | − | − | 591-1L | BB5 | 3 | 5 |
| 112 | + | − | − | − | 593-4L | BB5 | 3 | 5 |
| 119 | + | + | + | + | 593-4L | BB5 | 3 | 4 |

Example 12

Analysis of Autonomy and Integration of Mini-Chromosomes in Adchromosomal Broccoli Plants Southern Blot Southern blot analysis was carried out to analyze whether the mini-chromosome was autonomous or integrated into the genome of the of the adchromosomal T0 broccoli plants. An autonomous mini-chromosome will have the same restriction pattern as wild type plant DNA spiked with mini-chromosome DNA, while a mini-chromosome that has integrated into a host chromosome will have an altered restriction pattern and that altered restriction pattern is not predictable. If integration does occur and the junction between the host chromosome DN is in the centromeric region of the mini-chromosome, a restriction pattern similar to an autonomous mini-chromosome is expected. This is true because only the "gene region" (the part of the mini-chromosome excluding the centromere region) is subsequently used as a probe, as described below.

Plant tissue from the adchromosomal and control broccoli plants was ground to a fine powder in liquid nitrogen using mortar and pestle. Genomic DNA was isolated from the homogenized plant cells using phenol:chloroform:isoamyl alcohol extraction as taught by Csail et al., (Plant Mol. Biol. Rep. 16: 69-89, 1998). The DNA samples (5 µg) were digested with BglII restriction enzyme diluted in enzyme buffer, 100×BSA, 100 mM β-mercaptoethanol, 100 mM spermidine, dH$_2$O. The DNA was digested overnight at 37° C. Subsequently, an additional 2 µl of BglII was added to the DNA and allowed to digest a few additional hours. Loading buffer was added and the samples were separated on a 0.7% agarose gel. The DNA on the gel was visualized using ethidium bromide. The DNA on the gel was transferred to a nylon membrane using a Bio-Rad Vacuum Blotter (Model 785). The filters were probed with radiolabeled DNA complementary to the gene region of the mini-chromosome (entire sequence excluding the centromere region).

Southern blot analysis was carried out on 60 adchromosomal broccoli plants in which 32 events were tested, 7 centromeres were tested (6 broccoli centromeres and 1 soybean centromere). 40% of the samples were tested in duplicate.

The Southern Blot results are summarized in Table 41. In the majority of events, the gene region of the mini-chromosome was intact and the results indicate the mini-chromosomes were autonomous or integrated via the centromere sequence. BB5R4-1

TABLE 41

| Mini-chromosome | Centromere | No. of Events Tested | Consistent with Autonomy | Consistent with Integration | Not Detected |
|---|---|---|---|---|---|
| 5R4-1 | BB5 | 6 | 1 | 5 | — |
| 5R16-6 | BB5 | 1 | 1 | — | — |
| 817 | BB5R4-1 | 2 | 1 | — | 1 |
| 818 | BB5R4-1 | 1 | 1 | — | — |
| 819 | BB5R4-1 | 4 | 4 | — | — |
| 820 | BB5R4-1 | 1 | — | — | 1 |
| 823 | BB5R4-1 | 3 | 3 | — | — |
| 824 | BB5R4-1 | 2 | 1 | — | 1 |
| 591-1 | BB5R4-1 | 2 | 1 | — | 1 |
| 593-3L | BB5R4-1 | 1 | 1 | — | — |
| 593-4L | BB5R4-1 | 1 | — | 1 | — |
| 816-2 | BB5R4-1 | 2 | 2 | — | — |
| 965 | BB15R4-1 | 1 | 1 | — | — |
| 964-4 | BB15R4-1 | 1 | — | — | 1 |
| 967 | BB16R1-2 | 1 | 1 | — | — |
| 222R2-1 | BB222 | 1 | — | — | 1 |
| 972-5 | BB60R1-1 | 1 | 1 | — | — |
| SB986-1 | SB38R2-2 | 1 | 1 | — | — |
| Total | | 32 | 20 | 6 | 6 |

Fluorescence In Situ Hybridization

Fluorescence in situ hybridization (FISH) is carried out to determine the autonomy of the mini-chromosomes in root tips and anthers from the adchromosomal T0 broccoli plants. The tissues were probed with labeled pCHR151 and pCHR08, and BB5 PCRed BSAT and stained with DAPI. For analysis, the FISH chromosomal spreads needed to meet the following criteria: condensed and well-spread chromosomes, free of major background, strong centromere hybridization, 18 chromosomes, signal localized to approximately the same place on same chromosome. Integration is determined by detecting the mini-chromosome and it is associated with the genome and autonomy is determined by detecting the mini-chromosome and it was free of the genome. If the mini-chromosome is detected to be both free and associated with the genome it is both autonomous and integrated mini-chromosomes are present.

Example 13

Analysis of Mini-chromosomes in Ti Brassica Pollen and T1 *Brassica* Plants

To analyze the presence of the mini-chromosome in pollen isolated from a flowering adchromosomal T0 *Brassica* plant (T1 pollen), two anthers from each of three flowers were removed. The anthers were harvested from flowers that were open for more than a half a day and were shedding pollen. The anthers were streaked on a plate of sterile medium containing 1×MS salts, 13% sucrose, 0.8% tissue culture agar, pH 5.8, depositing a streak of pollen onto the surface of the plate. In a darkened room, the pollen was examined with a fluorescence stereo-microscope using 100× magnification and a rhodamine or FITC filter set. At least 500 pollen cells in groups of 100 were counted. Total pollen cells were counted under visible light and then examined under fluorescence.

T1 pollen was analyzed from adchromosomal T0 broccoli plants. The broccoli pollen visual data is summarized in Table 42.

TABLE 42

| Plant | Event | % of Pollen Grains Expressing DsRed |
|---|---|---|
| Pbo4A | 4 | 0% |
| pbo4E2 | 4 | no pollen |
| pbo7BCopy | 7 | 0% |
| pbo7C | 7 | no pollen |
| pbo7C1Copy | 7 | no pollen |
| pbo7S | 7 | 0% |
| pbo10C2 | 10 | no pollen |
| pbo10C2Copy | 10 | no pollen |
| pbo10D3 | 10 | no pollen |
| pbo15E1 | 15 | 0% |
| pbo15E2 | 15 | 7% |
| pbo15M1 | 15 | 1% |
| pbo15O | 15 | 0% |
| pbo17A1 | 17 | 0% |
| pbo17C2 | 17 | 0% |
| pbo17G1 | 17 | 0% |
| pbo17N1 | 17 | 0% |
| pbo18A | 18 | 1% |
| pbo18B | 18 | 0% |
| pbo19G3 | 19 | 4% |
| pbo28A | 28 | 0% |
| pbo39B1 | 39 | 0% |
| pbo39C | 39 | 0% |
| pbo40A | 40 | 32% |
| pbo40D | 40 | 25% |
| pbo51C | 51 | 4% |
| pbo51D | 51 | 0% |
| pbo52A | 52 | 0% |
| pbo52C | 52 | 1% |
| pbo53A | 53 | 8% |
| pbo55B | 55 | 4% |
| pbo69A1 | 69 | 0% |
| pbo83A1 | 83 | 0% |
| pbo112A3 | 112 | no pollen |
| pbo119A | 119 | no pollen |
| pbo126A | 126 | 0% |
| pbo126B | 126 | 3% |
| pbo173D | 173 | no pollen |
| pbo221A | 221 | 14% |
| pbo222E | 222 | 2% |

Adchromosomal T1 broccoli plants were generated by selfing or outcrossing. All crosses were done by bud pollination to overcome self-incompatibility and/or to ensure that the donor pollen gave rise to all seeds in the pod. To perform a bud pollination, an unopened flower was stripped of all sepals, petals and stamens, leaving only the immature pistil. Pollen from the appropriate plant was applied to the stigma. The flower was labeled and the pod allowed to develop normally The presence of the mini-chromosome in the adchromosomal T1 broccoli plants were analyzed visually and by PCR as described in Example 8. Three mini-chromosomes comprising one of two centromere sequences (with 2 and 4 genes) were analyzed. The data from the adchromosomal T1 broccoli plants is summarized in Table 43 and Table 44.

TABLE 43

T1 Adchromosomal Broccoli Plants

| | Visual scoring of T1 seedlings (outcross - male) | | Visual scoring of T1 seedlings (outcross - female) | | Visual Scoring of T1 seedlings (self) | | PCR on negative seedlings | |
|---|---|---|---|---|---|---|---|---|
| Event | tested | positive | tested | positive | tested | positive | tested | positive |
| 4 | 68 | 0 | 55 | 0 | — | — | 57 | 0 |
| 17 | 158 | 0 | — | — | 1 | 0 | 95 | 0 |
| 17 | 70 | 0 | — | — | 1 | 0 | — | — |
| 17 | 39 | 0 | 67 | 0 | 17 | 1 | — | — |
| 17 | 9 | 0 | 4 | 0 | — | — | 13 | 1 |
| 18 | 11 | 0 | 52 | 5 | — | — | — | — |
| 18 | 34 | 0 | — | — | — | — | — | — |
| 40 | 46 | 0 | 4 | 3 | 9 | 7 | 3 | 0 |

TABLE 44

T1 Adchromosomal Broccoli Plants

| | | Visual | | | | | | PCR of |
|---|---|---|---|---|---|---|---|---|
| | | Donor | | Recipient | | Self | | Negatives |
| Plant | Event | Tested | Positive | Tested | Positive | Tested | Positive | Tested | Positive |
| pbo4A | 4 | 69 | 0 | 55 | 0 | 0 | 0 | 57 | 0 |
| pbo17A1 | 17 | 258 | 0 | 51 | 0 | 9 | 0 | 98 | 0 |
| pbo17A3 | 17 | 77 | 0 | 1 | 0 | 1 | 0 | 0 | 0 |
| pbo17C2 | 17 | 43 | 0 | 65 | 0 | 20 | 0 | 0 | 0 |
| pbo17G1 | 17 | 0 | 0 | 4 | 1 | 0 | 0 | 0 | 0 |
| pbo17N1 | 17 | 9 | 0 | 4 | 0 | 10 | 0 | 13 | 0 |
| pbo18A | 18 | 248 | 0 | 52 | 0 | 6 | 0 | 0 | 0 |
| pbo18B | 18 | 50 | 0 | 29 | 0 | 0 | 0 | 0 | 0 |
| pbo22 | 22 | 66 | 0 | 0 | 0 | 0 | 0 | 0 | 0 |
| pbo40A | 40 | 56 | 28 | 3 | 1 | 9 | 7 | 59 | 27 |
| pbo40D | 40 | 65 | 32 | 22 | 13 | 40 | 31 | 0 | 0 |
| pbo51A | 51 | 64 | 0 | 0 | 0 | 12 | 0 | 0 | 0 |
| pbo51C | 51 | 101 | 0 | 63 | 2 | 0 | 0 | 0 | 0 |
| pbo51D | 51 | 0 | 0 | 0 | 0 | 2 | 0 | 0 | 0 |
| pbo52C | 52 | 83 | 0 | 236 | 6 | 59 | 0 | 0 | 0 |

Pollen was also analyzed from transformed T0 canola plants (*Brassica napus*) by visual analysis. The visual data is summarized in Table 45.

TABLE 45

Brassica napus pollen fluorescence summary

| Plant | Event # | Mini-C | # pollen counted | % fluorescent pollen | Flower size |
|---|---|---|---|---|---|
| 11-1-2 | 11 | pCHR820-1 | 568 | 87.5% | large |
| 11-1-4 | 11 | pCHR820-1 | 558 | 88.9% | large |
| 11-2 | 11 | pCHR820-1 | 637 | 68.8% | N.R. |
| 11-3-1-1 | 11 | pCHR820-1 | 613 | 52.7% | small |
| 11-3-1-2 | 11 | pCHR820-1 | 667 | 63.7% | small |
| 11-6-1 | 11 | pCHR820-1 | 591 | 98.0% | large |
| 11-6-2 | 11 | pCHR820-1 | 580 | 96.6% | large |
| 11-6-3 | 11 | pCHR820-1 | 640 | 93.8% | large |
| 11-6-4 | 11 | pCHR820-1 | 585 | 95.2% | large |
| 11-7 | 11 | pCHR820-1 | 607 | 67.2% | small |
| 11-8-1-1 | 11 | pCHR820-1 | 540 | 65.4% | N.R. |
| 11-8-1-2 | 11 | pCHR820-1 | 584 | 62.5% | small |
| 11-8-1-3 | 11 | pCHR820-1 | 512 | 64.8% | N.R. |
| 11-8-2 | 11 | pCHR820-1 | 542 | 66.4% | N.R. |
| 11-8-2-2 | 11 | pCHR820-1 | 652 | 69.8% | small |
| 11-8-2-3 | 11 | pCHR820-1 | 574 | 66.7% | small |
| 11-8-2-4 | 11 | pCHR820-1 | 610 | 63.1% | small |
| 11-12 | 11 | pCHR820-1 | 550 | 94.2% | N.R. |
| 11-14-1-1 | 11 | pCHR820-1 | 600 | 97.3% | large |
| 11-14-2 | 11 | pCHR820-1 | 569 | 97.7% | large |
| 11-15 | 11 | pCHR820-1 | 565 | 86.7% | large |
| 11-17 | 11 | pCHR820-1 | 605 | 98.0% | large |
| 16-2-2 | 16 | pCHR820-1 | >2000 | 0.0% | large/abnormal |
| 16-2-3 | 16 | pCHR820-1 | 655 | 61.1% | large/abnormal |
| 16-2-3 | 16 | pCHR820-1 | 589 | 48.9% | large/abnormal |
| 19-2 | 19 | pCHR820-1 | 573 | 40.1% | large |
| 19-3-1 | 19 | pCHR820-1 | 704 | 49.7% | large |
| 19-5-1 | 19 | pCHR820-1 | 666 | 49.7% | Large |

N.R. = not recorded

Pollen was also analyzed from adchromosomal T0 tobacco plants by visual analysis. The visual pollen data is summarized in Tables 46. In addition, adchromosomal T1 tobacco plants were analyzed visually and by PCR. The T1 plant data is summarized in Tables 47 and 48. T1 tomato pollen, harvested from adchromosomal T0 tomato plants was also visually analyzed. 537 pollen cells were counted and 153 were fluorescent (28.5%)

TABLE 46

Visual Analysis of Adchromosomal T0 Tobacco Plants

| Plant | Construct type | Construct | Fluorescent pollen | Total pollen | % |
|---|---|---|---|---|---|
| XNN | — | — | 0 | 2000 | 0 |
| pNt1E | mini-C | TB99R7-1 | 79 | 511 | 15.5 |
| pNt2A-3 | mini-C | TB99R10-1 | 289 | 531 | 54.4 |
| pNt2D-1 | mini-C | TB99R10-1 | 323 | 538 | 60.0 |
| pNt2H-2 | mini-C | TB99R10-1 | 251 | 520 | 48.0 |
| pNt2E | mini-C | TB99R10-1 | 268 | 507 | 53.0 |
| pNt2D | mini-C | TB99R10-1 | 195 | 508 | 38.0 |
| pNt2H | mini-C | TB99R10-1 | 76 | 507 | 15.0 |
| pNt4D-1 | mini-C | TB99R10-1 | 200 | 502 | 39.8 |
| pNt6A | mini-C | pCHR488 + TB99R1-5 | 18 | 120 | 15.0 |
| pNt8B | integrating | pCHR488 + 479 | 63 | 650 | 9.7 |

TABLE 46-continued

Visual Analysis of Adchromosomal T0 Tobacco Plants

| Plant | Construct type | Construct | Fluorescent pollen | Total pollen | % |
|---|---|---|---|---|---|
| pNt13D | integrating | pCHR488 + 480 | 188 | 519 | 36.2 |
| pNt15B | mini-C | TB99R8-1 | 249 | 500 | 49.8 |
| pNt15D | mini-C | TB99R8-1 | 272 | 506 | 54.0 |
| pNt16B | mini-C | TB132R8-1 | 202 | 501 | 40.0 |
| pNt16D | mini-C | TB132R8-1 | 277 | 506 | 55.0 |

TABLE 47

Visual Analysis of Adchromosomal T0 Tobacco Plants

| T0 Plant Event | Visual Score | Visual Scoring of T1 seedlings (self) counted | Red | % Red | PCR scoring of red (+) T1 seedlings (selfed) tested | positive | PCR scoring of non-Red (−) T1 seedlings (self) tested | positive |
|---|---|---|---|---|---|---|---|---|
| 1 | + | 192 | 174 | 90% | 10 | 6 | 16 | 0 |
| 1 | + | 91 | 79 | 87% | | | | |
| 2 | − | 294 | 0 | 0% | | | | |
| 2 | − | 393 | 1 | 0% | | | | |
| 2 | + | 208 | 163 | 78% | 10 | 10 | 25 | 0 |
| 2 | + | 177 | 126 | 71% | | | | |
| 2 | + | 200 | 145 | 73% | | | | |

TABLE 48

Visual Analysis of T1 Tobacco Seedlings

| Plant | Fluorescent Seedlings | Seedlings Counted | % Fluorescent |
|---|---|---|---|
| pNT 14B | 0 | 165 | 0% |
| pNT 15B | 36 | 61 | 62.30% |
| pNT 15D | 137 | 210 | 62.00% |
| pNT 1B(1) | 79 | 91 | 86.80% |
| pNT 1G(2) | 174 | 192 | 90% |
| pNT 2A-1 | 163 | 208 | 78% |
| pNT 2A-2 | 65 | 89 | 73.00% |
| pNT 2A-3(2) | 145 | 200 | 72.5% |
| pNT 2B-1 | 0 | 73 | 0% |
| pNT 2C(2) | 1 | 393 | 0.25% |
| pNT 2C-1 | 0 | 294 | 0% |
| pNT 2C-2(1) | 0 | 204 | 0% |
| pNT 2D(1) | 126 | 177 | 71.1% |
| pNT 2D(3) | | | |
| pNT 2E(1) | 185 | 238 | 77.7% |
| pNT 2F(1) | 0 | 228 | 0% |
| pNT 2F(2) | | | |
| pNT 2G(1) | 14 | 19 | 73.7% |
| pNT 2G(2) | 16 | 24 | 66.7% |
| pNT 2I(1) | 0 | 230 | 0% |
| pNT 2K(2) | 156 | 226 | 69.00% |
| pNT 2D(2) | | | |
| pNT 5A | 0 | 128 | 0 |
| pNT 15A | 0 | 78 | 0 |
| pNT 19A | 0 | 217 | 0 |

Example 14

Corn Centromere Discovery

BAC Library Construction

Two Bacterial Artificial Chromosome (BAC) libraries were constructed from corn genomic DNA. The corn genomic DNA was isolated from corn variety B73 and digested with the restriction enzymes BstYI or MboI. These enzymes were chosen because they are methylation insensitive and therefore can be used to enrich BAC libraries for centromere DNA sequences.

Probe Identification and Selection

Twenty-three groups of corn repetitive genomic or plastid sequences, including specific centromere-localized sequences, were initially compiled as candidate probes for hybridization with the BAC libraries (Table 49). These probes represented various classes of corn repetitive sequences including satellite repeats (heterochromatic/centromere-specific), retroelements, rDNA, B chromosome-specific repeats, chloroplast and mitochondrion DNA, hypermethylated or hypomethylated DNA fractions, and telomeric DNA.

TABLE 49

Maize Repetitive Sequences and Bac Library Probes

| Class | Class Name | Primers | Description | Reference | Comment | GenBank accession |
|---|---|---|---|---|---|---|
| 1 | CR (centromeric retrotransposable) element | CRJM-001 and 002 | gypsy-type localized to cen of all cereals. CentC and CRM co-IP with CEN H3 | Aragon-Alcaide et al 1996, Jiang et al 1996, Zhong et al 2002 | aka CRM, pSau3A9 (from sorghum), CRR (from rice) | AY1290008 |
| 2 | Cent-A | CHR 15 and 16 | centromere retrotransposon, includes MCS1A and B | | AF082532 Similar sequence | AF078917 |
| 3 | Huck | CRJM-005 and 006 | Ty3/gypsy | Meyers et al 2001 | (most frequent) | AF050438 |

TABLE 49-continued

Maize Repetitive Sequences and Bac Library Probes

| Class | Class Name | Primers | Description | Reference | Comment | GenBank accession |
|---|---|---|---|---|---|---|
| 4 | Grande | CRJM-056 and 057 | Ty3/gypsy | Meyers et al 2001 | | AF050437 |
| 5 | Cinful | CRJM-007 and 008 | Ty3/gypsy | Meyers et al 2001 | | AF049110 |
| 6 | Ji/Prem2 | LTR-5 CRJM-011 and 012 gag CRJM-013 and 014 | Ty1/copia | Meyers et al 2001 | | from alpha zein seq |
| 7 | Opie | | Ty1/copia | Meyers et al 2001 | 5' LTR | AF050453 |
| 8 | Tekay | CRJM-009 and 010 | | | 3' LTR | AF050452 |
| 9 | alpha zein | | | | | AF090447 |
| 10 | adh | | | | | AF123535 |
| 11 | bz | | | | | AF448416 |
| 12 | knob 180 | CHR 11 and 12 | | | many sequences! | gi|168710|gb| M32521.1| MZEZMA |
| 13 | MZEHETRO | CRJM-015 and 016 | maize heterochromatic repeat (knob) | Peacock et al PNAS. 78, 4490-4494 (1981) | | M35408 |
| 14 | TR-1(knob 360) | CHR 13 and 14 | Knob-specific | Hsu et al 2002 | 3 lengths, multi types. Type 1 BLASTs to all 3. Cuts w/RI | AF071126 |
| 15 | Cent-C | CHR 17 and 18 — CRJM-019 and 020 | 156 bp | Ananiev et al 1998 | all match well | AY321491 (Cent C27) AF078923 158a AF078922 156a |
| 16 | Cent4 | CRJM-021 and 022 | Chromosome 4 repeat homologous to B-chromosome cen repeat | Page et al, 2001 | | AF242891 |
| 17 | pZmBs and K5 | S67586 | B-specific repeats; B73 has no B chromosomes | Alfenito and Birchler 1993; Kaszas and Birchler 1993, 1998 | | AY173950 |
| 18 | rDNA | CRJM-023 and 024 | maize intergenic spacer | | | AF013103 |
| | | CRJM-025 and 026 | maize 5S | | | AF273104 |
| | | CRJM-027 and 028 | maize 17S | | | K0220 |
| 19 | chloroplast | CHHZ211 and 212 | *Arabidiosis* | | | |
| | | CRJM-030 and 031 | maize xpl rDNAs | | | X01365 |
| 20 | mito | CHHZ214 and 215 | *Arabidiosis* | | | |
| | | CRJM-032 and 033 | maize mito 26S rDNA | | | K01868 |
| 21 | hypermethylated fraction | purified | | | | complex mixture |
| 22 | hypomethylated fraction | purified | | | | complex mixture |
| 23 | telomere | | sub-telomeric repeat | | U39641 | U39642 |

Twelve probes were picked to interrogate the BAC libraries. These probes represent different groups of commonly found repetitive sequences in the corn genome. The twelve probes selected are shown in Table 49 and 50 and were: Cent-C (#15), Cent (#16), MZEHETRO (#13), TR-1 (#14), CentA (#2), CR (#1), Huck (#3), Grande (#4), 17S rDNA (#18), 5S rDNA (#18); B cen (#17), and xplmito (#19 and #20). The primers used to amplify these probes are identified in Table 49. Probes were prepared and labeled with standard molecular methods.

TABLE 50

| Class | Class Properties | Cent-C | CentA | CR | Huck | Grande | 17S rDNA | Cent4 | TR-1 | MZEHETRO | 5S rDNA | B cen | xplmito | # clones identified |
|---|---|---|---|---|---|---|---|---|---|---|---|---|---|---|
| I | HiC LoA | >=7 | <7 | <7 | <7 | <6 | N/A | N/A | N/A | N/A | N/A | N/A | N/A | 61 |
| II | HiC HiA | >=7 | >=6 | <7 | <=10 | <=10 | N/A | N/A | N/A | N/A | N/A | N/A | N/A | 61 |
| III | HiCR HiC | >=7 | <6 | >=6 | <=10 | <=10 | N/A | N/A | N/A | N/A | N/A | N/A | N/A | 30 |
| IV | HiA HiC HiCR | >=7 | >6 | >=6 | <=10 | <=10 | N/A | N/A | N/A | N/A | N/A | N/A | N/A | 30 |
| V | HiC Hi17s | >=7 | >0 | >0 | >0 | >0 | >5 | N/A | N/A | N/A | N/A | N/A | N/A | 30 |
| VI | Hi4 | >0 | >0 | >0 | >0 | N/A | N/A | >5 | N/A | N/A | N/A | N/A | N/A | 17 |
| VII | HiTr1 LoHet | >0 | >0 | N/A | N/A | N/A | >0 | N/A | >6 | <6 | N/A | N/A | N/A | 31 |
| VIII | LoTr1 HiHet | >0 | >0 | N/A | N/A | N/A | >0 | N/A | <5 | >7 | N/A | N/A | N/A | 31 |
| IX | HiTr1 HiHet | >0 | >0 | N/A | N/A | N/A | >0 | N/A | >6 | >6 | N/A | N/A | N/A | 24 |
| Total | | | | | | | | | | | | | | 315 |

*Values represent hybridization intensities of an individual BAC to each probe on a scale of 1 to 10. Values were normalized.

Library Interrogation and Data Analysis

The BAC clones from the libraries were spotted onto filters for further analysis. The filters were hybridized with each of the 12 probes to identify specific BAC clones that contain DNA from the group of sequences represented by the probe(s).

A total of 92,160 BAC clones from the two libraries (36,864 BAC clones from 2 filters from the BstYI library and 55,296 clones from 3 filters from the MboI library) were interrogated with each of the 12 probes described above sing the following hybridization conditions: 0.5×SSC 0.25% SDS at 65 degrees for 15 minutes, followed by a wash at 65 degrees for a half hour. The hybridization intensities of the BAC clones with each probe were scanned to quantitate hybridization intensity for each clone. Scores of 1 to 10 (based on the hybridization intensities, with 10 being the strongest hybridization) were imported into a relational database, for classification. The database contained a total of 24 tables, 12 from each library used in the interrogation. Each table contained the hybridization scores of each BAC clone from the BstY1 or MboI library, to one of the 12 probes. Data analysis was carried out using standard SQL (Structured Query Language) routines to find BACs that contain different groups of repetitive sequences.

Classification and Selection of BAC Clones for Mini-Chromosome Construction

BAC clones containing centromeric/heterochromatic DNA were identified by their hybridization scores to different probes. The goal was to select BAC clones that contained a diverse set of various repetitive sequences. Nine classes of centromeric BAC clones were eventually chosen to cover the broadest possible range of centromeric/heterochromatic sequences for mini-chromosome construction. Detailed descriptions of each class and probe hybridization values for each class are shown in Table 50.

Class I (HiC LoA) BAC clones had strong hybridization to probe Cent-C, but low hybridization to Cent-A, CR, Huck and Grande. Class II (HiC HiA) BAC clones had strong hybridization to both Cent-C and CentA, but low hybridization to CR. Class III (HiCR HiC) BAC clones had strong hybridization to both Cent-C and CR, but low hybridization to CentA. Class IV (HiA HiC HiCR) BAC clones had strong hybridization to Cent-C, CentA, and CR. Class V (HiC Hills) BAC clones had strong hybridization to Cent-C and 17S rDNA. Class VI (Hi4) BAC clones had strong hybridization to Cent4. Class VII (HiTri LoHet) BAC clones had strong hybridization to TR-1 but low hybridization to MZEHETRO. Class VIII (LoTr1 HiHet) BAC clones had strong hybridization to MZE-HETRO but low hybridization to TR-1. Class LX (HiTri HiHet) BAC clones had strong hybridization to both TR-1 and MZEHETRO.

A number of representative clones from each class were chosen to yield a total of 315 BAC clones for further analysis by restriction digest fingerprinting.

The 315 BAC clones were fingerprinted based on restriction sites found in the centromere specific sequence(s). Fingerprinting was used to evaluate the sequence composition of the large numbers of BAC clones and to compare their similarity to each other by comparing the restriction enzyme digest fragment patterns. A sequence with a tandem repeated sequence will show a single intense band of unit repeat size when digested with a restriction enzyme that cuts within the unit repeat. Second, BAC clones with similar sequences will show similar patterns of restriction fragments in a digest.

BAC DNA was extracted from bacteria using methods familiar to those in the art. Restriction enzymes HpaII and MspI were used to digest BAC clones in Classes I through VI, and restriction enzyme NdeI was used to digest BAC clones in classes VII through IX.

Z. mays (corn) BACs ZB19 and ZB113 were deposited with the American Type Culture Collection (ATCC) P.O. Box 1549 Manassas, Va. 20108, USA on Feb. 23, 2005 and assigned Accession No. PTA-6604 and PTA-6605, respectively.

Example 15

Construction of Maize Mini-Chromosomes

The 115 BAC clones identified in Example 1 were grown up and DNA was extracted for mini-chromosome construction using NucleoBond™ Purification Kit (Clontech). To determine the molecular weight of centromere fragments in the BAC libraries, a frozen sample of bacteria harboring a BAC clone was grown in selective liquid media and the BAC DNA harvested using a standard alkaline lysis method. The recovered BAC DNA was restriction digested and resolved on an agarose gel. Centromere fragment size was determined by comparing to a molecular weight standard.

For each BAC, two types of mini-chromosomes were generated, differing only by the promoter used to express the DsRed gene. Corn ADH promoter was used to express DsRed in mini-chromosomes constructed with pCHR667 and the Arabidopsis UBQ10 promoter was used to express DsRed in mini-chromosomes constructed with pCHR758. Mini-chromosome genetic elements within the pCHR667 and pCHR758 vectors are set out in Table 51 and 52, respectively.

TABLE 51

Donor Components of pCHR667

| Genetic Element | Size (base pair) | Location (bp) | Details |
|---|---|---|---|
| ADH Corn Promoter | 1189 | 14-1202 | PCR amplified maize promoter alcohol dehydrogenase 1 (ADH-1) for expression of DsRed in maize (used primers CRJM-42/43) |
| Maize ADH Intron | 579 | 1216-1794 | PCR amplified maize ADH intron with AUG mutation for stabilization of DsRed2 gene transcript and increase protein expression level (used primers CRJM-72/73) |
| DsRed2 + NLS | 780 | 1817-2596 | Nuclear localized red fluorescent protein from *Discosoma* sp. (Matz, M et. al *Nat Biotechnol* 1999 Dec.; 17(12): 1227). |
| ADH Terminator | 203 | 2725-2927 | Amplified maize terminator using primers CRJM-46/47 |
| Bacterial Kanamycin | 817 | 3066-3882 | Bacterial kanamycin selectable marker |
| Rps16A terminator | 489 | 4065-4553 | Amplified from *Arabidopsis thaliana* 40S ribosomal protein S16 (At2g09990) for termination of NptII gene |
| NPTII | 795 | 4617-5411 | Neomycin phosphotransferase II plant selectable marker |
| UBQ10 intron | 359 | 5439-5798 | PCR amplified *Arabidopsis thaliana* intron from UBQ10 gene (At4g05320) for stabilization of NptII gene transcript and increase protein expression level |
| YAT1 yeast promoter | 2000 | 5812-7811 | PCR amplified YAT1 promoter from chromosome I of *Saccharomyces cerevisiae* for expression of NptII in maize |
| LoxP | 34 | 10341-10374 and 7829-7862 | Recombination site for Cre mediated recombination (Arenski et. al 1983, Abremski et. al 1984) |

TABLE 52

Donor Components of pCHR758

| Genetic Element | Size (base pair) | Location (bp) | Details |
|---|---|---|---|
| UBQ10 promoter | 2038 | 14-2051 | *Arabidopsis thaliana* polyubiquitin promoter (At4g05320) |
| DsRed2 + NLS | 780 | 2088-2867 | Nuclear localized red fluorescent protein from *Discosoma* sp. (Matz, M et. al *Nat Biotechnol* 1999 Dec.; 17(12): 1227). |
| Pyruvate kinase terminator | 332 | 3002-3333 | *Arabidopsis thaliana* pyruvate kinase terminator (At5g52920) |
| Bacterial Kanamycin | 817 | 3478-4294 | Bacterial kanamycin selectable marker |
| Rps16A terminator | 489 | 4477-4965 | Amplified from *Arabidopsis thaliana* 40S ribosomal protein S16 (At2g09990) for termination of NptII gene |
| NPTII | 795 | 5029-5823 | Neomycin phosphotransferase II plant selectable marker |
| UBQ10 intron | 359 | 5851-6210 | PCR amplified *Arabidopsis thaliana* intron from UBQ10 gene (At4g05320) for stabilization of NptII gene transcript and increase protein expression level |
| YAT1 yeast promoter | 2000 | 6224-8223 | PCR amplified YAT1 promoter from chromosome I of *Saccharomyces cerevisiae* for expression of NptII in maize |

TABLE 52-continued

Donor Components of pCHR758

| Genetic Element | Size (base pair) | Location (bp) | Details |
| --- | --- | --- | --- |
| LoxP | 34 | 8243-8276 & 10755-10788 | Recombination site for Cre mediated recombination (Arenski et. al 1983, Abremski et. al 1984) |

Corn mini-chromosomes were constructed by following a two-step procedure: Step 1: Preparation of donor DNA for retrofitting with BAC centromere vectors and Step 2: Cre-Lox Recombination-BAC and Donor DNA to generate the mini-chromosome. A total of 230 corn mini-chromosomes were constructed using this assembly process, and were subsequently tested in several different corn cell lines.

Preparation of Donor DNA for Retrofitting

Cre recombinase-mediated exchange was used to construct mini-chromosomes by combining the plant centromere fragments cloned in pBeloBAC 11 with a donor plasmid (i.e. pCHR667 or pCHR758, tables 51 & 52). The recipient BAC vector carrying the plant centromere fragment contained a loxP recombination site; the donor plasmid contained two such sites, flanking the sequences to be inserted into the recipient BAC.

Cre recombinase-mediated exchange was used to construct mini-chromosomes by combining the plant centromere fragments cloned in pBeloBAC11 with a donor plasmid (i.e. pCHR667 & pCHR758, Tables 7 and 8). The recipient BAC vector carrying the plant centromere fragment contained a loxP recombination site; the donor plasmid contained two such sites, flanking the sequences to be inserted into the recipient BAC. Mini-chromosomes were constructed using a two-step method. First, the donor plasmid was linearized to allow free contact between the two loxP site; in this step the backbone of the donor plasmid is eliminated. In the second step, the donor molecules were combined with centromere BACs and were treated with Cre recombinase, generating circular mini-chromosomes with all the components of the donor and recipient DNA. Mini-chromosomes were delivered into E. coli and selected on medium containing kanamycin and chloramphenicol. Only vectors that successfully cre recombined and contained both selectable markers survived in the medium. Mini-chromosomes were extracted from bacteria and restriction digested to verify DNA composition and calculate centromere insert size.

To determine the molecular weight of the centromere fragments in the mini-chromosomes, three bacterial colonies from each transformation event were independently grown in selective liquid media and the mini-chromosome DNA harvested using a standard alkaline lysis method. The recovered mini-chromosome was restriction digested and resolved on an agarose gel. Centromere fragment size was determined by comparing to a molecular weight standard. If variation in centromere size was noted, the mini-chromosome with the largest centromere insert was used for further experimentation.

Functional Testing of Mini-Chromosomes Using Transient Assays

Maize mini-chromosomes were tested in several corn cell lines including PCI 117, HiII, and BMS, and the procedure was optimized for antibiotic selection, cell pre-treatments, and bombardment conditions. All assays were transient and fluorescent cells were counted at several time points. Preliminary results identified several mini-chromosomes that successfully generated fluorescent cell clusters.

Example 16

Transformation and Selection of Regenerable Cells and Corn Plant Regeneration

The biolistic delivery method using wet gold particles, described in Example 2, was used to deliver the mini-chromosomes into a number of different corn tissues including suspension cells, plate-grown calli, and immature embryos. For the purpose of transient delivery or selection of stable cell culture modified with a corn mini-chromosome, suspension cells were used for delivery using wet or dry gold delivery methods. An example of such a suspension culture is the publicly available line, PC1117.

To obtain trans-chromosomal corn plants modified with corn mini-chromosomes, standard protocols for corn tissue culture and transformation are followed. Such protocols include the Maize Embryo/Callus Bombardment Protocols available at Iowa Statue University, College of Agriculture web site.

The transformation process involved the preparation of regenerable tissues such as immature embryos from corn cultivars such as HiII, pre-culture of embryos on an auxin-enriched medium, delivery of miniC's into immature embryos or embryogenic calli, selection and isolation of fluorescent cell clusters, expansion of cell clusters and formation of transchromosomal embryos, maturation and regeneration of embryos into whole plants.

The invention claimed is:

1. A plant comprising at least one functional, stable, and autonomous mini-chromosome, wherein the mini-chromosome comprises a plant centromere, wherein the centromere (i) comprises a polynucleotide comprising at least 5 repeated nucleotide sequences, each comprising a nucleic acid sequence having at least 95% sequence identity with SEQ ID NO:24, and (ii) confers an ability to segregate the mini-chromosome to daughter cells through cell division.

2. The plant according to claim 1, wherein the mini-chromosome is 1000 kilobases or less in length.

3. The plant according to claim 1, wherein the mini-chromosome comprises a site for site-specific recombination.

4. The plant according to claim 1, wherein the mini-chromosome comprises a centromeric nucleic acid insert derived from a crop plant centromere.

5. The plant according to claim 1, wherein the mini-chromosome comprises a centromeric nucleic acid insert that comprises artificially synthesized repeated nucleotide sequences.

6. The plant according to claim 1, wherein the mini-chromosome is derived from a donor clone or a centromere clone and has substitutions, deletions, insertions, duplications or arrangements of one or more nucleotides in the mini-chromosome compared to the nucleotide sequence of the donor clone or centromere clone.

7. The plant of claim 1, wherein the mini-chromosome is obtained by passage of the mini-chromosome through one or more hosts.

8. The plant according to claim 1, wherein the mini-chromosome comprises one or more exogenous nucleic acids.

9. The plant according to claim 8, wherein at least one exogenous nucleic acid is operably linked to a heterologous regulatory sequence functional in plant cells.

10. The plant according to claim 1, wherein the mini-chromosome comprises an exogenous nucleic acid that confers herbicide resistance, insect resistance, disease resistance, or stress resistance on the plant.

11. The plant according to claim 1, wherein the centromere of the mini-chromosome comprises n copies of a repeated nucleotide sequence, wherein n is less than 1000.

12. The plant according claim 1, wherein the mini-chromosome comprises a telomere.

13. The plant according to claim 1, wherein the mini-chromosome is circular.

14. The plant according to claim 1, wherein the plant is a monocotyledon.

15. The plant according to claim 1, wherein the plant is a dicotyledone.

16. A part of the plant according to claim 1, wherein the plant part comprises the minichromosome.

17. A meiocyte, gamete, ovule, pollen, or endosperm of the plant according to claim 1, wherein the meiocyte, gamete, ovule, pollen or endosperm comprises the minichromosome.

18. A seed, embryo or propagule of the plant according to claim 1, wherein the seed, embryo or propagule comprises the minichromosome.

19. A progeny of the plant according to claim 1, wherein the progeny comprises the minichromosome.

20. The progeny of claim 19 wherein the progeny is the result of self-breeding.

21. The progeny of claim 19 wherein the progeny is the result of cross-breeding.

22. The progeny of claim 19 wherein the progeny is the result of apomyxis.

23. The progeny of claim 19 wherein the progeny is the result of clonal propagation.

24. A method of using a plant according to claim 1 to produce a food product comprising the steps of growing the plant, and harvesting or processing the plant.

25. A method of using a plant according to claim 1, to produce a recombinant protein comprising the step of growing a plant comprising a mini-chromosome that comprises an exogenous nucleic acid encoding the recombinant protein.

26. A method of using a plant according to claim 1 to produce a chemical product comprising the step of growing a plant comprising a mini-chromosome that comprises an exogenous nucleic acid encoding an enzyme involved in synthesis of the chemical product.

* * * * *

SEQUENCE LISTING

<160> NUMBER OF SEQ ID NOS: 52

<210> SEQ ID NO 1
<211> LENGTH: 484
<212> TYPE: DNA
<213> ORGANISM: Brassica oleraceae

```
<220> FEATURE:
<221> NAME/KEY: misc_feature
<222> LOCATION: (6)..(6)
<223> OTHER INFORMATION: n = a, c, g, or t

<400> SEQUENCE: 1
accctnccca aactgggaaa ctggaatcac ctgatttgaa agtgggataa cttcttcatg      60
ccaactccta tgagtttat  tcaacttcct ggtgattctc caccacttta tgtatccaaa    120
tcaagcttct tacaaagtga ttcatcctgg tttgattgga acgacgaaca agttgtgcta    180
ttcccaaact tggaaactgg aatcacctga cttgaaagtg ggataacttc ttcatcccaa    240
ctcctatgag atttattcaa cttcctggtg attctccacc actttatgta tccaaatcaa    300
gcttcttaca aagtgattca ttctggtttg tttggaacga cgaagaagcg ggatcctct    360 agagtcgacc tgcaggcatg caagcttgag tattctatag tgtcacctaa atagcttggc    420
gtaatcatgg tcatagctgt ttcctgtgtg aaattgttat ccgctcacaa ttccacacaa    480
cata                                                                 484

<210> SEQ ID NO 2
<211> LENGTH: 180
<212> TYPE: DNA
<213> ORGANISM: Brassica oleraceae
<220> FEATURE:
<221> NAME/KEY: misc_feature
<222> LOCATION: (129)..(129)
<223> OTHER INFORMATION: n = a, c, g, or t

<400> SEQUENCE: 2
ascttsattt ggatacataa agtagtggag aatcaccagg aagttgaata aatctcatag     60
gagttaggat gaagaagtta tcccactttc aaataaggtg atcccagttt ycctgtttgg    120
gaatatkana actthttcgh cattctadtc aaaccaggat gaatcgcgat gtaararvcy    180

<210> SEQ ID NO 3
<211> LENGTH: 661
<212> TYPE: DNA
<213> ORGANISM: Brassica oleraceae

<400> SEQUENCE: 3
ttgatctctt caactcaaac acacggctca gattagagat gttaccgtag accttttgga     60
gcgtatccca caggtccttt ggcgtctcac agtagctgta ggcttccagg attgaagctt    120
caagtgaccc atgtagtaca gtaagcacct tcaagtcatc ttgatcccac ttctcttgat    180
ctaccaccat cagctcttga ccgccttctc cttctttagc aactggtttc ggagctccat    240
ctgagatatg gctccataaa cccttgctcc caactgccgc tttcaccaag cgagaccaca    300
acaggtagtt agtaccaccc ttcaacttaa ccgcaaccga gagagccttg ctcttgcttt    360
cttccattcc aaattcttaa gaacaaccgt aaatgaaatg aagctgaaga ttactgagat    420
ttagaaacca ggaaatgggt aacctggctc tgataccatg aaagattaag agaatgaaat    480
gatttagaga agattaagga acagaatgag agattatgaa gagattagac tagaatcatg    540
attaagagag tatgaactta gagagataaa ctcagaactg tatggtttat tattaatgac    600
aagagttaca atatatagtg tgagatcata agggttttcg aaatcaaaga gctaagctaa    660
g                                                                    661

<210> SEQ ID NO 4
<211> LENGTH: 2139
<212> TYPE: DNA
<213> ORGANISM: Drosophila melanogaster
```

```
<400> SEQUENCE: 4
gttgtccgca gcggagatgc aactgatgca acccacattt cagatcaccg acaacgtgca      60
gcgcggcaac tacgccactc tgaccgacaa ggatgtggcg catttcgagc agctcctggg     120
caagaacttc gtgctcactg aggacctgga gggatacaac atctgcttcc ttaagaggat     180
tcgaggtagg ttgtgtaacc aaattcattc acattcgtgt gccctttaat gaatttctcc     240
gatgaattgc ttcaaccagg caacagcaag ttggtgctta agcccggaag cacggcggag     300
gtggccgcca tcctgaagta ctgcaacgag cgtcgtttgg cggtggtgcc gcagggcggg     360
aacacaggtc tagtgggcgg atccgtgccg atctgcgacg agattgtcct ttctctagcg     420
cgcctgaaca aggtgttatc cgtggacgag gtcaccggca ttgctgtcgt ggaggcgggc     480
tgcatcctgg agaacttcga tcagagggcc agagaggtgg gcttgacggt gccactggac     540
ctgggcgcca aggccagttg ccacatcggg ggcaatgtgt ccacaaacgc gggcggagtg     600
cgggtggtgc gttacggcaa tctgcacggc tctgttttgg gcgtggaggc ggtgctggcc     660
accggtcagg tgctggacct tatgtccaac ttcaagaagg acaacaccgg ctaccacatg     720
aagcacttgt tcataggatc cgagggcact ctgggcgtgg tcacgaagct ttcgatgctc     780
tgcccccatt cctcgcgagc ggtgaacgtg gccttcatcg gcctgaactc cttcgacgat     840
gtgctgaaga cttttgtcag tgccaagcgt aatctgggcg agattctaag ctcctgcgag     900
ctgattgacg agcgggcctt gaacaccgcc ctcgagcagt tcaagttcct gaagtgagtt     960
gcgccacctt tgtcttctct gagcgttacc aatcctgttc acaaacttat ttcccatagc    1020
tcccccattt cgggatttcc cttctacatg ctcatcgaga cctcgggcag caacggtgac    1080
cacgacgagg agaagatcaa ccagttcatt ggggacggta tggagcgtgg cgagatccag    1140
gatggcaccg taaccggtga tcccggcaag gtgcaggaga tctggaagat ccgcgaaatg    1200
gtgccgctgg gtctgatcga aagagcttc tgcttcaagt acgacatctc gctgcctctg    1260
cgggacttct acaacattgt ggacgtgatg cgagagaggt gcggtcccct ggccacagtt    1320
gtctgcggat acggccatct gggggactct aatctgcacc tgaacgtctc ctgcgaggag    1380
tttaacggcg agatctacaa gcgggtcgaa cccttcgtct acgagtacac ctccaagctg    1440
aagggcagca ttagtgcgga gcacggcatt ggcttcctga agaaggacta cctgcactac    1500
tccaaggacc cggtggccat ggctacatg cgcgagatga gaagctgct ggaccccaac    1560 agcatcctca atccctataa ggtgcttaac tgaaggcttc tacctaatag attctatttt    1620
ttttgtttgt gtgtaatttt cataacctta taatacagaa atggcattag aagtgaattt    1680
tgttaacttg tgaagttaaa aaggaccatc atatttggca cgaaaccaat gggcaaaact    1740
tacttataaa atagtccgaa aaaatagtat ataccagttt ttacagtacc acattatagg    1800
tactcggagg taataataga aaaaacacta tctttgcatt tactgttaca ctacgaagca    1860
ctatatttag tagcagtact cattagagtc cactcacaaa attagcacca accggcagta    1920
attggtcaag gatcggcgat agcttcaaac tccgaagttc aaagtcaaac tgccgccctg    1980
cgaaagcttc gcgagtggag ctttttctgca cttatcgata gctaacattg tggcgcgact    2040
atcgatcgac gagctgccgc ttaacagtgc catatataga ttgtaacatt agaagctcaa    2100
atcattgttg gagcacaaac cacaaagaac acacgaaac                           2139

<210> SEQ ID NO 5
<211> LENGTH: 2191
<212> TYPE: DNA
<213> ORGANISM: Drosophila melanogaster
```

<400> SEQUENCE: 5

```
aaaatatttc acctcatttt ccgcacacca tttataagca aagttacccc caacccataa        60
cttttatggt aagtaataca gaccctccaa gttcggcaaa tcgataccca gcgaccttga       120
gcttgacatt tatatatatg ccagaatata acgaccacgt gctgtcaact gtgtcaggaa       180
aagctcaccc acactttctt tggaggagct gtgctcccta aacgaatttc attgtcaagg       240
tcgcacgcac aaaaatgaag aggaaaagct gaatgtgggt ggaaatgccg gccggcacga       300
ccttgaagcc agttgggtga aaataaaaa gcttttgccg gtaggagact tgtggaacat        360
cacccacaag tggcggactt ggccttggcg atggccttgt tggagctccc tcagcaaaaa       420
tgttacatag ggggaggaaa taagctcaat tggctttatg ctttccgctc cctggaagtc       480
cttttctgga atgttaaagt gttaaatgac atttattgaa catttgggac agaggaggag       540
ataatacaat atacttgtct aattaaaaaa aatcgttatt atgatttatt ccatatgtaa       600
gatttttaatt catcatgatt gtaaataaat tatataaaac aaattcaata aatttacatt      660
attgataaaa tttatttttt catgaaatta tacccaaaaa ttattctcaa ttttttcttat     720
aatcagtttt gcataagtat actttcttca taccctctca ccacagccac tgctttcttg       780
actttgcaac tatccgggaa cagcttatca taatggatga gctgcagcta acggaaaatg       840
ggggagctgg gatcaaacat tttccaaggt tgaaattgtc gtcagcataa tgtttgaggg       900
agctggattc gcgttagctt gaaggtcaat ccatttgggt gccctttgtt atggtcaagt       960
ttaaggctgc aatagggga atcttcaagg accattacgc aaggttttcg catcaaagat       1020
ttgccgtgca agcttttga gttgaaggat gcttaacttg aaagcgggtt agtggttcca       1080
agagatttta ggtgaaggag actccgctgt tttgaaatat attaagtatg taaagaagta     1140
tactataaat aacccaaagt gatacaatgt aagaaaagat ctcgttggtc cctggtataa     1200
atttgtttgc cattaatgaa tattgaaaat aataattata ctaataatag gtacaataag     1260
caagattaaa ttgcatttaa tcaccaaaaa tcagtttcta tgcgaaccaa aatgtcataa     1320
caaacaattg ttgattcatc cgtagtgaaa tccaagttcg aaattcgaaa tgagcatacg     1380
acgaccaaac ttcccctcaa aattgctaga ctcagctaga gcaagtacgc ccaagttaac     1440
ccctgaaatt cgaaatgaat tcgatgccgc gcttcgaaca acgaaatccc aaagagctta     1500
cgttttatttt gacgtagcac tcttacgtga aatgattttc cccaattccg ctctcatttc    1560
ccgagtctct caccgcttct cagccacttt cccaccccct ttctagttcc gaagtaaagg    1620
taacaaaggc agccgtgtct ttggggtggt aaactggcgg tggtggtggc acattgtcag    1680
tggtgtgggt tcctgtggtt ggtggttcaa ttggttggtt gttggcataa acaaagcaca    1740
cacacaatac acacaaactc ccgggggtg gtggaaattg ggagggtgac attcactgcg     1800
agagaggaac tcgcttccta taggaaagta caaagagagc tatttttataa atgtgactgc    1860
agcaaggata tttacagtca gtccactctg aaacctcgac gagagaacat tgaataacaa     1920
gcggaagcga aaagcgcagt tgaaagttcg tcaaaaagcg acaagtttcc tcgttcgttt     1980
tcccgccaaa tgagtcagaa aaattttcca agtgctcgat acgaaacata aagacttaca    2040
agacttaaag tgcaagcagt gaatggaata tattattcct cagcgatatt gaaatcaaac     2100
attaaaaata tatgctacac taaagttata tattttttta aagattcata cgttttgtaa    2160
aatcacattt tgtattaaat taaataccgc c                                    2191
```

<210> SEQ ID NO 6
<211> LENGTH: 2035
<212> TYPE: DNA

<213> ORGANISM: Drosophila melanogaster

<400> SEQUENCE: 6

```
tgggtgcgtc gcaggtttca ctggaaaaca atttgcactt ttgtttgtgg agtcgacaac    60
aaaagcattc acttgtctaa gactctctca ttcataactc gcactttagt tcactgaacc   120
gcacgcaaaa ctttggggcg gacaacatgt tttcgaggtg ccaaaagctt cataaaacta   180
ccaatccatt agattaaatt ccaggcggta catcttttgg ggatgattca tgtggcaggg   240
gttctctact cgtttacaat catatcatca tcttcaagat catatagttt atcatatcag   300
tagagtacta caatataatg cataaactaa gccaaataac tttatgacgc gtgcttatgc   360
gaaagtaaac tttattatca aatttactta accgtgaaat caaaaccttt atataaacac   420
gaatattatt atctttgcta aataaaactc tcgcttaaca aacaatgaca cttcaattcc   480
aacatagagt ttatcttaag ccaataacca aaaacggaac ttacataact gccaacaaa    540
catatgaata tagctatttc ggatcgtggg agaccattat gcatacaagg cacgctccta   600
aaaccgtgt taaacaaata tatgtcaaat gtatatctta aaaaagcgcg cacatatctt    660
ttgaaatatc ttcacccaga gtatgtatga gattaaactg gattagcact aagccacagc   720
ttctgtagat agaaattta tgcagagagt agattatttg gctgctgagc aatttgacca    780
ccacaagata gcagagaaca tctgacattt tctatatcca tataataaaa ctgacttaac   840
actaagctga agtggtatgt ttaaatcctc cagctaataa atcgagacta aacgccctat   900
cttatagtga tatataatag tatctatatg tgtattgtca tttactgttt atgagtattt   960
gaaaaaacca ttctatattt tataggttag ttaataaata ttttgatata catatgtaga  1020
ttggctcaca cgtacttatg acccactaca taataaaatt gttttgtttt ttaatagaat  1080
aatggtttat aaaaagttta gactcacacg gaaatgataa actctttgca aatacagctt  1140
tcattttatt acaaattgca ctctttcaga tctgcagttg ctatgccaac cttttattcc  1200
ctttactaaa agggtatact aggcttactg aacagtatgt aactggtaaa gtaaagcgtt  1260
tccgattcta taaattatat atctaaactt ttgatcagtc gaatccatct gaacacattc  1320
tgtcacatta gattattcca gaaactcaac ttaaacatgt gtatttttta agaccattat  1380
caaggatatt aaaaatggtc tcctaaaatt taataaacaa agtgtcaca tcaaatttaa   1440
gacgtaaatt aatattttt ttctatggtg aaataattgt tatttccaa tgttgtgaaa   1500
taataaatgt atcttttcaa cgcacacatt ttcaaggttt taataataat agtgactcgt  1560
gcgtgaataa gagagaaatt aagattttaa aaaagaataa aattcagaga tgtgatctgt  1620
aaaaattatt taccaatttt catttacccc cgaaagtgat gctaatggtt aaaacggcat  1680
ttgcgactta tctcctacgt aatattgcaa aaataaggat ttggttagat gagtgtgaag  1740
taaacaagat gcaaagtttt ggagatagaa acatagcct tgagtcttgg tcatgtttac   1800
ttggcaccag gccgcgatta tcagcgctac tagtcgtaat ttgagttaga cctttaatac  1860
tctaagtgag agtgatgata tacgatttcc cagccacttg ctttctacga aatgcgctaa  1920
aaaaaatccc taactacaca aagatttgtg ttgttatcca ggtgttctga tataaaaggc  1980
ggcaaggaaa ttgatggcat catcagtatc aaagtgagag tgattgcagt cacac        2035
```

<210> SEQ ID NO 7
<211> LENGTH: 2136
<212> TYPE: DNA
<213> ORGANISM: Drosophila melanogaster

<400> SEQUENCE: 7

| | | |
|---|---|---|
| atgggacggt cctattctca gcaaaaattg acaagaacaa caacaatgtc tatggaaaat | 60 |
| cgaacttcat cccagcacct gcagaaatcc cgagcgagtc ggggaaaaag tatttaaccc | 120 |
| ccgaaagggt tttccccaaa ataatgaagt aatgaatgaa gcggaaaaca ctggccgcca | 180 |
| atctacctaa tactaatgag cgggccaacc cgaccaggaa tttttgcaag tcaggtactt | 240 |
| caacggatat atgggttcga caagtgcgga ttttcccgcg acatcaatga ggacttggcc | 300 |
| gggttatccg cggtgctcat cggcaattc cgcggccgag gacttcatcg tagtgatcat | 360 |
| taggtagata tgtgcatgga tgtgacatgg cgatcattgc gcggaataac acacgtaata | 420 |
| accgagatat ccgggatgac ccaccaggta ggatgtgagg acatatagaa aaccccccagc | 480 |
| cagttttcc actcgtcgtg gcttgttttg cttgagtttc gctgactgcg taattggata | 540 |
| agatgggaaa ttactttaaa tccttcgctg atccacatcc ggacattcgt cgaaggaaaa | 600 |
| tccattgcag ggaaatacga aatggaaatg cggctgggtt attggctcga catttcccat | 660 |
| cttccctcac gccattggtt gcaggatcgc ggggaattgg aattccgcgc tggaattttt | 720 |
| tgtcacctct tgggtttatc aaaacttttg ggtttgctat ggattttttc caattttacc | 780 |
| accgcgcctg gttttttttt tttgacgacg cggaaaatcg gacttggcta tgcgggcttg | 840 |
| tctgttttc cgggtacaaa gtctgcatgt cagcctccat gcgggagtgg gagttgggaa | 900 |
| agtttcccat cgatagttgg agggtggct tgaaagtctg gaggtgctag ctgggaaagt | 960 |
| tgtgtgtgcg cgatgaggca aggagtcaaa gatcagggga gttggaaagc gagaattgtg | 1020 |
| ggaatcgtcc aggactcagc tggatgctga ggggcagtat gattttttt acgttatcaa | 1080 |
| tcgaattgat tttaagacag cagaacttca catactaata agatgaccat gggattagtt | 1140 |
| aaaatgtgta actcgtattc gaatcgtcat tctttcacgg accaatcgtg gaacaggag | 1200 |
| atctcttcga tccaagctca caggagactt gacactcttc gtctattcct tgtcaagttt | 1260 |
| ttaatgacat ctcctatgcc ctgagctatg ttttcctagc tctcatcgat cgctgccaat | 1320 |
| gagccactgg agatgatcca taagtcagcg tagagtgcac cccagagttg acacttggtg | 1380 |
| tctcggaatt cggctcatta tcagtgctat ttttggaaca cctctctgcg aaggtgtcat | 1440 |
| ttttgtcagt gcgtatcgct caggttcaac tccccaccaa aaaccgaatt tagagcatcg | 1500 |
| gcagatgtac ttgaagcact caatctaagt gaggaaacca ccccatgaac gaagagtact | 1560 |
| aggagtccta tttgactcgt gcttaaaaat agaaaattac ttagggtgat ccataggtag | 1620 |
| ggaggcgata ttgtaacttg catttcggac ccggacctgc acgagttatt acgggtgggt | 1680 |
| tgtgagcgta tcgggaaatt ggagagccac cagatctgtc ataacttata cggggggatcc | 1740 |
| ttattcctgg gagggtgcgc ctgcgtctgc tcttccgaga gagaggtggg aaatggagga | 1800 |
| agagagagag agagagagtg agagagcagg tagagggaag tgagggaaat acgcaataag | 1860 |
| ggtatgggaa aagtgctgtt gttgttgcta ggtagcgacg cacacgtgcg agtgtttttc | 1920 |
| tgttttgaag aagaaccacc accaaatggc gacagcggcg tcgcagagg cgcagagttc | 1980 |
| cgggtataaa agagcgtgct cgactgttga cctgtcacag ccacctcagc tctcgttgag | 2040 |
| aacgcaacca ccgctctata ctcgatcccg aactatataa ctcgcctctc gatcgccgat | 2100 |
| ctcccgattt acccatctcg atcagtaccg gaaacc | 2136 |

```
<210> SEQ ID NO 8
<211> LENGTH: 2015
<212> TYPE: DNA
<213> ORGANISM: Drosophila melanogaster

<400> SEQUENCE: 8
```

-continued

```
atttggctcc ccatcgccat cggttgctcc aatgacacta gggaattgtg ggccgccgac      60
agctgtcctt aattacatgg aaatccacac tagattcgtg cccctcgccc cgtactcgca     120
gccgaagtcc ccacagagtc attcaccttg ccaccaccaa aaaaaaaacg aaagcaactg     180
aaggaaaagt tcgattcgaa ggctgaggga taccttaaaa gcccatttc ccggcttcgt      240
aaatcacatt tagttagcca tttagactac agcaagtctt ttaagataca ctgcaaaata     300
aataccatta cattaataga agtgtcatgt catcggtctg tattttttgtt accacagaat    360
agacttacat atatgataaa aaaatgttca acaataagtt acatcggtag ccaattctat     420
agatttaatt ccttacgaat atagtttcgt tggaatactc aatttgtaat tgtaattaat     480
tataattatt ataattttaa gaatttatat aagtaactaa aagacacggc agacacagaa     540
tgaaaacact ctatgttagg gaatgcaaaa aaacgtggcg gaagccaaaa ggcgcaagca     600
aaaatcgaaa ccaagtgaat ataacatatt atttcaacag gcaactcatt cagcatataa     660
tattaccacc catggagctt tatgtagttg atgtacgtag tctatgatgt ggagcccacg     720
ttggcggaac tgggaatggg gattggggtt tgagagctgt ggtaaattgg ggggttgaag     780
tatcaagggt ttgggttctg tagacctgcg gaatcgaggt gaataagcga agaacacatt    840
cacacacact aaaaggcaaa caaagggaaa tcaatctttg tacatacttt tagcatatgc    900
acacgtatga tctccaccca cttttccctc ccaatgaaac aaacacacac acacatgcaa    960
ggccgtacgt ttgtatatgt gtgcggttgt cggctttgcc gggaattggg gaatatttgc    1020
atgcctttgt gtacttttttc catatgattt atgacctaaa ttgttgctgc tcgcgcacat   1080
ataattacac acacatcgct gtggccatgt gtgtgtgtgt cgtcttggga cgcgcgccaa    1140
agtatgctac acttttttgtt ttatgagtta ataagtaggc gtggcccag cccaattgct     1200
acactctgat tatggcaccg gatacccaga tagacgccca tccaccccac tgtaagatgg    1260
gggaattttcc aaacctatat gtatgtgcag atcagatagg atagcacaga acttttttaaa   1320
gtacacttttt ggggcacgca atttagaaaa tgtacctcgg tgtcggagaa attatttttaa   1380
aagtcgactg aaccacctcg ttccatatgg agaagtctac gagttcaagt ttaatggagc    1440
agctgactgc actgaattttt gtagtttaat acacaaatcc gcaaattgca tctcacttca   1500
aatagcctgg tacatagtat ctactaacat aactcatatt aaaataaagc aaccaaccag    1560
agggccgaag ttctattaat aaaactaata tttaactatt atatatacat tttatttact    1620
tggtacgctt atgataacct tcgaaagaga accaacacaa tacgctttgt catttgaaaa    1680
ataaatatgc tgtaactact ttacaaggtg aaactcttgt cagaagataa gaggctaggt    1740
aagttgatta ttcaatcagt ttacttactg caacccaaaa tggtcactgc actaaccttc    1800
agatgagctg cactacaccc tcaatcgaga atcaatgcaa acgcagtgcc agcgaaaatg    1860
tcagcaaggg attaggccaa tcccaaacgg gtaatcccgc tgcgacaatg ctaatccaat    1920
tccgatgggc cgtataaaag ccccaagctg ggctggctgt gatttcgtct tggcccgcag    1980
accggagcat ggagtccggt aacgtgtcgt cgagc                               2015
```

<210> SEQ ID NO 9
<211> LENGTH: 2082
<212> TYPE: DNA
<213> ORGANISM: Drosophila melanogaster

<400> SEQUENCE: 9

```
atcgatgacg gcatcggctt gacctctcgg agtacgtttg attttataga acaagttttc     60
tcctttctta tactataagg aaaaattata aaaattgctg aaaatgaaac atggctagaa    120
```

```
ttcgttttttt aacattttttt caatctgaga aaaaatttcc gattagtctt aaaataacta    180
aaccaattcg tatacccgtt aatcgtagaa gaaaaatgaa attcatataa taagtagatg    240
gatttgctga cccggtgagg tatatatgta ttcctgaaca tgatcagtaa acgagtcgat    300
ctggccttat ccgtatgaac gtcgagatct cgggaaatac aaaagctaga aggttgagat    360
taagtatgca gattctagaa gaagacgcag cgcaagtttg cgactacgct gaatctactg    420
ctaaaaactg ccacgcccac acttcttaag aatttgattt attttcacaa gctgaggaac    480
ggtagggtcg aggaactcga ctacaacgtt ctgccttgtt tatttcttaa caaaaactta    540
gtagccgttt gggttggaaa ccacctgacc ttaggtctgg tagcagttat ttaatttatt    600 tttttttattt tatacaactt gctcgctgtt tgttccccct agccctgaaa cacaagctgt    660
caaacggtgg aggtgataag tctaatgaat gcgataagct ttatttcaat tcgcaatttt    720
cgtgtggcat tttggcaaaa aaaaaaactc gtcggacata catgttgcca caaacataaa    780
gtgaatacat aatgttgggt gaacgactca tacacgattg tggcaaatca aattctttta    840
acacgggacg gggaaaggcg agtgaagata ttttagcata tatttagcac atctgttaaa    900
tccatttttt tactctccgt tttcggccag atatggttag aaaagaaaaa aattagtaca    960 taccccccata tataataaga aaaaagagaa gagtcagcag aagtacgggg agcttaagtg   1020
tagcaatcag aacatcacaa atagtaaata aattaataat aataataatc atatccaaaa   1080
atatttttat tcctaaccta tcgcattgtt acatcgaggg tgaaattcaa aatagacaaa   1140
aagttgggga ataaaatgtg aaaaaagtgg taaaatgttt aatagtgtgg gcgttactgt   1200
tttgtcggtg tgaggtgcgt ggccaccaaa gtgttttttgg tataacgata gaaattggta   1260
agacaaacaa tattgcgaag aaaacccgaa gcatttttaa aaagtgcgaa cgtggcagtt   1320
ttaagggttt gtgggcgtgg caataatttt tggcaattcg ataaaaatgt acaggaccaa   1380
atatatgaag aaatataaaa tattttttcaa aatgacagcc agcaaccata catatatata   1440
aataaatgtc ggagacccctt ccttctacct gtaacatact tttccacgaa tctagtattg   1500
gttgatatat aattatgctg tgtataagac caaaatcagt gtacatttcc attggattca   1560
ccaaccggat ggttccggat ggtaatgcaa atattcatc taagaaacga aaacacctag   1620 aattaaaccct gaactgatat gacttatgca catatcagtg aggtgggcag ttcaaagcaa   1680
tcacgatgct ccaagttatt atcgcagtgc agtgaaaaat tcacagtcac cgtcgccaat   1740
tgccaataaa gatcggccat tatacaacag aaccgcgttg aagacgatcg acgaggtcgt   1800
gggtcttatc ttatcaccac ctgaattgag gcatgcctcc agaatgacga gggcatccga   1860
agataatgtg gcccgctatt ttcggccggg actggaccta tgcgacgacc tatgctgatg   1920 acggagtct gccgctgata tggtgcaatg caaggctcca gtcggggggta taaaagaccc   1980 agtttcggtg cagtcaagac aacagacttt aggtgttggt cgttgagcga accaaagccg   2040
gagcagttga ggaaccaaag aatagcagcg agaggaccaa gg                      2082
```

<210> SEQ ID NO 10
<211> LENGTH: 1999
<212> TYPE: DNA
<213> ORGANISM: Saccharomyces cerevisiae

<400> SEQUENCE: 10

```
tgtagggacc caaatccaat tgtagtagtt accttgatta tggttggctt gtccttcgat     60
agttttgcct tttccaaagc gctagaaatg gattccatat cgtcgtctcc tttatcgact    120
tccatgactt cccaaccata tgcctcgtat cgcttcaaaa catcttcgtc gaacgagtac    180
```

```
gaggttttac cgtcaatgga aatgctatta ctgtcataaa acgtaatcaa gttacccaat    240
tgcagatgtc ccgctaagga agaggtctcc gaagaaacac cctcttgtaa gcaaccatcc    300
cctacaatag caaacgtata tgagtcggaa atgggaaagc catcctcgtt ataagtggcg    360
gcaaagttgg cctgcgctat tgccatacca acagcatttg agatacctg gcctagcgga     420 ccggaagtga tttccactcc cgctgagtgg aattctggat gacccggtgt ccttgagttt    480
acttgtctaa attgtctcaa gtcctcgata gagtaatcgt atcctaatag atggagcatt    540
gagtacagaa gagcgcatga gtgaccgttc gacagaacaa acctgtctct attgatccaa    600
tgttcattgt tagggttaca gcgcagttgc ttgaaaatta catgggcaac tggtgccaat    660
cctagtggtg cacctgggtg gccagattgt gcgctttcca cctggtcaac ggaaagtaat    720
cttaaagtgg aaaccgcaag tttatcaatg tcggagaact gtgccatttt tttgttcttt    780
ttttgattag taaggtataa tcgtctacgt agaggttaca aatcgaagac tacagtaaga    840
ggggacaagc caattgaata tacgactgaa ataaatggaa taattctgca ttattacact    900
cgtttatata tccaaacagg tgatctggta ttctcttgac aacgaatgaa gctccctata    960
ttcgacactc cttattcagg actcctccca acaaggagaa gtaggtgttc cttgagctac   1020
cctttaaagc tggggagatg agcttgccct tcctgtcatc gccattatga cgagaaaagt   1080
aaaacatgta gaataaggtc cacccaaaca tgtccgagca atgacgttat atatcgtgtt   1140
ccctgttcaa agcatggcat atgtgccatt aaaggcgaat ttttgtccct agcaaaggag   1200
agacagcgag ccaccattaa gaagtgactt gaaagcaagc gaaatagct acacatatat    1260 atcaatatat tgacctataa acccaaaatg tgaaagaaat ttgataggtc aagatcaatg   1320
taaacaatta ctttgttatg tagagttttt ttagctacct atattccacc ataacatcaa   1380
tcatgcggtt gctggtgtat ttaccaataa tgtttaatgt atatatatat atatatat     1440 ggggccgtat acttacatat agtagatgtc aagcgtaggc gcttcccctg ccggctgtga   1500
gggcgccata accaaggtat ctatagaccg ccaatcagca aactacctcc gtacattcat   1560
gttgcaccca cacatttata cacccagacc gcgacaaatt acccataagg ttgtttgtga   1620
cggcgtcgta caagagaacg tgggaacttt ttaggctcac caaaaaagaa agaaaaaata   1680
cgagttgctg acagaagcct caagaaaaaa aaaattcttc ttcgactatg ctggaggcag   1740
agatgatcga gccggtagtt aactatatat agctaaattg gttccatcac cttcttttct   1800
ggtgtcgctc cttctagtgc tatttctggc ttttcctatt tttttttttc catttttctt   1860
tctctctttc taatatataa attctcttgc attttctatt tttctctcta tctattctac   1920
ttgtttattc ccttcaaggt ttttttttaa ggagtacttg tttttagaat atacggtcaa   1980
cgaactataa ttaactaaa                                                 1999

<210> SEQ ID NO 11
<211> LENGTH: 2001
<212> TYPE: DNA
<213> ORGANISM: Saccharomyces cerevisiae

<400> SEQUENCE: 11
tctgctatta ttgatgcttt gaagacctcc agacaaattt ttcacagaat gtactcttac    60
gttgtttacc gtattgcttt gtctctacat ttggaaatct tcttgggtct atggattgct   120
attttggata actctttgga cattgatttg attgttttca tcgctatttt cgctgatgtt   180
gctactttgg ctattgctta cgataatgct cctactctc caaagcccgt taaatggaac   240
ctaccaagat tatggggtat gtctattatt ttgggcatag ttttagctat aggttcttgg   300
```

```
                                         -continued attaccttga ctactatgtt cttaccaaag ggtggtatta tccaaaactt cggtgctatg    360
aacggtatta tgttcttgca aatttccttg actgaaaact ggttgatttt cattaccaga    420
gctgctggtc cattctggtc ttctatccca tcctggcaat ggctggtgc cgtcttcgct     480 gtcgacatca tcgctaccat gtttacctta ttcggttggt ggtctgaaaa ctggactgat    540
attgttactg tcgtccgtgt ctggatctgg tctatcggta tcttctgtgt tttgggtggt    600
ttctactacg aaatgtccac ttctgaagcc tttgacagat tgatgaacgg taagccaatg    660
aaggaaaaga agtctaccag aagtgtcgaa gacttcatgg ctgctatgca aagagtctct    720
actcaacacg aaaaggaaac ctaatcctgt tgaagtagca tttaatcata attttttgtca   780 cattttaatc aacttgattt ttctggttta attttttctaa ttttaatttt aattttttta   840
tcaatgggaa ctgatacact aaaaagaatt aggagccaac aagaataagc cgcttatttc    900
ctactagagt ttgcttaaaa tttcatctcg aattgtcatt ctaatatttt atccacacac    960
acaccttaaa attttagat taaatggcat caactcttag cttcacacac acacacacac    1020
cgaagctggt tgttttatttt gatttgatat aattggttc tctggatggt acttttttctt   1080 tcttggttat ttcctatttt aaaatatgaa acgcacacaa gtcataatta ttctaataga   1140
gcacaattca caacacgcac atttcaactt taatattttt ttagaaacac tttatttagt   1200
ctaattctta attttaata tatataatgc acacacacta atttattcat taatttttta   1260
ttgagtagga tttgaaaata tttggtatct ttgcaagatg tttgtataga gggacaaaga   1320
atcgtcttta ttatggtcaa ggctttacgt cataatagtt cctgcccagc tcttctataa   1380
tactttaaag atctcttctc gtttgctcca tttggaagtc tcgcttacgt ttatgcgccc   1440
atacagacac tcaagataca cacttacatg aacgtataca aatttactaa cactacttga   1500
aaatatgaac cacagtacat catattaaga cgtagtattc gatgattgaa ggccgcctcc   1560
gcgaaatacc tttactgatt ttgccggtta atcgcatcga aatttcttca tcacaagaaa   1620
gcaaacaaat cgccaggcca ttctacaagt ttcctttttct tatgaagatg taaaagctac   1680
taaggcgtca ttactctaga tgactcagtt tagtctgacc ttctatagta tactaccctg   1740
gcgctatgat gatgagcggt tctttttattg cggaaacgaa aattccggga ccggcgaaat   1800
ttgcccggtt ttgtccgtaa ccggcttcat gagtcggctt caatagtagt tgaatactta   1860
tttaaacagc agaacttaac tcactcatca cgctgtttcc gctgaatttt ctcaaaatat   1920
ctaagcagtc aacaaatata aagaatattg aaattgacag ttttttgtcgc tatcgatttt   1980 tattatttgc tgttttaaat c                                             2001

<210> SEQ ID NO 12
<211> LENGTH: 2000
<212> TYPE: DNA
<213> ORGANISM: Saccharomyces cerevisiae

<400> SEQUENCE: 12
ccaaatcatt cttattcggt ttccagacgg taacaatacc ctcgcccatc ccacacaaaa     60
gggtatctgc tacttcggga tcgacgaaac aaccacaaag aacttcgtcc tcctgatcat    120
cgctgatcaa aattttacca tcctcgtttc cagctacgtt cggtttggca tctttgtcgc    180
gaacgtcaaa ataagctaac gttgtctggc ccaaagaaat gaattatat gcagatcttt    240 tatcaaagtg gaaaatatcg ttgatagagt cgccaaaatg tatcgaacga atggaatttg    300
ataatgccaa gttttccgag tttattacgt gtatattacc ggattcatcg cctattaaaa    360
tgaatgggtg agtttgagag gcgcataatt tcgtaaattt atcattttttt ttctcttcag    420
```

-continued

| | |
|---|---|
| aattaaacag tgagcttaag tttaccttt tgacgactt gccggtcata gtattggcct | 480 |
| tttttaaaac attatccgat ccaacagaaa aaatattgtc acctttagaa tcaaagcaca | 540 |
| tggcacggac actacctta tgtcttttag tcttccaaag tgtttttacg cccaagtctt | 600 |
| catcttttcc tgtttgcttt tgttgctgtt gttcttcaat atcaacaaat ttcaaatctc | 660 |
| cagtttctag gtctatatct aatctaatcc aagggcatac acctttcttt gcatccttgc | 720 |
| ctgtagttgc agtgtcaatt ctacgtctac gatctaggtg cgattgcaac ttagcggggt | 780 |
| cataacgatg gcacacaata tgtcctgtac caaagccagt tattataatg gcagttcag | 840 |
| gatgtaaaag agactggaaa atgggagctt taatgatag taattctaga atgggcaggt | 900 |
| ttgttgaatc gacaacatct gtttttttt tgctctttgc catagctgat gcgtggattg | 960 |
| tttctaattt cccagctgct tcctcttcca attgtggcga tgatgccatg atttctatgt | 1020 |
| taaaatttt ctaaccatga aatttttttt ttctagcgag aaaaaaaatc agaaaaatta | 1080 |
| ctattagtga gtattggaga cattgtcaat gggagatgtt ctctttataa tatcttcaac | 1140 |
| aggttctttc aactctggaa attcatccac aatcttgtca gcaagtgaat ctcttaattg | 1200 |
| cttcaatcca tgcatcttgc ctcttttgata ttggttggat cttcttatgg cttccacgaa | 1260 |
| ctctcttgtg taaatatctg gatttctacc gtcctcaatg tattgaacaa cttccaaggg | 1320 |
| aatgtccacc ttagacaagc tggattgagg atcgttgctt ctcacgttca gcttgtacaa | 1380 |
| gcgatccaca tttctttgca agttggtgat cattcccttg gtggcttctg gagtaccagg | 1440 |
| aaaatcatat atcgagacac ctaattcaac gaaggactca ataatcgaag ccacttggtc | 1500 |
| ttgagtagtg gccagttctt gctgcaattg ttcattgtta gtgctgtttc cattcatctt | 1560 |
| atcggtttat ttttctatat atttgcctct tctcaaaca ggagttagta gttaaaagta | 1620 |
| cgaagttctt gttctttaat gcgcgctgac aaaagaattg gataaaagag aatggtgggg | 1680 |
| ggacaagaag gaaatttgtc ctagtttaac atgaatggca tcttgttacc gggtggacat | 1740 |
| cacctattga ttctaaatat ctttacggtt tatcatactg ttctttattc cgtcgttatt | 1800 |
| cttttattt ttatcatcat ttcacgtggc tagtaaaaga aaagccacaa catgactcag | 1860 |
| caaatctcga caaagtaaaa gctcatagag atagtattat attgatataa aaaagtata | 1920 |
| ctgtactgtt tgtaaccttt tcaatgcttt aagatcaaaa ctaaggccag caaaggtatc | 1980 |
| aacccatagc aactcataaa | 2000 |

<210> SEQ ID NO 13
<211> LENGTH: 2001
<212> TYPE: DNA
<213> ORGANISM: Saccharomyces cerevisiae

<400> SEQUENCE: 13

| | |
|---|---|
| gaaaccatta aatcatattt aataaattgt tgcgacatgc aagaagttcg cggatggtca | 60 |
| tgcgtattta agaatagtca agtaacaatt tgcttattcg ttgatgatat gatattattc | 120 |
| agcaaagact taaatgcaaa taagaaaatc ataacaacac tcaagaaaca atacgataca | 180 |
| aagataataa atctgggtga aagtgataac gaaattcagt acgacatact tggattagag | 240 |
| atcaaatatc aaagaagcaa gtacatgaaa ttaggtatgg aaaaatcctt gacagaaaaa | 300 |
| ttacccaaac taaacgtacc tttgaaccca aaaggaaaga aacttagagc tccaggtcaa | 360 |
| ccaggtcatt atatagacca ggatgaacta gaaatagatg aagatgaata caaagagaaa | 420 |
| gtacatgaaa tgcaaaagtt gattggtcta gcttcatatg ttggatataa atttagattt | 480 |
| gacttactat actacatcaa cacattgctc aaccatatac tattcccctc taggcaagtt | 540 |

```
ttagacatga catatgagtt aatacaattc atgtgggaca ctagagataa acaattaata      600
tggcacaaaa acaaacctac caagccagat aataaactag tcgcaataag cgatgcttca      660
tatggtaacc aaccatatta caagtcacaa attggtaaca ttttcctact caacggaaaa      720
gtgattggag gaaagtcgac aaaggcttcg ttaacatgca cttcaactac agaagcagaa      780
atacacgcgg tcagtgaagc tattccgcta ttgaataacc tcagtcacct tgtgcaagaa      840
cttaacaaga aaccaattat taaaggctta cttactgata gtagatcaac gatcagtata      900
attaagtcta caaatgaaga gaaatttaga aacagatttt ttggcacaaa ggcaatgaga      960
cttagagatg aagtatcagg taataattta tacgtatact acatcgagac caagaagaac     1020
attgctgatg tgatgacaaa acctcttccg ataaaaacat ttaaactatt aactaacaaa     1080
tggattcatt agatctatta cattatgggt ggtatgttgg aataaaaatc aactatcatc     1140
tactaactag tatttacgtt actagtatat tatcatatac ggtgttagaa gatgacgcaa     1200
atgatgagaa atagtcatct aaattagtgg aagctgaaac gcaaggattg ataatgtaat     1260
aggatcaatg aatattaaca tataaaatga tgataataat atttatagaa ttgtgtagaa     1320
ttgcagattc ccttttatgg attcctaaat cctcgaggag aacttctagt atatctacat     1380
acctaatatt attgccttat taaaaatgga atcccaacaa ttacatcaaa atccacattc     1440
tcttcaaaat caattgtcct gtacttcctt gttcatgtgt gttcaaaaac gttatattta     1500
taggataatt atactctatt tctcaacaag taattggttg tttggccgag cggtctaagg     1560
cgcctgattc aagaaaatatc ttgaccgcag ttaactgtgg gaatactcag gtatcgtaag     1620
atgcaagagt tcgaatctct tagcaaccat tatttttttc ctcaacataa cgagaacaca     1680
caggggcgct atcgcacaga atcaaattcg atgactggaa attttttgtt aatttcagag     1740
gtcgcctgac gcatataccgt ttttcaactg aaaaattggg agaaaaagga aaggtgagag     1800
ccgcggaacc ggcttttcat atagaataga gaagcgttca tgactaaatg cttgcatcac     1860
aatacttgaa gttgacaata ttatttaagg acctattgtt ttttccaata ggtggttagc     1920
aatcgtctta ctttctaact tttcttacct tttacatttc agcaatatat atatatatat     1980
ttcaaggata taccattcta a                                               2001
```

`<210>` SEQ ID NO 14
`<211>` LENGTH: 2001
`<212>` TYPE: DNA
`<213>` ORGANISM: Saccharomyces cerevisiae

`<400>` SEQUENCE: 14

```
cactaccacc actacggttg tccatgacgt atcctgcgat tttttgaatt aatgattcaa       60
tagttgacat ttgctcgtca ttggggttcg actgagctgc ggatgtcaac ttcgcaacag      120
cttctgcatg gtttccttga gaaaaatgag actcagcctc tgagattaac ttatccgtat      180
ccatttcaga tctttgctat acgtttgtat cgctatatgt acgttctttt aatgaacttt      240
ctcctttctt tatcgtgtag cttgcttggg tatcttttaa tgagttgcgg acagtgagat      300
ttttcagaag ggcaattggc caagacacca aaaacgtttg gacgagacag gcatcaaagg      360
acaaggtaaa aggcgttgag ctgtggctgg ctgtgtatgc gtttgaaata ccatggatag      420
atatcaaaga aagataggat gtttcataca aatcccaaat ttggggcgcg gacaactgaa      480
atacgtgggt ccagtggaca cgaaagctgg aatgtttgct ggtgtagact tacttgccaa      540
cattggtaag aacgatggat cattcatggg gaagaagtat tttcaaacag agtatcctca      600
aagtggacta tttatccagt tgcaaaaagt cgcatcattg atcgagaagg catcgatatc      660
```

```
gcaaacctcg agaagaacga cgatggaacc gctatcaata cccaaaaaca gatctattgt    720
gaggctcact aaccagttct ctcccatgga tgatcctaaa tcccccacac ccatgagaag    780
tttccggatc accagtcggc acagcggtaa tcaacagtcg atggaccagg aggcatcgga    840
tcaccatcaa cagcaagaat ttggttacga taacagagaa gacagaatgg aggtcgactc    900
tatcctgtca tcagacagaa aggctaatca caacaccacc agcgattgga aaccggacaa    960
tggccacatg aatgacctca atagcagcga agttacaatt gaattacgag aagcccaatt   1020
gaccatcgaa aagctacaaa ggaaacaact acactacaaa aggctactcg atgaccaaag   1080
aatggtcctc gaagaagtgc aaccgacttt tgataggtat gaagccacaa tacaagaaag   1140
agagaaagag atagaccatc tcaagcaaca attggagctc gaacgcagac agcaagccaa   1200
acaaaagcag ttttttgacg ctgagaatga acagctactt gctgtcgtaa gccaactaca   1260
cgaagagatc aaagaaaacg aagagagaaa tctttctcat aatcaaccca ctggtgccaa   1320
cgaagatgtc gaactcctga aaaaacagct ggaacaatta cgcaacatag aagaccaatt   1380
tgagttacac aagacaaagt gggctaaaga acgcgaacaa ttgaaaatgc ataacgattc   1440
gctcagtaaa gaataccaaa atttgagcaa ggaactattt ttgacaaaac cacaagattc   1500
ctcatcggaa gaggtggcat ccttaacgaa aaaacttgaa gaggctaatg aaaaaatcaa   1560
acagttggaa caggctcaag cacaaacagc cgtggaatcg ttgccaattt tcgaccccc   1620
tgcaccagtc gataccacgg caggaagaca acagtggtgt gagcattgcg atacgatggg   1680
tcataataca gcagaatgcc cccatcacaa tcctgacaac cagcagttct tctaggcagt   1740
cgaactgact ctaatagtga ctccggtaaa ttagttaatt aattgctaaa cccatgcaca   1800
gtgactcacg ttttttatc agtcattcga tatagaaggt aagaaaagga tatgactatg   1860
aacagtagta tactgtgtat ataatagata tggaacgtta tattcacctc cgatgtgtgt   1920
tgtacataca taaaaatatc atagcacaac tgcgctgtgt aatagtaata caatagttta   1980
caaaatttttt tttctgaata c                                            2001

<210> SEQ ID NO 15
<211> LENGTH: 2001
<212> TYPE: DNA
<213> ORGANISM: Saccharomyces cerevisiae

<400> SEQUENCE: 15
acaatgagga agaacatgcc gttttacaag aattaaatag tttaacccaa agaattaatg     60
aactaggcat ggaaagtata aattcaaact ccgattcgga cagaataaac gggtcatatt    120
cacaagtgga ttttggtaac aataacgacg aggacgatat gaacctgttc gacccagatt    180
ttatggcaca agaccaattg cgtgctgaag aaagagacta caacaaggat gatagaacac    240
ccttagctaa ggtccctgcg gcctttcaat caactggatt gggcataacc cccgatgacg    300
atatcgagag acaatacata acggaacaca gatcacgaca tgaagtgcca aagcggtctc    360
ccgagaaacc ctccaacccg ctggaaatag gtaacccata cgcgaaacct ggcacaaggt    420
tgaataccac tcacacccac agcaaaactg atcgtagcat taccccctcag aggggccagc    480
cagtcccatc aggccagcag atttcctcct acgtgcagcc agcaaacatt aatagtccta    540
acaaaatgta tggtgcaaac aactcggcaa tgggttcgcc caggaatcca agacgagag    600
cgccaccagg tccatacaat cagggatgga ataaccgccc ctcgccttca atatttacc    660
aacgtcctca tccctcagat acacaaccac aagcatatca tctccccgga aacccatact    720
caacggggaa caggccaaac atgcaagcgc aatatcaccc gcagcaggtg cccatgccta    780
```

```
tcctgcagca gcccaatcgc ccgtaccaac cttatgcgat gaatacgcac atgggctctc      840
ctggcggata tgctggggca gcaccaccat ttcagccagc taacgtcaac tacaatacta      900
ggcctcagca gccatggcct acacctaact caccatccgc acactaccgt ccgcccccta      960
acctgaacca gcctcaaaac ggtagtgctg gttactatcg tccgccggca ccacaattgc     1020
aaaactccca agcccgtcca caaagaagg acggattctc acagttcatg ccatctgcaa      1080
ctacgaagaa cccatatgcc cagtaactcg accgactggt tgtaatttta caaaaagaga    1140
gacaattaag aaaagaaaca agcgccaggc ttccgtatcc cagttttttca tctcactttc   1200 tgggcacgat tgtaataata cttcatgata ataactaaac tatataagta gtgtctcatc    1260
cgtaaatata catttagaca gattcttgta ttttctccgg gcaatttttta acttttttttc  1320 tgttagggca catgacactt gcctattatg gacagccagt aaagatgtgc catatattgc    1380 ccccttacg ctctctgcca gtattagtgg gaaaaaaaaa actgaaaaaa aaaaaatcgc     1440
agactactaa taatcacgtg atatttcttt tcactctctt cataaagttg ctaaaaacac    1500
acaatcgaat gagcctctga gcagtataaa ttgtacttca aagcactagt catgaaaaac    1560
gcttacatta gttcagtttg tcaaggttat gctattactt gtacttattt cttgctattg    1620
ttagtggctc cccacattga cgtatttttca cgtgatgcgc ctcactgcgg aaggcgccac   1680
acattgcctg caaaaaattg tggatgcact catttgatag taaactaagt catgttaatc   1740
gtttggattt ggcacacacc cacaaatata cacattacat atatatatat attcaaaata   1800
cagctgcgtc caatagatga gcttccgctt cgttgtacaa cctacctgct atcttgttca   1860
cggatatttc ttgcttttaa taaacaaaag taactctaga acagtcaagt cttcgataat   1920 tttttttagtc acagggtccg tctaaagttt ctctttattt ggaataatag aaaagaaaga  1980
aaaaaacgta gtataaaagg a                                            2001

<210> SEQ ID NO 16
<211> LENGTH: 2000
<212> TYPE: DNA
<213> ORGANISM: Saccharomyces cerevisiae

<400> SEQUENCE: 16
aaggatggca ataccccaat cggaggaact cgaacacttc agtatctgtg tcttctagtg       60
agtctttagc ggaagttatt cagccatctt ccttcaaaag tgggagtagt tcattgcatt     120
atctatcgtc ttctatctca agccaacctg gttcgtacgg ttcttggttc aacaaaaggc     180
caacaatttc tcagttcttt caaccaagcc cttctttaaa acacaacgag tcgtgggaga    240
ggctgcaaac aactgctgga atatgcaaa ggacttcaag ttcgtcttct ttgcagcaag      300
caacctccag gttatcacta accactccgc aacaatcacc gtctatcagc gaatatgatg    360
agtatccttg gatgggcaca cctggctctc ctaatgttgg agatgtgtct cacgcacccc   420
cattggttaa gaatatatca tataaatttc cactaaagaa cgttgagttg aaagagatt    480 gccaaaggat ctctcaggat gatctttgg atgaggcttt tgaaagaata tgtcagccct     540
ctttggctga ccttaattcc acttacgaaa tttttccagg taactcttct tatgcggata    600
ttttgactac tgattctgat attgatgatg gcttgatgaa taaacctctg gaactattgc    660
cgaaatatac aatgtatta acccatttta acaattttttt ccagttgcaa gcatgtcctg   720
ctggtcaaga atcagagagc agaataacaa attctatgaa gattgacctg ttaaaggcgg   780
attacacaag aagtctatta gtatcgttac gttcaaggga cattagggat gtcgcattga    840
aaagagagtt tactggcaat aacaacaata acagcaacca gaatatctat gatgagaatt    900
```

```
ttgtcggaaa aaggaagtac gtgttgaaac agaagaccag aaaaatctttt tcctgtggca    960
agattggcaa gctaagtact agtttggaaa actgcgttaa ttttgttgaa aatagtataa   1020
agagtgcaat gatgttatat gatgataatg gaatagatag tgagcttcgc gattcagaag   1080
ctttacggat ttttcatct cttgttcatt attgtaatgc aggttaatgt tttctccttc    1140
tttacatgtt taatatattc caagttacct aagaggtgta cgatattttt ttcttttata   1200
tatatgattt tctctattca tttttagtt tttttgata cataagcgaa tcgcacattg     1260
cgcaacttca atttgttgat tcgccaaagt attcttacca taaaacaacc attcgttgct   1320
ttacccttc gtaatcattt accgtgataa ccataatcag aaactattat tttcagccta    1380
gtagaccggc caagcaggcc ttgtaatgtt tctcttgatt gcttgaatct tttaagcagc   1440
caaatctttc caaaaaaatg caattatcag aacaaaacta tttaaggtga cttctccgta   1500
tttacaccac cagaagcgtt ctggctcccc ttttctctaa acgttaaaca ttttacaatt   1560
gaaatgttac caatcctata ttattgtacc acattgccag atttatgaac tctgggtatg   1620
ggtgctaatt ttcgttagaa gcgctggtac aattttctct gtcattgtga cactaattag   1680
gaaacttctc gactatcaat gtgtaaatga aggaataatg gcggaaactt tgaaactttg   1740
tcaataattg catcattgga tgcgtttcat ttggccgtta tcacggagag gcagagttct   1800
ctccacaatt tgggcagaag tcttttgaaa agacatatat atatatatat atgtatatga   1860
gtggatgctt aagtaagaa taatttctga attcccaagt attcattttg tgcagtattc    1920
acatattcta tttattgct tttaacttt agaggcaatt aaatttgtgt aggaaaggca     1980
aaatactatc aaaattttcc                                               2000
```

<210> SEQ ID NO 17
<211> LENGTH: 2001
<212> TYPE: DNA
<213> ORGANISM: Saccharomyces cerevisiae
<400> SEQUENCE: 17

```
ttgccttcaa gatctacttt cctaagaaga tcattattac aaacacaact gcactcaaag     60
atgactgctc atactaatat caaacagcac aaacactgtc atgaggacca tcctatcaga   120
agatcggact ctgccgtgtc aattgtacat ttgaaacgtg cgcccttcaa ggttacagtg   180
attggttctg gtaactgggg gaccaccatc gccaaagtca ttgcggaaaa cacagaattg   240
cattcccata tcttcgagcc agaggtgaga atgtgggttt tgatgaaaaa gatcggcgac   300
gaaaatctga cggatatcat aaatacaaga caccagaacg ttaaatatct acccaatatt   360
gacctgcccc ataatctagt ggccgatcct gatctttac actccatcaa gggtgctgac   420
atccttgttt tcaacatccc tcatcaattt ttaccaaaca tagtcaaaca attgcaaggc   480
cacgtggccc ctcatgtaag ggccatctcg tgtctaaaag ggttcgagtt gggctccaag   540
ggtgtgcaat gctatcctc ctatgttact gatgagttag gaatccaatg tggcgcacta   600
tctggtgcaa acttggcacc ggaagtggcc aaggagcatt ggtccgaaac caccgtggct   660
taccaactac caaggatta tcaaggtgat ggcaaggatg tagatcataa gattttgaaa    720
ttgctgttcc acagacctta cttccacgtc aatgtcatcg atgatgttgc tggtatatcc   780
attgccggtg ccttgaagaa cgtcgtgca cttgcatgtg gtttcgtaga aggtatggga    840
tggggtaaca atgcctccgc agccattcaa aggctgggtt taggtgaaat tatcaagttc   900
ggtagaatgt ttttcccaga atccaaagtc gagacctact atcaagaatc cgctggtgtt   960
gcagatctga tcaccacctg ctcaggcggt agaaacgtca aggttgccac atacatggcc  1020
```

| | | | | |
|---|---|---|---|---|
| aagaccggta | agtcagcctt | ggaagcagaa | aaggaattgc | ttaacggtca atccgcccaa | 1080 |
| gggataatca | catgcagaga | agttcacgag | tggctacaaa | catgtgagtt gacccaagaa | 1140 |
| ttcccattat | tcgaggcagt | ctaccagata | gtctacaaca | acgtccgcat ggaagaccta | 1200 |
| ccggagatga | ttgaagagct | agacatcgat | gacgaataga | cactctcccc ccccctcccc | 1260 |
| ctctgatctt | tcctgttgcc | tcttttcccc | ccaaccaatt | tatcattata cacaagttct | 1320 |
| acaactacta | ctagtaacat | tactacagtt | attataattt | tctattctct ttttctttaa | 1380 |
| gaatctatca | ttaacgttaa | tttctatata | tacataacta | ccattataca cgctattatc | 1440 |
| gtttacatat | cacatcaccg | ttaatgaaag | atacgacacc | ctgtacacta acacaattaa | 1500 |
| ataatcgcca | taaccttttc | tgttatctat | agcccttaaa | gctgtttctt cgagcttttt | 1560 |
| cactgcagta | attctccaca | tgggcccagc | cactgagata | agagcgctat gttagtcact | 1620 |
| actgacggct | ctccagtcat | ttatgtgatt | ttttagtgac | tcatgtcgca tttggcccgt | 1680 |
| ttttttccgc | tgtcgcaacc | tatttccatt | aacggtgccg | tatggaagag tcatttaaag | 1740 |
| gcaggagaga | gagattactc | atcttcattg | gatcagattg | atgactgcgt acggcagata | 1800 |
| gtgtaatctg | agcagttgcg | agacccgac | tggcactgtc | tcaatagtat attaatgggc | 1860 |
| atacattcgt | actcccttgt | tcttgcccac | agttctctct | ctctttactt cttgtatctt | 1920 |
| gtctccccat | tgtgcagcga | taaggaacat | tgttctaata | tacacggata caaaagaaat | 1980 |
| acacataatt | gcataaaata | c | | | 2001 |

<210> SEQ ID NO 18
<211> LENGTH: 1999
<212> TYPE: DNA
<213> ORGANISM: Saccharomyces cerevisiae

<400> SEQUENCE: 18

| | | | | |
|---|---|---|---|---|
| ttttgtaaga | aattattcac | cgcatcttca | tctggcaaac | gaatgggaga ctttgaggaa | 60 |
| cccaatccat | ttctgaataa | cggagattta | gaaatgtaaa | aggtagcaaa tgtaaaaagt | 120 |
| gccaggacca | tcacagcagt | caatgccaac | accaatttcc | cttgccatga cactgttgga | 180 |
| tcttttgaag | gagatttgta | acctggaatc | tcactataat | gaacacattc accggattca | 240 |
| cacttcaaag | taatataagg | gtcaccaaac | acggtcaata | tcaaatcatt catagaaggc | 300 |
| tcactgaatt | tacattgcct | tgtttctaaa | tcacagctga | aatctcctgg ccctttatt | 360 |
| gtctctgtca | ggaaatccga | gatatctata | gaccccttag | caccacacaa cacagtgtcg | 420 |
| ggaacgcatt | tgcattgaac | gtcattacac | ttataatggg | aggtattctg ttccaagtcg | 480 |
| tattcaaagg | cacaatcact | taagccacaa | tagaagcttt | ctaactgatc tatccaaaac | 540 |
| tgaaaattac | attcttgatt | aggtttatca | caggcaaatg | taatttgtgg tatttgccg | 600 |
| ttcaaaatct | gtagaatttt | ctcattggtc | acattacaac | ctgaaaatac tttatctaca | 660 |
| atcataccat | tcttataaca | tgtcccctta | atactaggat | caggcatgaa cgcatcacag | 720 |
| acaaaatctt | cttgacaaac | gtcacaattg | atccctcccc | atccgttatc acaatgacag | 780 |
| gtgtcatttt | tgtgctcttat | gggacgatcc | ttattaccgc | tttcatccgg tgatagaccg | 840 |
| ccacagaggg | gcagagagca | atcatcacct | gcaaacccctt | ctatacactc acatctacca | 900 |
| gtgtacgaat | tgcattcaga | aaactgtttg | cattcaaaaa | taggtagcat acaattaaaa | 960 |
| catggcgggc | atgtatcatt | gcccttatct | tgtgcagtta | gacgcgaatt tttcgaagaa | 1020 |
| gtaccttcaa | agaatggggt | cttatcttgt | tttgcaagta | ccactgagca ggataataat | 1080 |
| agaaatgata | atatactata | gtagagataa | cgtcgatgac | ttcccatact gtaattgctt | 1140 |

```
ttagttgtgt attttttagtg tgcaagtttc tgtaaatcga ttaatttttt tttctttcct   1200 cttttttatta accttaattt ttattttaga ttcctgactt caactcaaga cgcacagata   1260
ttataacatc tgcataatag gcatttgcaa gaattactcg tgagtaagga aagagtgagg   1320
aactatcgca tacctgcatt taaagatgcc gatttgggcg cgaatccttt attttggctt   1380
caccctcata ctattatcag ggccagaaaa aggaagtgtt tccctccttc ttgaattgat   1440
gttaccctca taaagcacgt ggcctcttat cgagaaagaa attaccgtcg ctcgtgattt   1500
gtttgcaaaa agaacaaaac tgaaaaaacc cagacacgct cgacttcctg tcttcctatt   1560
gattgcagct tccaatttcg tcacacaaca aggtcctagc gacggctcac aggttttgta   1620
acaagcaatc gaaggttctg gaatggcggg aaagggttta gtaccacatg ctatgatgcc   1680
cactgtgatc tccagagcaa agttcgttcg atcgtactgt tactctctct ctttcaaaca   1740
gaattgtccg aatcgtgtga caacaacagc ctgttctcac acactctttt cttctaacca   1800 aggggggtggt ttagtttagt agaacctcgt gaaacttaca tttacatata tataaacttg   1860
cataaattgg tcaatgcaag aaatacatat ttggtctttt ctaattcgta gttttttcaag   1920 ttcttagatg ctttcttttt ctctttttta cagatcatca aggaagtaat tatctacttt   1980
ttacaacaaa tataaaaca                                                 1999

<210> SEQ ID NO 19
<211> LENGTH: 1999
<212> TYPE: DNA
<213> ORGANISM: Saccharomyces cerevisiae

<400> SEQUENCE: 19
aaacaaatgg caaaaataac gggcttcacc attgttcctg tatggtgtat tagaacatag     60
ctgaaaatac ttctgcctca aaaaagtgtt aaaaaaaaga ggcattatat agaggtaaag    120
cctacaggcg caagataaca catcaccgct ctcccccctc tcatgaaaag tcatcgctaa    180
agaggaacac tgaaggttcc cgtaggttgt ctttggcaca aggtagtaca tggtaaaaac    240
tcaggatgga ataattcaaa ttcaccaatt tcaacgtccc ttgtttaaaa agaaaagaat    300
ttttctcttt aaggtagcac taatgcatta tcgatgatgt aaccattcac acaggttatt    360
tagcttttga tccttgaacc attaattaac ccagaaatag aaattaccca agtggggctc    420
tccaacacaa tgagaggaaa ggtgactttt taaggggggcc agaccctgtt aaaaaccttt    480
gatggctatg taataatagt aaattaagtg caaacatgta agaaagattc tcggtaacga    540
ccatacaaat attgggcgtg tggcgtagtc ggtagcgcgc tccccttagca tgggagaggt    600 ctccggttcg attccggact cgtccaaatt atttttttact ttccgcggtg ccgagatgca    660
gacgtggcca actgtgtctg ccgtcgcaaa atgatttgaa ttttgcgtcg cgcacgtttc    720
tcacgtacat aataagtatt ttcatacagt tctagcaaga cgaggtggtc aaaatagaag    780
cgtcctatgt tttacagtac aagacagtcc atactgaaat gacaacgtac ttgacttttc    840 agtatttct ttttctcaca gtctggttat ttttgaaagc gcacgaaata tatgtaggca    900
agcattttct gagtctgctg acctctaaaa ttaatgctat tgtgcacctt agtaacccaa    960
ggcaggacag ttaccttgcg tggtgttact atggccggaa gcccgaaaga gttatcgtta   1020
ctccgattat tttgtacagc tgatgggacc ttgccgtctt catttttttt tttttttcacc   1080 tatagagccg ggcagagctg cccggcttaa ctaagggccg gaaaaaaaac ggaaaaaaga   1140
aagccaagcg tgtagacgta gtataacagt atatctgaca cgcacgtgat gaccacgtaa   1200
tcgcatcgcc cctcacctct cacctctcac cgctgactca gcttcactaa aaaggaaaat   1260
```

-continued

```
atatactctt tcccaggcaa ggtgacagcg gtccccgtct cctccacaaa ggcctctcct    1320
ggggtttgag caagtctaag tttacgtagc ataaaaattc tcggattgcg tcaaataata    1380
aaaaaagtaa ccccacttct acttctacat cggaaaaaca ttccattcac atatcgtctt    1440
tggcctatct tgttttgtcc tcggtagatc aggtcagtac aaacgcaaca cgaaagaaca    1500
aaaaaagaag aaaacagaag gccaagacag ggtcaatgag actgttgtcc tcctactgtc    1560
cctatgtctc tggccgatca cgcgccattg tccctcagaa acaaatcaaa cacccacacc    1620
ccgggcaccc aaagtcccca cccacaccac caatacgtaa acggggcgcc ccctgcaggc    1680
cctcctgcgc gcggcctccc gccttgcttc tctccccttc cttttctttt tccagttttc    1740
cctattttgt ccсttttttcc gcacaacaag tatcagaatg ggttcatcaa atctatccaa    1800
cctaattcgc acgtagactg gcttggtatt ggcagtttcg tagttatata tatactacca    1860
tgagtgaaac tgttacgtta ccttaaattc tttctccctt taattttctt ttatcttact    1920
ctcctacata agacatcaag aaacaattgt atattgtaca ccccccccct ccacaaacac    1980
aaatattgat aatataaag                                                 1999

<210> SEQ ID NO 20
<211> LENGTH: 2009
<212> TYPE: DNA
<213> ORGANISM: Saccharomyces cerevisiae

<400> SEQUENCE: 20
ggatgagaaa cgagtgcggt ttcgagagta gatattcaac ccacccgaag tagccttcag      60
gaactggttc cgttctctct tcctccggaa tagtctgaat gtccttaaga gaccgtggct     120
cgtatactct tctattcttg ggccgcaata gcaaaaagag ccagacaaac acgacggcgg     180
taagaccgta gataatcagg gttgaaatga acgccgaagt cgaagaactg tcagccatag     240
tacgtatgtg ctataaatat ctaacctttc gctgctttga atatgatgtg ctcaaatata     300
acttaatata atagtataac aaaaaggagt actatttgct aaatatcgta gacgtagtag     360
acatagtaaa tacaataaag gatagataac caagaaccca catcaagcga atacatacat     420
atatatatac tcgatgtata catgtttcta agcacttgcg cacatacgta tttaaagtat     480
ttcagggaga ttaacgtatt aaaacaagaa gagggttgac tacatcacga tgaggggat     540 cgaagaaatg atggtaaatg aaataggaaa tcaaggagca tgaaggcaaa agacaaatat     600
aagggtcgaa cgaaaaataa agtgaaaagt gttgatatga tgtatttggc tttgcggcgc     660 cgaaaaacg agtttacgca attgcacaat catgctgact ctgtggcgga cccgcgctct     720
tgccggcccg gcgataacgc tgggcgtgag gctgtgcccg gcggagtttt tgcgcctgc     780 attttccaag gttacccctg cgctaagggg cgagattgga gaagcaataa gaatgccggt     840
tggggttgcg atgatgacga ccacgacaac tggtgtcatt atttaagttg ccgaaagaac     900
ctgagtgcat ttgcaacatg agtatactag aagaatgagc caagacttgc gagacgcgag     960
tttgccggtg gtgcgaacaa tagagcgacc atgaccttga aggtgagacg cgcataaccg    1020
ctagagtact ttgaagagga aacagcaata gggttgctac cagtataaat agacaggtac    1080
atacaacact ggaaatggtt gtctgtttga gtacgctttc aattcatttg ggtgtgcact    1140
ttattatgtt acaatatgga agggaaccттт acacttctcc tatgcacata tattaattaa    1200
agtccaatgc tagtagagaa gggggggтaac acccctccgc gctcttttcc gatttttttc    1260
taaaccgtgg aatatttcgg atatcctttt gttgttccg ggtgtacaat atggacttcc    1320
tcttttctgg caaccaaacc catacatcgg gattcctata ataccttcgt tggtctccct    1380
```

-continued

| | | | | | |
|---|---|---|---|---|---|
| aacatgtagg | tggcggaggg | gagatataca | atagaacaga | taccagacaa | gacataatgg | 1440 |
| gctaaacaag | actacaccaa | ttacactgcc | tcattgatgg | tggtacataa | cgaactaata | 1500 |
| ctgtagccct | agacttgata | gccatcatca | tatcgaagtt | tcactaccct | ttttccattt | 1560 |
| gccatctatt | gaagtaataa | taggcgcatg | caacttcttt | tcttttttt | tcttttctct | 1620 |
| ctccccgtt | gttgtctcac | catatccgca | atgacaaaaa | aatgatggaa | gacactaaag | 1680 |
| gaaaaatta | acgacaaaga | cagcaccaac | agatgtcgtt | gttccagagc | tgatgagggg | 1740 |
| tatctcgaag | cacacgaaac | tttttccttc | cttcattcac | gcacactact | ctctaatgag | 1800 |
| caacggtata | cggccttcct | tccagttact | tgaatttgaa | ataaaaaaaa | gtttgctgtc | 1860 |
| ttgctatcaa | gtataaatag | acctgcaatt | attaatcttt | tgtttcctcg | tcattgttct | 1920 |
| cgttccctt | cttccttgtt | tctttttctg | cacaatattt | caagctatac | caagcataca | 1980 |
| atcaactatc | tcatatacaa | tgtctatcc | | | | 2009 |

<210> SEQ ID NO 21
<211> LENGTH: 1943
<212> TYPE: DNA
<213> ORGANISM: Saccharomyces cerevisiae

<400> SEQUENCE: 21

| | | | | | |
|---|---|---|---|---|---|
| ggcagtcatc | aggatcgtag | gagataagca | ccctgacaag | taacatgccg | atgaagttgt | 60 |
| ttggttcatt | gggcaaaaaa | atcgggattc | tagaaaaccc | tgagttgaag | attttttcga | 120 |
| cagtttatc | gtctaggatg | gtatcggcac | tcattgtgaa | cacgttttca | atcggagtca | 180 |
| tgatttcctc | aaccctcttt | gcctttagat | ccaaaacagc | agagatgatt | gtaacttcgt | 240 |
| ctttagtcaa | ccgttccacc | cccatggtcc | tatgcaaggt | gaccaaagtc | tttaagccgg | 300 |
| attttttgta | catcgtacca | tgatcttcac | ccagcatata | gtccaggaga | gtcgcgatcg | 360 |
| gatatgcgac | tgggtacatc | agatacatca | gtacaagaac | aaaggggcag | aagaatgccc | 420 |
| caacttgcag | cccgtattta | acacagacac | tctgcggaat | aatttccacg | aagatcacaa | 480 |
| ttagaatagt | tgacgacact | acagcctgcc | aaccaccccc | aagacacctg | tccaaaacaa | 540 |
| taggcaatgt | ttcgttggtt | ataacattag | aaagcagcag | tgtgactaga | acccaatgct | 600 |
| tcccctaga | tattaggtca | agcacccgct | tggccagttt | cttttcagaa | ttcgagcctg | 660 |
| aagtgctgat | taccttcagg | tagacttcat | cttgacccat | caaccccagc | gtcaatcctg | 720 |
| caaatacacc | acccagcagc | actaggatga | tagagataat | atagtacgtg | gtaacgcttg | 780 |
| cctcatcacc | tacgctatgg | ccggaatcgg | caacatccct | agaattgagt | acgtgtgatc | 840 |
| cggataacaa | cggcagtgaa | tatatcttcg | gtatcgtaaa | gatgtgatat | aagatgatgt | 900 |
| atacccaatg | aggagcgcct | gatcgtgacc | tagaccttag | tggcaaaaac | gacatatcta | 960 |
| ttatagtggg | gagagtttcg | tgcaaataac | agacgcagca | gcaagtaact | gtgacgatat | 1020 |
| caactctttt | tttattatgt | aataagcaaa | caagcacgaa | tggggaaagc | ctatgtgcaa | 1080 |
| tcaccaaggt | cgtccctttt | ttcccatttg | ctaatttaga | atttaaagaa | accaaaagaa | 1140 |
| tgaagaaaga | aaacaaatac | tagccctaac | cctgacttcg | tttctatgat | aatacccctgc | 1200 |
| tttaatgaac | ggtatgccct | agggtatatc | tcactctgta | cgttacaaac | tccggttatt | 1260 |
| ttatcggaac | atccgagcac | ccgcgccttc | ctcaacccag | gcaccgcccc | caggtaaccg | 1320 |
| tgcgcgatga | gctaatcctg | agccatcacc | caccccaccc | gttgatgaca | gcaattcggg | 1380 |
| agggcgaaaa | ataaaaactg | gagcaaggaa | ttaccatcac | cgtcaccatc | accatcatat | 1440 |
| cgccttagcc | tctagccata | gccatcatgc | aagcgtgtat | cttctaagat | tcagtcatca | 1500 |

```
tcattaccga gtttgttttc cttcacatga tgaagaaggt ttgagtatgc tcgaaacaat   1560
aagacgacga tggctctgcc attgttatat tacgcttttg cggcgaggtg ccgatgggtt   1620
gctgagggga agagtgttta gcttacggac ctattgccat tgttattccg attaatctat   1680
tgttcagcag ctcttctcta ccctgtcatt ctagtatttt ttttttttt ttttggtttt   1740 actttttttt cttcttgcct ttttttcttg ttactttttt tctagttttt tttccttcca   1800
ctaagctttt tccttgattt atccttgggt tcttctttct actcctttag attttttttt   1860
tatatattaa tttttaagtt tatgtatttt ggtagattca attctctttc cctttccttt   1920
tccttcgctc cccttcctta tca                                           1943
```

<210> SEQ ID NO 22
<211> LENGTH: 2001
<212> TYPE: DNA
<213> ORGANISM: Saccharomyces cerevisiae

<400> SEQUENCE: 22

```
tgacaacgag taccaggaaa tcagtgcttc tgctttgaag aaggctcgta agggctgtga     60
tggtttgaag aaaaaggcag tcaagcaaaa ggaacaggtt tgaagaaac aacaaaaaga    120 ggcagaaaat gctgccaagc aattgtctgc tttgaatatc accattaagg aggacgaatc    180
gctaccagct gccattaaga ctagaattta tgactcttat tccaaggtcg acaaagagt    240 taaggtttcc ggttggatcc atagattacg ttctaacaag aaggttattt tcgtcgtcct    300
cagagacgga tctggtttca ttcaatgtgt cttgtccggt gatttggcat ggctcaaca    360 aactttggac ctgactttgg aatccaccgt tactctgtac ggtaccatag tcaaattgcc    420
tgagggtaaa accgctccag gtggtgttga attgaatgtc gactattacg aagttgtagg    480
tttggccccc ggtggtgaag actcctttac aaacaaaatc gcagagggct cagacccttc    540
tttactgttg gaccaacgtc atttggcctt gagaggagat gccttgtctg cagtcatgaa    600
agtccgtgct gctctactga aaagcgttag acgtgtttat gatgaagaac atttgacaga    660 agttaccccca ccatgtatgg tgcaaactca agtcgaaggt ggttccactt tgttcaagat    720
gaactattac ggcgaggaag cttacttgac ccaaagttcc caattatatt tagaaacctg    780
tttggcctcc ctaggtgatg tttataccat ccaagaatct ttcagagctg aaaagtccca    840
cacaagaaga catttgtccg aatatacccca tatcgaagct gaattggcct tcttgacttt    900
cgacgatcta ttacaacata ttgaaacttt gatcgtcaaa tccgtgcaat acgttttgga    960
agacccaatt gctggcccac tcgtaaaaca attgaatcca aacttaagg ctccaaaggc    1020 tccattcatg agattacagt acaaggatgc cattacctgg ttgaacgaac acgacatcaa    1080
gaacgaagag ggcgaagact ttaaatttgg tgacgatatt gcagaagctg ctgaaagaaa    1140
gatgaccgat accatcggcg tcccaatctt tttgacgaga ttcccagtag aaatcaagtc    1200
tttctacatg aagcgttgtt ctgacgaccc ccgcgtcact gaatccgtcg acgttttgat    1260
gccaaacgtt ggtgaaatca ctggtggttc tatgagaatc gacgacatgg acgaactaat    1320
ggcagggttt aagcgtgagg gtattgatac cgacgcctac tactggttca ttgaccaaag    1380
aaaatacggt acttgcccac atggtggtta cggtatcggt accgaacgta ttttagcctg    1440
gttgtgtgac agattcactg tcagagactg ttccttgtat ccacgtttca gcggtagatg    1500
taagccatga tctttagtta ctgaagagta cgtgagcgct cacatatata caaatattta    1560
taccgattaa tatttacgtt cctccctctc tctaattatt cattgattta ttcagaattt    1620
agcgttataa caataaatgg ttggcgcagg caattaattt ttctttactc ttccaaaccc    1680
```

```
tctgttaacg acaatcaaat aacctgatct gccaaggctc catcatatct ggcctagaac      1740
agtttttttt tttcgattat ttgttcgttc ttgtggtggt tactcattgg cagaatcccg      1800
aaaatcatga ttagtagatg aatgactcac ttttggata agctggcgca aattgaaaca      1860
```
*(line 1860 as shown)*

```
aaaatcatga ttagtagatg aatgactcac tttttggata agctggcgca aattgaaaca      1860
tgtgaaaaaa aaaaaaaagg attataaaag gtcagcgaag cacagaactc tgagataaga      1920
ctacctttct ttagctaggg gagaatattc gcaattgaag agctcaaaag caggtaacta      1980
tataacaaga ctaaggcaaa c                                                2001
```

<210> SEQ ID NO 23
<211> LENGTH: 1999
<212> TYPE: DNA
<213> ORGANISM: Saccharomyces cerevisiae

<400> SEQUENCE: 23

```
tcctaaggac atattccgtt cgtacttgag ttattggatc tatgaaatcg ctcgctatac        60
accagtcatg attttgtccc tggtaatagg ggttttggtt ttattaatta tatttttaa       120 tgacaacgaa gcttgtgttt tcaattctgc aatatttgct tttacttctc ttgtaggttt      180
gttaataata ttaagtgatg gtaatccaaa gctagtcagt cgtcgaaatt ttaggaccga      240
gcttttagtg gatgtcatca cacgtaaacc ggcggtagaa gggaaagaat ggaggatcat      300
cacatacaac atgaaccaat atttgtttaa tcatgggcaa tggcatactc cgtattactt      360
ttacagcgat gaggattgct accgttattt tctacgcctt gttgagggag taaccccccaa     420 gaagcaaaca gccacgtcaa ttggcaattc tccggtcacc gctaagcctg aagatgccat      480
cgagtcagct tctcctagtt ccagactgaa ttatcaaaac ttttttgctca aggcagcgga     540 gatcgaacga caagctcagg aaaattactg gcgaaggcgg catcccaata tcgatgcgct      600
tcttaaaaag acggaatagc ttagagacac taccatacgt aaagcgaaca taaactagag      660
tatgatatat aatcagcact aactggccgg aaaacggccg aaggaagcct cgaaaagtcg      720
attcgtgttg gacccatttg ctgaacaaag tggttcattg cctacctatt atggtagtag      780
tcgtgataat cgtgtggttg gttttgtcaa cggtgcattt gcattttcat gacaataaac      840
cttgcgtttt cgttctcggg atattacttt ccctccactt ctttcgcctc aatagctcct      900
ataagcattc tcagggcgta tgtcggtgat cgagatttcc aagcaagctt ttagtggaaa      960
tcatcgcgcg caagccagcg gtaaagggaa agaacggag gacgattaca tacaagatga      1020
acgaataaat aaattaataa taaataataa taaaaagtac agtagcatta aatattatta      1080
agtttaatga ttaaaaattg gttaattgtc aagaaaatct aaggtattaa taaataaata      1140
atactatgac aacttgcagc gaaagcatca gccccaatga aaattaatca gaattgaatc      1200
tgagcgtatt tatttgataa cggtttacgt aactgttgga ataaaaatca actatcatct      1260
actaactagt gtttacgtta ctagtatatt atcatatacg gtgttagaag atgacgcaaa      1320
tgatgagaaa tagtcatcgt tttcaacgga agctgaaata caaggattga taatgtaata      1380
ggatcaatga atatcaacat ataaaacgat gataataata tttatagaat tgtgtagaat      1440
tgcagattcc cttttatgga ttcctaaatc ctcgagaaga acttctagta tatctacgta      1500
cctaatatta ttgccttatt aaaaatggaa tcccaacaat tatctcaaaa ttcccccaat      1560
tctcatcagt aacaccccac cccgtattac ttttaccgtg atgaagattg gcatcgttac      1620
tttctaaacg taggacgtgc ggaatgacaa aaccatcagc agtgtcacga tctctccagt      1680
cacaatggca atcatgagtg catagtccaa agtaaggggg caaggaaaag catgattgaa      1740
aggactcccc atctggactc tatatgtcat cagcggctaa aaaaaagcat atagcacaac      1800
```

```
atcagcatca gcatcagcac tagagtcatc ggcccggcgg tccgcggtca tccccgcgga    1860 cttttccgtcc gcccggcggg ctgtatcagc gtcaactgga acgcgcatat atatacaaga    1920
cacacataac atagaagcac acccacgaca ataaccacac gacaataacc acacccgccc    1980
acccctcctt tccgtatac                                                  1999

<210> SEQ ID NO 24
<211> LENGTH: 91
<212> TYPE: DNA
<213> ORGANISM: Glycine max

<400> SEQUENCE: 24
aaawtcaaac gacaataact tttkactcgg atgtccgatt gwgtcccgta rtatatcgag    60
acgctcgwaa ttgaaaacwg aagctctrag m                                   91

<210> SEQ ID NO 25
<211> LENGTH: 92
<212> TYPE: DNA
<213> ORGANISM: Glycine max

<400> SEQUENCE: 25
aaattcaaat ggtcataact tttmacwcgg akgtccgatt caggcgcata atatatcgag    60
acgctcgaaa ttgaacaayg gaagctctcg ag                                  92

<210> SEQ ID NO 26
<211> LENGTH: 91
<212> TYPE: DNA
<213> ORGANISM: Glycine max

<400> SEQUENCE: 26
aaattcaaac gacaataact ttttactcgg atgtcygatt gagtcccgta atatatcgag    60
acgctcgaaa ttgaatrytg aagctctgag c                                   91

<210> SEQ ID NO 27
<211> LENGTH: 266
<212> TYPE: DNA
<213> ORGANISM: Brassica oleraceae
<220> FEATURE:
<221> NAME/KEY: misc_feature
<222> LOCATION: (38)..(38)
<223> OTHER INFORMATION: n = a, c, g, or t
<220> FEATURE:
<221> NAME/KEY: misc_feature
<222> LOCATION: (242)..(242)
<223> OTHER INFORMATION: n = a, c, g, or t

<400> SEQUENCE: 27
gatttagatt gtactcattc caattaccag actcgaanag cccggtattg ttatttattg    60
tcactacctc cccgtgtcag gattgggtaa tttgcgcgcc tgctgccttc cttggatgtg   120
gtagccgttt ctcaggctcc ctctccggaa tcgaaccct attctccgtc acccgttacc    180
accatggtag gccactatcc taccatcgaa agttgatagg gcagaaattt gaatgatgcg    240
tngccagcac taaggccatg cgatcg                                         266

<210> SEQ ID NO 28
<211> LENGTH: 345
<212> TYPE: DNA
<213> ORGANISM: Brassica oleraceae
<220> FEATURE:
<221> NAME/KEY: misc_feature
<222> LOCATION: (9)..(9)
<223> OTHER INFORMATION: n = a, c, g, or t
<220> FEATURE:
```

```
<221> NAME/KEY: misc_feature
<222> LOCATION: (17)..(17)
<223> OTHER INFORMATION: n = a, c, g, or t
<220> FEATURE:
<221> NAME/KEY: misc_feature
<222> LOCATION: (27)..(27)
<223> OTHER INFORMATION: n = a, c, g, or t
<220> FEATURE:
<221> NAME/KEY: misc_feature
<222> LOCATION: (41)..(41)
<223> OTHER INFORMATION: n = a, c, g, or t

<400> SEQUENCE: 28
aaactgggna aactggnaat cacctgnatt tgaaagtggg nataacttct tcatgccaac      60
tcctatgagt tttattcaac ttcctggtga ttctccacca ctttatgtat ccaaatcaag     120
cttcttacaa agtgattcat cctggtttga ttggaacgac gaacaagttg tgctattccc     180
aaacttggaa actggaatca cctgacttga aagtgggata acttcttcat cccaactcct     240
atgagattta ttcaacttcc tggtgattct ccaccacttt atgtatccaa atcaagcttc     300
ttacaaagtg attcattctg gtttgtttgg aacgacgaag aagcg                     345

<210> SEQ ID NO 29
<211> LENGTH: 40
<212> TYPE: DNA
<213> ORGANISM: Artificial sequence
<220> FEATURE:
<223> OTHER INFORMATION: Synthetic primer

<400> SEQUENCE: 29
ggtggtcggc cggagcacaa gcgggccaag cccatgcttg                            40

<210> SEQ ID NO 30
<211> LENGTH: 41
<212> TYPE: DNA
<213> ORGANISM: Artificial sequence
<220> FEATURE:
<223> OTHER INFORMATION: Synthetic primer

<400> SEQUENCE: 30
ggtggtcggc cgcaggttgc atatgaatct ttaactgaca g                          41

<210> SEQ ID NO 31
<211> LENGTH: 41
<212> TYPE: DNA
<213> ORGANISM: Artificial sequence
<220> FEATURE:
<223> OTHER INFORMATION: Synthetic primer

<400> SEQUENCE: 31
ggtggtcggc cgcgagcaca agcgggccaa gcccatgctt g                          41

<210> SEQ ID NO 32
<211> LENGTH: 42
<212> TYPE: DNA
<213> ORGANISM: Artificial sequence
<220> FEATURE:
<223> OTHER INFORMATION: Sytnthetic primer

<400> SEQUENCE: 32
ggtggtcggc cgtcaggttg catatgaatc tttaactgac ag                         42

<210> SEQ ID NO 33
<211> LENGTH: 39
<212> TYPE: DNA
<213> ORGANISM: Artificial sequence
<220> FEATURE:
```

<223> OTHER INFORMATION: Synthetic primer

<400> SEQUENCE: 33
ggtggtcggc cgtcgtcggc acttggcagc gaaatctcc                                39

<210> SEQ ID NO 34
<211> LENGTH: 42
<212> TYPE: DNA
<213> ORGANISM: Artificial sequence
<220> FEATURE:
<223> OTHER INFORMATION: Synthetic primer

<400> SEQUENCE: 34
ggtggtcggc cgcattatca tataattatg ttttgctgct tc                            42

<210> SEQ ID NO 35
<211> LENGTH: 38
<212> TYPE: DNA
<213> ORGANISM: Artificial sequence
<220> FEATURE:
<223> OTHER INFORMATION: Synthetic primer

<400> SEQUENCE: 35
ggtggtcggc cgcgtcggca cttggcagcg aaatctcc                                 38

<210> SEQ ID NO 36
<211> LENGTH: 41
<212> TYPE: DNA
<213> ORGANISM: Artificial sequence
<220> FEATURE:
<223> OTHER INFORMATION: Synthetic primer

<400> SEQUENCE: 36
ggtggtcggc cgattatcat ataattatgt tttgctgctt c                             41

<210> SEQ ID NO 37
<211> LENGTH: 105
<212> TYPE: DNA
<213> ORGANISM: Lycopersicum
<220> FEATURE:
<221> NAME/KEY: misc_feature
<222> LOCATION: (18)..(18)
<223> OTHER INFORMATION: n = a, c, g, or t
<220> FEATURE:
<221> NAME/KEY: misc_feature
<222> LOCATION: (29)..(29)
<223> OTHER INFORMATION: n = a, c, g, or t

<400> SEQUENCE: 37
accaaatttg ttcgtggnac gtcctcaana cgttgtctat gcatacggtt ggccatcacg         60
gcctttccga cccatttgga aggtcaaacg aaccccgaag tgagc                        105

<210> SEQ ID NO 38
<211> LENGTH: 105
<212> TYPE: DNA
<213> ORGANISM: Lycopersicum
<220> FEATURE:
<221> NAME/KEY: misc_feature
<222> LOCATION: (40)..(40)
<223> OTHER INFORMATION: n = a, c, g, or t

<400> SEQUENCE: 38
ggttttctag gccgtttggg aaggtcaaac gagccccggn acgagcatac gcctcatttt         60
gacgattttc gtgtgctatt gcacaccatt ttttgggtga tcgag                        105

<210> SEQ ID NO 39

-continued

<211> LENGTH: 256
<212> TYPE: DNA
<213> ORGANISM: Lycopersicum

<400> SEQUENCE: 39

| gtaacgacct gtttagtcgt tttgagcagc agattttatt tctggaaaaa caggctgaga | 60 |
| cgacggaaac cacgacggac cgtcatgggc acgacggacc gtcgaggggg tctcgttcca | 120 |
| aaacacttag aattctgaaa tttgggtact gaaatcgact ctctgaactt cgtgaagaag | 180 |
| tggcaggacg gaccgtcgtg ggcacgacgg accgtcacag gcccttcaat aatttcagtc | 240 |
| tctgaactct gtgacg | 256 |

<210> SEQ ID NO 40
<211> LENGTH: 574
<212> TYPE: DNA
<213> ORGANISM: Plant Telomere probe

<400> SEQUENCE: 40

| aggcgcgcca cctgcaggag agctcggtct catcgagaca cagggtttag ggtttagggt | 60 |
| ttagggttta gggttttag gggtttaggg tttaggtttt agggttagg gtttaggtt tagggtttag | 120 |
| ggtttagggt ttagggttta gggtttaggg tttagggttt agggtttagg gtttagggtt | 180 |
| tagggtttag ggtttagggt ttagggttta gggtttaggg tttagggttt agggtttagg | 240 |
| gtttagggtt tagggtttag ggtttagggt ttagggttta gggtttaggg tttagggttt | 300 |
| agggtttagg gtttagggtt tagggtttag ggtttagggt ttagggttta gggtttaggg | 360 |
| tttagggttt agggtttagg gtttagggtt tagggtttag ggtttagggt ttagggttta | 420 |
| gggtttaggg tttagggttt agggtttagg gtttagggtt tagggtttag ggtttagggt | 480 |
| ttagggttta gggtttaggg tttagggttt agggtttagg gtttagggtt tagggtttag | 540 |
| gtgagcccgg gtttaaacgc ccgggccgtc gacc | 574 |

<210> SEQ ID NO 41
<211> LENGTH: 41
<212> TYPE: DNA
<213> ORGANISM: Artificial sequence
<220> FEATURE:
<223> OTHER INFORMATION: Synthetic primer

<400> SEQUENCE: 41

| aggcgcgcca cctgcaggag agctcggtct catcgagaca c | 41 |

<210> SEQ ID NO 42
<211> LENGTH: 34
<212> TYPE: DNA
<213> ORGANISM: Artificial sequence
<220> FEATURE:
<223> OTHER INFORMATION: Synthetic primer

<400> SEQUENCE: 42

| ggtcgacggc ccgggcgttt aaacccgggc tcac | 34 |

<210> SEQ ID NO 43
<211> LENGTH: 155
<212> TYPE: DNA
<213> ORGANISM: Glycine max
<220> FEATURE:
<221> NAME/KEY: misc_feature
<222> LOCATION: (4)..(4)
<223> OTHER INFORMATION: n = a, c, g, or t
<220> FEATURE:
<221> NAME/KEY: misc_feature
<222> LOCATION: (26)..(26)

<223> OTHER INFORMATION: n = a, c, g, or t

<400> SEQUENCE: 43
gttnttgtcg tttgaatttg ctgagnacct tcaacattca atttcgagcg tctcgatata    60
ttacgggact taatcagaca atcgagtaaa aagttattgt cgtttgaatt tgctcagagc   120
ttctgttttc aattacgagc gtctcgatat attac                              155

<210> SEQ ID NO 44
<211> LENGTH: 167
<212> TYPE: DNA
<213> ORGANISM: Glycine max
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (13)..(13)
<223> OTHER INFORMATION: n = a, c, g, or t
<220> FEATURE:
<221> NAME/KEY: misc_feature
<222> LOCATION: (31)..(31)
<223> OTHER INFORMATION: n = a, c, g, or t
<220> FEATURE:
<221> NAME/KEY: misc_feature
<222> LOCATION: (39)..(39)
<223> OTHER INFORMATION: n = a, c, g, or t
<220> FEATURE:
<221> NAME/KEY: misc_feature
<222> LOCATION: (54)..(54)
<223> OTHER INFORMATION: n = a, c, g, or t
<220> FEATURE:
<221> NAME/KEY: misc_feature
<222> LOCATION: (65)..(65)
<223> OTHER INFORMATION: n = a, c, g, or t
<220> FEATURE:
<221> NAME/KEY: misc_feature
<222> LOCATION: (96)..(96)
<223> OTHER INFORMATION: n = a, c, g, or t

<400> SEQUENCE: 44
gtccgnatca ggncgcataa tatatgcgag nacgctagna aattgaataa tggnaagcac    60
tcganaaatt caaatggtca taactttcca cacggnaggt tagattcaag cgcataatat   120
atagagaagc tcgaaatata acaactaaag ctctcgcgaa attcaaa                 167

<210> SEQ ID NO 45
<211> LENGTH: 216
<212> TYPE: DNA
<213> ORGANISM: Glycine max
<220> FEATURE:
<221> NAME/KEY: misc_feature
<222> LOCATION: (34)..(34)
<223> OTHER INFORMATION: n = a, c, g, or t

<400> SEQUENCE: 45
ggcagagttt ttggtttttt catgttgtca aagnagttga acaatgaaaa tggatgacta    60
gtgcctgatc gaattgatcg gatcatgtag gaacaaggtt caagtctacc ggtctgttag   120
gatgcctcag ctgcatacat cactgcactt ccacttgaca cctatcatta attagaaacg   180
gctcgtctcg ccgtgacctt ctcttgaatt ctcaaa                             216

<210> SEQ ID NO 46
<211> LENGTH: 605
<212> TYPE: DNA
<213> ORGANISM: Glycine max
<220> FEATURE:
<221> NAME/KEY: misc_feature
<222> LOCATION: (368)..(368)

<223> OTHER INFORMATION: n = a, c, g, or t

<400> SEQUENCE: 46

```
ggtgttgggc ctttaaaaat gatccttttta acttggtaag aaaagctgag ataaaacttt    60
caaatctttt tttagtgatt ttttggtgga cgagcttgac ttggcgaatt gattttagcc   120
ttagtttcgc tttagttatt agtcaattca attaagaatg ataaatccca aagagaaaat   180
gtccgattga tttttgtgct tcattttact aaaagatatt cttttgatta ttatattatt   240
attttacctc tttttttgat ttccaacgtg gttacggcac gaccgagcgg ttggaactcc   300
ttttaacaga aattaatgaa tactacaatt caaatgatcg atggaaattt attttatttt   360
tagattangc gcgaaatgac ttaaataaat gactgaagca tgtcaaaagg gggtatggaa   420
agtaatgaaa ataagaataa aaatacatga aacacaatgt ggaccactac gggtacatag   480
aatgaatcga aaagcttggt tcgaggtact tacccgttga agatcgaaga acgatgaaga   540
acgaatgaag aacgtcgaag aacgattgaa agctttgcga gattcctcac gggaaaacgt   600
tacgg                                                              605
```

<210> SEQ ID NO 47
<211> LENGTH: 24
<212> TYPE: DNA
<213> ORGANISM: Artificial sequence
<220> FEATURE:
<223> OTHER INFORMATION: Synthetic probe

<400> SEQUENCE: 47

```
tgaacggcca cgagttcgag atcg                                          24
```

<210> SEQ ID NO 48
<211> LENGTH: 24
<212> TYPE: DNA
<213> ORGANISM: Artificial sequence
<220> FEATURE:
<223> OTHER INFORMATION: Synthetic probe

<400> SEQUENCE: 48

```
gtcctcgttg tgggaggtga tgtc                                          24
```

<210> SEQ ID NO 49
<211> LENGTH: 24
<212> TYPE: DNA
<213> ORGANISM: Artificial sequence
<220> FEATURE:
<223> OTHER INFORMATION: Synthetic probe

<400> SEQUENCE: 49

```
ctgccactcc atttccttct cggc                                          24
```

<210> SEQ ID NO 50
<211> LENGTH: 24
<212> TYPE: DNA
<213> ORGANISM: Artificial sequence
<220> FEATURE:
<223> OTHER INFORMATION: Synthetic probe

<400> SEQUENCE: 50

```
acttatccgg tcctagatca tcag                                          24
```

<210> SEQ ID NO 51
<211> LENGTH: 176
<212> TYPE: DNA
<213> ORGANISM: Brassica oleraceae

```
<400> SEQUENCE: 51
agcttgattt ggatacataa agtggtggag aatcaccagg aagttgaata aatctcatag        60
gagttggcat gaagaagtta tcccmctttc aaatcaggtg attccagttt cccagtttgg       120
gaatagcaca gcttcttcgt cgttccaatc aaaccaggat gaatctcttt gtaaga           176

<210> SEQ ID NO 52
<211> LENGTH: 176
<212> TYPE: DNA
<213> ORGANISM: Brassica oleraceae

<400> SEQUENCE: 52
accttcattt ggatacataa agtagtgkag aatcaccagg aagttgaata aatctcatag        60
gagttaggat gaagaagtta tcccactttc aaataaggtg atcccagttt ycctgtttgg      120
gaatatgaca acttcttcgt cattctaatc aaaccaggat gaatckygat gtwaga          176
```